United States Patent [19]

Misra et al.

[11] Patent Number: 5,153,327
[45] Date of Patent: Oct. 6, 1992

[54] 7-OXABICYCLOHEPTYL SUBSTITUTED HETEROCYCLIC AMIDE OR ESTER PROSTAGLANDIN ANALOGS USEFUL IN THE TREATMENT OF THROMBOTIC AND VASOSPASTIC DISEASE

[75] Inventors: Raj N. Misra, Hopewell; Philip M. Sher, Plainsboro; Philip D. Stein, Princeton; Steven E. Hall, Trenton; David Floyd, Pennington, all of N.J.; Joel C. Barrish, Holland, Pa.

[73] Assignee: E. R. Squibb & Sons, Inc., Princeton, N.J.

[21] Appl. No.: 774,424

[22] Filed: Oct. 10, 1991

Related U.S. Application Data

[60] Division of Ser. No. 540,026, Jun. 18, 1990, Pat. No. 5,100,889, which is a continuation-in-part of Ser. No. 442,818, Nov. 28, 1989, abandoned, which is a continuation-in-part of Ser. No. 433,301, Nov. 8, 1989, abandoned, which is a continuation of Ser. No. 288,826, Dec. 23, 1988, abandoned, and a continuation-in-part of Ser. No. 334,070, Apr. 3, 1989, abandoned.

[51] Int. Cl.$^5$ .......................... C07D 413/04
[52] U.S. Cl. .......................... 548/237
[58] Field of Search .......................... 548/237

[56] References Cited

U.S. PATENT DOCUMENTS

| | | | |
|---|---|---|---|
| 4,416,896 | 11/1983 | NaKane et al. | 514/469 |
| 4,418,076 | 11/1983 | NaKane et al. | 514/212 |
| 4,463,015 | 7/1984 | Haslanger et al. | 514/212 |
| 4,474,804 | 10/1984 | Das et al. | 514/469 |
| 4,522,949 | 6/1985 | Das et al. | 514/469 |
| 4,536,513 | 8/1985 | Das et al. | 514/469 |
| 4,663,336 | 5/1987 | NaKane et al. | 514/381 |
| 4,663,337 | 5/1987 | Das et al. | 514/469 |

OTHER PUBLICATIONS

As Belo Bioorg Chem, 04.03.81-SU278256 (23.11.87).
Chem Abs. SA Selects: Prostaglandins Issue 12, 1988 108:198903m. Kuz'mitskii, B. B. et al.
CA Selects: Prostaglandins, Issue 12, 1988, 108:204363d, Lakhvich, F..A. et al.
CA 114:164202r Preparation of . . . vaso relaxants Misra, p. 776, 1991.
CA 114:62093p Preparation of . . . vasospastic disease. Sher et al., p. 690, 1991.
Reagents for Organic Synthesis, Fieser and Fieser, p. 165, 1967.

*Primary Examiner*—Mary C. Lee
*Assistant Examiner*—Joseph K. McKane
*Attorney, Agent, or Firm*—Burton Rodney

[57] ABSTRACT

7-Oxabicycloheptane substituted prostaglandin analogs useful in treating thrombotic and vasospastic disease have the structural formula

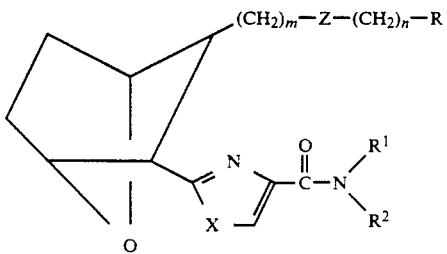

wherein m is 1, 2 or 3; n is 1, 2, 3 or 4; Z is —(CH$_2$)$_2$—, —CH=CH— or

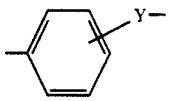

wherein Y is O, a single bond or vinyl, with the proviso that when n is O, if Z is

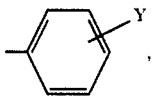

then Y cannot be O, and when Z is —CH=CH—, n is 1, 2, 3 or 4; and when Y=vinyl, n=; R is CO$_2$H, CO$_2$lower alkyl, CH$_2$OH, CO$_2$alkali metal, CONHSOR$^3$m CONHR$^{3a}$ or —CH$_2$-5-tetrazolyl, X is O, S or NH; and where R$^1$, R$^2$, R$^3$ and R$^{3a}$ are as defined herein.

4 Claims, No Drawings

7-OXABICYCLOHEPTYL SUBSTITUTED HETEROCYCLIC AMIDE OR ESTER PROSTAGLANDIN ANALOGS USEFUL IN THE TREATMENT OF THROMBOTIC AND VASOSPASTIC DISEASE

This is a division of application Ser. No. 540,026, filed Jun. 18, 1990, U.S. Pat. No. 5,100,889 which is a continuation-in-part of application Ser. No. 442,818, filed Nov. 28, 1989, now abandoned which is a continuation-in-part of application Ser. No. 433,301, filed Nov. 8, 1989, now abandoned which is a continuation of application Ser. No. 288,826, filed Dec. 23, 1988, now abandoned and is a continuation-in-part of application Ser. No. 334,070, filed Apr. 3, 1989 now abandoned.

DESCRIPTION OF THE INVENTION

The present invention relates to 7-oxabicycloheptyl substituted heterocyclic amide prostaglandin analogs which are thromboxane $A_2$ ($TXA_2$) receptor antagonists or combined thromboxane $A_2$ receptor antagonist/thromboxane synthetase inhibitors useful, for example, in the treatment of thrombotic and/or vasospastic disease, and have good duration of action. These compounds have the structural formula I

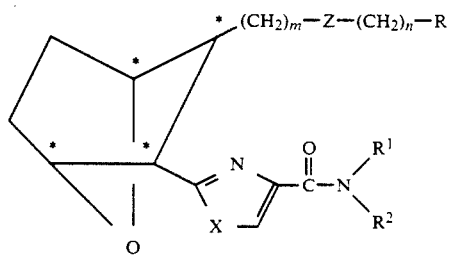

and including all stereoisomers thereof, wherein
m is 1, 2 or 3; n is 0, 1, 2, 3 or 4;
Z is $-(CH_2)_2-$, $-CH=CH-$ or

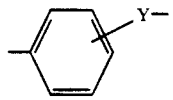

wherein Y is O, a single bond or vinyl ($-CH=CH-$), with the provisos that when n is 0, if Z is

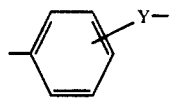

then Y cannot be O; and when Z is $-CH=CH-$, n is 1,2,3, or 4; and when Y=vinyl, n=0;
R is $CO_2H$, $CO_2$lower alkyl, $CO_2$alkali metal, $CH_2OH$, $CONHSO_2R^3$, $CONHR^{3a}$, or

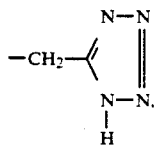

($-CH_2-$5-tetrazolyl);
X is O, S or NH;
$R^1$ is hydrogen, lower alkyl, lower alkenyl, lower alkynyl, aralkyl, aryl, cycloalkyl, cycloalkylalkyl, cycloheteroalkyl, cycloheteroalkylalkyl, heteroaryl or heteroarylalkyl, or amide

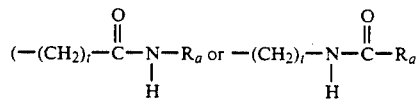

wherein t is 1 to 12 and $R_a$ is lower alkyl, aryl, cycloalkyl, or cycloalkylalkyl), each of $R^1$ being unsubstituted or optionally substituted with a lower alkyl, aryl, cycloalkyl, or cycloalkylalkyl group;
$R^2$ is hydrogen, lower alkyl, aryl, or aralkyl; or
$R^1$ and $R^2$ together with the nitrogen to which they are linked may form a 5- to 8- membered ring;
$R^3$ is lower alkyl, aryl or aralkyl; and
$R^{3a}$ is hydrogen, lower alkyl, aryl or aralkyl.

Thus, the compounds of the invention include the following types of compounds:

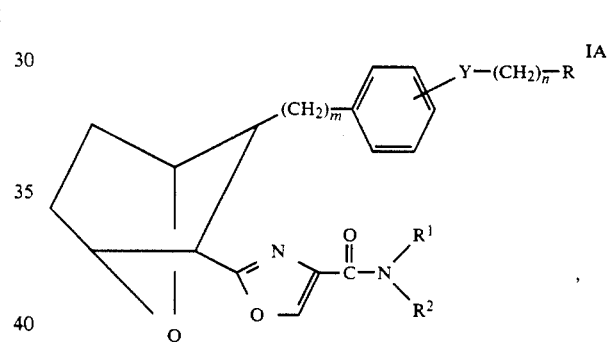

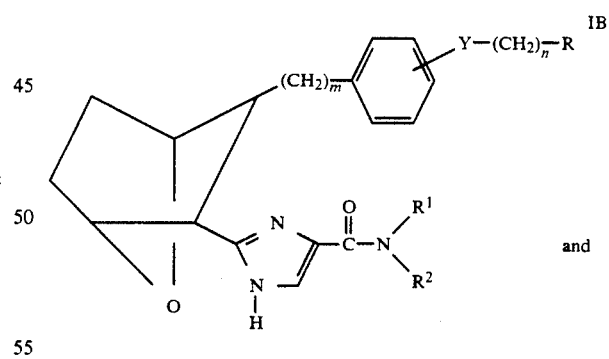

and

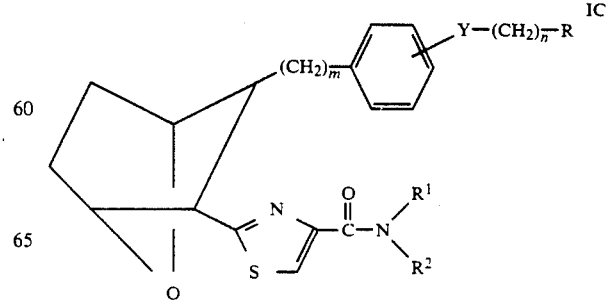

-continued

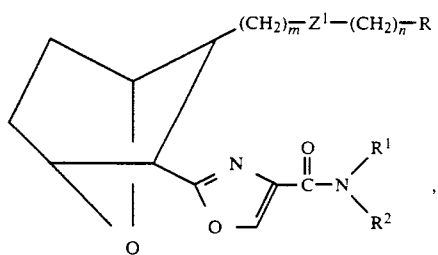
ID

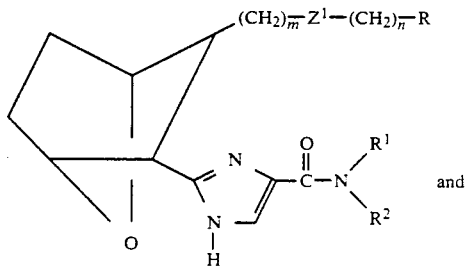
IE

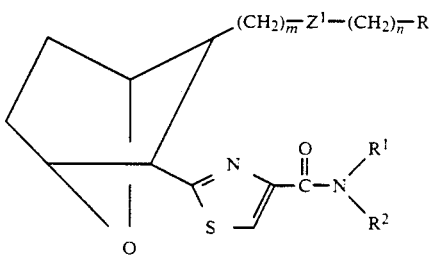
IF wherein in formulae ID, IE and IF, $Z^1$ is —CH=CH— or —(CH$_2$)$_2$—.

In addition, in accordance with the present invention, a compound is provided having the structure $I_x$

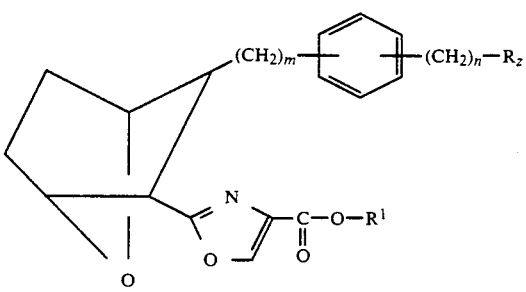
$I_x$ wherein m, n, and $R^1$ are as defined hereinbefore except that it will not include H and $R_z$ is CO$_2$H, CO$_2$ alkyl or CO$_2$ alkali metal.

Preferred are compounds of formula $I_x$ having the formula $I_y$

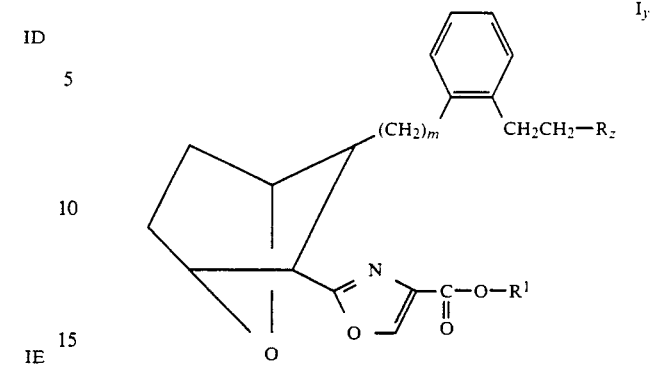
$I_y$ where $R_z$ is CO$_2$H and $R^1$ is cycloalkylalkyl.

The term "lower alkyl" or "alkyl" as employed herein includes both straight and branched chain radicals of up to 18 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including 1, 2 or 3 halo substituents, an aryl substituent, an alkyl-aryl substituent, a haloaryl substituent, a cycloalkyl substituent, an alkylcycloalkyl substituent, hydroxy or a carboxy substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with substituents such as halogen, lower alkyl, alkoxy and/or hydroxy group.

The term "aryl" or "Ar" as employed herein refers to monocyclic or bicyclic aromatic groups containing from 6 to 10 carbons in the ring portion, such as phenyl, naphthyl. Aryl (or Ar), phenyl or naphthyl may include substituted aryl, substituted phenyl or substituted naphthyl, which may include 1 or 2 substituents on either the phenyl or naphthyl such as lower alkyl, trifluoromethyl, halogen (Cl, Br, I or F), lower alkoxy, arylalkoxy, hydroxy, alkylthio, alkylsulfinyl, alkylsulfonyl, arylthio, arylsulfinyl and/or arylsulfonyl.

The term "aralkyl", "aryl-alkyl" or "aryl-lower alkyl" as used herein refers to lower alkyl groups as discussed above having an aryl substituent, such as benzyl.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "lower alkenyl" or "alkenyl" as employed herein with respect to the $R^1$ substituent includes a carbon chain of up to 16 carbons, preferably 3 to 10 carbons, containing one double bond which will be separated from "N" by at least one saturated carbon moiety such as —(CH$_2$)$_q$— where q can be 1 to 14, such as 2-propenyl, 2-butenyl, 3-butenyl, 2-pentenyl, 4-pentenyl and the like, and may include a halogen substituent such as I, Cl, or F.

The term "lower alkynyl" or "alkynyl" as employed herein with respect to the $R^1$ substituent includes a carbon chain of up to 16 carbons, preferably 3 to 10 carbons, containing one triple bond which will be separated from "N" by at least one saturated carbon moiety such as —(CH$_2$)$_{q'}$— where q' can be 1 to 14, such as 2-propynyl, 2-butynyl, 3-butynyl and the like.

The term "cycloheteroalkyl" as used herein as an R$^1$ substituent refers to a 5-, 6- or 7-membered saturated ring which includes 1 or 2 hetero atoms such as nitrogen, oxygen and/or sulfur, and which is linked to the "N" of the

group through a carbon atom either beta or gamma to a heteroatom, such as

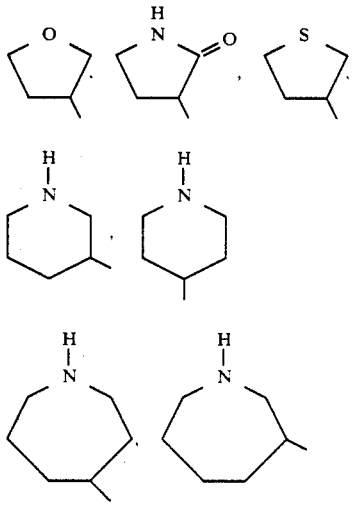

and the like.

The term "heteroaryl" or heteroaromatic as an R$^1$ substituent refers to a 5- or 6-membered aromatic ring which includes 1 or 2 hetero atoms such as nitrogen, oxygen or sulfur, which are not directly linked through a hetero atom to the "N" of the

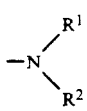

group, such as

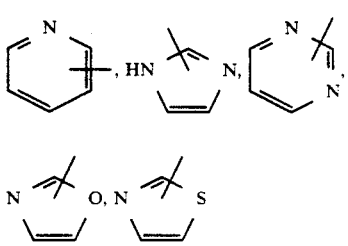

and the like

The term "cycloheteroalkylalkyl" as defined by R$^1$ refers to 5-, 6- or 7-membered saturated ring which includes 1 or 2 heteroatoms such as nitrogen, oxygen or sulfur, and is linked to the "N" of the

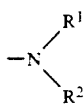

group through a (C$_2$)$_x$ chain wherein x is 1 to 12, preferably 1 to 8, such as

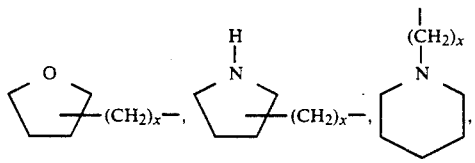

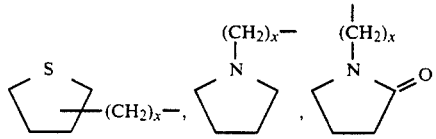

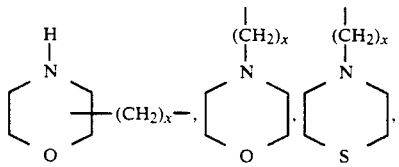

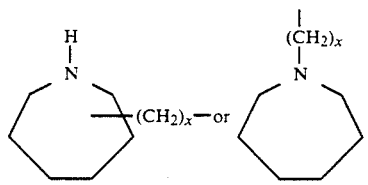

The term "heteroarylalkyl" as defined by R$^1$ refers to a 5-, 6- or 7-membered aromatic ring which includes 1, 2, 3 or 4 heteroatoms such as nitrogen, oxygen or sulfur, and is linked to the "N" of the

group through a —(CH$_2$)$_{x'}$— chain where x' is 1 to 12, preferably 1 to 8, such as

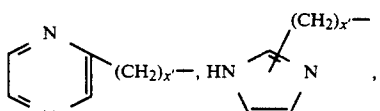

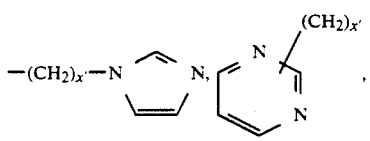

-continued

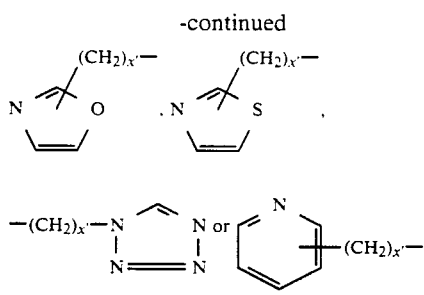

Preferred are those compounds of formula I wherein Z is

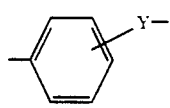

and X is O. More preferred are compound of formula I wherein Z— is

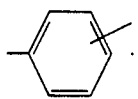

, m is 1, n is 1 or 2, Y is a single bond, X is O, R is $CO_2H$, $R^1$ is substituted alkyl or a cycloheteroalkylalkyl and $R^2$ is H or lower alkyl, and $-Y-(CH_2)_n-R$ is in the ortho or meta position.

Also preferred are compounds of formula I wherein Z is $-CH=CH-$ in the cis configuration, m is 1, n is 2 or 3, R is $CO_2H$, $R^1$ is substituted phenylalkyl or cyclohexylalkyl and $R^2$ is H or methyl.

The compounds of formula I of the invention may be prepared as follows.

The various compounds of the invention wherein Z is

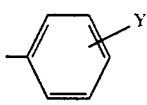

may be prepared as outlined below.

Compounds of the invention where Y is a single bond, n is 1, 2, 3 or 4 and X is O are prepared starting with bromophenylalkyl alcohol A

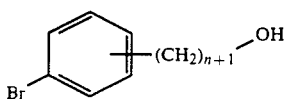

wherein n is 1, 2, 3 or 4 which is treated with a protecting compound such as t-butylchlorodiphenylsilane, in the presence of an amine base such as triethylamine and an inert solvent, employing conventional procedures, to form the protected bromophenylalkyl compound B

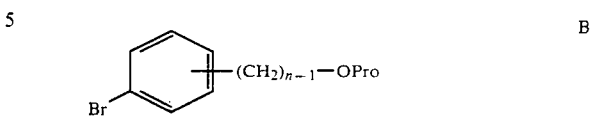

wherein Pro represents a protecting group.

Examples of protecting compounds suitable for use herein in reacting with bromophenalkyl alcohol A include but are not limited to

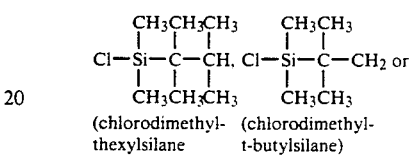

(chlorodimethyl-   (chlorodimethyl-
thexylsilane)      t-butylsilane)

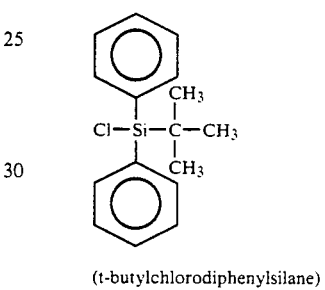

(t-butylchlorodiphenylsilane)

The protected compound B is then transmetallated by treatment with $t-C_7H_9Li$ or $n-C_7H_9Li$ in the presence of diethyl ether or tetrahydrofuran at reduced temperature of from about $-100°$ to about $0°$ C. or is preferably subjected to a Grignard reaction by treatment with magnesium in the presence of an inert organic solvent such as tetrahydrofuran (THF) or diethyl ether and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

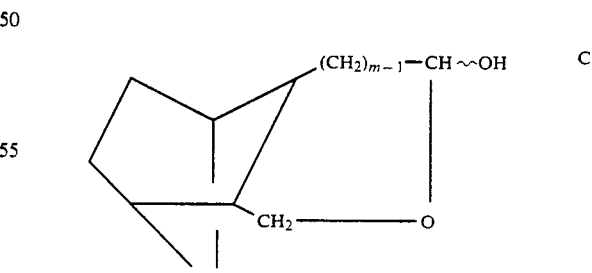

employing a molar ratio of C:B of within the range of from about 1:2 to about 1:4, in the presence of an inert organic solvent such as THF at a reduced temperature of from about $-78°$ to about $25°$ C., to form the condensed 7-oxabicycloheptane compound II

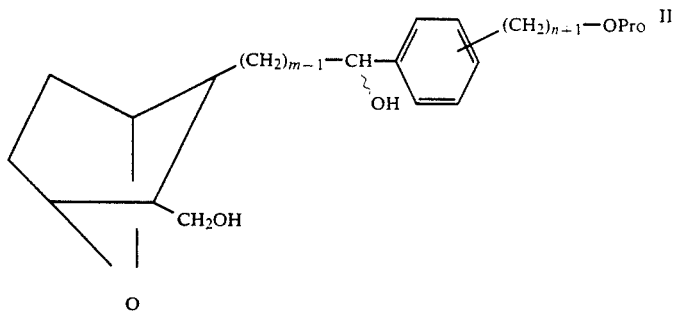

The condensed compound II is then subjected to hydrogenolysis by treatment with hydrogen in the presence of a catalyst such as palladium hydroxide on charcoal in acetic acid or an inert organic solvent such as ethyl acetate, to form the alcohol III

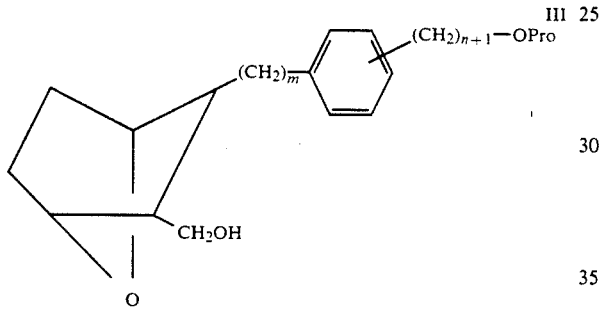

When the protecting group (Pro) in III is thexyldimethylsilyl or t-butyldimethylsilyl, alcohol III may be subjected to acetylation by treatment with acetyl chloride in the presence of pyridine and methylene chloride to acetylate the free alcohol and the so-formed acetate is deprotected by conventional procedures, for example, by treatment with aqueous hydrofluoric acid in the presence of acetonitrile to cleave off the silyl protecting group to form IIIA

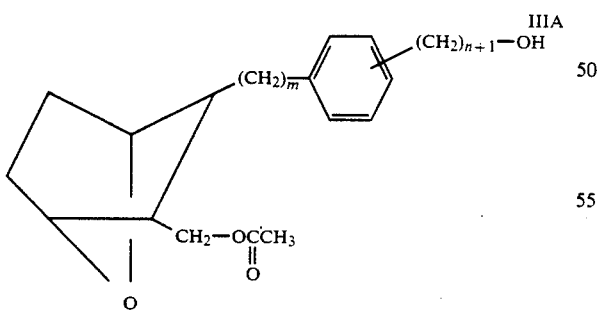

IIIA is then treated with a protecting compound such as t-butyldiphenylsilyl chloride in the presence of a catalyst such as 4,4-dimethylaminopyridine and an amine such as triethylamine and methylene chloride to add the protecting group and then the acetate is removed by treatment with aqueous hydroxide in tetrahydrofuran or excess methyllithium in the presence of an inert solvent such as diethyl ether to form IIIB

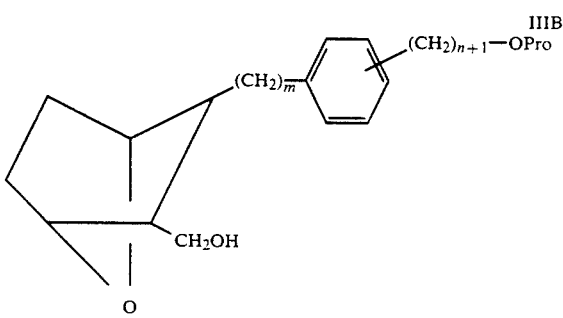

(where Pro is t-butyldiphenylsilyl)

The protected alcohol IIIB is then subjected to a Jones oxidation wherein a solution of protected alcohol IIIB in acetone cooled to from about −10° to about 25° C. is treated with Jones reagent (that is, CrO₃ dissolved or suspended in sulfuric acid in the presence of water, prepared as described in Fieser & Fieser, "Reagents for Organic Synthesis," Vol. 1, p. 142 (1967)) to form acid IV

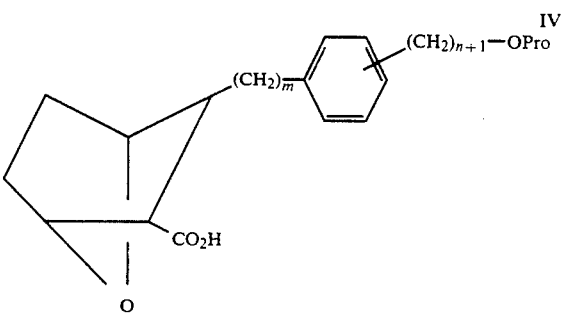

Acid IV, in an inert organic solvent, such as tetrahydrofuran, is then made to undergo a carbodiimide coupling reaction with amine hydrochloride D

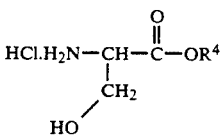

where $R^4$ is lower alkyl such as methyl or ethyl, or arylalkyl, such as benzyl, in the presence of dicyclohexylcarbodiimide (DCC) or 1-(3-dimethylaminopropyl)-3-ethylcarbodiimide hydrochloride (WSC) and 1-hydroxybenzotriazole and triethylamine under an inert atmosphere such as argon employing a molar ratio of D:IV of within the range of from about 1.2:1 to about 1:1, to form hydroxyamide V

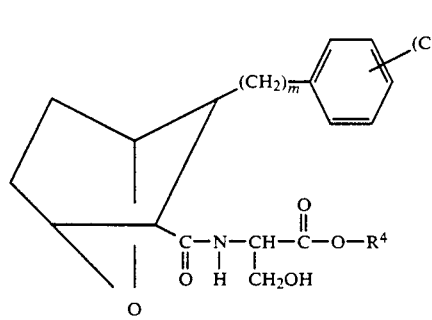

Hydroxyamide V is then subjected to cyclodehydration wherein a solution of V in an inert organic solvent such as tetrahydrofuran, acetonitrile or chloroform, under an inert atmosphere such as argon, is treated with triphenylphosphine (employing a molar ratio of V:triphenylphosphine of from about 0.8:1 to about 1:1) and carbon tetrachloride in the presence of an amine base such as triethylamine or diisopropylethylamine, to form oxazoline VI

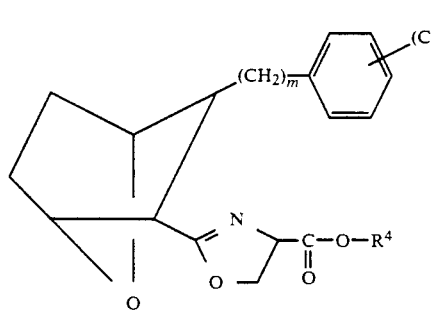

Oxazoline VI is oxidized by treatment with manganese dioxide or preferably nickel peroxide (Nakagawa et al, J. Org. Chem., 1962, 27, 1597) to form the oxazole VII

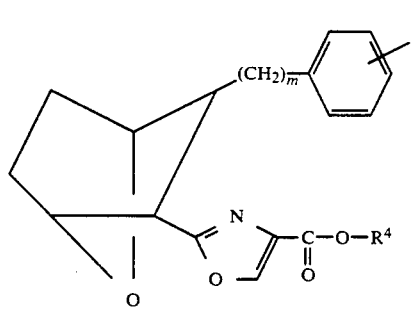

Oxazole VII is converted to the corresponding acid by treating VII with a base, such as lithium hydroxide, sodium hydroxide or potassium hydroxide to form the corresponding alkali metal salt, followed by neutralization with an acid, such as dilute hydrochloric acid or oxalic acid to form acid compound VIII

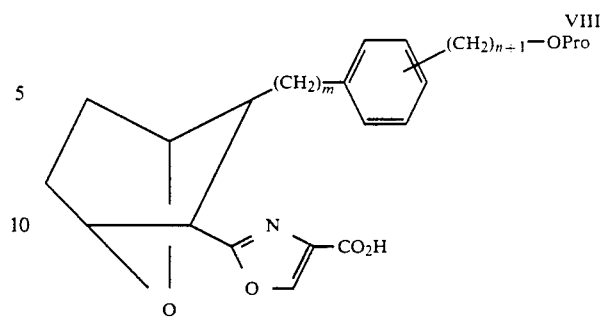

Acid VIII is converted to the corresponding acid chloride by treating VIII with oxalyl chloride optionally in the presence of catalytic amounts of dimethylformamide, and a solvent such as benzene, toluene or methylene chloride. The so-formed acid chloride is dissolved in an inert solvent such as methylene chloride or toluene cooled to a temperature within the range of from about $-10°$ C. to about $+10°$ C., and amine base such as triethylamine or pyridine and amine E, or a salt thereof, are added

employing a molar ratio of E:VIII of within the range of from about 1.1:1 to about 1.5:1, form the oxazole IX

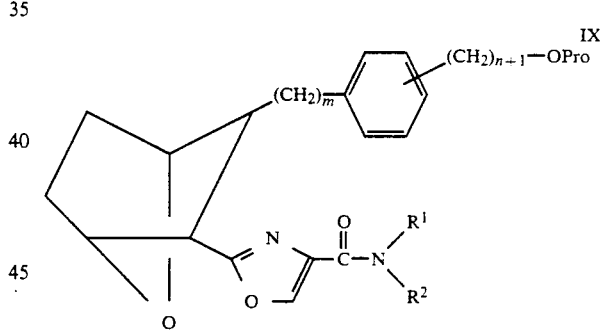

Silyl ether IX is then deprotected using conventional procedures, for example, by treatment with aqueous hydrofluoric acid in the presence of acetonitrile and methylene chloride and is then subjected to a Jones oxidation employing procedures described hereinbefore to form the oxazole IG of the invention

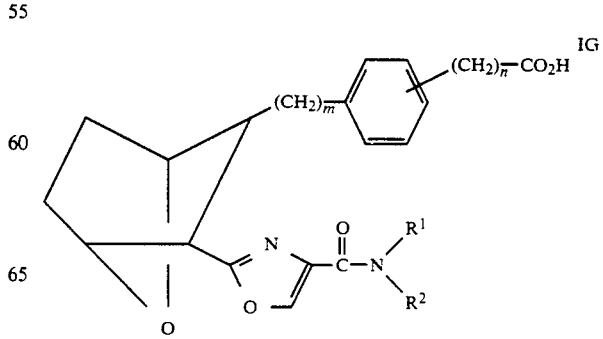

In a more preferred procedure, compounds of formula I wherein Y is a single bond, n is 1, 2, 3 or 4 and X is O may be prepared starting with alcohol III by protecting the alcohol function thereof by treatment, for example, with a solution of acetic anhydride, pyridine and 4-dimethylaminopyridine to form the protected alcohol X

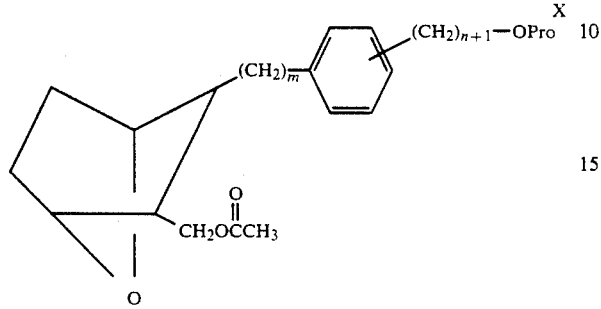

Alternatively, compound II can be protected by treatment with, for example, a solution of acetic anhydride and pyridine to form compound XI

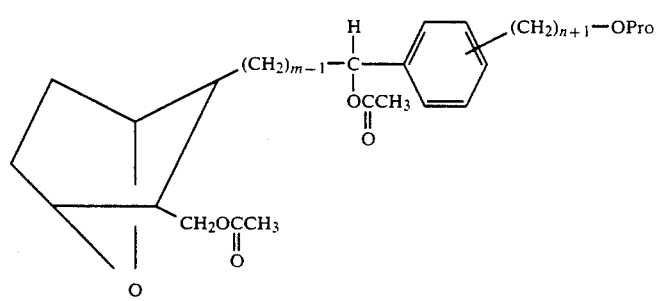

which is then subjected to hydrogenolysis as described above to provide compound X.

The protected alcohol X wherein Pro is t-butyldimethylsilyl or dimethyl(1,1,2-trimethylpropyl)silyl is subjected to a Jones oxidation employing procedures described hereinbefore to form crude acid which is deacetylated by reaction with aqueous hydroxide in the presence of inert organic solvent such as THF and then esterified, for example, by treatment with diazoalkane, such as diazomethane, or acidic alcohol such as methanolic HCl, to form the alcohol ester XII

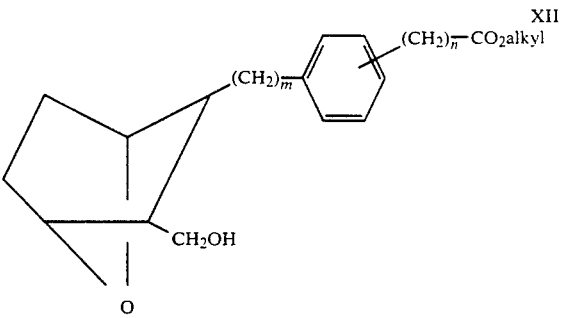

In an alternative method for forming alcohol ester XII, protected alcohol XI is subjected to a Jones oxidation and esterification to form ester XIa

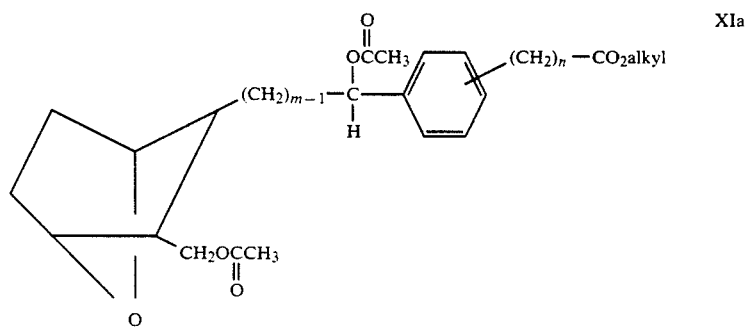

which is then made to undergo hydrogenolysis and subsequent removal of the acetate protecting group by transesterification to afford alcohol ester XII.

Next, the alcohol ester XII is subjected to a Jones oxidation to form the acid XIII

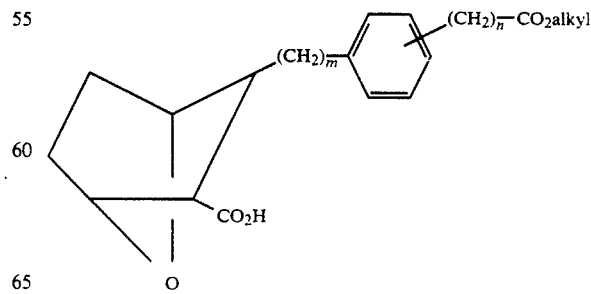

In an alternative procedure, acid XIII wherein n is 1, Z is

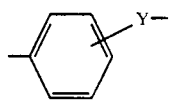

where Y is a single bond, may be prepared from alcohol III by treating III with acetic anhydride in the presence of pyridine or other organic base such as triethylamine, under an inert atmosphere such as argon, to form the corresponding acetate and treating the acetate with a deprotecting agent such as $(n-C_7H_9)_rNF$ to remove the protecting group and form acetate alcohol IIIC

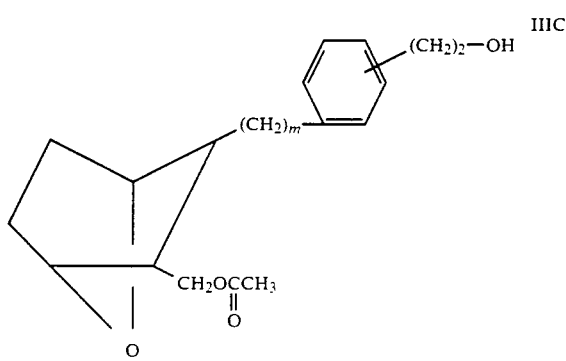

Acetate alcohol IIIC is then made to undergo a Dess-Martin oxidation by treating a mixture of IIIC in dry methylene chloride with Dess-Martin periodinane (J. Org. Chem. 1983, 48, 4155) to form the aldehyde IIID

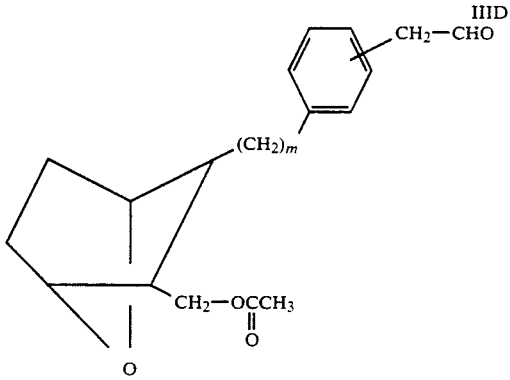

which is then oxidized by treating IIID with N-iodosuccinamide (NIS) in the presence of potassium carbonate in methanol to form acetate ester IIIE

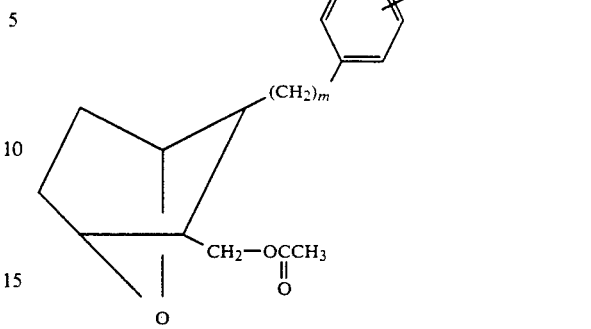

Acetate ester IIIE in methanol is deprotected by treatment with a weak base such as potassium carbonate, and the resulting alcohol is then subjected to a Jones oxidation as described herein to form acid XIII, where n is 1.

The acid XIII is then made to undergo a carbodiimide coupling reaction with amine hydrochloride D, where $R^4$ is benzyl, as described hereinbefore (with respect to coupling of acid IV) to form the amide XIV

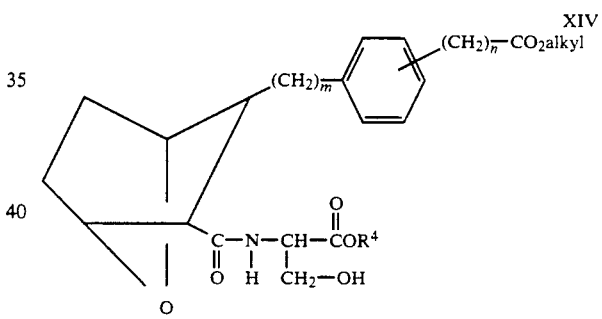

Amide XIV is then subjected to cyclodehydration (using a procedure similar to the cyclodehydration of amide V) to form oxazoline XV

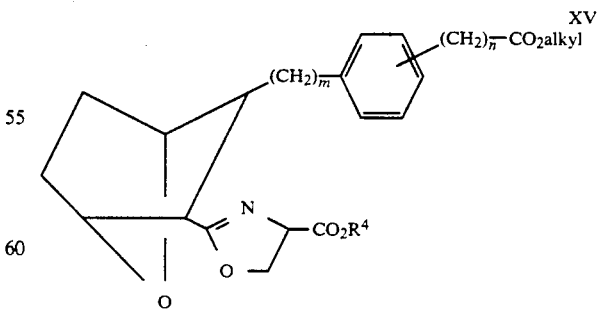

which is made to undergo oxidation using manganese dioxide, or nickel peroxide, or preferably cupric bromide and 1,8-diazabicyclo[5.4.0]undec-7-ene (DBU) to form the oxazole XVI

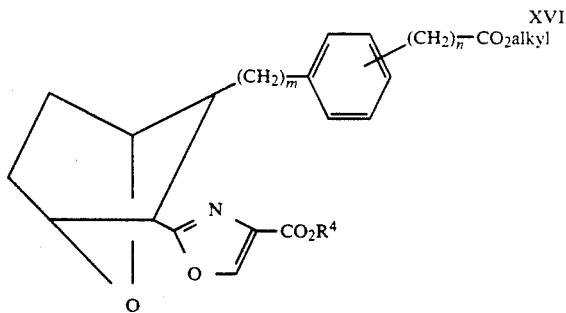

XVI

The cupric bromide oxidation is carried out at a temperature of within the range of from about 20° C. to about 70° C., employing a molar ratio of cupric bromide to XV of within the range of from about 2:1 to about 6:1 and a molar ratio of cupric bromide to DBU of within the range of from about 1:1 to about 1:3 in an inert solvent such as ethyl acetate or preferably ethylacetate/chloroform (1:1, v/v).

The latter oxidation is a novel method in accordance with the present invention.

Oxazole XVI is then deprotected to remove $R^{4\cdot}$ for example, by treatment with palladium hydroxide on charcoal and hydrogen in the presence of an inert solvent such as ethyl acetate, to form the corresponding acid XVII

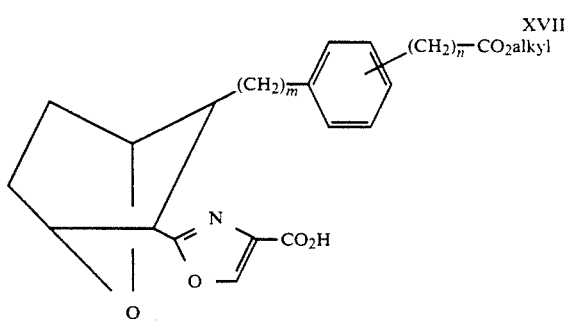

XVII

Acid XVII is then converted to the corresponding acid chloride employing a procedure similar to that described with respect to acid VIII and the resulting acid chloride is treated with amine E employing a procedure and molar ratio of E:XVII similar to that described hereinbefore with respect to acid VIII to form the ester of the invention IH

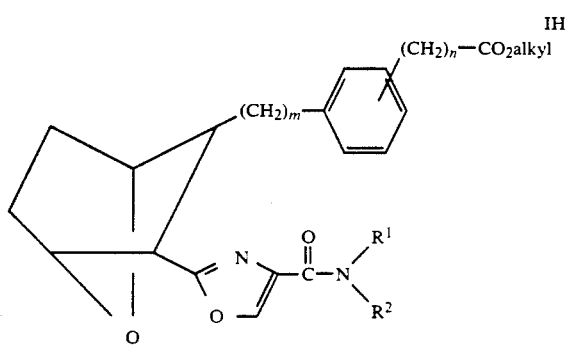

IH

In an alternate preferred procedure for the preparation of IH acid XIII is made to undergo a carbodiimide coupling reaction with amine Da

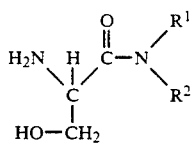

Da in the presence of dicyclohexylcarbodiimide or 1-(3-dimethylaminopropyl)-3-ethylcarbodiimide hydrochloride and 1-hydroxybenzotriazole and triethylamine as described hereinbefore to form hydroxy amide XIV'.

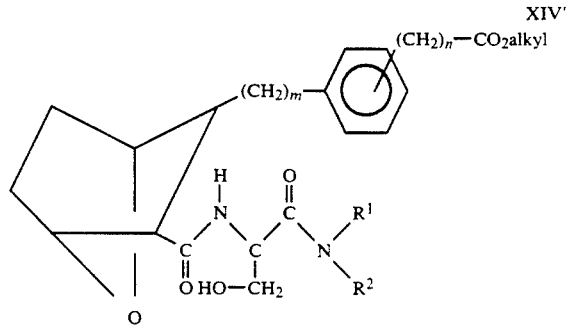

XIV'

Hydroxy amide XIV' is then subjected to cyclodehydration as described hereinbefore (with respect to the preparation of VI). A preferred method for this conversion involves treatment of XIV' with an alkylsulfonyl chloride, such as methanesulfonyl chloride in the presence of an amine such as triethylamine or pyridine followed by treatment of the resulting alkylsulfonate intermediate with potassium carbonate in acetone to form oxazoline XV'

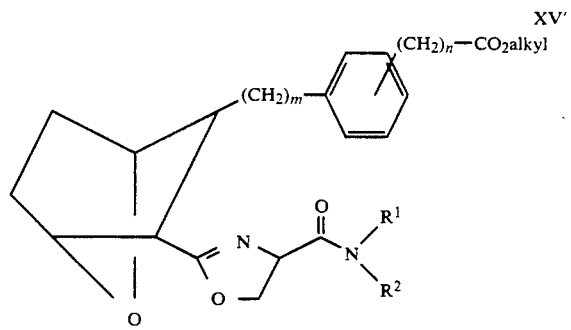

XV' which is made to undergo oxidation as described hereinbefore (with respect to the preparation of XVI) to form oxazole IH.

Ester IH may then be hydrolyzed by treatment with an aqueous solution of alkali metal base and then aqueous acid to form the corresponding acid IG.

Compounds of the invention wherein Y is O and X is 0 may be prepared as follows:

Bromophenol $A^1$

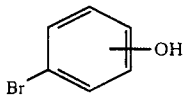

is treated with a protecting compound such as chloro-t-butyldimethylsilane, benzyl bromide or bromomethyl methyl ether, preferably benzyl bromide or bromomethyl methyl ether for ortho-bromophenol, employing conventional procedures to form the protected bromophenyl compound $B^1$

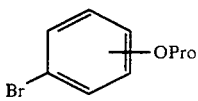

wherein Pro represents a protecting group.

Examples of protecting compounds suitable for use herein in reacting with bromophenol $A^1$ include those set out hereinbefore with respect to protection of alcohol A.

Protected compound $B^1$ is then transmetallated (using a procedure similar to that set out above with respect to transmetallation of B using n-butyllithium in THF) and condensed with hemiacetal C to form the condensed 7-oxabicycloheptane compound XXII

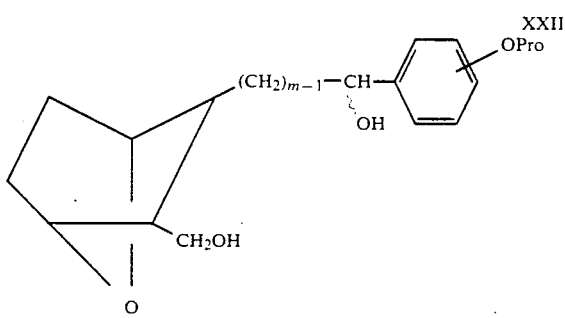

The condensed compound XXII is then subjected to hydrogenolysis by treatment with hydrogen in the presence of a catalyst such as palladium on charcoal in acetic acid, to form the alcohol XXIII in the case where Pro is a silyl or methoxymethyl ether protecting group or to form XXIV directly when Pro is benzyl.

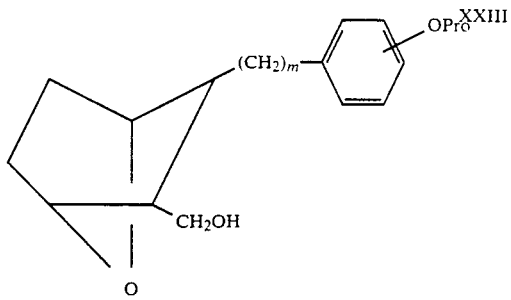

When Pro is a silyl protecting group, compound XXIII is deprotected by treatment with, for example, a solution of acetonitrile and aqueous hydrofluoric acid to form the deprotected alcohol XXIV

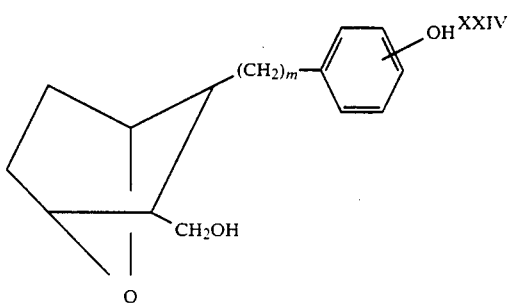

The alcohol XXIV is then alkylated by treating a solution of alcohol XXIV in tetrahydrofuran with a molar equivalent of sodium hydride or one to four equivalents of a carbonate base such as potassium carbonate. The resulting phenoxide solution is alkylated by treating with a haloalkanoic acid ester F $$Hal-(CH_2)_n-CO_2alkyl \qquad F$$

employing a molar ratio of F:XXIV of from about 1:1 to about 3:1, in the presence of an inert organic solvent such as THF or dimethylformamide or dimethoxyethane, to form ester XXV

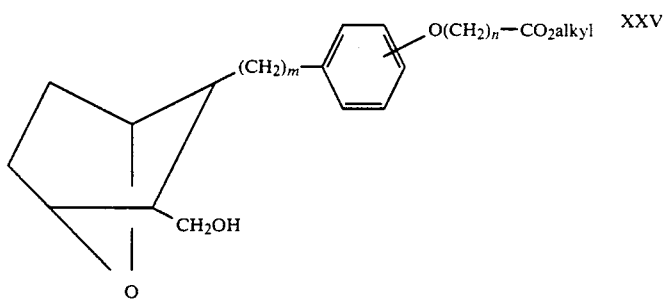

Alternatively, when the protecting group in XXIII is methoxymethyl, the free hydroxyl is protected as a benzyl ether. The methoxymethyl protecting group is removed by treatment with aqueous acid. The resulting phenol is alkylated with ethyl bromoacetate as described above for the alkylation of XXIV. The benzyl protecting group is then removed by hydrogenolysis with palladium hydroxide and hydrogen to give XXV.

Alternatively, alcohol ester starting materials of formula XXV may be prepared by following the procedure as described in U.S. Pat. No. 4,536,513.

Next, the alcohol ester XXV is subjected to a Jones oxidation as described hereinbefore with respect to the oxidation of alcohol IIIB, to form acid XXVI

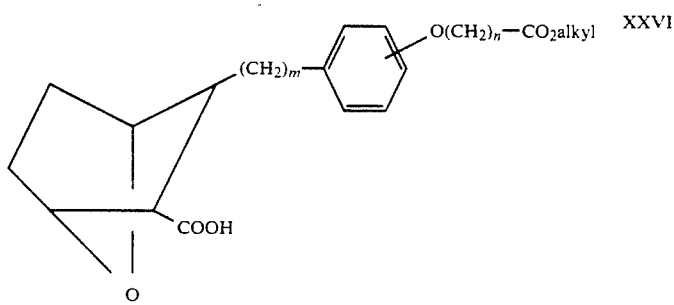

The acid XXVI is then used to prepare compounds of the invention of formula IJ and IK using the procedures set out hereinbefore with respect to conversion of acid XIII to ester IH

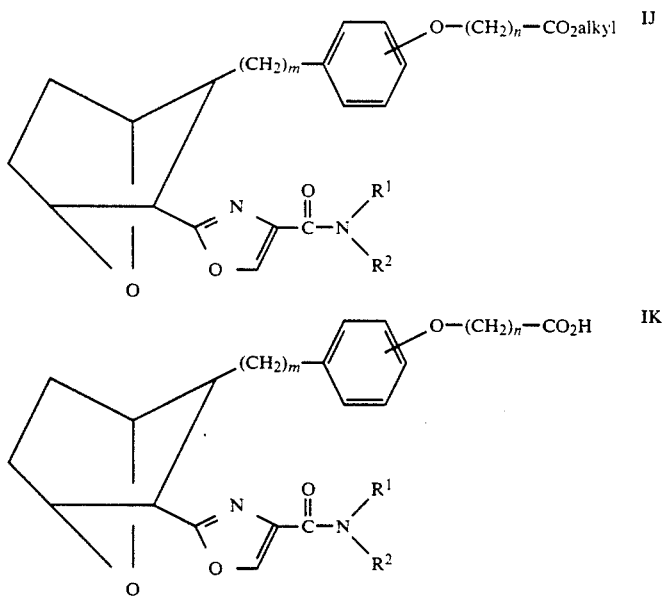

Compounds of the invention wherein Y is a single bond or O and X is S may be prepared starting with acid XIII or XXVI as follows:

Acid XIII or XXVI is reacted with oxalyl chloride, optionally in the presence of catalytic amounts of dimethylformamide, in methylene chloride, to form the corresponding acid chloride which is amidated by reacting with ammonia to form the amide XXVII

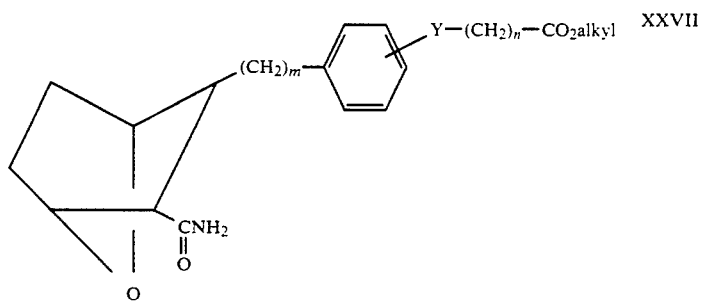

Alternatively, acid XIII or XXVI is reacted with an alkylchloroformate in the presence of an amine such as triethylamine to form the mixed anhydride which is amidated by reacting with methanol-ammonia solution or concentrated aqueous ammonia solution to form amide XXVII.

Amide XXVII is then treated with phosphorus pentasulfide ($P_2S_5$) or Lawesson's Reagent (2,4-bis(4-methoxyphenyl)-1,3-dithia-2,4-diphosphetane-2,4-disulfide) to form the corresponding thioamide XXVIII

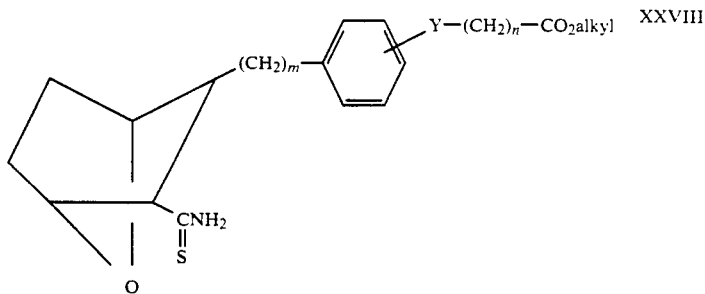

which is treated with bromopyruvic acid

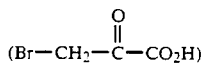

in a polar solvent such as dimethylformamide in the presence of a weak base such as K₂CO₃ employing a molar ratio of XXVIII: bromopyruvic acid of within the range of from about 1:1 to about 1:1.5 to form thiazoline XXIX

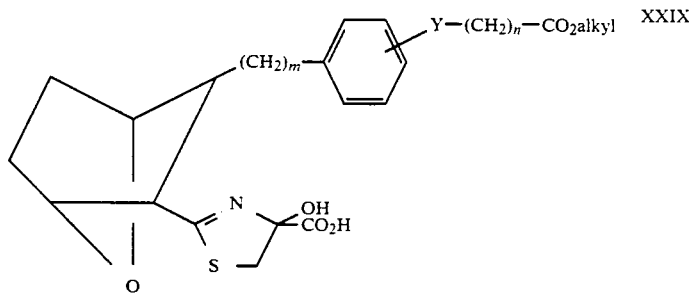

Thiazoline XXIX is then dehydrated by treatment with a sulfonyl chloride such as methanesulfonyl chlorine in the presence of a base such as triethylamine to form thiazole acid XXX

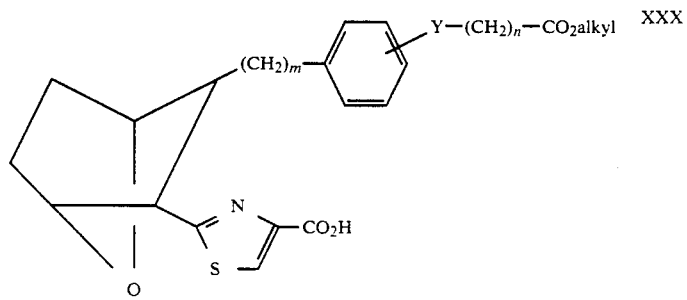

which is then made to undergo a carbodiimide coupling reaction with amine

in the presence of DCC or WSC under an inert atmosphere such as argon employing a molar ratio of E:XXX of within the range of from about 1:1 to about 2:1, to form amide IL

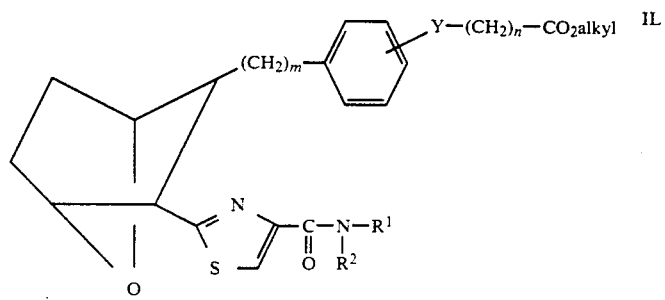

Alternatively, acid XXX can be activated by conversion to the corresponding acid chloride by treating acid XXX with oxalyl chloride in a nonpolar solvent such as benzene. The acid chloride is then coupled with amine E using an amine base such as triethylamine or pyridine to form IL.

Compounds of the invention where Y is a single bond or O and X is NH are prepared starting with acid XIII or XXVI which is made to undergo a coupling reaction with amine G

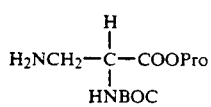

where BOC is t-butyloxycarbonyl and Pro is a protecting group such as benzyl, in the presence of a coupling agent such as 1-(3-dimethylaminopropyl)-3-ethylcarbodiimide hydrochloride (WSC) and 1-hydroxybenzotriazole (HOBT) and methylene chloride employing a molar ratio of XIII or XXVI:G of within the range of from about 1.2:1 to about 1:1, for a period of from about 12 to about 90 hours. The resulting amide is made to undergo a thionation reaction by treating the amide with Lawesson's reagent in the presence of benzene at a temperature of from about 50° to about 75° C. for a period of from about 1 to about 4 hours, to form the ester XXXI

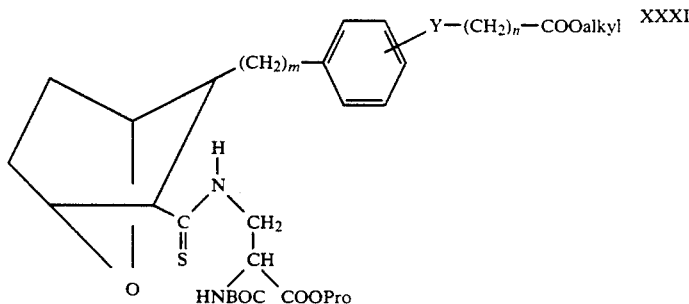

The ester XXXI is cyclized by treating a solution of XXXI in an inert solvent such as acetonitrile, chloroform or tetrahydrofuran with triphenylphosphine (employing a molar ratio of XXXI:triphenylphosphine of from about 0.8:1 to about 1:1) and carbon tetrachloride in the presence of an amine base such as triethylamine or diisopropylethylamine, to form imidazoline XXXII

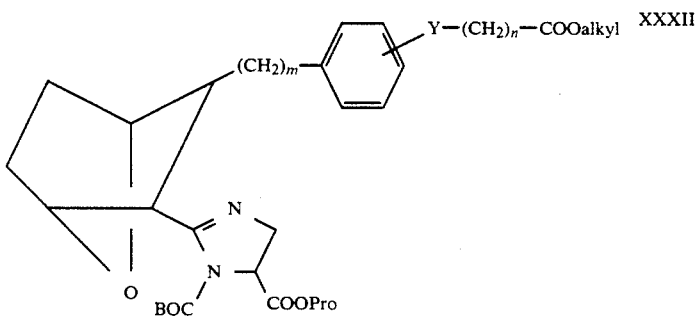

Imidazoline XXXII is then deprotected to remove the Pro protecting group, using conventional procedures for example, by hydrogenation when Pro is benzyl, to form the acid XXXIII

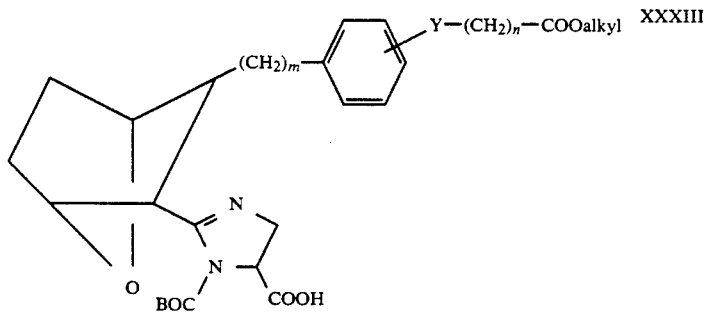

Next, the acid XXXIII is made to undergo a coupling reaction with amine E in the presence of an amine base such as pyridine or triethylamine under an inert atmosphere such as argon in the presence of a coupling agent such as WSC and HOBT and chloroform, employing a molar ratio of E:XXXIII of within the range of from about 0.8:1 to about 1.2:1 to form amine XXXIV

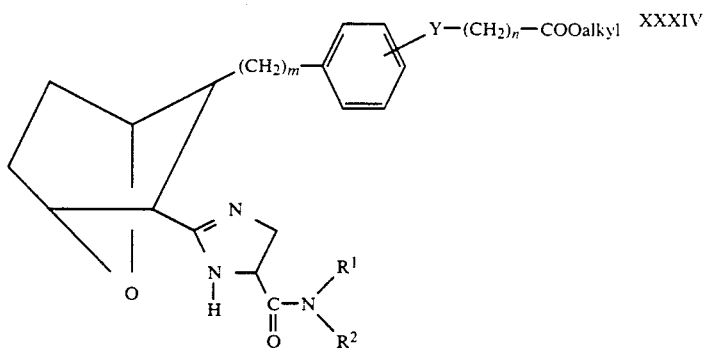

The amine XXXIV in solution in methylene chloride is then treated with trifluoroacetic acid to remove the BOC group and form amide XXXV

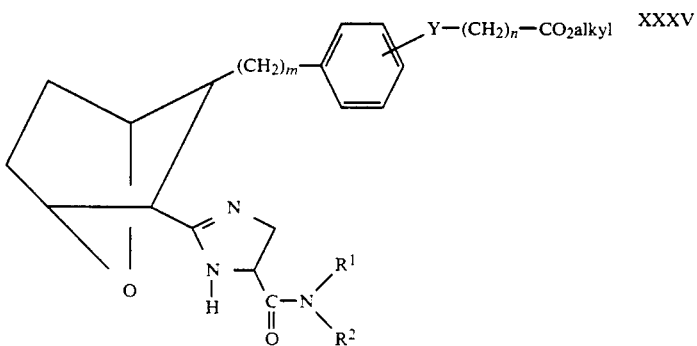

Amide XXXV is oxidized by treatment with an oxidizing agent such as manganese dioxide in the presence of an inert solvent such as chloroform to form ester IM

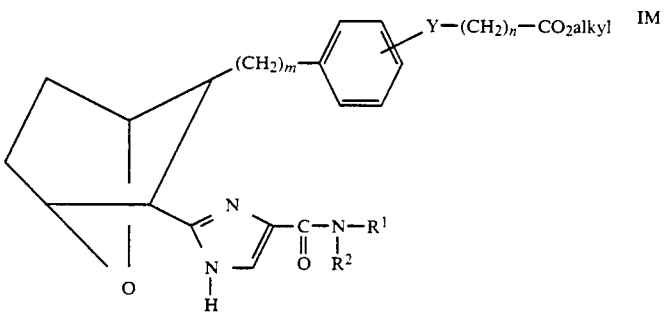

Compounds of the invention wherein n is 0 and Y is a single bond, that is benzoic acids or derivatives thereof of the structure IN

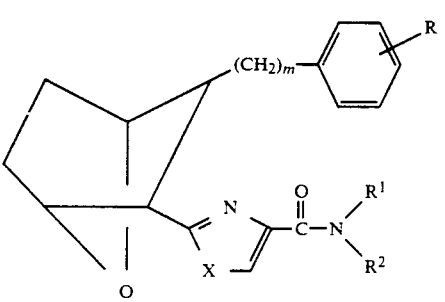

may be prepared starting with bromobenzyl alcohol $A^2$

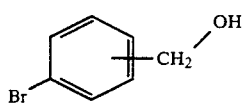

which is treated with a protecting compound such as t-butylchlorodiphenylsilane, in the presence of 4-dimethylaminopyridine and an amine base such as triethylamine and an inert solvent, such as methylene chloride, employing conventional procedures, to form the protected bromobenzyl compound $B^2$

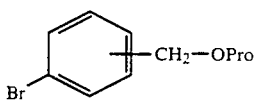

wherein Pro represents a protecting group.

Examples of protecting compounds suitable for use herein with the exclusion of benzyl bromide are as set out hereinbefore in reacting with bromophenalkyl alcohol A.

The protected compound $B^2$ is then transmetallated by treatment with t-$C_4H_9Li$ or n-$C_4H_9Li$ in the presence of diethyl ether or tetrahydrofuran at reduced temperature of from about $-100°$ to about $0°$ C. (or is subjected to a Grignard reaction by treatment with magnesium in the presence of an inert organic solvent such as tetrahydrofuran (THF) or diethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

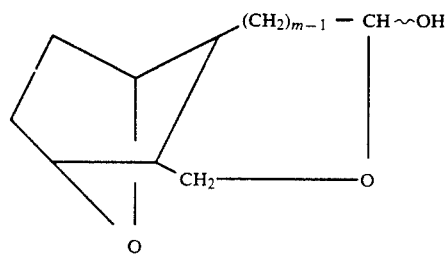

employing a molar ratio of C:$B^2$ of within the range of from about 1:2 to about 1:4, in the presence of an inert organic solvent such as THF at a reduced temperature of from about $-78°$ to about $25°$ C., to form the condensed 7-oxabicycloheptane compound IIA

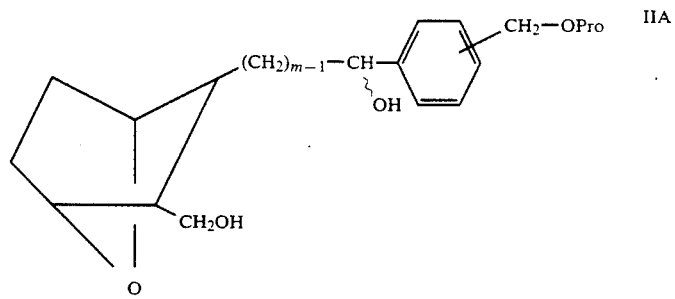

Compound IIA is then protected by treatment with, for example, a solution of acetic anhydride and pyridine in the presence of 4-dimethylaminopyridine to form compound XIA

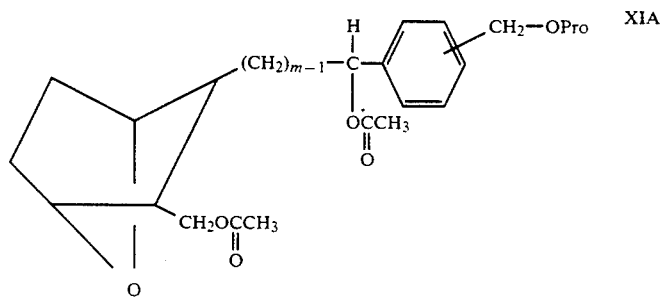

The protected alcohol XIA is then deprotected using conventional procedures and the resulting alcohol subjected to a Jones oxidation employing procedures described hereinbefore to form crude acid. The crude acid is deacetylated by reaction with aqueous hydroxide in the presence of inert organic solvent such as THF and then esterified, for example, by treatment with diazoalkane, such as diazomethane, or acidic alcohol, to form the alcohol ester XIIA

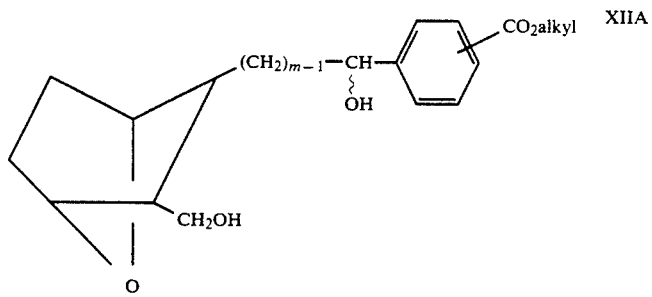

The alcohol ester is then subjected to hydrogenolysis as described above to provide alcohol ester compound XIIB

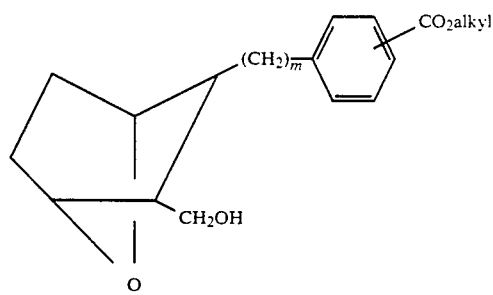
XIIB

Next, the alcohol ester XIIB is subjected to a Jones oxidation to form the acid XIIIA

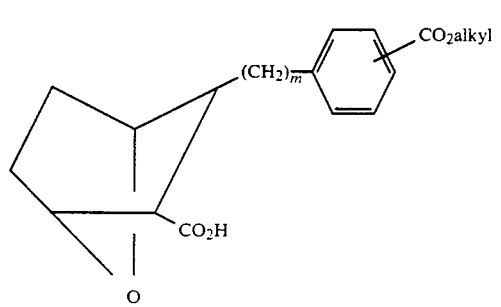
XIIIA

In a preferred method, compounds of the invention wherein n is O, m is 1 and Y is a single bond, and R is in the ortho position, that is benzoic acids or derivatives thereof of the structure INa

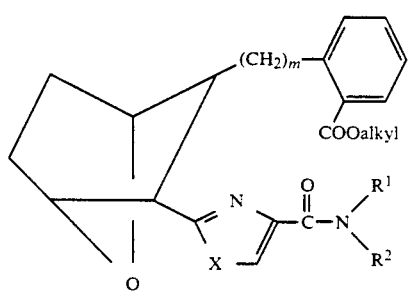
INa may be prepared starting with oxazoline $B^3$

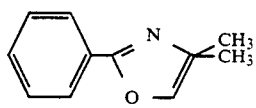
$B^3$ (prepared as described by A. I. Meyers et al in J. Org. Chem. 39, 2787 (1974)) which is metallated by treatment with t-$C_4H_9Li$ or n-$C_4H_9Li$ in the presence of diethyl ether or tetrahydrofuran at reduced temperature of from about $-100°$ to about $0°$ C. and then is condensed with (exo)octahydro-4,7-epoxyisobenzofuran-1ol (prepared as described in U.S. Pat. No. 4,143,054) of the structure Ca

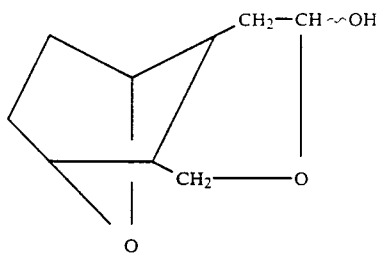
Ca employing a molar ratio of Ca:$B^3$ of within the range of from about 1:2 to about 1:4, in the presence of an inert organic solvent such as THF at a reduced temperature of from about $-78°$ to about $0°$ C., to form the condensed 7-oxabicycloheptane compound IIA'

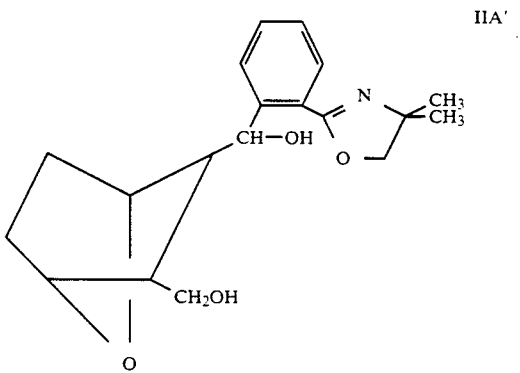
IIA'

Compound IIA' is then subjected to aqueous acidic hydrolysis by treatment with aqueous oxalic acid to form compound XIA'

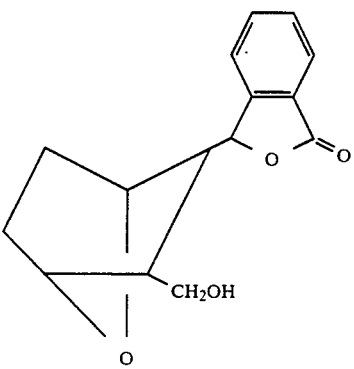
XIA'

XIA' is then subjected to hydrogenolysis as described above and esterification to provide alcohol ester compound XIIB'

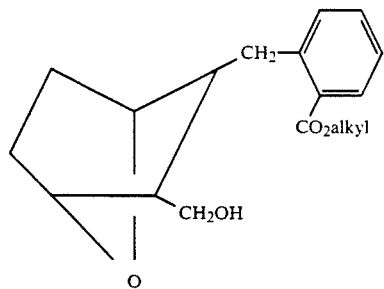
XIIB'

Compound XIIB' may be used in place of XIIB to form acid XIIIA'

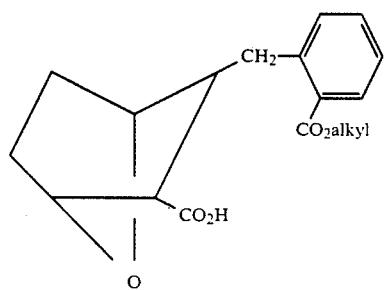
XIIIA'

The acid XIIIA or XIIIA' is then used in place of acid XIII to form the corresponding benzoic acids of structure IO

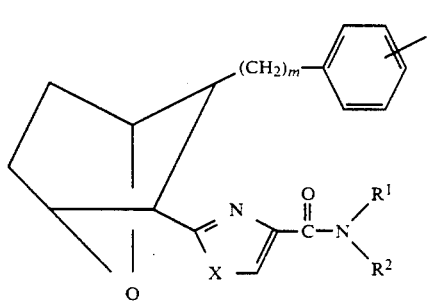
IO including

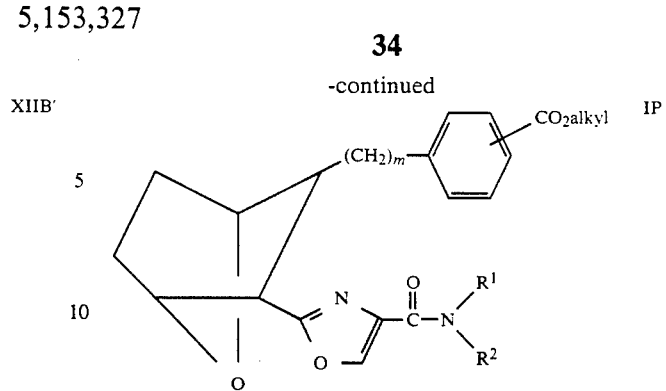
IP

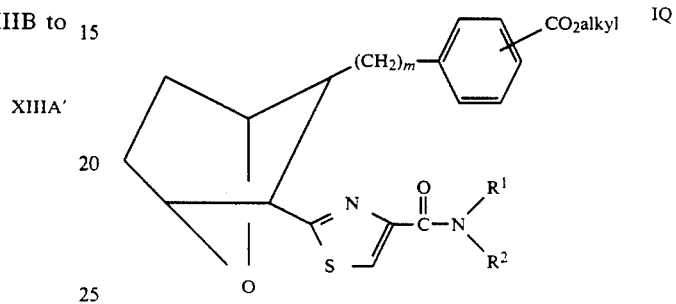
IQ

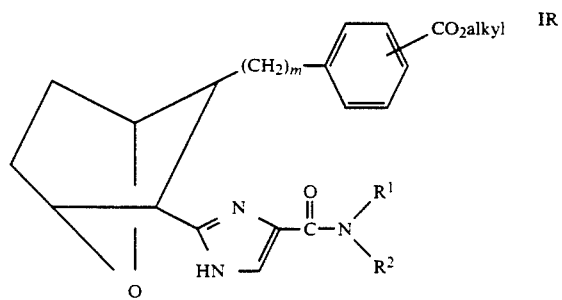
IR

Compounds of formula I wherein Z is

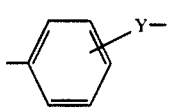

and Y is —CH=CH— may be prepared starting with alcohol XII wherein n is 2 which is treated with a silane protecting compound as described hereinbefore in the presence of an amine base, such as triethylamine and an inert solvent such as methylene chloride and N,N-dimethylaminopyridine (DMAP) to form the protected alcohol XIIa.

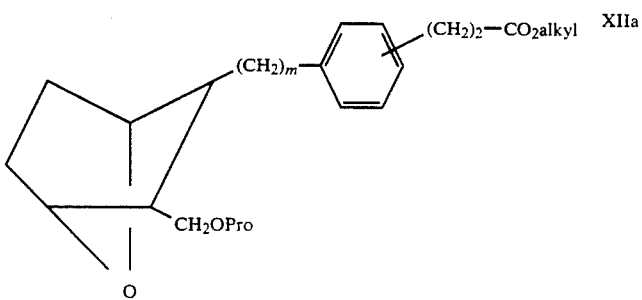
XIIa

The protected alcohol XIIa is then treated with lithium diisopropylamide in the form of a cooled (−78° to 0°

C.) mixture of diisopropylamine and t-butyllithium or n-butyllithium, under argon. The resulting mixture is treated with diphenyl diselenide at a temperature of within the range of from about −78° to about 25° C., to form the corresponding selenide.

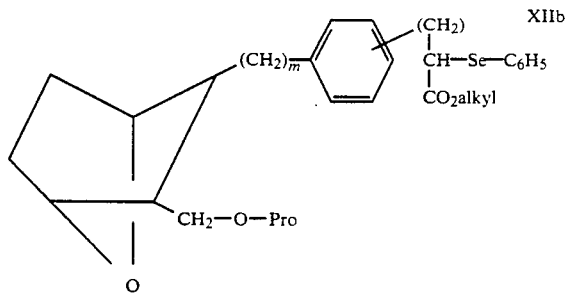

Selenide XIIb in an inert organic solvent such as ethyl acetate and/or methanol is treated with an oxidizing agent such as aqueous hydrogen peroxide to form the cinnamate XIIc

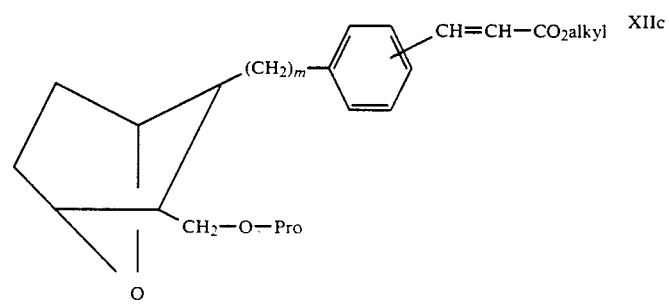

The protecting group is removed from XIIc by treated XIIc with acetyl chloride in the presence of an organic solvent such as methanol to form the alcohol XIId.

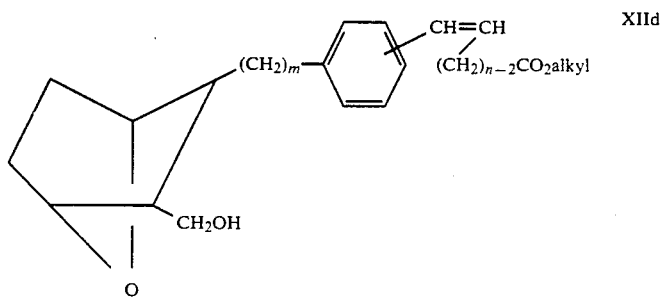

Alcohol XIId may then be employed to form compounds of formula I wherein Z is

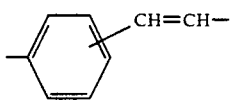

employing procedures described hereinbefore.

Compounds of formula Ix may be prepared by treating a compound of formula I wherein X is O, $R^2$ is H, Z is

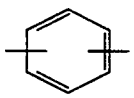

and R is $CO_2H$ with a protecting compound such as benzyl bromide in the presence of base such as potassium carbonate or sodium hydride and an inert organic solvent such as dimethylformamide to form the protected compound $I_{xa}$

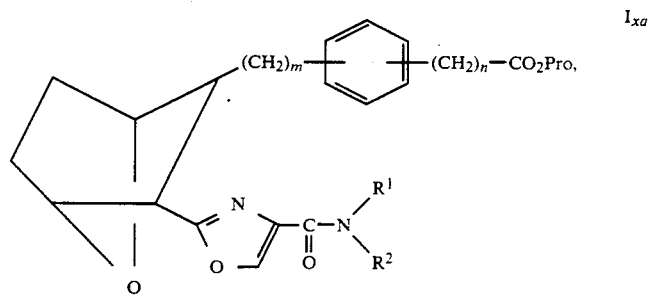

causing $I_{xa}$ to undergo an oxidative rearrangement by treating $I_{xa}$ with sodium nitrite in the presence of organic acid such as acetic acid and acetic anhydride, or nitrogen tetroxide or nitrosyl chloride, and a solvent such as dioxane at temperatures of from about 85° to about 105° C., to form the corresponding ester $I_{xb}$

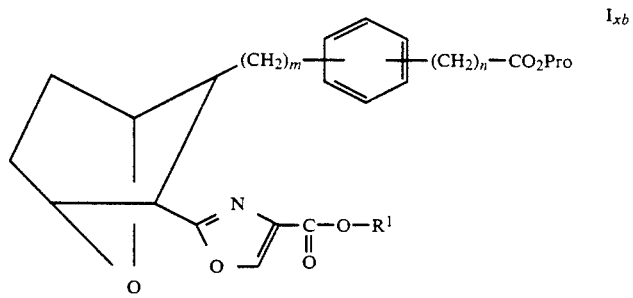

$I_{xb}$ and removing the protecting group by hydrogenation in the presence of a hydrogenation catalysis such as palladium on charcoal to form $I_x$.

The starting bromophenylalkyl alcohol A where n is 2 may be prepared by subjecting aldehyde M

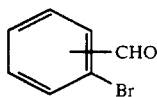

M to a Wittig reaction with $(C_6H_5)_3PCHCO_2CH_3$ to form the ester N

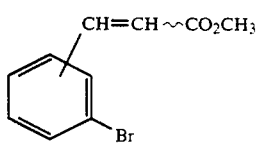

N which is made to undergo a double bond reduction by treatment with hydrogen in the presence of rhodium on alumina catalyst in the presence of methanol to form ester O

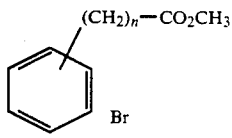

O

Ester O is then reduced by treatment with diisobutylaluminum hydride in the presence of toluene solvent to form alcohol A.

The compounds of formula I of the invention wherein Z is —CH=CH or —(C₂)₂— may be prepared as follows.

Compounds of the invention where Z is —CH=CH— and preferably in the cis form, and X is O are prepared starting with the hydroxymethyl compound AA

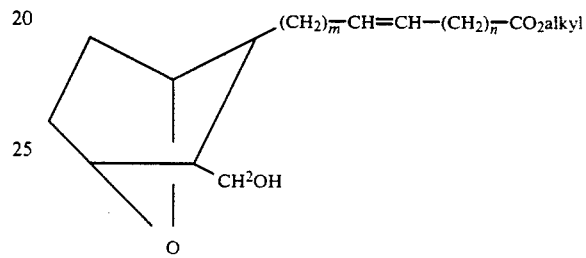

AA (which is prepared as described in U.S. Pat. No. 4,143,054) which is subjected to a Jones oxidation wherein AA is reacted with Jones' Reagent ($CrO_3$ dissolved or suspended in aqueous sulfuric acid, prepared as described in Fieser & Fieser, "Reagents for Organic Synthesis", Vol I, p. 142 (1967)) in the presence of acetone, under an inert atmosphere such as argon at a temperature within the range of from about −10° to about 20° C., to form the corresponding carboxylic acid BB

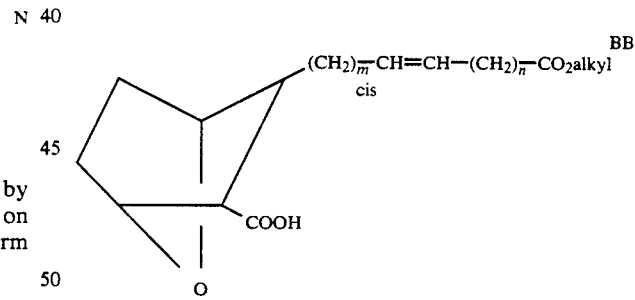

BB

Acid BB, in an inert organic solvent, such as tetrahydrofuran, is then made to undergo a carbodiimide coupling reaction with amide Da

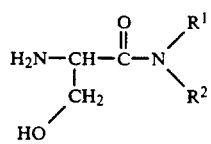

Da in the presence of dicyclohexylcarbodiimide (DCC) or 1-(3-dimethylaminopropyl)-3-ethylcarbodiimide hydrochloride (WSC) and 1-hydroxybenzotriazole under an inert atmosphere such as argon employing a molar ratio of Da:BB of within the range of from about 1.2:1 to about 1:1, to form hydroxybisamide IIa

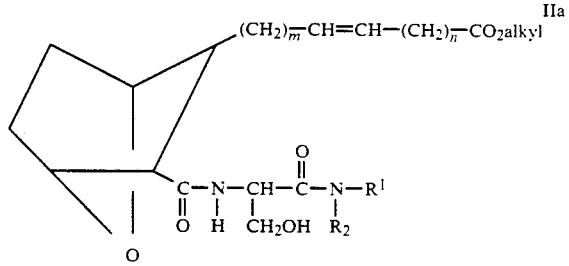

Hydroxybisamide IIa is then subjected to cyclodehydration wherein a solution of IIa in an inert organic solvent such as tetrahydrofuran, acetonitrile or chloroform, under an inert atmosphere such as argon, is treated with triphenylphosphine and carbon tetrachloride in the presence of an amine base such as triethylamine, to form oxazoline IIIa.

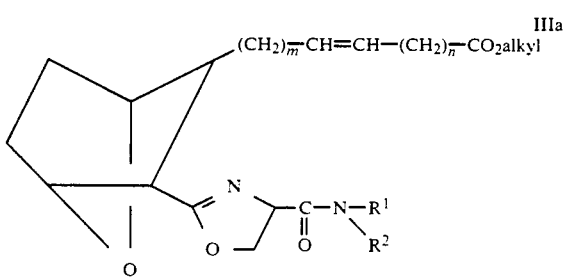

Alternatively, hydroxybisamide IIa is treated with a sulfonyl chloride, such as methane sulfonyl chloride, and an amine base such as triethylamine followed by treatment with potassium carbonate in acetone to form oxazoline IIIa.

Oxazoline IIIa is oxidized by treatment with manganese dioxide or nickel peroxide preferably nickel peroxide to form the oxazole IDa

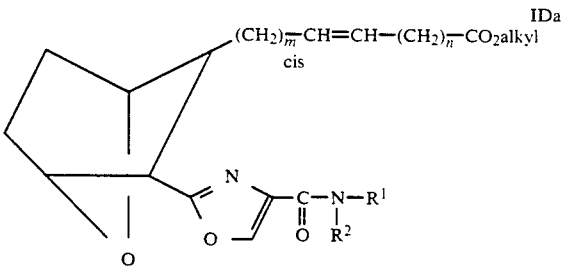

Alternatively, oxazole IDa can be prepared from acid BB

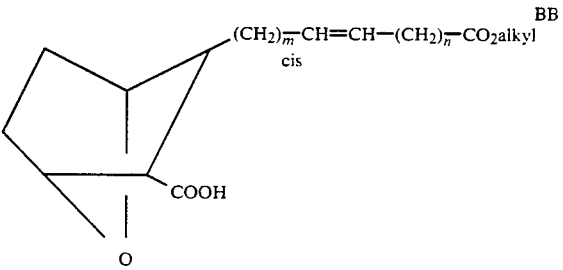

by a carbodiimide coupling as described previously except substituting CCa for Da to obtain IIb.

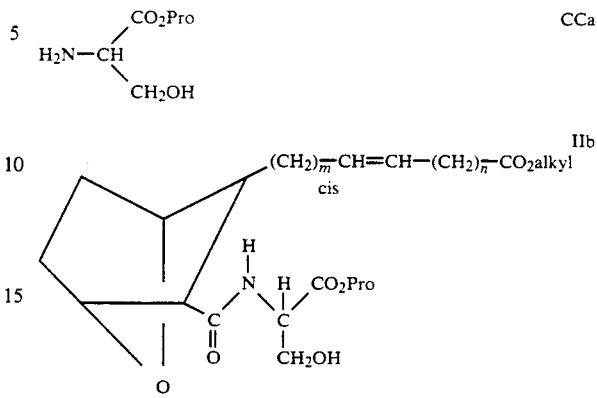

where Pro is a conventional protecting group. Hydroxyamide IIb is then subjected to a cyclodehydration and oxidation as described for IIa and IIIa to form ID'

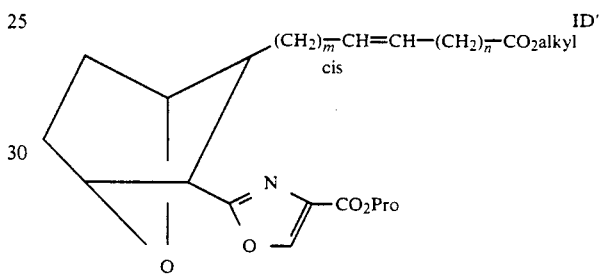

The protecting group of ID' can be removed to form the corresponding acid ID" which is treated with excess

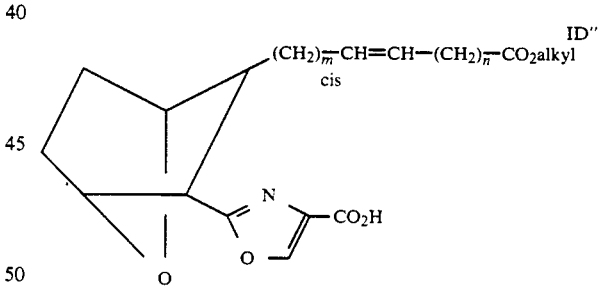

oxalyl chloride in the presence of an inert organic solvent such as toluene, methylene chloride, or chloroform, and optionally a catalytic amount of dimethylformamide, while stirring under an inert atmosphere such as argon, to form the crude acid chloride IDa"

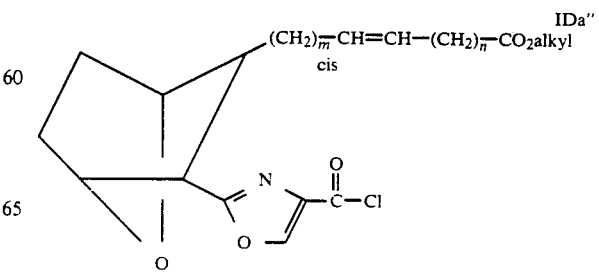

which is treated with amine hydrochloride E'

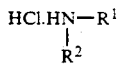

in the presence of an organic base such as triethylamine under an inert atmosphere such as argon, employing a molar ratio of IDa'':E' of within the range of from about 0.5:1 to about 2:1 and preferably from about 0.8:1 to about 1:1, to form IDa'''.

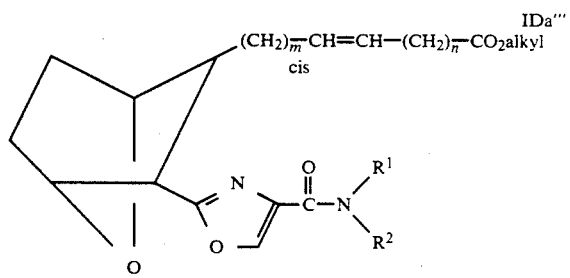

Compounds of formula I wherein Z represents —CH=CH— which is the trans double bond isomer may be prepared starting with hydroxymethyl compound AA which includes a cis double bond. Compound AA is treated with a protecting compound such as t-butyldimethylsilyl chloride or other silyl protecting group as described hereinbefore in the presence of imidazole or triethylamine and an inert organic solvent such as methylene chloride or tetrahydrofuran, to form the protected compound AA'

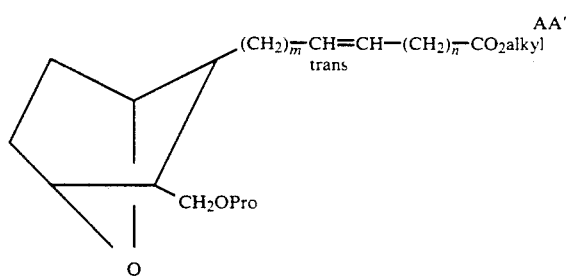

A solution of the protected alcohol in an inert organic solvent such as methylene chloride or acetone is treated with excess ozone at reduced temperature of from about −78° to about −60° C. followed by treatment with dimethyl sulfide (molar ratio of AA':(CH$_3$)$_2$S of within the range of from about 0.01:1 to about 0.2:1), to form the aldehyde AA$^2$

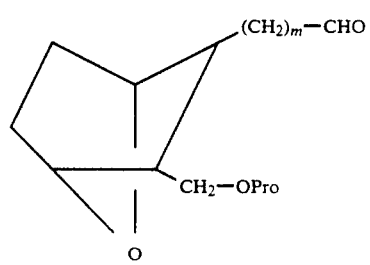

Aldehyde AA$^2$ is then treated with a mixture of lithium bromide or lithium chloride and trimethylphosphonoacetate and triethylamine in an inert organic solvent such as methylene chloride or chloroform to form the ester AA$^3$

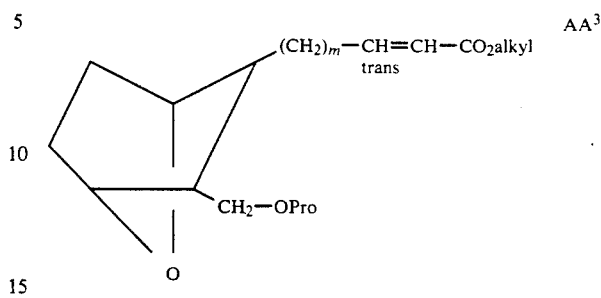

A solution of ester AA$^3$ in an inert organic solvent such as tetrahydrofuran, diethyl ether or dimethyoxyethane is cooled to a temperature of from about −78° to 0° C. and reacted with diisobutylaluminum hydride in an aromatic solvent such as toluene for a period of from about 0.5 to about 4 hours to form alcohol AA$^4$

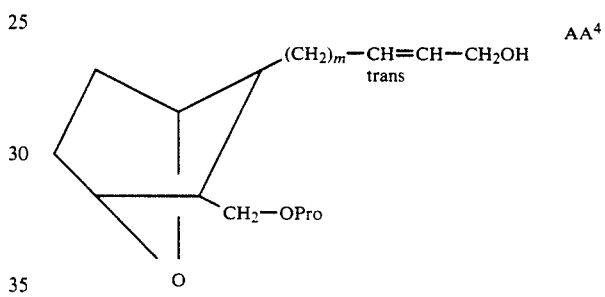

Alcohol AA$^4$ is treated with bromotriphenylphosphonium bromide (formed by adding bromine to triphenylphosphine in toluene or other aromatic solvent under an inert atmosphere such as argon, at a reduced temperature of from about −10° to about 10° C.) in the presence of pyridine and toluene, at a reduced temperature of from about −10° to about 10° C., to form bromide AA$^5$

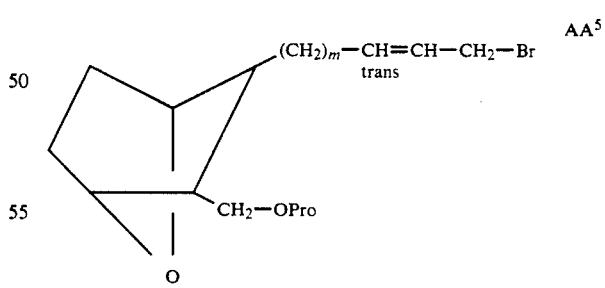

An acetic acid ester such as t-butyl acetate or ethyl acetate is treated with a solution of LDA (lithium diisopropylamide) in an inert organic solvent such as tetrahydrofuran and at a reduced temperature of from about −78° to about −60° C. for a period of from about 0.5 to about 2 hours followed by addition of a solution of bromide AA$^5$ in an inert solvent such as tetrahydrofuran to form ester AA$^6$ (n is 2)

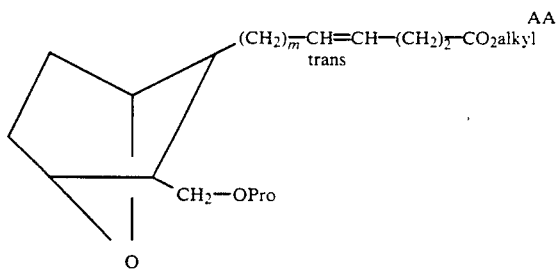

AA⁶

For compounds of the invention where Z=—CH=CH— in the trans form and n is 1, 3, or 4, aldehyde XI is allowed to react with a phosphonium salt of formula P

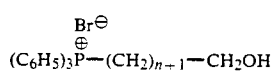

P in the presence of a strong base such as potassium t-amylate in toluene or NaH/dimethylsulfoxide to give XIII'

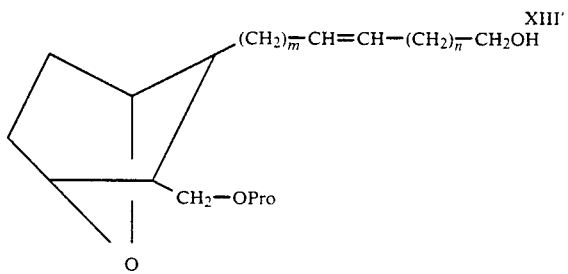

XIII' which is oxidized and esterified using procedures known to those skilled in the art to form ester AA⁶ (where n=1, 3, or 4).

Ester AA⁶ is then deprotected by treating AA⁶ in methanol under an inert atmosphere such as argon with hydrochloric acid in methanol (prepared by adding acetyl chloride to methanol) to form alcohol AA⁷

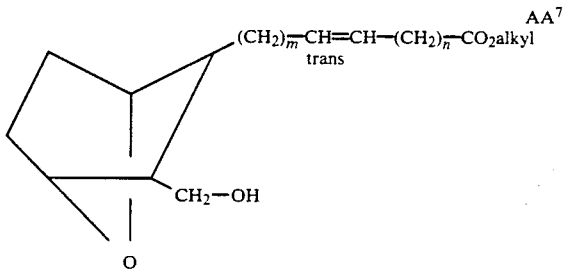

AA⁷

AA⁷ may then be used in place of AA as a starting material following the procedure hereinbefore described to form acid AA⁸

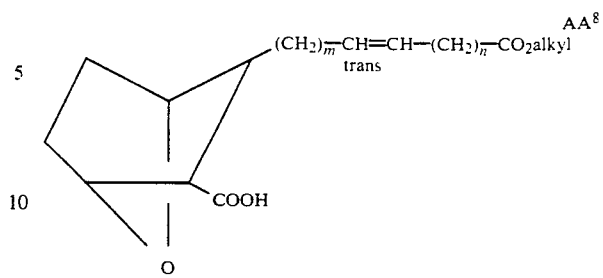

AA⁸ and subsequently to form the trans compound of formula IDaa of the invention

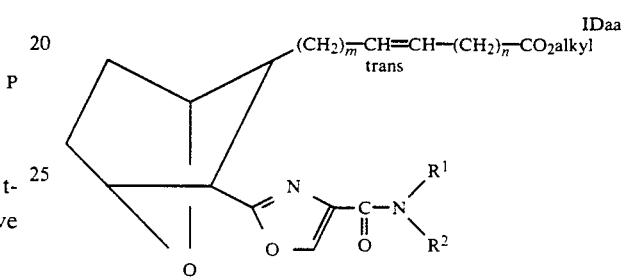

IDaa

Compounds of the invention IB wherein Z is —CH=CH— and X is S may be prepared starting with acid BB or AA⁸ as follows:

Acid BB or AA⁸ is reacted with oxalyl chloride, optionally in the presence of catalytic amounts of dimethylformamide, in methylene chloride, to form the corresponding acid chloride which is amidated by reacting with ammonia to form the amide XXXVII

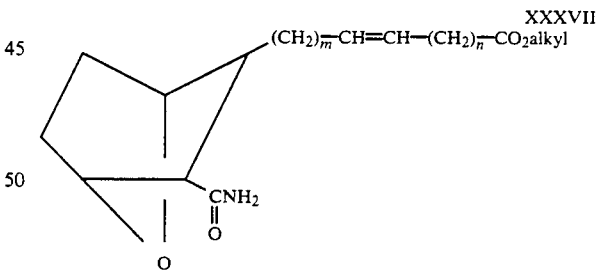

XXXVII

Alternatively, acid BB or AA⁸ is reacted with an alkylchloroformate in the presence of an amine such as triethylamine to form the mixed anhydride which is amidated by reacting with methanol-ammonia solution or concentrated aqueous ammonia solution to form amide XXXVII.

Amide XXXVII is then treated with phosphorus pentasulfide ($P_2S_5$) or Lawesson's Reagent (2,4-bis(4-methoxyphenyl)-1,3-dithia-2,4-diphosphetane-2,4-disulfide) to form the corresponding thioamide XXXVIII

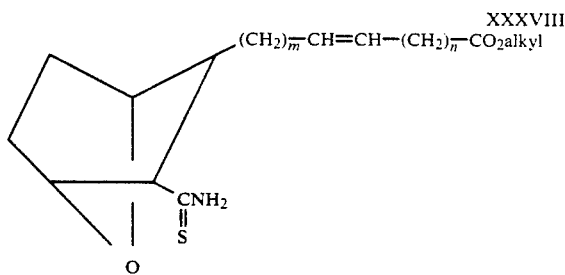

which is treated with bromopyruvic acid

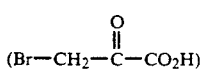

in a polar solvent such as dimethylformamide in the presence of a weak base such as $K_2CO_3$ employing a molar ratio of XXXVIII: bromopyruvic acid of within the range of from about 1:1 to about 1:1.5 to form thiazoline XXXIX

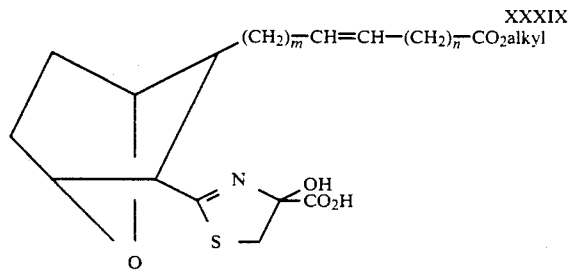

Thiazoline XXXIX is then dehydrated by treatment with a sulfonyl chloride such as methanesulfonyl chloride in the presence of a base such as triethylamine to form thiazole acid XL

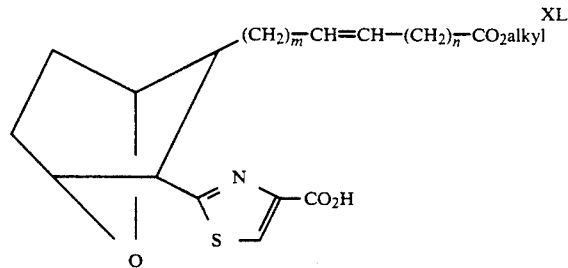

which is then made to undergo a carbodiimide coupling reaction with amine

in the presence of DCC or WSC under an inert atmosphere such as argon employing a molar ratio of A‴:XL of within the range of from about 1:1 to about 2:1, to form amide $IF_a$

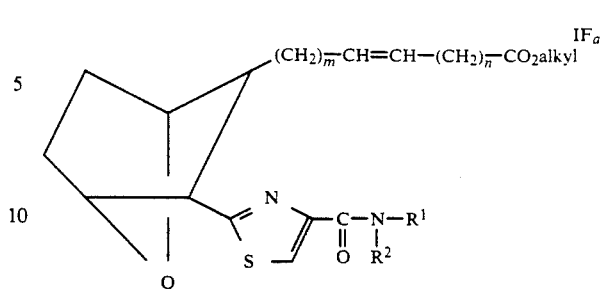

Compounds of the invention IE where X is NH and $Z^1$ is —CH=CH— are prepared starting with acid BB or $AA^8$ which is made to undergo a coupling reaction with amine Q

where Boc is t-butyloxycarbonyl and Pro is a protecting group such as preferably —$CH_2CH_2Si(CH_3)_3$, in the presence of a coupling agent such as 1-(3-dimethylaminopropyl)-3-ethylcarbodiimide hydrochloride (WSC) and 1-hydroxybenzotriazole (HOBT) and methylene chloride employing a molar ratio of BB or $AA^8$:Q of within the range of from about 1.2:1 to about 1:1, for a period of from about 12 to about 90 hours. The resulting amide is made to undergo a thionation reaction by treating the amide with Lawesson's reagent in the presence of benzene at a temperature of from about 50 to about 75° C. for a period of from about 1 to about 4 hours, to form the ester XLI

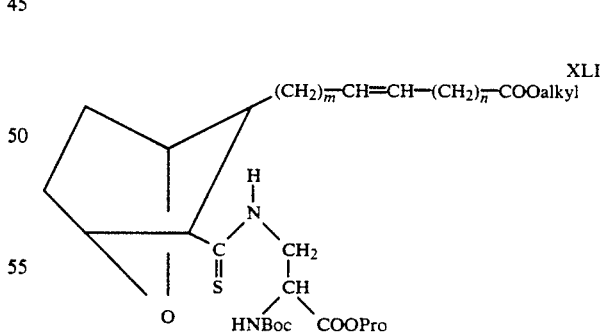

The ester XLI is cyclized by treating a solution of XLI in an inert solvent such as acetonitrile, chloroform or tetrahydrofuran, with triphenylphosphine (employing a molar ratio of XLI:triphenylphosphine of from about 0.8:1 to about 1:1) and carbon tetrachloride in the presence of an amine base such as triethylamine or diisopropylethylamine, to form imidazoline XLII

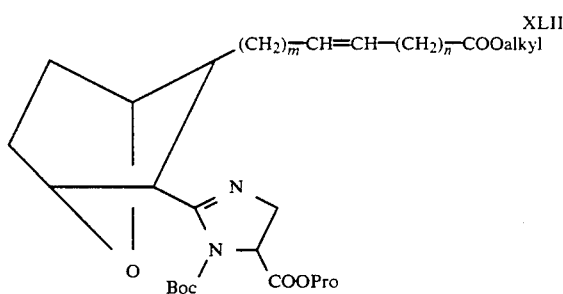

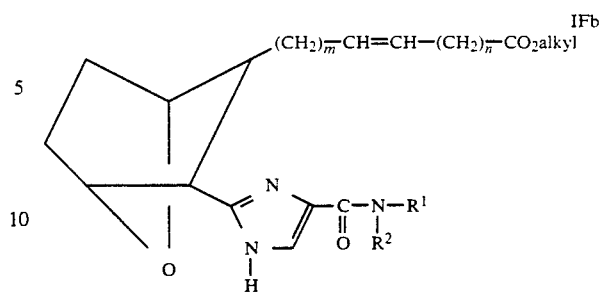

Imidazoline XLII is then deprotected to remove the Pro protecting group, using conventional procedures, for example, by treatment with trifluoroacetic acid in the presence of methylene chloride, to form the acid XLIII

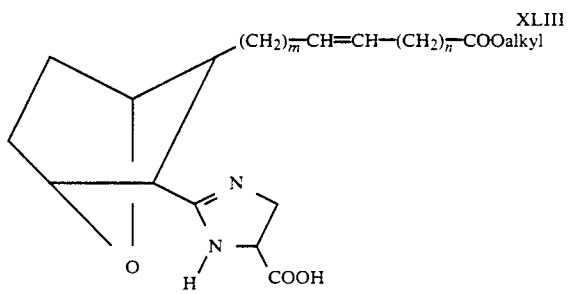

Next, the acid XLIII is made to undergo a coupling reaction with amine A''' in the presence of an amine base such as pyridine or triethylamine under an inert atmosphere such as argon in the presence of a coupling agent such as WSC and HOBT and chloroform, employing a molar ratio of A''':XLIII of within the range of from about 0.8:1 to about 1.2:1 to form amide XLIV

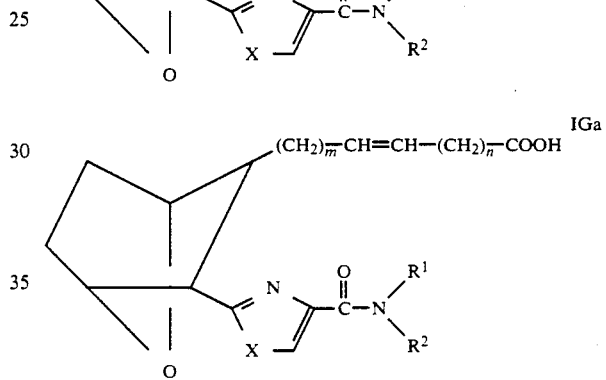

Amide XLIV is oxidized by treatment with an oxidizing agent such as manganese dioxide in the presence of an inert solvent such as chloroform to form ester IFb The aforementioned esters of the invention may be converted to the corresponding acids, that is IS

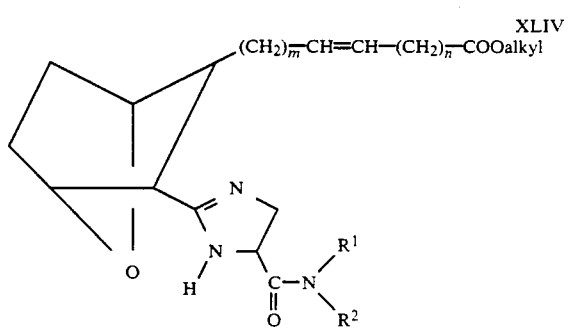

by treating the esters with a base, such as lithium hydroxide, sodium hydroxide or potassium hydroxide to form the corresponding alkali metal salt, followed by neutralization with an acid, such as dilute hydrochloric acid or oxalic acid to form the acid compounds of the invention.

Compounds of formula I wherein Z is —(CH$_2$)$_2$— may be prepared from acid IGa by subjecting IGa to hydrogenation using, for example, a hydrogenation catalyst, such as palladium on carbon, in an inert organic solvent such as ethyl acetate (EtOAc) or acetic acid (AcOH) to form acid of the invention IGa'

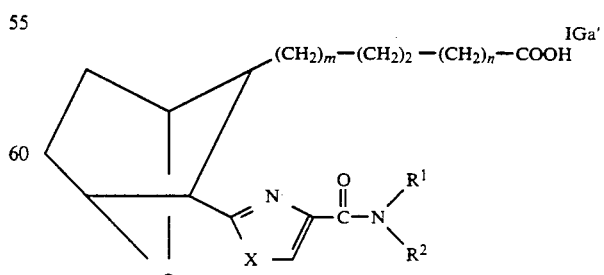

Compounds of the invention wherein R is CONH-SO$_2$R$^3$, that is IT

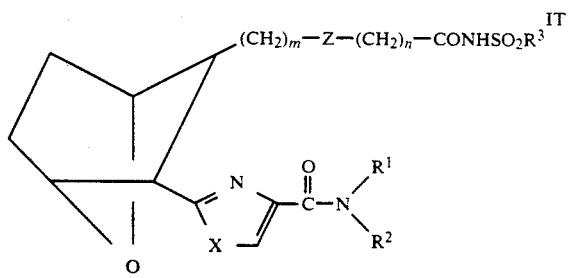

are prepared by treating acid IS, IGa or IGa' with a sulfonamide of the structure H

in the presence of a coupling agent such as carbonyldiimidazole or WSC in the presence of an amine such as dimethylaminopyridine under an inert atmosphere such as argon employing a molar ratio of H:IS or IG, or IGa' of within the range of from about 0.8:1 to about 1.2:1, to form sulfonamide IT.

Acids IS, IGa and IGa' may be converted to the corresponding alkyl esters by treating the acids IS, IGa and IGa' with the appropriate alcohol under acid catalysis to form the esters.

Compounds of the invention wherein R is —CH$_2$-5-tetrazolyl, Z is

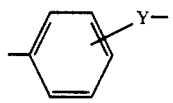

and Y is a single bond, or Z is —(CH$_2$)$_2$— that is IU where Y is a single bond

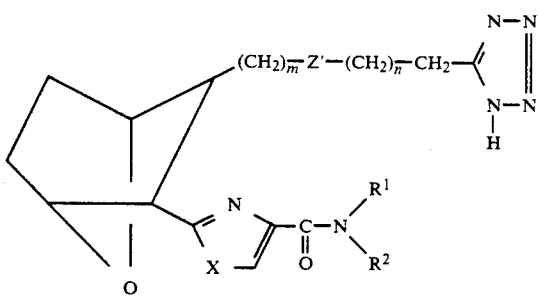

where Z' is

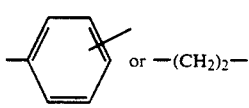

are prepared by subjecting esters IH, IJ, IL, IM, IP, IMa, IQ or IR or the esters of IS, IGa or IGa' where Z is

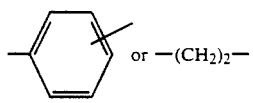

to reduction with a hydride reagent such as lithium borohydride or sodium borohydride to afford alcohol XXXVIIA

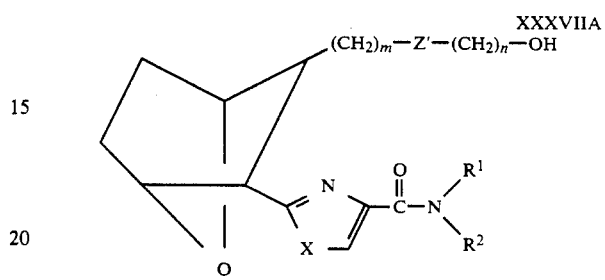

which is converted to the bromide on treatment with triphenylphosphonium dibromide in an inert solvent such as toluene. The bromide is then converted to nitrile XXXVIIIA on treatment with an alkali metal cyanide in a polar solvent such as methanol/water.

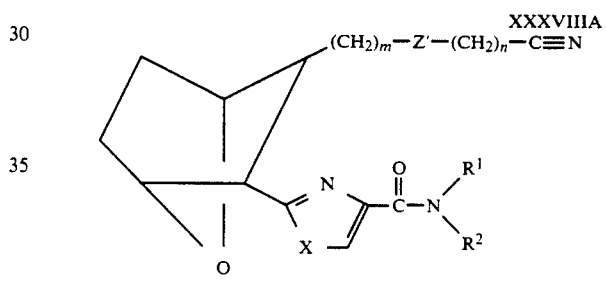

The nitrile XXXVIIIA is then subjected to a cycloaddition reaction by treating XXXVIIIA with sodium azide in the presence of ammonium chloride, dimethylformamide and lithium chloride at a temperature of from about 100° C. to about 130° C. to form IU.

Compounds of the invention wherein R is —CH$_2$—5-tetrazolyl and Y=O, that is IU where Y is O, are prepared by conversion of alcohol XXIII to ether XXXIXA using the procedures set out hereinbefore for the conversion of XII to esters IE, IH and IJ

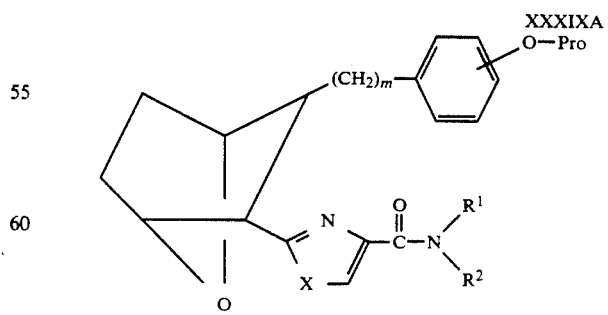

which are converted to nitrile by deprotection, for example with aqueous HF, followed by alkylation with halonitrile J in the J X—(CH$_2$)$_n$—CN    J presence of a base such as sodium hydride or potassium carbonate.

The nitrile is then subjected to a cycloaddition reaction by treating with sodium azide in the presence of ammonium chloride, dimethylformamide and lithium chloride at temperatures from about 100° C. to about 130° C. to form IU.

Compounds of the invention wherein R is —CH$_2$—5-tetrazolyl, that is IJa

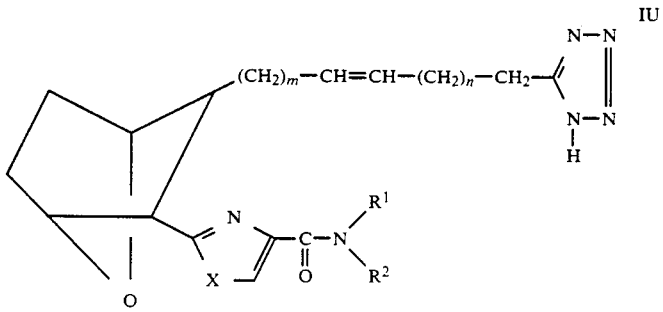

are prepared by treating alcohol Ka (prepared as described in U.S. Pat. No. 4,654,356)

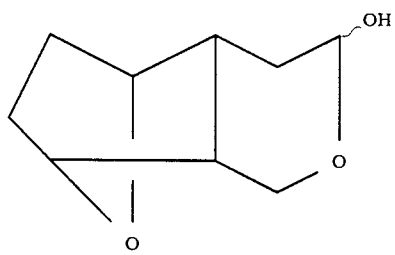

Ka with a Wittig reagent of the structure La

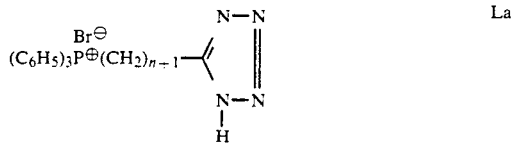

La in the presence of a base, such as potassium t-butoxide or sodium hydride-dimethyl sulfoxide employing a molar ratio of Ka:La of within the range of from about 1:1 to about 0.2:1 to form the hydroxymethyl compound XIIa

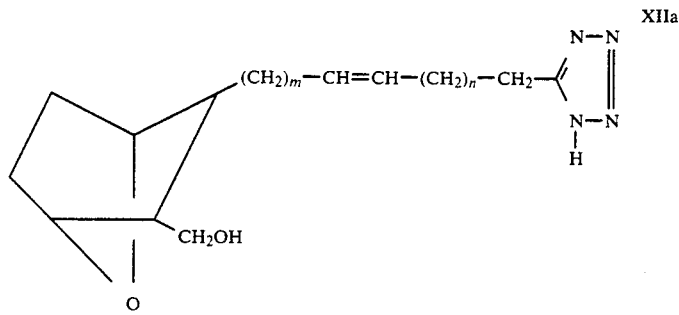

XIIa which is treated with protecting compound Ma
Ma Pro-Halide
for example,
bromomethyl methyl ether to form the protected tetrazole XIIIa

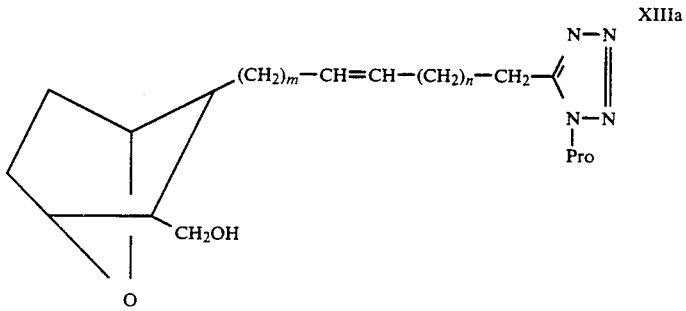

XIIIa

The protected tetrazole XIa may then be used in place of hydroxymethyl compound AA to form the various compounds of the formula XIVa wherein X is O, S or NH

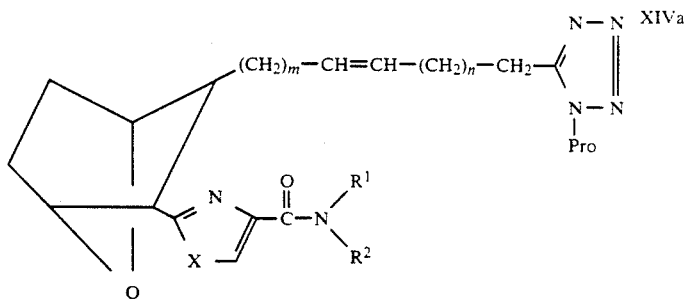

which is deprotected by treatment with aqueous acid such as aqueous hydrochloric acid to form compounds of the invention IJ.

Compounds of formula I wherein R is $CONHR^{3a}$ wherein $R^{3a}$ is other than H may be prepared from the corresponding acid

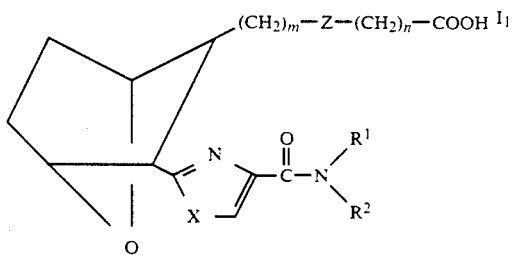

by treating acid $I_1$ with WSC in the presence of dimethylformamide and HOBT, organic basic such as triethylamine and amine E″

$HNHR^{3a}$      E″ to form the amide of the invention $I_2$

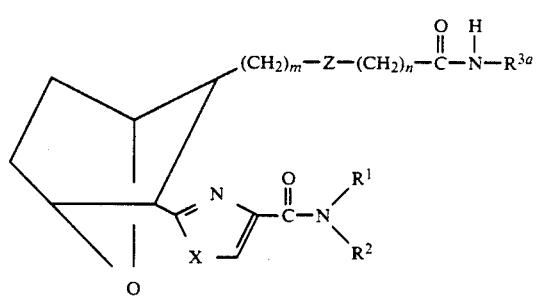

where $R^{3a}$ is lower alkyl, aryl or aralkyl.

Compounds of formula I wherein R is $CONH_2$ may be prepared from the corresponding acid I, employing the procedure as described above for making amide $I_2$ except that ammonium chloride is employed in place of amine E″ to form the amide of the invention $I_3$

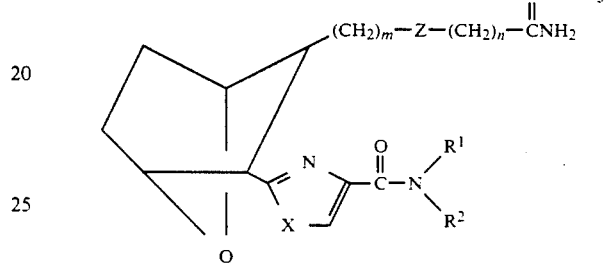

Compounds of formula I wherein R is $CH_2OH$ may be prepared from the corresponding ester $I_4$

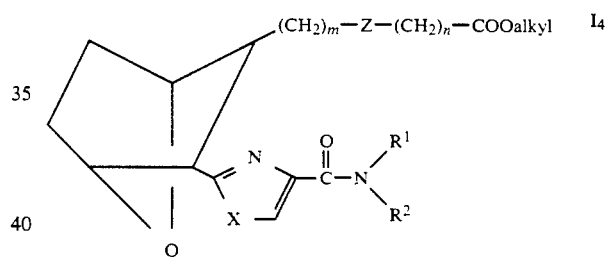

which is treated with a reducing agent such as lithium borohydride ($LiBH_4$) in the presence of diethyl ether and tetrahydrofuran to form the alcohol $I_5$

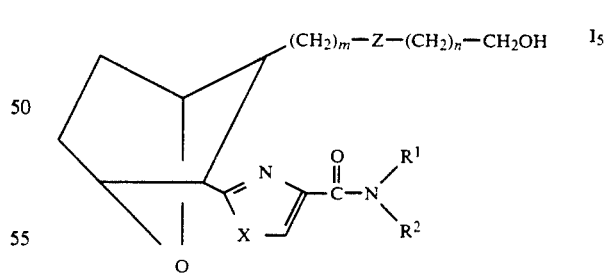

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cisendo and all trans forms and stereoisomeric pairs may be prepared by employing starting materials and following the procedures as outlined in U.S. Pat. No. 4,143,054. Examples of such stereoisomers are set out below.

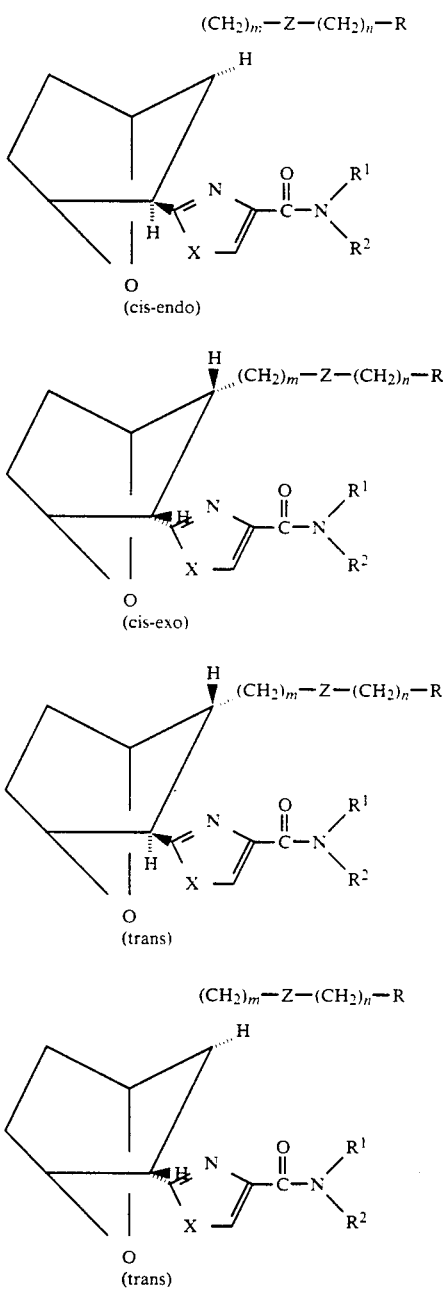

The nucleus in each of the compounds of the invention is depicted as

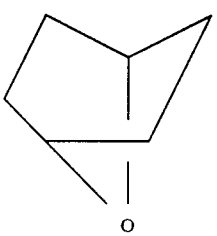

for matter of convenience; it will also be appreciated that the nucleus in the compounds of the invention may be depicted as

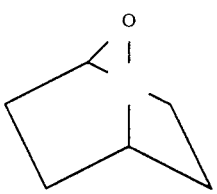

The compounds of this invention are thromboxane receptor antagonists and as such are useful as inhibitors of thromboxane receptor mediated actions. The term "thromboxane receptor antagonist" includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diureticinduced diuresis.

In addition, the thromboxane receptor antagonists of the invention may be used with a thrombolytic agent such as t-PA, streptokinase, urokinase, prourokinase or anisoylated plasminogenstreptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The oxazole derivatives of the invention, that is compounds of formula I where X is O have particularly long duration of action and these may, if desired, be administered in the above dosages once daily, once every other day, or if desired once daily two times a week.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

The following Examples represent preferred embodiments of the present invention. Unless otherwise indicated, all temperatures are expressed in degrees Centigrade.

The following Examples represent preferred embodiments of the present invention. Unless otherwise indicated, all temperatures are expressed in degrees Centigrade.

EXAMPLE 1

[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzenepropanoic acid

A. 3-(2-Bromophenyl)-2-propenoic acid, methyl ester

To a stirred solution of 161.2 g (871 mmol) of 2-bromobenzaldehyde in 700 mL of dry THF (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg) eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

TLC (silica gel, 5% EtOAc in hexane - $I_2$):

| 2-bromobenzaldehyde | 0.29 |
|---|---|
| title compound | 0.20 |

B. 2-Bromobenzenepropanoic acid, methyl ester

A mixture of 201.5 g (836 mmol) of Part A acrylate and 8.4 g of 5% rhodium on alumina catalyst (MCB) in 1.0 L of methanol was stirred at room temperature under an atmosphere of hydrogen (balloon) for in excess of 8 hours. $^1$H NMR analysis of an aliquot showed about a 1:1 mixture of title compound and trans Part A compound with no cis Part A compound. The mixture was diluted with 500 mL additional methanol (MeOH) and 12.6 g more catalyst was added. After hydrogenation overnight the reaction was complete. The reaction mixture was passed through Celite and a Millipore/Fluropore membrane filter (0.5 μm FH) with a prefilter pad, and the filtrate was concentrated in vacuo to obtain two immiscible oils. One of the oils was water soluble and gave a highly acid, i.e. aqueous solution Solid $NaHCO_3$ and $Na_2SO_4$ were carefully added (gas was evolved). The mixture was diluted with $CH_2Cl_2$, filtered, and evaporated (and re-evaporated with $CH_2Cl_2$ to drive off MeOH) to obtain 196.9 g of clear oil. This oil was 95% pure title compound with 5% of debromo title compound. The corrected yield of title compound was 92% (187.1 g).

TLC (silica gel, 15% EtOAc in hexane - UV):

| Part A compound | 0.36 |
|---|---|
| (much more strongly UV absorbing) | |
| title compound | 0.40 |

C. 2-Bromobenzenepropanol

To a stirring solution of 196.9 g (95% pure = 187.1 g, 770 mmol) of Part B compound in 770 mL of toluene under argon cooled to 0° (ice bath), was added over 45 minutes 830 mL of 1.0M diisobutylaluminum hydride (DIBAl-H) in toluene solution (830 mmol, Aldrich). The reaction was not very exothermic. After the mixture was stirred for 1 hour, TLC indicated approximately half of the starting material remained. Next, 580 mL of 1.5M DIBAl-H in toluene solution (870 mmol, Aldrich) was added slowly. The ice bath was removed and stirring was continued for 2 hours. The mixture was then poured slowly into 1.2 L of 6M aqueous HCl stirring in an ice bath. This quench was exothermic and gas was evolved. After the mixture was recooled to 0°, the layers were separated, and the organic layer was washed with 1M aqueous HCl and brine. It was then dried over $Na_2SO_4$ and $MgSO_4$ and evaporated (and re-evaporated with $CH_2Cl_2$ to drive off toluene) to obtain 173.0 g of clear, colorless oil. This oil was 95% pure title compound with 5% of debromo- title compound. The corrected yield of title compound was 99% (164.3 g).

TLC (silica gel, 15% EtOAc in hexane - anisaldehyde, UV):

| | |
|---|---|
| Part B compound (faintly staining) | 0.49 |
| Title compound | 0.11 |

D.
[3-(2-Bromophenyl)propoxy]dimethyl-(1,1,2-trimethylpropyl)silane

To a stirring solution of 173.0 g (95% pure = 164.3 g, 764 mmol) of Part C compound and 57.8 g of imidazole (850 mmol) in 1.0 L of $CHCl_3$ at room temperature was added slowly 136.6 g (764 mmol) of thexyldimethylchlorosilane. The reaction was mildly exothermic and a precipitate formed. After stirring overnight, $^1$H NMR analysis of an aliquot showed a trace of Part C compound remaining. Additional thexyldimethylchlorosilane (6.8 g, 38 mmol, 0.05 equiv) was added. After 2 days the mixture was evaporated. The residue was diluted with hexane and filtered. The filtrate was evaporated and distilled (150°–180° at 1.2 torr) to obtain 262.8 g of slightly cloudy, colorless oil. This oil was 94% pure title compound with 5% of debromo-title compound. The corrected yield of title compound was 91% (247.0 g). TLC (silica gel, 15% EtOAc in hexane anisaldehyde):

| | |
|---|---|
| Part C compound | 0.11 |
| Title compound | 0.89 |

E.
Bromo[2-[3-[[dimethyl(1,1,2-trimethylpropyl)silyl]oxy]propyl]phenyl]magnesium A 2-L oven-dried flask containing a magnetic stir-bar was charged with 19.0 g of hammer-crushed Mg turnings (782 mmol, Mallinckrodt) and placed under an argon atmosphere. After 440 mL dry THF (distilled from potassium/benzophenone) was added, the Mg was activated at room temperature by introduction of a crystal of iodine and 2 mL of 1,2-dibromoethane (gas was evolved). This was followed by addition of 207.4 g (94% pure = 195.0 g, 546 mmol) of Part D compound in a single portion. The reaction mixture briefly turned colorless, then amber. The exothermic reaction brought the mixture to reflux. Additional dry THF (120 mL) was introduced to ensure product solubility on eventual cooling. Although the reaction was not violently exothermic, foaming made it necessary to cool the mixture with a water bath. The water bath was used intermittently until the exotherm subsided. The mixture was then heated to a gentle reflux for 1 hour and cooled to room temperature. No precipitate formed. The mixture consisted of a brown, clear solution of title compound and some unreacted Mg. This solution was used the same day to prepare title compound F as follows.

F.
[1S-(1α,2α,3α,4α)]-α-[2-[3-[[Dimethyl-(1,1,2-trimethylpropyl)silyl]oxy]propyl]phenyl]-7-oxabicyclo[2.2.1]heptane-2,3-dimethanol A 5-L flask containing a magnetic stir-bar was charged with 63.1 g of [3aR-(3aα,4β,7β,7aα)]-octahydro-4,7-epoxyisobenzofuran-1-ol (SQ 30,674) (405 mmol) and placed under an argon atmosphere. After 400 mL dry THF (distilled from potassium/ benzophenone) was added, SQ 30,674 was dissolved by stirring. The resulting solution was cooled to 0°, and by syringe over 30 minutes, 192 mL of 2.0M $C_2H_5MgBr$ (Aldrich, prewarmed to 30° to ensure homogeneity, 385 mmol, 0.95 equiv) was added. Gas was evolved. After the addition was complete, stirring at 0° was continued for 1 hour. The solution of previously prepared Part E magnesium compound (546 mmol, 1.35 equiv theoretical) was introduced by cannula over 1 hour. The temperature was maintained at 0° during the addition and for several hours afterward. A small amount of precipitate formed. The mixture was warmed to room temperature, and 50 mL dry THF was added. Some precipitate remained. This mixture was stirred for 6 days before 290 mL of a saturated, aqueous solution of (83 g) $NH_4Cl$ was slowly added. The quench was slightly exothermic, the mixture warming itself to about 40°. The mixture was stirred for 2 hours, and the inorganics formed a white paste. To the mixture was added 1.0 L of $CH_2Cl_2$. The organic supernatant was decanted from the paste. The paste was then stirred with 500 mL $CH_2Cl_2$. The organic layer was decanted, and this procedure was repeated. The combined organic layers were dried over 115 g $Na_2SO_4$ (total volume 3.5 L), and concentrated in vacuo. To drive off THF the residue was re-concentrated after addition of 200 mL $CH_2Cl_2$. This yielded 230 g of an oil. The oil was then quickly dissolved in 2.0 L hexane. Crystallization began in minutes. The mixture was refrigerated with periodic agitation for 5 days. The crystals which formed were filtered (cold) and washed with two 500 mL portions of refrigerated hexane. After exposure to vacuum, 145 9 g of crystals (mp 99.5°–100.5°) were obtained. The crystals, pure, and a single diastereomer of Part F compound, represented an 83% yield. The mother liquors were evaporated, redissolved in 200 mL hexane, and placed in the freezer for 30 days. A second crop of crystals (8.7 g, pure, single diastereomer of Part F compound, 5% additional yield) was collected as above. (In an earlier run, yields of the cospotting major and minor diastereomers were 94% and 5% respectively. The minor diastereomer is an oil).

TLC (silica gel, 100% EtOAc - anisaldehyde):

| | |
|---|---|
| SQ 30,674 | 0.35 |
| Part F compound | 0.78 |

$^{13}$C NMR (67.8 MHz in CDCl$_3$): 141.8, 138.7, 129.5, 127.3, 126.2, 125.5, 79.5, 77.3, 67.4, 62.2, 61.7, 51.7, 49.0, 34.2, 34.1, 29.7, 29.7, 28.0, 25.2, 20.3, 18.5, −3.3.

G.
[1S-(1α,2α,3α,4α)]-2-[[2-[3-[[Dimethyl(1,1,2-trimethyl-propyl)silyl]oxy]propyl]-phenyl]methyl]-7-oxabicyclo[2.2.1]heptane-3-methanol A mixture of 143.0 g (329 mmol) of Part F compound and 28.6 g of 20% palladium hydroxide on carbon catalyst (moist, <50% water, Aldrich) in 2.0 L of glacial acetic acid was stirred rapidly under an atmosphere of hydrogen (balloon) at room temperature for 30 hours. The reaction mixture was filtered through filter paper to remove most of the catalyst. The filtrate was evaporated to 500 mL on a rotovapor in a 30° water bath under high vacuum. This was then passed through a Millipore/Fluropore membrane filter (0.5 μm FH) with a prefilter pad. Evaporation as above was followed by azeotropic removal of acetic acid (AcOH) with toluene (500 mL three times) and re-evaporation with CH$_2$Cl$_2$ to drive off toluene. The crude product, 144.9 g of an oil, consisted largely of title compound (approximately 90%) with small amounts of solvent, the acetate of title compound (identical with Part H compound, less than 5%), and desilylated title compound (diol, less than 5%).

TLC (silica gel, 25% EtOAc in hexane - anisaldehyde):

| Part F compound | 0.07 |
|---|---|
| Title compound | 0.16 |
| Part H compound | 0.50 |
| desilylated title compound (diol) | 0.00 |

TLC (silica gel, 100% EtOAc - anisaldehyde):

| Part F compound | 0.82 |
|---|---|
| Title compound | 0.85 |
| Part G compound | 0.93 |
| desilylated G (diol) | 0.20 |

H.
[1S-(1α,2α,3α,4α)]-2-[[2-[3-[[Dimethyl-(1,1,2-trimethyl-propyl)silyl]oxy]propyl]-phenyl]methyl-7-oxabicyclo[2.2.1]hept-2-yl]-heptane-3-methanol, acetate ester A solution of 144.9 g (<329 mmol) of crude Part G compound in 200 mL pyridine (Burdick & Jackson) was stirred magnetically under argon at room temperature while 50 mL (54 g, 530 mmol) of acetic anhydride was added in a single portion The reaction mixture warmed to a peak temperature of about 41° after 30 minutes. After 16 hours the homogeneous mixture was rotoevaporated using a 70° water bath. The residue was coevaporated three times with toluene (500 mL). This gave 163.5 g of an oil, crude title compound. The crude product contained toluene, but no residual pyridine.

TLC (silica gel, 25% EtOAc in hexane - anisaldehyde):

| Part G compound | 0.20 |
|---|---|
| Part H compound | 0.54 |

$^{13}$C NMR (67.8 MHz in CDCl$_3$): 170.9, 140.4, 138.7, 129.6, 129.4, 126.2, 125.9, 79.3, 79.2, 63.8, 62.4, 46.9, 46.0, 34.2, 34.0, 30.6, 29.5, 29.5, 28.9, 25.1, 21.0, 20.4, 18.5, −3.4.

I.
[1S-(1α,2α,3α,4α)]-2-[[3-[(Acetyloxy)-methyl]-7-oxabicyclo[2.2.1]hept-2-yl]-methyl]benzenepropanoic acid To a stirring solution of 163.5 g of crude Part H compound in 2.0 L acetone in a room temperature bath, was added slowly (over about 1 hour in 50 mL portions) 240 mL of Jones' Reagent with Mn$^{+2}$. Exothermic reaction brought the mixture to near reflux. As precipitate formed stirring became very difficult. The red color of the reagent persisted after the last portion was introduced. The excess reagent was quenched 30 minutes later by addition of 50 mL 2-propanol. The precipitated Cr salts were easily filtered. The salts were washed with acetone. The filtrate (2.4 L) was evaporated, and two immiscible oils were obtained. After addition of 500 mL CH$_2$Cl$_2$, 100 mL brine, and 300 mL water, separation of the organic and aqueous layers was difficult. Introduction of 300 mL CHCl$_3$ allowed good separation. The aqueous layer was re-extracted twice with 300 mL CHCl$_3$, and the combined extracts were dried over Na$_2$SO$_4$ and evaporated in vacuo. This provided 164.5 g of crude title compound (containing desilylation by-product), a clear oil.

TLC [silica gel, 50% (5% CH$_3$COOH in ethyl acetate (EtOAc)) in hexane - anisaldehyde]:

| Part H compound | 0.89 |
|---|---|
| Title compound | 0.42 |

J.
[1S-(1α,2α,3α,4α)]-2-[[3-(Hydroxymethyl)-7-oxabicyclo[2.2.1]hept-2-yl]methyl]benzene-propanoic acid, methyl ester A solution of 164.5 g of crude Part I compound in 1.0 L of acidic methanol (prepared by cautious addition of 10 mL of acetyl chloride to 1.0 L of methanol) was stirred under argon in a 2-L flask. TLC indicated that the reaction proceeded predominantly through one distinct intermediate. After 16 hours 30 g of NaHCO$_3$ was added cautiously over 10 minutes. Neutralization was not exothermic, but gas was evolved. The mixture was stirred for 30 minutes before it was cautiously evaporated. The residue was diluted with 500 mL CH$_2$Cl$_2$, dried over Na$_2$SO$_4$, and filtered. After the filtrate was evaporated, the crude product was coevaporated in vacuo twice with toluene (60° bath, to remove some of the desilylation by-product). This gave 119.3 g of an oil. Crude title compound was judged to be roughly 75% pure with only about a third of an equivalent of desilylation by-product and a little diol (Part G by-product).

TLC (silica gel, 50% (5% CH$_3$COOH in EtOAc) in hexane - anisaldehyde):

| Part I compound | 0.35 |
|---|---|
| intermediate | 0.53 |
| title compound | 0.31 |
| diol | 0.11 |

K.
[1S-(1α,2α,3α,4α)]-2-[(3-Carboxy-7-oxabicyclo[2.2.1-]hept-2-yl)methyl]-benzenepropanoic acid, methyl ester To a stirring solution of 93.6 g (78% of the sample) of crude Part J compound in 1.5 L acetone in a room temperature bath, was added slowly (over about 1 hour in 50 mL portions) 150 mL of Jones' Reagent with $Mn^{+2}$. (Jones' Reagent was prepared as described in Fieser & Fieser, "Reagents for Organic Synthesis", vol. 1, p. 142 - Djerassi procedure. Into this Jones' Reagent was dissolved 1.0 g $MnSO_4 \cdot H_2O$ per L.). Exothermic reaction brought the mixture to near reflux. As precipitate formed stirring became very difficult. The red color of the reagent persisted after the last portion was introduced. The excess reagent was quenched 30 minutes later by addition of 50 mL 2-propanol. The precipitated Cr salts were easily filtered. The salts were washed with acetone. The filtrate was evaporated, and two immiscible oils were obtained. After addition of 500 mL $CHCl_3$, 100 mL brine, and 300 mL water, separation of the organic and aqueous layers was uncomplicated. The aqueous layer was re-extracted twice with 250 mL $CHCl_3$, and the combined extracts were dried over $Na_2SO_4$ and evaporated. This provided 109.6 g of crude title acid, a pale green, clear oil. A portion (30.6 g, 28%) of the crude title acid was flash chromatographed (1.0 kg Merck silica gel, 40% to 100% (5%$CH_3COOH$ in EtOAc) in hexane gradient). This provided 18.2 g of pure title acid as a viscous oil. Also isolated was 1.4 g of the diacid corresponding to title acid, a solid. The overall yields from Part F compound were 80% and 6%, respectively.

TLC (silica gel, 50% (5% $CH_3COOH$ in EtOAc) in Hexane - anisaldehyde):

| Part J compound | 0.33 |
|---|---|
| diol | 0.12 |
| title acid | 0.31 |
| diacid | 0.13 |

L. N-(Cyclohexylbutyl)-L-serinamide

To a solution of 14.3 g of 4-cyclohexylbutylamine hydrochloride (74.7 mmol), 16.1 g t-butoxycarbonyl (BOC)-(L)-serine (78.4 mmol, 1.05 equiv), 10.1 g 1-hydroxybenzotriazole hydrate (74.7 mmol, 1.00 equiv), and 7.9 g N-methylmorpholine (78.4 mmol, 1.05 equiv) in 200 mL N,N-dimethyl formamide (DMF) (Burdick & Jackson) stirring under argon at 0°, was added 15.0 g WSC (78.4 mmol, 1.05 equiv) in a single portion. All of the WSC dissolved. The reaction mixture was allowed to slowly warm to room temperature overnight, and a precipitate formed. The mixture was rotoevaporated (60° bath) to 90 g of oil plus solid. This was diluted with 400 mL EtOAc and washed with 200 mL 0.3 M aqueous HCl twice (all solids dissolved at this point), then 200 mL 1.0 M aqueous $NaHCO_3$ twice. To the organic layer was added 500 mL toluene, and this was dried over $Na_2SO_4$ and evaporated. After coevaporation with toluene, 28.4 g of a thick solidifying oil was obtained. This material, BOC-title compound, H was dissolved in 150 mL $CH_2Cl_2$, and while stirring at room temperature under argon, 100 mL trifluoroacetic acid was added (gas was evolved). After 4 hours the solvent was evaporated, and after coevaporation with $CHCl_3$, the crude product was flash chromatographed (1.0 kg silica gel, 10% (10% conc. aq. $NH_3$ in $CH_3OH$) in $CH_2Cl_2$) to obtain 13.4 g of 95% pure title compound as a white solid. The corrected yield of title compound was 70% (12.7 g) overall from 4-cyclohexylbutylamine hydrochloride TLC (silica gel, 10% (10% conc. aq. $NH_3$ in $CH_3OH$) in $CH_2Cl_2$ - anisaldehyde):

| 4-Cyclohexylbutylamine | 0.27 |
|---|---|
| BOC-title compound | 0.43 |
| title compound | 0.17 |

M.
[1S-(1α,2α,3α(R*),4α)]-2-[[3-[[2-[(4-Cyclohexylbutyl)amino]-1-(hydroxymethyl)-2-oxoethyl]amino]carbonyl]-7-oxabicyclo-[2.2.1]hept-2-yl]methyl]benzenepropanoic acid, methyl ester To a stirred solution of 16.7 g of Part K compound (52.5 mmol), 13.4 g of Part L compound (95% pure = 12.7 g, 52.5 mmol), 7.8 g of 1-hydroxybenzenetriazole monohydrate (57.8 mmol, 1.10 equiv), and 5.8 g of N-methylmorpholine (57.8 mmol, 1.10 equiv) in 250 mL of DMF (Burdick & Jackson) under argon at 0°, was added 11.1 g of WSC (57.8 mmol, 1.10 equiv). The WSC dissolved completely. The mixture was allowed to warm to room temperature overnight. No precipitate formed. The mixture was rotoevaporated (60° bath). The residue was diluted with 700 mL EtOAc—solids did not all dissolve—and washed with 250 mL 0.3M aqueous HCl, then 250 mL 1.0 M aqueous $NaHCO_3$. The still undissolved solid was desired product according to TLC. Addition of 200 mL $CH_2Cl_2$ did not give a solution. This was washed with 150 mL 0.3M aqueous HCl plus 50 mL brine, then 250 mL 1.0M aqueous $NaHCO_3$. After addition of 500 mL more $CH_2Cl_2$ a solution formed. This was dried over $Na_2SO_4$ and evaporated in vacuo. Crude title compound, 30.7 g of white solid, was obtained. This material was about 93% pure. The corrected yield (28.5 g) of title compound (a single diastereomer) was 100%.

TLC (silica gel, 10% (10% conc. aq. $NH_3$ in $CH_3OH$) in $CH_2Cl_2$ - anisaldehyde):

| Part K compound | 0.42 |
|---|---|
| Part L compound | 0.25 |
| Title compound | 0.48 |

TLC (silica gel, 50% (5% $CH_3COOH$ in EtOAc) in hexane - anisaldehyde):

| Part K compound | 0.34 |
|---|---|
| Part L compound | 0.00 |
| Title compound | 0.12 |

N.
[1S-(1α,2α,3α,4α)]-2-[[3-[4-[[(4-Cyclohexylbutyl)amino]carbonyl]-4,5-dihydro2-oxazolyl]-7-oxabicyclo[2.2.1]hept-2-yl]methyl]benzenepropanoic acid, methyl ester A stirred solution of 30.7 g of crude Part M compound (93% pure=28.5 g, 52.5 mmol) in 800 mL of dry $CH_2Cl_2$ under argon at room temperature was cooled to 0°. As the starting material began to precipitate, 12.1 g of $(C_2H_5)_3N$ (120 mmol), then 6.9 g of methanesulfonyl chloride (60 mmol) were added. The precipitate redissolved. After 40 minutes the mixture was warmed to room temperature, and 30 minutes later it was evaporated. To the residue (crude mesylate of Part M compound) under argon, was added 1.0 L of acetone and 27.6 g K$_2$CO$_3$ (200 mmol). The mixture was refluxed for 2 hours and refrigerated overnight. The solid was filtered off and rinsed with acetone. TLC indicated that the solid contained product even after extensive rinsing. After further rinsing with CH$_2$Cl$_2$, almost all of product was extracted. The filtrate was evaporated and flash chromatographed (500 g silica gel, 20% acetone in toluene) to obtain 24.9 g of a solid. $^1$H NMR indicated either pure title compound as an unequal mixture of two diastereomers (90% yield) or one diastereomer of title compound plus an impurity.

TLC (silica gel, 20% acetone in toluene-anisaldehyde):

| Part M compound | 0.13 |
|---|---|
| mesylate of Part M compound | 0.21 |
| title compound | 0.34 |

O.
[1S-(1α,2α,3α,4α)]-2-[[3-[4-[[(4-Cyclohexylbutyl)amino]carbonyl]-2-oxazolyl]7-oxabicyclo[2.2.1]hept-2-yl]methyl]-benzenepropanoic acid, methyl ester To a stirred suspension of 22.3 g (100 mmol) of cupric bromide in 250 mL of EtOAc (Burdick & Jackson) at room temperature under argon, was added 30.4 g (200 mmol) of 1,8-diazabicyclo[5.4.0]undec-7ene (DBU). The resulting dark mixture was stirred for 15 minutes before a solution of 24.9 g of Part N compound (if pure, 47.5 mmol) in 250 mL of CHCl$_3$ (Burdick & Jackson) was added. The mixture warmed to about 45° (simply due to the heat of mixing of the two solvents). After 18 hours 22.3 g cupric bromide and 15.2 g DBU were added. After another 25 hours (TLC showed almost complete reaction), 11.2 g cupric bromide and 7.6 g DBU were added. After 4 hours more, the reaction mixture was poured into a 6-L separatory funnel. A residual heavy syrup was transferred by dissolving with CH$_2$Cl$_2$. This was shaken with 1.0 L of EtOAc and 1.4 L of a 1:1 (vol:vol) mixture of saturated aqueous NH$_4$Cl and concentrated aqueous ammonia. Separation was poor. Addition of 750 mL diethyl ether (Et$_2$O) allowed good separation. Two further extractions of the aqueous layer with 800 mL EtOAc proceeded smoothly. The extracts were dried over Na$_2$SO$_4$ and evaporated. Flash chromatography (750 g silica gel, 25% to 40% EtOAc in hexane gradient) allowed isolation of 16.5 g of pure title compound as a white solid. The yield of title compound was 67% assuming pure Part N compound. Also isolated was 1.8 g (6% yield) of bromo-title compound (brominated at the 5 position of the oxazole ring) as a gum.

TLC (silica gel, 20% acetone in toluene-anisaldehyde):

| Part N compound | 0.31 |
|---|---|
| title compound | 0.47 |
| bromo-title compound | 0.61 |

P.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]-methyl]benzenepropanoic acid A homogeneous solution of 16.5 g Part O ester (31.6 mmol) in 100 mL of THF, 500 mL of CH30H, and 200 mL of 1.0M aqueous NaOH was prepared and stirred at room temperature for 5 hours. Acidification with 300 mL 1.0M aqueous HCl was followed by extraction three times with CH$_2$Cl$_2$ (500 mL, 250 mL, 250 mL). The combined extracts were dried over Na$_2$SO$_4$ and evaporated. The crude product was recrystallized by dissolving in 1.8 L of boiling CH$_3$CN (Burdick & Jackson, minimum volume) and cooling slowly, ultimately in the freezer for 20 hours. Crystals of title compound (not visibly highly crystalline) were filtered, washed with refrigerated CH$_3$CN, and dried under high vacuum. This provided 14.35 g of pure title compound (89% yield), as a white solid. (The mother liquors were evaporated to 1.7 g of approximately 90% pure product—corrected additional yield 9%, 1.5 g). The product appeared to be microcrystalline as judged by its powder X-ray diffraction pattern, mp 167.5°–168.5°. [α]$_D^\circ$ = +14.1° in CHCl$_3$ at c=2.9 g/100 mL. HPLC HI=99.64% (balance was three or more compounds, C18 column, 220 nm detector, 43% CH$_3$CN: 29% of 0.2% aqueous H$_3$PO$_4$:28% CH$_3$OH isocratic eluent).

TLC (silica gel, 50% (5% CH$_3$COOH in EtOAc) in hexane - anisaldehyde):

| Part O compound | 0.51 |
|---|---|
| title compound | 0.36 |

$^{13}$C NMR (67.8 MHz in CDCl$_3$): 176.5, 163.9, 160.8, 141.0, 138.5, 137.8, 135.9, 129.7, 129.0, 126.7, 126.5, 79.7, 78.6, 50.0, 46.9, 39.2, 37.5, 37.1, 34.8, 33.3, 32.5, 29.8, 28.9, 27.4, 26.7, 26.3, 24.2.

EXAMPLE 2
[1S-(1α,2α,3α,4α)]-2-[[3-[4-[[[4-(4-Chlorophenyl)butyl]amino]carbonyl]-2-oxazolyl]-7-oxabicyclo[2.2.1]hept-2-yl]methyl]benzenepropanoic acid A. 1-Bromo-2-[3-[[Dimethyl(1,1,2-trimethyl-propyl)silyl]oxy]propyl]benzene To a solution of 29.0 g (135 mmol) of crude Example 1 Part C alcohol and 24.1 g (135 mmol, Petrarch) of thexyldimethylchlorosilane in 200 mL of dry methylene chloride (distilled from phosphorous pentoxide) was added at room temperature 20 mL (143 mmol, distilled from calcium hydride) of triethylamine then 200 mg (1.64 mmol, Aldrich) of 4-dimethylaminopyridine. The reaction mixture was stirred at room temperature for 18 hours. The resulting slurry was diluted with 100 mL of hexane, cooled to 0° with stirring for 15 minutes then filtered to remove solid triethylamine hydrochloride. The filtrate was concentrated in vacuo to give an oil. The crude oil was purified by flash chromatography (Merck silica, 15×10 cm, 1:9 ethyl acetate/petroleum ether) to afford 45.5 g (127 mmol, 94%) of title compound as a colorless liquid.

B.
[1S-(1α,2α,3α,4α)]-[2-[3-[[Dimethyl-(1,1,2-trimethylpropyl)silyl]oxy]propyl]-phenyl]-7-oxabicyclo2.2.1-]heptane-2,3-dimethanol To a solution of 5.00 g (14.0 mmol) of Part A compound in 30 mL of dry diethyl ether (distilled from ketyl) cooled to −100° was added dropwise 15 mL (1.7M in pentane, 25 mmol, Aldrich) of t-butyllithium solution over 15 minutes. The reaction mixture was stirred at −100° for 15 minutes then at 0° for 15 minutes. The resulting pale yellow anion solution was re-cooled to -78° then 30 mL of dry THF (distilled from ketyl) was introduced followed by the rapid addition of a solution of 875 mg (5.61 mmol) of [3aR-(3aα,4β,7β,-7aα)]-octahydro-4,7-epoxy-isobenzofuran-1-ol in 10 mL of THF. The reaction mixture was warmed to 0°, stirred for 1 hour, quenched with 5 mL of water then partitioned between 100 mL of water and 25 mL of ethyl acetate. The organic layer was separated and the aqueous layer was extracted with an additional 25 mL of ethyl acetate. The organic extracts were combined, dried (magnesium sulfate) and concentrated in vacuo to give an oil. The crude oil was purified by flash chromatography (Merck silica, 12×5.0 cm, 1:4 ethyl acetate/petroleum ether then 4:1 ethyl acetate/petroleum ether) to afford 2.35 g (5.41 mmol, 97%) of title diasteromeric alcohols as a colorless oil.

C.[1S-(1α,2α,3α,4α)]-2-[[2-[3-[[Dimethyl(1,1,2-trimethylpropyl)-silyl]oxy]propyl]phenyl]methyl]-7-oxabicyclo[2.2.1]heptane-3-methanol A mixture of 1.90 g (4.38 mmol) of Part B diastereomeric alcohols and 1.9 g of 20% palladium hydroxide on carbon catalyst (moist, <50% water, Aldrich) in 60 mL of glacial acetic acid was stirred rapidly under an atmosphere of hydrogen (balloon) for 5 hours. The reaction mixture was filtered through a 4μM polycarbonate membrane and the filtrate was concentrated in vacuo (room temperature bath). The residue was partitioned between 50 mL of water and 50 mL of ethyl acetate. The organic layer was separated, washed with 50 mL of 1M aqueous sodium hydroxide solution, dried (magnesium sulfate) and concentrated in vacuo to give an oil. The crude material was purified by flash chromatography (Merck silica, 12×5.0 cm, 1:2 ethyl acetate/petroleum ether) to afford 1.03 g (2.39 mmol, 55%) of title compound as a colorless oil. In addition, 573 mg (1.37 mmol, 30%) of Part C starting material (as a single diastereomer) was recovered.

D.
[1S-[1α,2α,3α,4α)]-2-[[3-(Hydroxy-methyl)-7-oxabicyclo[2.2.1]hept-2-yl]-methyl]benzenepropanoic acid, methyl ester A solution of 1.00 g (2.39 mmol) of Part C compound and 50 mg (0.41 mmol, Aldrich) of 4dimethylaminopyridine in 6 mL of 1:1 dry pyridine/ acetic anhydride was stirred at room temperature for 2 hours. The reaction mixture was concentrated in vacuo and the residue partitioned between 25 mL of ethyl acetate and 20 mL 1M aqueous HCl solution The organic layer was separated, washed with 20 mL of 1M aqueous NaOH then 20 mL of brine, dried (magnesium sulfate) and concentrated in vacuo to afford the crude acetate as an oil.

To a solution of the crude acetate in 15 mL of reagent acetone cooled to 0° was added rapidly 3.3 mL (2.6M in $Cr^{+6}$, for preparation see Fieser & Fieser, "Reagents for Organic Synthesis," Vol. 1, p. 142) of Jones reagent. The reaction mixture was stirred for 2 hours, quenched by addition of 1 mL of isopropanol and stirred for an additional 30 minutes. The resulting green slurry was filtered through a pad of Celite. The filtrate was concentrated in vacuo and the residue partitioned between 25 mL of diethyl ether and 25 mL of water. The organic layer was separated and concentrated in vacuo to give the crude acetate-acid as an oil.

A solution of the crude acetate-acid in 15 mL of 2:1 1M aqueous NaOH/THF was stirred at room temperature for 30 minutes. The reaction mixture was cooled in an ice-bath, quenched by addition of 15 mL of 1M aqueous HCl solution then extracted with two-25 mL portions of diethyl ether. The ether extracts were combined, washed with 25 mL of brine and concentrated in vacuo to give the crude alcohol-acid as an oil.

A solution of the crude alcohol-acid in 10 mL of acidic methanol (prepared by addition of 0.5 mL of acetyl chloride to 10 mL of dry methanol at 0°) was stirred at 0° for 2 hours then concentrated in vacuo. The resulting oil was purified by flash chromatography (Merck silica, 15×3.0 cm, ethyl acetate) to afford 526 mg (1.76 mmol, 74% from Part C compound) of title compound as a colorless oil.

E.
[1S-(1α,2α,3α,4α)]-2-[[3-Carboxy-7-oxabicyclo2.2.1-]hept-2-yl]methyl]-benzenepropanoic acid, methyl ester To a solution of 495 mg (1.63 mmol) of Part D compound in 5 mL of reagent acetone cooled to 0° was added rapidly 2.0 mL (2.6M in $Cr^{+6}$) of Jones reagent. The reaction mixture was warmed to room temperature, stirred for 2 hours then quenched by addition of ∼1 mL of isopropanol. After 15 minutes the resulting green slurry was filtered through a pad of Celite. The filtrate was partitioned between 20 mL of diethyl ether and 20 mL of water. The organic layer was separated and the aqueous layer was extracted with an additional 20 mL of diethyl ether. The ether extracts were combined, dried (magnesium sulfate) and concentrated in vacuo to give 560 mg (1.59 mmol, 98%) of crude title compound as a colorless oil.

F.
[1S-(1α,2α,3α,4α)]-2-[[3-[[1-(Hydroxymethyl)-2-oxo-2-(phenylmethoxy)-ethyl]amino]carbonyl]-7-oxabicyclo-[2.2.1]hept-2-yl]methyl]benzene-propanoic acid, methyl ester To a solution of 490 mg (1.54 mmol) of Part E acid in 10 mL of dry THF (distilled from ketyl) cooled to 0° was added 392 mg (1.69 mmol, Sigma) of L-serine benzyl ester hydrochloride, 228 mg (1.69 mmol, Aldrich) of 1-hydroxybenzotriazole hydrate and 530 μL (3.8 mmol, distilled from calcium hydride) of triethylamine. The mixture was stirred for 5 minutes then 348 mg (1.69 mmol, Aldrich) of dicyclohexylcarbodiimide was added in one portion. The reaction was stirred at 0° for 3 hours then warmed to room temperature for 16 hours. The resulting slurry was diluted with 10 mL of ethyl acetate, cooled to 0° for 15 minutes then filtered. The filtrate was concentrated in vacuo to give an oil. The crude material was purified by flash chromatography (Merck silica, 15×3.0 cm, ethyl acetate) to afford 540 mg (1.09 mmol, 71%) of title compound as a white solid.

G.
[1S-(1α,2α,3α,4α)]-2-[[3-[4,5-Dihydro-4-[(phenylmethoxy)carbonyl]-2-oxazolyl]-7-oxabicyclo[2.2.1]hept-2-yl]-methyl]benzenepropanoic acid, methyl ester To a solution of 525 mg (1.06 mmol) of Part F compound, 843 mg (3.10 mmol, Aldrich) of triphenylphosphine and 540 μL (3.1 mmol, Aldrich) of diisopropylethylamine in 6 mL of 5:1 dry acetonitrile/ methylene chloride was added at room temperature 300 μL (3.1 mmol, Mallinckrodt) of reagent carbon tetrachloride. The reaction mixture was stirred for 2 hours then diluted with 15 mL of ethyl acetate followed by the slow addition of 15 mL of saturated aqueous sodium bicarbonate solution. The resulting mixture was stirred for 5 minutes then partitioned between 20 mL of ethyl acetate and 20 mL of water. The organic layer was separated, washed with 20 mL of brine, dried (sodium sulfate) and concentrated in vacuo to give a yellow oily solid. The crude material was purified by flash chromatography (Merck silica, 20×3.0 cm, 2:1 ethyl acetate/petroleum ether) to afford 380 mg (0.80 mmol, 75%) of title oxazoline as a pale yellow solid.

H.
[1S-(1α,2α,3α,4α)]-2-[[3-[4-[(Phenylmethoxy)carbonyl]-2-oxazolyl]-7-oxabicyclo[2.2.1]hept-2-yl]methyl]-benzenepropanoic acid, methyl ester To a solution of 375 mg (0.79 mmol) of Part G oxazoline in 10 mL of dry methylene chloride (distilled from phosphorous pentoxide) was added 750 mg of Example 1, Part J, nickel peroxide oxidant (K. Nakagawa et al, J. Org. Chem. 27, 1597 (62)) at room temperature. The reaction mixture was stirred for 1 hour then an additional 190 mg of oxidant was added. After 30 minutes the reaction mixture was diluted with 20 mL of ethyl acetate followed by the addition of 10 mL of 3M aqueous sodium bisulfite solution. The resulting mixture was stirred rapidly for 20 minutes then 10 mL of water was added. The organic layer was separated and the aqueous layer extracted with an additional 20 mL of ethyl acetate. The organic extracts were combined, washed with 25 mL of 1M aqueous sodium citrate solution, dried (magnesium sulfate) and concentrated in vacuo to give an oil. The crude material was purified by flash chromatography (Merck silica, 15×5.0 cm, 2:3 ethyl acetate/petroleum ether) to afford 180 mg (0.38 mmol, 48%) of title oxazole as an oil.

I. 4-(4-Chlorophenyl)butylamine (a) 3-(4-Chloropenyl)propanol

To a stirred solution of 5.0 g (27 mmol) of 3-(4-chlorophenyl)propionic acid in 30 ml of tetrahydrofuran at 0° C., 30 ml (1M in THF, 30 mmol) of borane-tetrahydrofuran solution was added dropwise. The reaction was stirred for 15 hours. The reaction mixture was concentrated in vacuo. The residue was quenched with water and partitioned between diethyl ether and saturated sodium bicarbonate. The organic layer was separated and the aqueous layer was extracted twice with 40 ml of diethyl ether. The organic layers were combined and washed with brine, dried over MgSO4 and concentrated in vacuo to obtain 3.9 g of a colorless oil.

<sup>13</sup>C NMR (CDCl3, 67.8 MHz)δ: 140.0, 131.0, 129.9, 129.0, 161.0, 132.5, 131.0.

(b) 3-(4-Chlorophenyl)propyl bromide

To a stirred solution of 4.15 g (15.8 mmol) of triphenylphosphine in 100 ml of toluene at 0° C., 1.51 ml (15.8 mmol) of bromine was added dropwise. This mixture was stirred for 3 hours then a solution of 3.90 g (22.9 mmol) of Part (a) alcohol and 1.63 ml (15.8 mmol) of pyridine in 20 ml of toluene was added. A solution of 25 ml hexane and 25 ml diethyl ether was added, and a brown mass was formed. The liquid was decanted and concentrated in vacuo. The residue was triturated with hexane:ethyl acetate and triphenylphosphine oxide was precipitated. The solid was filtered and the filtrate was concentrated in vacuo to give a yellow oil. The oil was purified by flash chromatography to obtain 1.80 g (7.72 mmol, 49%) of the desired product.

<sup>13</sup>C NMR (CDCl3)δ: 138.7, 131.6, 129.6, 128.3, 33.7, 33.0, 32.5.

(c) 4-(4-Chlorophenyl)butyronitrile

To a solution of 3.10 g (13.3 mmol) of Part (b) bromide in 36 ml of ethanol stirred under argon at room temperature, was added a solution of 4.26 g (65.4 mmol) of potassium cyanide in 12 ml of water. The reaction was incomplete after 5 hours as indicated by TLC. To the reaction mixture 4 ml of THF and 4 ml of water were added, and a homogeneous reaction mixture was obtained. After stirring for 12 hours, water and diethyl ether were added. The organic layer was separated. The aqueous layer was extracted twice with 50 ml of diethyl ether. The organic layers were combined, washed with water, brine, dried over MgSO4 and concentrated in vacuo to give an oil. The oil was purified by flash chromatography (Merck silica gel 90:10 hexane:ethyl acetate) to obtain 1.80 g (10.1 mmol, 76%)of title nitrile as a clear oil.

<sup>13</sup>C NMR (CDCl3)δ: 138.0, 132.1, 129.6, 128.6, 33.5, 26.6, 16.2

(d) 4-(4-Chlorophenyl)butylamine

To a solution of 1.80 g (10 mmol) of Part (c) nitrile in 70 ml of diethyl ether stirred under argon at 0° C., was added 0.38 g (10 mmol) of lithium aluminum hydride. Gas was evolved. After 20 minutes, the reaction mixture was quenched with 0.4 ml of water, then 0.4 ml of 1N NaOH, then 1.2 ml water, stirring for a few minutes after each addition. The resulting white precipitate was filtered and the filtrate was concentrated in vacuo to obtain 1.5 g (8.20 mmol, 82%) of title amine as a clear oil.

<sup>13</sup>C NMR (CDCl3)δ: 140.7, 131.2, 129.5, 128.2, 41.8, 3499, 33.0, 28.4

J.
[1S-(1α,2α,3α,4α)]-2-[[3-4-[[[4-(4-Chlorophenyl)butyl]amino]carbonyl]-2-oxazolyl]-7-oxabicyclo[2.2.1]hept-2-yl]methyl]benzenepropanoic acid, methyl ester A mixture of 175 mg (0.37 mmol) of Part H oxazole and 30 mg of 20% palladium hydroxide on carbon catalyst (moist, <50% water, Aldrich) in 5 mL of reagent ethyl acetate was stirred under an atmosphere of hydrogen (balloon) for 1 hour. The catalyst was removed by filtration through a 4μM polycarbonate membrane. The filtrate was concentrated in vacuo to afford 141 mg (0.37 mmol, 100%) of the crude acid ([1S-(1α,2α3α,-4α)]-2-[[3-[4-]carboxy]-2-oxazolyl]-7-oxabicyclo[2.2.1-

]hept-2yl]methyl]benzenepropanoic acid, methyl ester) as a white solid, mp 156°-158°.

To a solution of 135 mg (0.35 mmol) of the crude acid in 3 mL of dry methylene chloride (distilled from phosphorous pentoxide) was added at room temperature a small drop of DMF then 40 μL (0.46 mmol, Aldrich) of oxalyl chloride. The reaction mixture was stirred for 30 minutes then concentrated in vacuo to give the crude acid chloride as a yellow solid. The acid chloride was solubilized in 3 mL of dry methylene chloride then cooled to 0° and a solution of 84 mg (0.46 mmol) of Part I amine and 70 μL (0.50 mmol, distilled from calcium hydride) of triethylamine in 1 mL of dry methylene chloride was added rapidly. The reaction mixture was stirred for 30 minutes then partitioned between 25 mL of ethyl acetate and 15 mL of 1M aqueous HCl solution. The organic layer was separated and the aqueous layer was extracted with an additional 10 mL of ethyl acetate. The organic extracts were combined, dried (magnesium sulfate) and concentrated in vacuo to give a yellow solid. The crude material was purified by flash chromatography (Merck silica, 18×1.5 cm, 3:1 ethyl acetate/petroleum ether) to afford 161 mg (0.29 mmol, 83%) of title compound as a white solid, mp 140°-142°.

K.

[1S-(1α,2α,3α,4α)]-2-[[3-[4-[[[4-(4-Chlorophenyl)butyl]amino]carbonyl]-2oxazolyl]-7-oxabicyclo[2.2.1]hept-2-yl]methyl]benzenepropanoic acid A solution of 158 mg (0.29 mmol) of Part J compound and 25 mg (0.60 mmol, Aldrich) of lithium hydroxide monohydrate in 6 mL of 2:1 THF/water was stirred rapidly at room temperature for 1.5 hours. The reaction was acidified by addition of 2 mL of 1M aqueous HCl solution then partitioned between 20 mL of ethyl acetate and 20 mL of water. The organic layer was separated, washed with 20 mL of brine, dried (magnesium sulfate) and concentrated in vacuo to afford 152 mg (0.28 mmol, 98%) of title product as a solid white foam.

IR (KBr): 3413, 2940, 1724, 1652, 1602, 1522, 1491, 1203, 1175, 1105 cm$^{-1}$

Partial 270 MHz $^1$NMR (CDCl$_3$): δ2.19 (dd, 1H), 2.32 (t, J=11, 1H), 2.55 (m, 5H), 2.89 (t, J=8, 2H), 3.39 (m, 3H), 4.39 (d, J=4, 1H), 4.96 (d, J=4, 1H), 7.12 (m, 9H), 8.14 (s, 1H) 67.5 MHz $^{13}$C NMR (CDCl$_3$): δ 27.4, 28.5, 28.8, 29.0, 29.4, 32.4, 34.7, 38.8, 46.9, 50.0, 78.7, 79.7, 126.5, 126.7, 128.4, 129.0, 129.7, 131.4, 135.8, 137.7, 138.4, 140.5, 141.1, 160.9, 163.9, 176.5.

MS(CI): 537, 539 (M+H)+

OR: [α]$_D$= +9.9° (c=1.0 in methanol)

TLC: R$_f$(silica gel, 1:9 methanol/methylene chloride)=0.50, ammonium molybdate/ceric sulfate and UV, homogeneous Analysis Calc'd for C$_{30}$H$_{33}$ClN$_2$O$_5$: C, 67.09; H, 6.19; N, 5.22, Cl, 6.60 Found: C, 67.33; H, 6.35; N, 5.13; Cl, 6.45

EXAMPLE 3

[1S-(1α,2α,3α,4α)-3-[3-[4-[[(4-Cyclohexylbutyl)amino]carbonyl]-2-oxazolyl]-7-oxabicyclo[2.2.1]hept-2-yl]methyl]benzeneacetic acid

A. (3-Bromophenethyl)oxythexyldimethylsilane

To a stirred solution of 3-bromophenylacetic acid (55.8 g, 260 mmol, Aldrich) under argon at 0° C. was added 1M diborane/tetrahydrofuran (THF) solution dropwise (300 mL, 300 mmol) over one hour. This mixture was stirred at 0° C. for 5.5 hours and then quenched slowly with water. The resulting mixture was concentrated in vacuo and the residue added to 300 mL of saturated NaHCO$_3$ solution and extracted with diethyl ether (4×40 mL). The combined ether extracts were dried (MgSO$_4$), and concentrated in vacuo to give 51.7 g of crude alcohol. To a stirred solution of this alcohol and triethylamine (75 mL, 538 mmol) in 500 mL of dry CH$_2$Cl$_2$ under argon at 0° C. was added thexyldimethylsilylchloride (56.2 mL, 286 mmol) over 15 minutes. The reaction mixture was stirred at 0° C. for 75 minutes and then at room temperature for 15 hours. This mixture was diluted with 500 mL of diethyl ether and the precipitate was filtered off. The solid was rinsed with diethyl ether (3×300 mL). The filtrate was concentrated in vacuo and partitioned between 300 mL of saturated NH$_4$Cl solution and diethyl ether (4×300 mL). The combined ether extracts were dried (MgSO$_4$) and concentrated in vacuo. This crude product was distilled to give 76.9 g (87%) of title compound, bp 148°-154° (~0.5 mm).

B.

[1S-(1α,2α,3α,4α)]-2-[3-[[3-(Hydroxymethyl)-7-oxabicyclo[2.2.1]hept-2-yl]hydroxymethyl]benzene]ethoxy]dimethyl(1,1,2-trimethylpropyl)silane To a solution of 10.0 g (29.1 mmol) of Part A compound in 60 mL of dry diethyl ether cooled to −78° was added dropwise 30 mL (1.7 m in pentane, 51 mmol, Aldrich) of t-butyllithium solution over ~15 minutes. The reaction mixture was stirred at −78° for 15 minutes then at 0° for 30 minutes. The resulting anion solution was re-cooled to −78°, 40 mL of dry tetrahydrofuran was introduced and then a solution of 1.87 g (12.0 mmol) of [3aR-(3aα,4β,7β,7aα)]octahydro-4,7-epoxyisobenzofuran-1-ol in 20 mL of tetrahydrofuran was added dropwise. After 15 minutes the reaction was warmed to 0°. After an additional 1 hour at 0°, the reaction was quenched with 5 mL of water, then added to 200 mL of water and extracted with two-75 mL portions of ethyl acetate. The organic extracts were combined, dried (magnesium sulfate) and concentrated in vacuo to give an oil. The crude oil was purified by flash chromatography (Merck silica, 23×5.0 cm, 1:4 ethyl acetate/petroleum ether then ethyl acetate) to afford 4.10 g (10.1 mmol, 85%) of title compound as a colorless oil.

C.

[1S-(1α,2α,3α,4α)]-2-[3-[[3-(Hydroxymethyl)-7-oxabicyclo[2.2.1]hept-2-yl]

methyl]benzene]ethoxy]dimethyl(1,1,2-trimethylpropyl)silane

A mixture of 4.05 g (10.0 mmol) of Part B compound and 5.50 g of 10% palladium on activated carbon (Aldrich) in 80 mL of glacial acetic acid was shaken under an atmosphere of hydrogen (40 psi) on a Parr apparatus for 24 hours. The resulting mixture was passed through a polycarbonate filter to remove the catalyst and the filtrate was concentrated in vacuo to give an oil. The crude oil was partitioned between 100 mL of ethyl acetate and 100 mL of water. The organic layer was separated, dried (magnesium sulfate) and concentrated in vacuo to afford 3.72 g (9.60 mmol, 96%) of crude title alcohol as a colorless oil.

D.
[1S-(1α,2α,3α,4α)]-3-[[3-[(Acetyloxy)methyl]-7-oxabicyclo[2.2.1]hept-2-yl]methyl]benzeneethanol

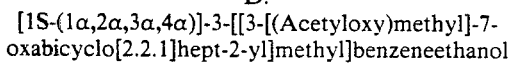

To a solution of 4.56 g (11.3 mmol) of Part C alcohol and 1.3 mL (16 mmol, Burdick and Jackson) of pyridine in 50 mL of dry methylene chloride (distilled from phosphorous pentoxide) cooled to 0° was added dropwise a solution of 1.0 mL (14 mmol, Mallinckrodt) of acetyl chloride in 3 mL of methylene chloride. The reaction mixture was stirred for 30 minutes then added to 50 mL of 1M aqueous HCl solution. The organic phase was separated, washed with 50 mL of 1M aqueous NaOH solution, dried (magnesium sulfate) and concentrated in vacuo to afford 5.05 g (11.4 mmol, quant) of crude acetate as a colorless oil. To a solution of the crude acetate in 30 mL of acetonitrile (Brudick and Jackson) cooled to 0° was added 1.5 mL of 48% aqueous hydrofluoric acid solution. The reaction was stirred for 1 hour then quenched by slow addition of 20 mL of saturated aqueous sodium bicarbonate solution. The resulting mixture was added to 100 mL of water and extracted with two-50 mL portions of ethyl acetate. The organic extracts were combined, dried (magnesium sulfate) and concentrated in vacuo to give an oil. The crude material was purified by flash chromatography (Merck silica, 20×5 cm, ethyl acetate) to afford 3.01 g (9.90 mmol, 88%) of title alcohol as a colorless oil.

E.
[1S-(1α,2α,3α,4α]-2-[[3-[2-[[(1,1-Dimethylethyl)diphenylsilyl]oxy]ethyl]phenyl]-methyl]-7-oxabicyclo[2.2.1]heptane-3-methanol

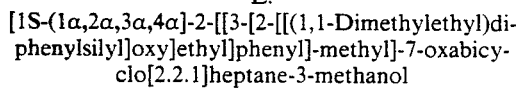

To a solution of 3.00 g (9.87 mmol) of Part D alcohol and 2.75 g (10.0 mmol, Petrarch) of t-butylchlorodiphenylsilane in 50 mL of dry methylene chloride (distilled from phosphorous pentoxide) was added at 0° 1.7 mL (12 mmol, distilled from calcium hydride) of triethylamine then 200 mg (1.6 mmol, Aldrich) of 4-dimethylaminopyridine. The reaction mixture was warmed to room temperature, stirred for 2 hours and the resulting slurry washed with 50 mL of 1M aqueous hydrochloric acid then 50 mL of water, dried (magnesium sulfate) and concentrated in vacuo to give the crude silyl ether as an oil. To a solution of the crude silyl ether in 50 mL of anhydrous diethyl ether (Mallinckrodt) cooled to −78° was added 20 mL (1.4M in diethyl ether, 28 mmol, Aldrich) of methyllithium solution dropwise over 15 minutes. After 5 minutes the reaction was quenched with 1 mL of methanol then warmed to room temperature and partitioned between 50 mL of diethyl ether and 100 mL of water. The organic layer was separated, washed with 50 mL of brine, dried (magnesium sulfate) and concentrated in vacuo to give an oil. The crude material was purified by flash chromatography (Merck silica, 20×5 cm, 1:1 ethyl acetate/petroleum ether) to afford 4.41 g (8.82 mmol, 89%) of title alcohol as a colorless glass.

F.
[1S-(1α,2α,3α,4α)]-2-[[3-[2-[[(1,1-Dimethylethyl)diphenylsilyl]oxy]ethyl]phenyl]methyl]-7-oxabicyclo[2.2.1]heptane-3-carboxylic acid

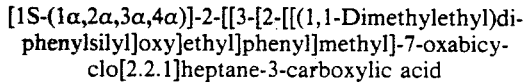

To a solution of 1.75 g (3.50 mmol) of Part E alcohol in 25 mL of reagent acetone cooled to 0° was added 3.5 mL of Jones reagent (2.6M, Fieser and Fieser, "Reagents for Organic Synthesis," vol. 1, p. 142) dropwise over 5 minutes. The reaction was stirred at 0° for 1.5 hours then quenched by addition of ~1 mL of isopropyl alcohol. The mixture was stirred for 30 minutes then the resulting green slurry was filtered through a pad of Celite. The filtrate was partitioned between 100 mL of water and 75 mL of ethyl acetate. The organic layer was separated, washed with 100 mL of water, 50 mL of brine, dried (magnesium sulfate) and concentrated in vacuo to give 1.82 g (3.54 mmol, 101%) of crude acid as a solid white foam.

G.
[1S-(1α,2α,3α,4α)]-2-[[[2-[[3-[2-[[(1,1-Dimethylethyl)diphenylsilyl]oxy]ethyl]phenyl]methyl]-7-oxabicyclo[2.2.1]hept-3-yl]carbonyl]amino]-3-hydroxypropanoic acid, methyl ester

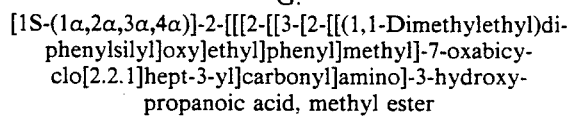

To a solution of 1.86 g (3.72 mmol) of Part F acid, 577 mg (3.72 mmol, Aldrich) of L-serine methyl ester hydrochloride and 502 mg (3.72 mmol, Aldrich) of 1-hydroxybenzotriazole hydrate in 20 mL of dry THF (distilled from potassium/benzophenone) cooled to 0° was added 1.1 mL (7.8 mmol, distilled from calcium hydride) of triethylamine, then after 5 minutes, 766 mg (3.72 mmol, Aldrich) of 1,3-dicyclohexylcarbodiimide. The reaction mixture was allowed to warm to room temperature, stirred for 16 hours and the resulting slurry filtered. The filtrate was concentrated in vacuo to give an oil.

The crude material was purified by flash chromatography (Merck silica, 15×5 cm, ethyl acetate) to afford 1.75 g (2.84 mmol, 76%) of title amide as a white foam.

H.
[1S-(1α,2α,3α,4α)]-2-[2-[[3-[2-[[(1,1-Dimethylethyl)diphenylsilyl]oxy]ethyl]phenyl]methyl]-7-oxabicyclo[2.2.1]hept-3-yl]-4,5-dihydro-4-oxazolecarboxylic acid, methyl ester

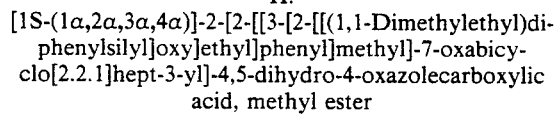

To a solution of 1.65 g (2.76 mmol) of Part G amide and 2.89 g (11.0 mmol, Aldrich) of triphenylphosphine in 40 mL of sieve-dried acetonitrile (Burdick and Jackson) was added 0.70 mL (7.2 mmol) of carbon tetrachloride then 1.1 mL (7.8 mmol, distilled from calcium hydride) of triethylamine. The solution was heated to 65° for 30 minutes then cooled to room temperature and the resulting dark solution was partitioned between 120 mL of saturated aqueous sodium bicarbonate solution and 50 mL of ethyl acetate. The organic layer was separated and the aqueous layer was extracted with an additional 50 mL of ethyl acetate. The organic extracts were combined, dried (sodium sulfate) and concentrated in vacuo to give a dark oil. The crude material was purified by flash chromatography (Merck silica, 20×5 cm, 1:2 acetone/hexane) to afford 515 mg (0.86 mmol, 31%) of title oxazoline as a yellow oil.

I.
[1S-(1α,2α,3α,4α)]-2-[2-[[3-[2-[[(1,1-Dimethylethyl)diphenylsilyl]oxy]ethyl]phenyl]methyl]-7-oxabicyclo[2.2.1]hept-3-yl]-4-oxazolecarboxylic acid, methyl ester

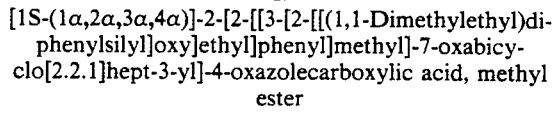

To a solution of 505 mg (0.85 mmol) of Part H oxazoline in 20 mL of dry methylene chloride (distilled from phosphorous pentoxide) was added at room temperature in one portion 1.0 g of Example 2, Part H, nickel peroxide. The reaction mixture was stirred for 1 hour then an additional 1.0 g portion of nickel peroxide was added. The reaction was again stirred for 1 hour then added was 40 mL of ethyl acetate followed by 25 mL of 3M aqueous sodium bisulfite solution. The mixture was stirred rapidly for 20 minutes then to the resulting blue-green emulsion was added 50 mL of 1M aqueous sodium citrate solution. The mixture was stirred for an additional 20 minutes then the organic layer was separated and the aqueous layer was extracted with 25 mL of ethyl acetate. The organic extracts were combined, dried (magnesium sulfate) and concentrated in vacuo to give an oil. The crude oil was purified by flash chromatography (Merck silica, 15×3 cm, 1:1 ethyl acetate/petroleum ether) to yield 247 mg 0.42 mmol, 49%) of title oxazole as a colorless oil.

J.
[1S-(1α,2α,3α,4α)]-N-(4-Cyclohexylbutyl)-2-[2-[[3-[2-[[(1,1-dimethylethyl)diphenylsilyl]oxy]ethyl]phenyl]-methyl]-7-oxabicyclo[2.2.1]hept-3-yl]-4-oxazolecarboxamide A solution of 240 mg (0.40 mmol) of Part I oxazole and 34 mg (0.81 mmol, Aldrich) of lithium hydroxide monohydrate in 5 mL of 4:1 THF/water was stirred rapidly at room temperature for 1.5 hours. The reaction mixture was acidified with 2 mL of 1M aqueous HCl solution then added to 20 mL of water and extracted with two-20 mL portions of ethyl acetate. The organic extracts were combined, dried (magnesium sulfate) and concentrated in vacuo to afford the crude acid as an oil. The acid was solubilized in toluene and concentrated in vacuo to remove residual water. To the resulting oil was added 5 mL of sieve-dried toluene (Burdick and Jackson), a small drop of DMF then dropwise at room temperature 50 µL (0.52 mmol, Aldrich) of oxalyl chloride. The reaction mixture was stirred for 1 hour then concentrated in vacuo to give the crude acid chloride as an oil. To a solution of the crude acid chloride in 5 mL of dry THF (distilled from potassium/benzophenone) cooled to 0° was added 95 mg (0.50 mmol) of cyclohexylbutylamine hydrochloride then 170 µL (1.2 mmol, distilled from calcium hydride) of triethylamine. The reaction was stirred for 1 hour then added to 20 mL of 1M aqueous HCl solution and extracted with two-20 mL portions of ethyl acetate. The organic extracts were combined, dried (magnesium sulfate) and concentrated in vacuo to give an oil. The oil was purified by flash chromatography (Merck silica, 20×3 cm, 2:3 ethyl acetate/petroleum ether) to afford 238 mg (0.33 mmol, 83%) of title oxazole as a colorless oil.

K.
[1S-(1α,2α,3α,4α)]-3-[[3-[4-[[(4-Cyclohexylbutyl)amino]carbonyl]-2-oxazolyl]-7-oxabicyclo[2.2.1]hept-2-yl]methyl]benzeneacetic acid To a solution of 235 mg (0.33 mmol) of Part J oxazole in 7.5 mL of 2:1 acetonitrile/methylene chloride was added at room temperature 0.35 mL of 48% aqueous hydrofluoric acid. The reaction mixture was stirred for 2 hours then added to 20 mL of saturated aqueous sodium bicarbonate solution and extracted with 20 mL of ethyl acetate and 20 mL of methylene chloride. The organic extracts were combined, dried (magnesium sulfate) and concentrated in vacuo to give an oil. The oil was purified by flash chromatography (Merck silica, 15×3 cm, ethyl acetate) to afford 147 mg (0.31 mmol, 94%) of the alcohol as a white solid.

To a solution of 135 mg (0.28 mmol) of the alcohol from above in 5 mL of reagent acetone at room temperature was added 0.35 mL (2.6M in $Cr^{+6}$, Fieser & Fieser, Vol. 1, p. 142) of Jones reagent. The reaction mixture was stirred for 45 minutes then quenched with several drops of isopropyl alcohol. After 15 minutes 20 mL of ethyl acetate was added followed by 20 mL of 3M aqueous sodium bisulfite solution. The mixture was stirred rapidly for 15 minutes then the organic layer was separated and the aqueous layer extracted with 20 mL of methylene chloride. The organic extracts were combined, dried (magnesium sulfate) and concentrated in vacuo to a volume of ~10 mL. The resulting solution was cooled to 0° and treated with excess ethereal diazomethane (until a yellow color persisted). The excess diazomethane was quenched with glacial acetic acid and the solution concentrated in vacuo to give an oil. The oil was purified by flash chromatography (Merck silica, 15×1.5 cm, 3:2 ethyl acetate/petroleum ether) to yield 63 mg (0.12 mmol, 43%) of methyl ester of the title acid as a white foam.

A solution of 60 mg (0.12 mmol) of methyl ester and 20 mg (0.48 mmol, Aldrich) of lithium hydroxide monohydrate in 2.5 ml of 4:1 THF/water was stirred at room temperature for 3 hours. The reaction was acidified by addition of 1 ml of 1M aqueous HCl solution then partitioned between 20 ml of ethyl acetate and 20 ml of water. The organic layer was separated, dried (magnesium sulfate) and concentrated in vacuo to give 58 mg (0.12 mmol, 100% from methyl ester) of title acid as a solid white foam.

IR (KBr): 3409 (broad), 2923, 1712, 1649, 1604, 1513 $cm^{-1}$

Partial 270 MHz $^1$H NMR (CDCl$_3$): δ2.20 (m, 1H), 2.40 (t, J=10, 1H), 2.62 (m, 1H), 3.32 (d, J=9, 1H), 3.36 (m, 2H), 3.56 (s, 2H), 4.39 (d, J=4, 1H), 4.90 (d, J=4, 1H), 6.90-7.30 (m, 4H), 8.04 (s, 1H)

67.5 MHz $^{13}$C NMR (CDCl$_3$): δ 24.2, 26.3, 26.7, 29.0, 29.7, 29.8, 33.3, 35.9, 37.0, 37.5, 39.2, 41.0, 46.6, 50.6, 79.2, 79.9, 127.2, 127.3, 128.6, 129.7, 133.9, 135.7, 140.0, 140.8, 161.0, 163.9, 175.0.

MS(CI): 495 (M+H)$^+$

TLC: $R_f$ (silica gel, 1:9 methanol/methylene chloride)=0.38, ammonium molybdate/ceric sulfate and UV Analysis for $C_{29}H_{38}N_2O_5$: C, 70.42; H, 7.74; N, 5.67
Found: C, 70.54; H, 7.78; N, 5.57

EXAMPLE 4
[1S-(1α,2α,3α,4α)]-2-[[3[4-[[(4-Cyclohexylbutyl)amino]carbonyl]-2-thiazolyl]-7-oxabicyclo2.2.1]hept-2-yl]methyl]benzenepropanoic acid

A.
[1S-(1α,2α,3α,4α)]-2-[[3-(Aminocarbonyl)-7-oxabicyclo[2.2.1]hept-2-yl]methyl]benzenepropanoic acid, methyl ester To a solution of Example 2 Part E intermediate acid (9.13 mmol) in dry benzene (100 mL) is added, dropwise over a 10 minute period, oxalyl chloride (0.96 mL, 11 mmol). After stirring for 5 hours, the reaction is concentrated in vacuo, dissolved in dry THF (10 mL) and added dropwise over a 5 minute period to a 0° C. solution of concentrated ammonium hydroxide (3 mL) in THF (100 mL). The reaction is then concentrated in vacuo. The residual solid is partitioned between ethyl acetate (150 mL) and 0.25 M K$_2$CO$_3$ (25 mL). The aqueous layer is extracted with ethyl acetate (25 mL). The combined organic layers are dried (Na$_2$SO$_4$) and concentrated in vacuo. The residue is suspended in boiling diethyl ether (100 mL). Ethyl acetate (ca. 10 mL) is added to effect solution. The mixture is concentrated to ca. 50 mL on a steam bath, cooled to room temperature, seeded and chilled overnight. Title amide is obtained by filtration.

B.
[1S-(1α,2α,3α,4α)]-2-[[3-(Aminothiocarbonyl)-7-oxabicyclo[2.2.1]hept-2-yl]methyl]benzenepropanoic acid, methyl ester To a 60° C. solution of Part A amide (0.999 mmol) in dry toluene (10 mL) is added Lawesson's Reagent (222 mg, 0.55 mmol). The reaction is stirred at 60° C. for 30 minutes, diluted with diethyl ether (50 mL), and washed with half-saturated NaHCO$_3$ (2×5 mL). The organic layer is dried (Na$_2$SO$_4$) and concentrated in vacuo. The residue is passed through a short silica plug using 50% ethyl acetate/hexanes to yield the title thioamide.

C.
[1S-(1α,2α,3α,4α)]-2-[[3-(4-Carboxy-2-thiazolyl)-7-oxabicyclo[2.2.1]hept-2-yl]methyl]benzenepropanoic acid, methyl ester To a solution of Part B thioamide (1.41 mmol) and powdered anhydrous K$_2$CO$_3$ (390 mg, 2.82 mmol) in dry DMF (10 mL) is added, in several portions, bromopyruvic acid (contains 0.4 mol water/mol bromoacid, 295 mg, 1.69 mmol). The reaction is allowed to stir at room temperature for 30 minutes. After this time, an additional 29.5 mg portion of bromopyruvic acid is added. After an additional 1 hour, the solvent is removed in vacuo below 30° C. The residue is suspended/dissolved in methylene chloride (10 mL). Triethylamine (0.59 mL, 4.2 mmol) is added followed by the dropwise addition of methanesulfonyl chloride (0.33 mL, 4.2 mmol). After stirring for 5 minutes, the reaction is diluted with diethyl ether (40 mL). The organic layer is extracted with 0.5M K$_2$CO$_3$ (9×10 mL). The combined aqueous layers are brought to pH 1.5 with 6 N HCl and extracted with diethyl ether (6×25 mL). These combined organic layers are dried (Na$_2$SO$_4$) and concentrated in vacuo.

D.
[1S-(1α,2α,3α,4α)]-2-[[3-[4-[[(4-Cyclohexylbutyl)amino]carbonyl]-2-thiazolyl]-7-oxabicyclo[2.2.1]hept-2-yl]methyl]benzenepropanoic acid, methyl ester To a solution of Part C acid (0.120 mmol) in dry DMF 1 mL) is added 1,1'-carbonyldiimidazole (20.3 mg, 0.125 mmol). The reaction is allowed to stir for 1 hour. A solution of (cyclohexylbutyl)amine hydrochloride (23.4 mg, 0.131 mmol) and triethylamine (0.020 mL, 0.14 mmol) in dry DMF (0.5 mL) is then added. The reaction is stirred for 1 hour, and concentrated to remove DMF. The residue is taken up in diethyl ether (20 mL) and 0.5 N HCl (5 mL). The organic layer is dried (Na$_2$SO$_4$) and concentrated in vacuo. The resultant material is chromatographed (silica, ethyl acetate/hexanes) to yield title ester.

E.
[1S-(1α,2α,3α,4α)]-2-[[3-[4-[[(4-Cyclohexylbutyl)amino]carbonyl]-2-thiazolyl]-7-oxabicyclo[2.2.1]hept-2-yl]methyl]benzenepropanoic acid To a solution of Part D amide in methanol (1 mL) is added 2 N KOH (0.3 mL). The reaction is stirred for 2 hours. An additional 0.3 mL portion of KOH is added. After an additional 1 hour, the reaction is concentrated to remove methanol. The residue is dissolved in water (1 mL) and 1 N HCl is added to bring the pH to 2. The mixture is extracted with methylene chloride (3×5 mL). the combined organic layers are dried (Na$_2$SO$_4$) and concentrated in vacuo to yield title compound.

EXAMPLE 5
[1S-(1α,2α,3α,4α)]-2-[[3-[4-[[(4-Cyclohexylbutyl)amino]carbonyl]-1H-imidazol-2-yl]-7-oxabicyclo[2.2.1]hept-2-yl]methyl]benzenepropanoic acid

A.
[1S-(1α,2α,3α,4α)]-2-[[3-Cyano-7-oxabicyclo[2.2.1]hept-2-yl]methyl]benzenepropanoic acid, methyl ester Vilsmeier reagent is prepared by the addition of oxalyl chloride (1 mmol) to a 0° C. acetonitrile solution of DMF (1 mmol). To the reagent is added Example 4, Part A amide (1 mmol). After 45 minutes, pyridine (2 mmol) is added. The reaction is then partitioned between diethyl ether and 1N HCl. The title nitrile is isolated by drying and concentrating the organic phase.

B.
[1S-(1α,2α,3α,4α)]-2-[[3-(Iminomethoxymethyl)-7-oxabicyclo-[2.2.1]hept-2-yl]methyl]benzenepropanoic acid, methyl ester HCl salt Gaseous HCl is bubbled into a 0° C. solution of part A nitrile (1 mmol) and methanol (2 mmol) in diethyl ether (10 mL) for 5 minutes. The mixture is allowed to stand at 0° C. for 7 days and is then concentrated to yield the title compound.

C.
[1S-(1α,2α,3α,4α]-2-[[3-[Methoxy[[2-oxo-2-[2-(trimethylsilyl)ethoxy]ethyl]imino]methyl]-7-oxabicyclo-[2.2.1]hept-2-yl]methyl]benzenepropanoic acid, methyl ester Part B iminoether (1 mmol) is suspended in 10 mL of THF and stirred with glycine, 2-(trimethylsilyl)ethyl ester HCl salt (2 mmol) and triethylamine (2 mmol). After 1 hour, the organic layer is diluted with diethyl ether, washed with NaHCO$_3$ solution, dried and concentrated to yield title ester which is used for the subsequent step.

D.
[1S-(1α,2α,3α,4α)]-2-[[3-[[[1-(Hydroxymethylene)-2-oxo-2-[2-(trimethylsilyl)ethoxy]ethyl]imino]methoxymethyl]-7-oxabicyclo[2.2.1]hept-2-yl]methyl]benzenepropanoic acid, methyl ester, monopotassium salt To a 0° C. solution of potassium methoxide (2 mmol) is added dropwise, a solution of ethyl formate (4 mmol) and Part C ester (1 mmol). After hours, the potassium salt is collected by filtration and used immediately for the next step.

E.
[1S-(1α,2α,3α,4α)]-2-[[3-[4-[[2-(Trimethylsilyl)ethoxy]carbonyl]-1H-imidazol-2-yl]-7-oxabicyclo[2.2.1]hept-2-yl]methyl]benzenepropanoic acid, methyl ester The Part D ester is dissolved in concentrated ammonia. After 3 hours, the solution is bubbled with N$_2$ to purge excess NH$_3$ and the residue neutralized with 1N HCl. The mixture is extracted with CH$_2$Cl$_2$. The organic layers are concentrated in vacuo after drying to yield title imidazole.

F.
[1S-(1α,2α,3α,4α)]-2-[[3-(4-Carboxy-1H-imidazol-2-yl)-7-oxabicyclo[2.2.1]hept-2-yl]methyl]benzenepropanoic acid, methyl ester To a solution of Part E imidazole (1 mmol) in THF (10 mL) is added 1.1 mL of 1M tetra-n-butylammonium fluoride (in THF). After stirring for 1 hour, the reaction is concentrated, diluted with water, brought to pH 7 with 1N HCl, and extracted with methylene chloride. The organic layer is concentrated after drying to yield title acid.

G.
[1S-(1α,2α,3α,4α)]-2-[3-[[(4-Cyclohexylbutyl)amino]-carbonyl]-1H-imidazol-2-yl]-7-oxabicyclo[2.2.1]hept-2-yl]-methyl]benzenepropanoic acid, methyl ester To a stirred mixture of 1.0 mmol of Part F acid, 1.0 mmol of 4-cyclohexylbutylamine hydrochloride, 1.0 mmol of 1-hydroxybenzotriazole in 10 mL of dry dimethylformamide under argon at 0° C. is added triethylamine (1.5 mmol). The mixture is stirred at 0° C. for 10 minutes at which time 1-(3-dimethylaminopropyl)-3-ethylcarbodiimide hydrochloride (1 mmol) is added. The reaction mixture is stirred at 23° C. for 24 hours and concentrated in vacuo. The residue is dissolved in ethyl acetate and washed with saturated NaHCO$_3$, dried (MgSO$_4$), filtered and concentrated in vacuo to provide title amide.

H.
[1S-(1α,2α,3α,4α)]-2-[[3-[4-[[(4-Cyclohexylbutyl)amino]carbonyl]-1H-imidazol-2-yl]-7-oxabicyclo[2.2.1]hept-2-yl]methyl]benzenepropanoic acid To a solution of Part G amide (1 mmol) in 10 mL of methanol is added 2 mL of 2N KOH. After stirring for 4 hours, the reaction is concentrated to remove methanol. The residue is diluted with water and brought to pH 2 with 1N HCl. The mixture is concentrated and the solid is extracted into methanol. The methanol is concentrated and the residue is extracted into 5:1 chloroform/methanol. The organics are concentrated to yield crude title acid which can be purified by chromatography on silica using ethyl acetate/pyridine/acetic acid/water.

EXAMPLE 6
[1S-(1α,2α,3α,4α)]-2-[3-[4-[[(4-Cyclohexylbutyl)amino]carbonyl]-2-oxazolyl]-7-oxabicyclo[2.2.1]hept-2-yl]methyl]-N-(phenylsulfonyl)benzene propanamide To a stirred mixture of 1-(3-dimethylaminopropyl)-3-ethylcarbodiimide hydrochloride (1.0 mmol) and 4-dimethylaminopyridine (1.0 mmol) in 8 mL of dimethylformamide is added 1.0 mmol of benzenesulfonamide and 2.0 mmol of triethylamine followed by 1.0 mmol of Example 1 title acid. This mixture is stirred at room temperature for 48 hours and concentrated in vacuo. The residue is partitioned between water and ethyl acetate. The aqueous layer is acidified and extracted with ethyl acetate. Combined ethyl acetate layers are concentrated in vacuo to afford title sulfonamide.

EXAMPLE 7
[1S-(1α,2α,3α,4α)]-3-[[3-[4-[[[4-(4-Chlorophenyl)butyl]amino]carbonyl]-2-oxazolyl]-7-oxabicyclo2.2.1]hept-2-yl]methyl]benzoic acid A. 3-Bromobenzenemethanol To a solution of 50.0 g (0.25 mols, Aldrich) of 3-bromobenzoic acid in 100 ml of dry tetrahydrofuran (THF) cooled to 0° is added slowly 100 ml (1.0M in THF, 100 mmols, Aldrich) of borane-tetrahydrofuran complex. The reaction is stirred at 0° for 1 hour then at room temperature for 18 hours. The reaction is quenched by dropwise addition of water then concentrated in vacuo to remove solvent. The residue is partitioned between diethyl ether and 1M aqueous HCl. The organic layer is separated, washed with 1M aqueous sodium hydroxide, brine, dried (magnesium sulfate) and concentrated in vacuo to afford title compound.

B.
3-Bromo-1-[[[dimethyl(1,1,2-trimethylpropyl)silyl]oxy]methyl]benzene

To a solution of 25.2 g (135 mmol) of crude Part A alcohol and 24.1 g (135 mmol, Petrarch) of thexyldimethylchlorosilane in 200 ml of dry methylene chloride (distilled from phosphorous pentoxide) is added at room temperature 20 ml (143 mmol, distilled from calcium hydride) of triethylamine then 200 mg (1.64 mmol, Aldrich) of 4-dimethylaminopyridine. The reaction mixture is stirred at room temperature for 18 hours. The resulting slurry is diluted with 100 ml of hexane, cooled to 0° with stirring for 15 minutes then filtered to remove solid triethylamine hydrochloride. The filtrate is concentrated in vacuo to give an oil. The crude oil is purified by flash chromatography (Merck silica) to afford title compound.

C.
[1S-(1α,2α,3α,4α)]-[3-[[[Dimethylsilyl(1,1,2-trimethylpropyl)]oxy]methyl]phenyl]7-oxabicyclo[2.2.1]heptane-2,3-dimethanol To a solution of 4.61 g (14.0 mmol) of Part B compound in 30 ml of dry diethyl ether (distilled from ketyl) cooled to −100° is added dropwise 15 ml (1.7M in pentane, 25 mmol, Aldrich) of t-butyllithium solution over 15 minutes. The reaction mixture is stirred at −100° for 15 minutes then at 0° for 15 minutes. The resulting anion solution is re-cooled to −78° then 30 ml of dry THF (distilled from ketyl) is introduced followed by the rapid addition of a solution of 875 mg (5.61 mmol) of [3aR-(3aα,4β,7β,7aα)]-octahydro-4,7-epoxyisobenzofuran-1-ol in 10 ml of THF. The reaction mixture is warmed to 0°, stirred for 1 hour, quenched with 5 ml of water then partitioned between 100 ml of water and 25 ml of ethyl acetate. The organic layer is separated and the aqueous layer is extracted with an additional 25 ml of ethyl acetate. The organic extracts are combined, dried (magnesium sulfate) and concentrated in vacuo to give an oil. The crude oil is purified by flash chromatography (Merck silica) to afford title diastereomeric alcohols.

D.
[1S-(1α,2α,3α,4α)]-3-[[[Dimethylsilyl(1,1,2-trimethylpropyl)]oxy]methyl]-phenyl]-7-oxabicyclo[2.2.1]heptane-2,3-dimethanol, diacetate A solution of 2.20 g (5.41 mmol) of Part C diol and 50 mg (0.41 mmol, Aldrich) of 4-dimethylaminopyridine in 10 ml of 1:1 acetic anhydride/pyridine is stirred at room temperature for 6 hours. The reaction mixture is concentrated in vacuo and the residue partitioned between 25 ml of ethyl acetate and 25 ml of 1M aqueous HCl. The organic layer is separated, washed with 25 ml of 1M aqueous sodium hydroxide, dried (magnesium sulfate) and concentrated in vacuo to give title compound.

E.
[1S-(1α,2α,3α,4α]-3-[Hydroxy[3-(hydroxymethyl)-7-oxabicyclo[2.2.1]hept-2-yl]methyl]benzoic acid, methyl ester To a solution of 1.10 g (2.24 mmol) of Part D diacetate in 15 ml of reagent acetone cooled to 0° is added rapidly 3.3 ml (2.6M in $Cr^{+6}$, for preparation see Fieser and Fieser, "Reagents for Organic Synthesis", vol. 1, p. 142) of Jones reagent. The reaction mixture is stirred for 2 hours, quenched by addition of 1 ml of isopropanol and stirred for an additional 30 minutes. The resulting green slurry is filtered through a pad of Celite. The filtrate is concentrated in vacuo and the residue partitioned between 25 ml of diethyl ether and 25 ml of water. The organic layer is separated and concentrated in vacuo to give the crude diacetate-acid as an oil.

A solution of the crude diacetate-acid in 15 ml of 2:1 1M aqueous NaOH/THF is stirred at room temperature for 90 minutes. The reaction mixture is cooled in an ice-bath, quenched by addition of 15 ml of 1M aqueous HCl solution then extracted with two-25 ml portions of diethyl ether. The ether extracts are combined, washed with 25 ml of brine and concentrated in vacuo to give the crude diol-acid.

A solution of the crude diol-acid in 10 ml of diethyl ether is treated with ethereal diazomethane at 0° then concentrated in vacuo. The resulting oil is purified by flash chromatography (Merck silica) to afford title compound.

F.
[1S-(1α,2α,3α,4α)]-3-[[3-(Hydroxymethyl)-7-oxabicyclo[2.2.1]hept-2-yl]methyl]benzoic acid, methyl ester A mixture of 450 mg (1.54 mmol) of Part E diol and 450 mg of 10% palladium on carbon catalyst (Aldrich) in 10 ml of glacial acetic acid is shaken under an atmosphere of hydrogen (50 psi) for 24 hours. The reaction is filtered and the filtrate concentrated in vacuo to give an oil. The crude material is purified by flash chromatography (Merck silica) to give title product.

G.
[1S-(1α,2α,3α,4α)]-3-[[3-Carboxy-7-oxabicyclo[2.2.1]hept-2-yl]methyl]benzoic acid, methyl ester To a solution of 450 mg (1.63 mmol) of Part F alcohol in 5 ml of reagent acetone cooled to 0° is added rapidly 2.0 ml (2.6M in $Cr^{+6}$) of Jones reagent. The reaction mixture is warmed to room temperature, stirred for 2 hours then quenched by addition of ~1 ml of isopropanol. After 15 minutes the resulting green slurry is filtered through a pad of Celite. The filtrate is partitioned between 20 ml of diethyl ether and 20 ml of water. The organic layer is separated and the aqueous layer is extracted with an additional 20 ml of diethyl ether. The ether extracts are combined, dried (magnesium sulfate) and concentrated in vacuo to give the crude title acid.

H.
[1S-(1α,2α,3α,4α)]-3-[[3-[[[1-(Hydroxymethyl)-2-oxo-2-(phenylmethoxy)ethyl]amino]carbonyl]-7-oxabicyclo[2.2.1]hept-2-yl]methyl]benzoic acid, methyl ester To a solution of 447 mg (1.54 mmol) of Part G acid in 10 ml of dry THF (distilled from ketyl) cooled to 0° is added 392 mg (1.69 mmol, Sigma) of L-serine benzyl ester hydrochloride, 228 mg (1.69 mmol, Aldrich) of 1-hydroxybenzotriazole hydrate and 530 µl (3.8 mmol, distilled from calcium hydride) of triethylamine. The mixture is stirred for 5 minutes then 348 mg (1.69 mmol, Aldrich) of dicyclohexylcarbodiimide is added in one portion. The reaction is stirred at 0° for 3 hours then warmed to room temperature for 16 hours. The resulting slurry is diluted with 10 ml of ethyl acetate, cooled to 0° for 15 minutes then filtered. The filtrate is concentrated in vacuo to give an oil. The crude material is purified by flash chromatography (Merck silica) to afford title ester.

I.
[1S-(1α,2α,3α,4α)]-3-[[3-[4,5-Dihydro-4-[(phenylmethoxy)carbonyl]-2-oxazolyl]-7-oxabicyclo[2.2.1]hept-2-yl]methyl]benzoic acid, methyl ester To a solution of 495 mg (1.06 mmol) of Part H ester, 843 mg (3.10 mmol, Aldrich) of triphenylphosphine and 540 µL (3.1 mmol, Aldrich) of diisopropylethylamine in 6 ml of 5:1 dry acetonitrile/methylene chloride is added at room temperature 300 µL (3.1 mmol, Mallinckrodt) of reagent carbon tetrachloride. The reaction mixture is stirred for 2 hours then diluted with 15 ml of ethyl acetate followed by the slow addition of 15 ml of saturated aqueous sodium bicarbonate solution. The resulting mixture is stirred for 5 minutes then partitioned between 20 ml of ethyl acetate and 20 ml of water. The organic layer is separated, washed with 20 ml of brine, dried (sodium sulfate) and concentrated in vacuo. The crude material is purified by flash chromatography (Merck silica) to afford title oxazoline.

J.
[1S-(1α,2α,3α,4α)]-3-[[3-[4-[(Phenylmethoxy)carbonyl]-2-oxazolyl]-7-oxabicyclo[2.2.1]hept-2-yl]methyl]benzoic acid, methyl ester To a solution of 355 mg (0.79 mmol) of Part I oxazoline in 10 ml of dry methylene chloride (distilled from phosphorous pentoxide) is added 750 mg of nickel peroxide oxidant (prepared as described in Example 2 Part H) at room temperature. The reaction mixture is stirred for 1 hour then an additional 750 mg of oxidant is added. After 30 minutes the reaction mixture is diluted with 20 ml of ethyl acetate followed by the addition of 10 ml of 3M aqueous sodium bisulfite solution. The resulting mixture is stirred rapidly for 20 minutes then 10 ml of water is added. The organic layer is separated and the aqueous layer extracted with an additional 20 ml of ethyl acetate. The organic extracts are combined, washed with 25 ml of 1M aqueous sodium citrate solution, dried (magnesium sulfate) and concentrated in vacuo to give an oil. The crude material is purified by flash chromatography (Merck silica) to afford title oxazole.

K.
[1S-(1α,2α,3α,4α)]-3-[[3-[4-[[[4-(4-Chlorophenyl)butyl]amino]carbonyl]-2-oxazolyl]-7-oxabicyclo[2.2.1]hept-2-yl]methyl]benzoic acid, methyl ester A mixture of 165 mg (0.37 mmol) of Part J oxazole and 30 mg of 20% palladium hydroxide on carbon catalyst (moist, <50% water, Aldrich) in 5 ml of reagent ethyl acetate is stirred under an atmosphere of hydrogen (balloon) for 1 hour. The catalyst is removed by filtration through a 4 μM polycarbonate membrane. The filtrate is concentrated in vacuo to afford crude acid.

To a solution of 125 mg (0.35 mmol) of the crude acid in 3 ml of dry methylene chloride (distilled from phosphorous pentoxide) is added at room temperature a small drop of dimethylformamide (DMF) then 40 μl (0.46 mmol, Aldrich) of oxalyl chloride. The reaction mixture is stirred for 30 minutes then concentrated in vacuo to give the crude acid chloride. The acid chloride is solubilized in 3 ml of dry methylene chloride then cooled to 0° and a solution of 84 mg (0.46 mmol) of 4-chlorophenylbutylamine and 70 μl (0.50 mmol, distilled from calcium hydride) of triethylamine in 1 ml of dry methylene chloride is added rapidly. The reaction mixture is stirred for 30 minutes then partitioned between 25 ml of ethyl acetate and 15 ml of 1M aqueous HCl solution. The organic layer is separated and the aqueous layer is extracted with an additional 10 ml of ethyl acetate. The organic extracts are combined, dried (magnesium sulfate) and concentrated in vacuo. The crude material is purified by flash chromatography (Merck silica) to afford title ester.

L.
[1S-(1α,2α,3α,4α)]-3-[[3-[4-[[[4-(4-Chlorophenyl)butyl]amino]carbonyl]-2-oxazolyl]-7-oxabicyclo[2.2.1]hept-2-yl]methyl]benzoic acid A solution of 151 mg (0.29 mmol) of Part K ester and 25 mg (0.60 mmol, Aldrich) of lithium hydroxide monohydrate in 6 ml of 2:1 THF/water is stirred rapidly at room temperature for 1.5 hours. The reaction is acidified by addition of 2 ml of 1M aqueous HCl solution then partitioned between 20 ml of ethyl acetate and 20 ml of water. The organic layer is separated, washed with 20 ml of brine, dried (magnesium sulfate) and concentrated in vacuo to afford title product.

EXAMPLE 8
[1S-(1α,2α,3α,4α)]-5-[[3-[[3-[4-[[(4-Cyclohexylbutyl)amino]carbonyl]-2-oxazolyl]-7-oxabicyclo[2.2.1]hept-2-yl]methyl]phenyl]methyl]-1H-tetrazole

A.
[1S-(1α,2α,3α,4α)]-3-[[3-[4-Cyclohexylbutyl)amino]-carbonyl]-2-oxazolyl]-7-oxabicyclo[2.2.1]hept-2-yl]methyl]benzeneacetonitrile To a solution of 1 mmol of Example 7, Part K ester in 10 mL of tetrahydrofuran is added 2 mmol of lithium borohydride. The reaction mixture is stirred for 1 hour at 23° C. and then is quenched by the addition of 1M HCl solution. The aqueous layer is extracted with ethyl acetate. The organic layers are dried, filtered and concentrated in vacuo to afford the crude alcohol. This alcohol is converted to the title nitrile using the procedures of Example 2 Part I(b) and I(c).

B.
[1S-(1α,2α,3α,4α)]-5-[[3-[[3-[4-[[(4-Cyclohexylbutyl)amino]carbonyl]-2-oxazolyl]-7-oxabicyclo[2.2.1]hept-2-yl]methyl]phenyl]-methyl]-1H-tetrazole A mixture of 300 mg (0.61 mmol) of Part A nitrile, 65 mg (1.0 mmol) of sodium azide, 53 mg (1.0 mmol) of ammonium chloride and 42 mg (1.0 mmol) of lithium chloride in 5 ml of dry dimethylformamide is heated to 125° for 24 hours. The reaction is cooled and filtered. The filtrate is concentrated in vacuo and the residue partitioned between water and ethyl acetate. The aqueous layer is adjusted to pH=2 with 1M aqueous HCl. The organic layer is separated, dried (MgSO$_4$) and concentrated in vacuo to give an oil. The crude material is purified by flash chromatography (Merck silica) to give title compound.

EXAMPLE 9
[1S-(1α,2α,3α,4α)]-[2-[[3-[4-[[(4-Cyclohexylbutyl)amino]carbonyl-2-oxazolyl]-7-oxabicyclo[2.2.1]hept-2-yl]methyl]phenoxy]acetic acid

A. 1-Bromo-2-(methoxymethoxy)benzene

The oil was removed from 4.5 g (60% in oil, 112 mmol, Aldrich) of sodium hydride dispersion by three-20 mL washes with hexane then the residue was covered with 75 mL of dimethylformamide (Burdick and Jackson). The resulting mixture was heated to about 50° and 18.1 g (105 mmol, Aldrich) of 2-bromophenol was added dropwise over 15 minutes. Vigorous gas evolution was observed. The reaction was stirred for an additional 30 minutes then the resulting gray-brown solution was cooled to 0° and 9.6 mL (117 mmol, Aldrich) of bromomethyl methyl ether was added dropwise over 15 minutes. The reaction mixture was stirred for 1 hour at 0° then at room temperature for 16 hours. The resulting slurry was partitioned between 200 mL of 1M aqueous sodium hydroxide solution and 150 mL of 4:1 hexane/diethyl ether. The aqueous layer was separated and extracted with an additional 100 mL of 4:1 hexane/diethyl ether. The organic extracts were combined, washed with two-200 mL portions of water, dried (magnesium sulfate) and concentrated in vacuo to give 22.2 g (102 mmol, 97%) of title compound as a pale yellow liquid.

B.
[1S-(1α,2α,3α,4α)]-[2-(Methoxymethoxy)phenyl]-7-oxabicyclo[2.2.1]heptane-2,3-dimethanol To a solution of 16.7 g (77.0 mmol) of Part A aryl bromide in 150 mL of dry THF (distilled from potassium/benzophenone) cooled to −78° was added dropwise 48 mL (1.6M in hexane, 77 mmol, Aldrich) of n-butyllithium over 30 minutes. The reaction mixture was stirred at −78° for 1 hour. To the resulting white slurry of the anion was added a solution of 4.80 g (30.8 mmol, of [3aR-[3aα,4β,7β,7aα)]-octahydro-4,7-epoxyisobenzofuran-1-ol in 30 mL of dry THF over 5 minutes. The reaction was warmed to 0° (becomes homogeneous), stirred for 2 hours then quenched with 5 mL of methanol and concentrated in vacuo. The residue was partitioned between 100 mL of brine and 100 mL of ethyl acetate then an additional 50 mL of water was added. The aqueous layer was separated and extracted with 100 mL of ethyl acetate. The organic extracts were combined, dried (magnesium sulfate) and concentrated in vacuo to give an oil. The crude material was purified by flash chromatography (Merck silica, 22×5.0 cm, 1:2 ethyl acetate/petroleum ether then ethyl acetate) to afford 8.49 g (28.9 mmol, 94%) of title diol as an oil.

C.
[1S-(1α,2α,3α,4α)]-2-[[2-(Methoxymethoxy)phenyl]methyl]-7-oxabicyclo-[2.2.1]heptane-3-methanol A mixture of 8.40 g (28.6 mmol) of Part B diol and 8.0 g of 10% palladium on carbon catalyst (Aldrich) in 75 mL of glacial acetic acid was stirred under an atmosphere of hydrogen (balloon) for 18 hours. The resulting mixture was filtered on a Buchner funnel then passed through a polycarbonate membrane. The filtrate was concentrated in vacuo (oil pump vacuum) to give an oil. The oil was partitioned between 75 mL of ethyl acetate and 100 mL of 1M aqueous sodium hydroxide solution (pH=12 of aqueous) then an equal volume of brine was added (100 mL). The aqueous layer was separated and extracted with an additional 50 mL of ethyl acetate. The organic extracts were combined, dried (magnesium sulfate) and concentrated in vacuo to afford 7.56 g (27.2 mmol, 95%) of title alcohol as a colorless oil.

D.
[1S-(1α,2α,3α,4α)]-2-[[2-(Methoxymethoxy)phenyl]methyl]-3-[(phenylmethoxy)methyl]-7-oxabicyclo[2.2.1]heptane The oil was removed from 552 mg (60% in oil, 13.8 mmol, Aldrich) of sodium hydride dispersion by three washes with petroleum ether then the residue was covered with 15 mL of dry THF (distilled from potassium/benzophenone). The mixture was heated to about 50° then added dropwise was a solution of 3.50 g (12.6 mmol) of Part C alcohol in 15 mL of dry THF. Vigorous gas evolution was observed. The reaction was stirred for an additional 30 minutes then cooled to 0°. To the resulting anion solution was added 465 mg (1.26 mmol, Fluka) of tetra-n-butylammonium iodide then dropwise 1.6 mL (14 mmol, Aldrich) of benzyl bromide. The reaction was stirred at 0° for 2 hours then at room temperature for 16 hours. The resulting mixture was quenched with 5 mL of water then partitioned between 100 mL of 1M aqueous HCl solution and 50 mL of ethyl acetate. The aqueous layer was separated and extracted with an additional 50 mL of ethyl acetate. The organic extracts were combined, washed with 100 mL of 1M aqueous sodium hydroxide solution, dried (magnesium sulfate) and concentrated in vacuo to give 4.55 g (12.4 mmol, 98%) of crude title compound as a yellow oil.

E.
[1S-(1α,2α,3α,4α)]-2-[[3-[(Phenylmethoxy)methyl]-7-oxabicyclo[2.2.1]-hept-2-yl]methyl]phenol To a solution of 4.53 g (12.3 mmol) of Part D title compound in 12 mL of dioxane (Burdick and Jackson) was added at room temperature 30 mL of 1:4 concentrated HCl/methanol. The reaction was stirred for 5 hours then concentrated in vacuo. The residue was partitioned between 50 mL of 1M aqueous HCl solution and 75 mL of ethyl acetate then 50 mL of brine was added. The organic layer was separated, dried (magnesium sulfate) and concentrated in vacuo to give an orange oil. The crude oil was purified by flash chromatography (Merck silica, 12×5.0 cm, 1:1:3 ethyl acetate/methylene chloride/hexane) to afford 3.46 g (10.7 mmol, 87%) of title phenol as a pale yellow glass.

F.
[1S-(11α,2α,3α,4α)]-2-[[3-[(Phenylmethoxy)methyl]-7-oxabicyclo[2.2.1]hept-2-yl]methyl]phenoxy]acetic acid, ethyl ester The oil was removed from 420 mg (60% in oil, 11 mmol, Aldrich) of sodium hydride dispersion by three washes with hexane then 15 mL of dry THF (distilled from potassium/benzophenone) was added. To the resulting stirred mixture at room temperature was added dropwise a solution of 3.30 g (10.2 mmol) of Part E phenol in 20 mL of dry THF over about 15 minutes. Vigorous gas evolution was observed. The reaction was stirred for an additional 30 minutes then cooled to 0° and a solution of 1.75 g (10.5 mmol, Aldrich) of ethyl bromoacetate in 2 mL of THF was added dropwise. The reaction mixture was stirred for 1.5 hours then quenched with 50 mL of 1M aqueous HCl solution. The resulting mixture was added to 50 mL of brine then extracted with 75 mL of ethyl acetate. The organic extract was dried (magnesium sulfate) and concentrated in vacuo to give an oil. The crude oil was purified by flash chromatography (Merck silica, 12×5.0 cm, 1:2 ethyl acetate/hexane) to afford 3.87 g (9.44 mmol, 93%) of title ester as a pale yellow oil.

G.
[1S-(1α,2α,3α,4α]-2-[[3-(Hydroxymethyl)-7-oxabicyclo[2.2.19 hept-2-yl]methyl]phenoxy]acetic acid, ethyl ester A mixture of 3.60 g (8.78 mmol) Part F ester and 180 mg of 20% palladium hydroxide on carbon catalyst (moist, Aldrich) in 25 mL of ethyl acetate was stirred under hydrogen (balloon) for 2 hours (TLC showed little reaction). Added to the reaction was 12 mL of absolute ethanol then 0.3 mL of concentrated HCl. The reaction was stirred for 2 hours (TLC showed little reaction) then an additional 360 mg of catalyst was added. The resulting mixture was stirred for 20 hours, filtered on a Buchner funnel then through a polycarbonate membrane. The filtrate was concentrated in vacuo to give an oil. The crude oil was purified by flash chromatography (Merck silica, 15×5.0 cm, 2:1 ethyl acetate/hexane) to afford 1.20 g (3.75 mmol, 43%) of desired title alcohol as an oil and 1.48 g (4.09 mmol, 47%) of corresponding acetate as an oil.

H.
[1S-(1α,2α,3α,4α)]-2-[[3-Carboxy-7-oxabicyclo[2.2.1]hept-2-yl]methyl]phenoxy]acetic acid, ethyl ester To a solution of 1.17 g (3.66 mmol) of Part G alcohol in 15 mL of reagent acetone cooled to 0° was added rapidly 2.5 mL (2.6M in $Cr^{+6}$, 6.5 mmol) of Jones reagent. The reaction was stirred for 1 hour at 0° then 30 minutes at room temperature. The mixture was recooled to 0°, quenched with 2 mL of isopropanol and stirred for an additional 30 minutes. The resulting green slurry was filtered through a pad of Celite. The filtrate was concentrated in vacuo and the residue partitioned between 20 mL of 1M HCl solution and 20 mL of ethyl acetate. The organic extract was separated, washed with 20 mL of brine, dried (magnesium sulfate) and concentrated in vacuo to give 1.19 g 3.56 mmol, 97%) of crude title acid as an oil.

I.
[1S-(1α,2α,3α,4α)]-2-[[3-[[[1-(Hydroxymethyl)-2-oxo-2-(phenylmethoxy)ethyl]amino]carbonyl]-7-oxabicyclo[2.2.1]hept-2-yl]methyl]phenoxy]acetic acid, ethyl ester To a solution of 1.19 g (3.69 mmol) of crude Part H acid in 15 mL of dry THF (distilled from potassium/benzophenone) cooled to 0° was added 540 mg (4.00 mmol, Aldrich) of 1-hydroxybenzotriazole hydrate, 928 mg (4.00 mmol, Sigma) of L-serine benzyl ester hydrochloride then 1.2 mL (8.5 mmol, distilled from calcium hydride) of triethylamine. The slurry was stirred for 5 minutes then 824 mg (4.00 mmol, Aldrich) of dicyclohexylcarbodiimide was added. The reaction mixture was stirred at 0° for 3 hours then at room temperature for 16 hours. The resulting slurry was diluted with 15 mL of ethyl acetate then filtered. The filtrate was concentrated in vacuo to give an oil. The crude material was purified by flash chromatography (Merck silica, 12×5.0 cm, ethyl acetate) to afford 1.33 g (2.60 mmol, 73%) of title amide as a solid.

J.
[1S-(1α,2α,3α,4α)]-2-[[3-[4,5-Dihydro-4-[(phenylmethoxy)carbonyl]-2-oxazolyl]-7-oxabicyclo[2.2.1]hept-2-yl]methyl]phenoxy]acetic acid, ethyl ester To a solution of 1.32 g (2.58 mmol) of Part I amide, 1.02 g (3.90 mmol, Aldrich) of triphenylphosphine and 0.70 mL (4.0 mmol, Aldrich) of diisopropylethylamine in 12 mL of 5:1 dry acetonitrile/methylene chloride was added at room temperature 380 mL (3.9 mmol) of reagent carbon tetrachloride. The reaction was stirred for 2.5 hours then added was 30 mL of ethyl acetate and 30 mL of saturated sodium bicarbonate solution. The organic layer was separated, washed with 30 mL of brine, dried (sodium sulfate) and concentrated in vacuo to give an oily solid. The crude material was purified by flash chromatography (Merck silica, 15×5.0 cm, 4:1 ethyl acetate/hexane) to afford 883 mg (1.79 mmol, 69%) of title oxazoline as an oil.

K.
[1S-(1α,2α,3α,4α)]-2-[[3-[4-[(Phenylmethoxy)carbonyl]-2-oxazolyl]-7-oxabicyclo[2.2.1]hept-2-yl]methyl]phenoxy]acetic acid, ethyl ester To a solution of 860 mg (1.74 mmol) of Part J oxazoline in 15 mL of dry methylene chloride (distilled from phosphorous pentoxide) was added at room temperature 1.7 g of nickel peroxide oxidant (prepared as described in Example 2, Part H), in one portion. The reaction was stirred for 45 minutes (incomplete by TLC) then an additional 1.7 g of oxidant was added. After 45 minutes an additional 0.85 g of oxidant was added. The reaction mixture was stirred for 45 minutes (starting material consumed by TLC) then 50 mL of ethyl acetate was added followed by 100 mL of 3M aqueous sodium bisulfite solution. The mixture was stirred rapidly for 30 minutes (green emulsion) then 50 mL of 1M aqueous sodium citrate solution was added. After stirring for 15 minutes two layers formed. The organic layer was separated and the aqueous layer was extracted with an additional 50 mL of ethyl acetate. The combined organic extracts were dried (magnesium sulfate) and concentrated in vacuo to give an oil. The crude material was purified by flash chromatography (Merck silica, 15×3.0 cm, 2:3 ethyl acetate/hexane) to afford 390 mg (0.79 mmol, 45%) of title oxazole as a foam.

L.
[1S-(1α,2α,3α,4α)]-2-[[3-(4-Carboxy-2-oxazolyl)-7-oxabicyclo[2.2.1]hept-2-yl]methyl]phenoxy]acetic acid, ethyl ester A mixture of 385 mg (0.78 mmol) of Part K oxazole and 38 mg of 20% palladium hydroxide on carbon catalyst (moist, Aldrich) in 10 mL of ethyl acetate was stirred rapidly under an atmosphere of hydrogen (balloon) for 1.5 hours then magnesium sulfate was added. The reaction mixture was passed through a polycarbonate membrane. The filtrate was concentrated in vacuo to give 314 mg (0.78 mmol, 100%) of title oxazole acid as a white solid, mp 151°–154°.

M.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]-phenoxy]acetic acid, ethyl ester To a solution of 310 mg (0.77 mmol) of Part L oxazole acid in 5 mL of dry methylene chloride (distilled from phosphorous pentoxide) was added a small drop of dimethylformamide then 90 μL (1.0 mmol, Aldrich) of oxalyl chloride. The reaction was stirred until gas evolution ceased, about 30 minutes, then concentrated in vacuo to give the crude acid chloride as a yellow foam. The acid chloride was solubilized in 3 mL of dry methylene chloride then cooled to 0° and added dropwise was solution of 192 mg (1.00 mmol) of cyclohexylbutylamine hydrochloride and 280 μL (2.0 mmol, distilled from calcium hydride) of triethylamine in 5 mL of dry methylene chloride. The reaction mixture was stirred for 15 minutes then partitioned between 15 mL of 1M aqueous HCl solution and 25 mL of ethyl acetate. The organic layer was separated, washed with 15 mL of brine, dried (magnesium sulfate) and concentrated in vacuo to give a solid. The crude material was purified by flash chromatography (Merck silica, 10×3.0 cm, 1:1 ethyl acetate/hexane) to afford 332 mg (0.62 mmol, 80%) of title oxazole amide as a white solid, mp 135°–136°.

N.
[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]phenoxy]acetic acid, A mixture of 295 mg (0.55 mmol) of Part M ester and 46 mg (1.1 mmol, Aldrich) of lithium hydroxide monohydrate in 2.5 mL of 4:1 THF/water was stirred at room temperature for 1.5 hours. The reaction mixture was acidified with 2.2 mL of 1M aqueous HCl solution then partitioned between 20 mL of ethyl acetate and 20 mL of water. The organic layer was separated, dried (magnesium sulfate) and concentrated in vacuo to afford 281 mg (0.55 mmol, 100%) of title product as a white solid, mp 190°–191°.

IR (KBr): 3416, 2921, 1741, 1644, 1602, 1520, 1492 cm$^1$.

270 MHz $^1$H NMR (CDCl$_3$): 30 0.70–1.90 (m, 22H), 2.18 (dd, 1H), 2.37 (dd, J=12,12,1H), 2.70 (m, 1H) 3.40 (m, 3H), 4.53 (d, J=15, 1H), 4.67 (d, J=15, 1H), 5.04 (d, 1H), 6.76 (d, J=8, 1H), 6.93 (dd, J=7,7, 1H), 7.15 (m, 3H), 8.17 (s, 1H)

67.5 MHZ $^{13}$C NMR (CDCl$_3$) 170.4, 164.2, 161.1, 155.4, 141.2, 135.7, 131.0, 128.8, 127.7, 121.7, 111.3, 80.0, 78.9, 65.1, 49.2, 46.9, 39.3, 37.5, 37.1, 33.3, 30.7, 29.9, 29.8, 28.7, 26.7, 26.4, 24.2. MS(CI): 511 (M+H)+

OR: $[\alpha]_D = +41.8°$ (c=1.0 in chloroform)

TLC: $R_f$ (silica gel, 1:10:90, acetic acid/methanol/methylene chloride)=0.46, ammonium molybdate/ceric sulfate and UV, homogeneous.

Analysis Calc'd for $C_{29}H_{38}N_2O_6$: C, 68.21; H, 7.50; N, 5.49 Found: C, 68.35; H, 7.81; N, 5.42

EXAMPLE 10

[1S-(1α,2α,3α,4α)]-2-[[3-[4-[[(7,7-Dimethyloctyl)amino]carbonyl]-2-oxazolyl]-7-oxabicyclo[2.2.1]hept-2-yl]methyl]benzenepropanoic acid

A. 7,7-Dimethyl-1-octanamine (1) 3,3-Dimethylbutanal

To a solution of 9.4 mL (107 mmol) of oxalyl chloride in 500 mL of dry $CH_2Cl_2$ at $-60°$ was added a solution of 15.4 mL (18.5 g, 235 mmol) of dimethyl sulfoxide in 25 mL of $CH_2Cl_2$ dropwise over 10 minutes. The reaction mixture was stirred for 10 minutes then 10 g (98 mmol, Aldrich) of 3,3-dimethyl-1-butanol was added slowly. Stirring was continued for an additional 20 minutes then 68.1 mL (489 mmol) of triethylamine was added, and the reaction mixture was allowed to warm to room temperature. Water (50 mL) was then added, the organic layer was separated and the aqueous layer was extracted with $CH_2Cl_2$ (30 mL). The organic layers were combined, washed sequentially with 1% aqueous HCl, water, aqueous saturated $NaHCO_3$, water and brine, dried (magnesium sulfate) and concentrated in vacuo to obtain 3.3 g (33%) of title compound as a volatile yellow oil.

(2) (3-Carboxypropyl)triphenylphosphonium bromide

A mixture of 100 g (599 mmol, Aldrich) of 4-bromobutyric acid and 157 g (599 mmol, Aldrich) of triphenylphosphine was heated to 130° for 2 hours. The reaction was cooled to room temperature. The resulting solid was solubilized in 250 mL of hot chloroform then diluted with 200 mL of diethyl ether. The mixture was cooled to room temperature then 0°. The solid which formed was collected by filtration and then dried under vacuum to afford 240 g (559 mmol, 93%) of title compound.

(3) 7,7-Dimethyl-4-octenoic acid

To a stirred solution of 13.7 g (31.9 mmol) of Part A(2) phosphonium bromide in 60 mL of dry THF under argon at $-15°$ was added dropwise 32 mL (1.72 M in toluene, 57.9 mmol, Callery Chem) of potassium t-amylate solution over 10 minutes. The mixture was stirred for 0.5 hour then to the resulting orange reaction mixture was added slowly a solution of 2.00 g (19.9 mmol) of Part A(1) aldehyde in 5 mL of THF. The reaction mixture was stirred at $-15°$ C. for 1 hour then at room temperature for 20 hours and quenched with 12 mL of glacial acetic acid. The resulting solution was concentrated in vacuo and the residue was partitioned between ethyl acetate (100 mL) and saturated $NaHCO_3$ (100 mL). The organic layer was separated and the aqueous layer was extracted twice with ethyl acetate (100 mL). The combined organic layers were washed sequentially with 1% aqueous HCl, water, saturated aqueous $NaHCO_3$, water, and brine, then dried (magnesium sulfate), and concentrated in vacuo. The residue was purified by flash chromatography (Merck silica, gradient: 1% to 100% ethyl acetate in hexane, with 0.3% glacial acetic acid) to obtain 1.75 g (51%) of title compound.

(4) 7,7-Dimethyloctanoic acid

To a stirred solution of 1.2 g (7.0 mmol) of Part A(3) compound in 8 mL of glacial acetic acid was added 0.2 g of platinum oxide catalyst. This mixture was stirred for 14 hours under an atmosphere of hydrogen (balloon). The reaction mixture was filtered through a Celite pad and the filtrate was concentrated in vacuo. The residue was diluted with 50 mL toluene and concentrated again. This process was repeated to obtain 1.2 g (100%) of title compound as oil.

(5) 7,7-Dimethyloctanamide

To a stirred solution of 1.21 g (7.02 mmol) of Part A(4) compound in 50 mL of toluene was added 3 mL (134 mmol) of oxalyl chloride. The reaction mixture was stirred for 1 hour at room temperature under argon and then concentrated in vacuo. The residue was diluted with 20 mL of toluene and concentrated again. This was repeated to remove traces of oxalyl chloride. The residue of the crude acid chloride was stirred in 5 mL of methanol and then 1.17 mL (8.43 mmol) of triethylamine and 2 mL (9M, 18 mmol) of methanolic ammonia were added at room temperature under argon. After stirring for 16 hours, the reaction mixture was partitioned between 3 mL water and 20 mL ethyl acetate. The organic layer was separated and the aqueous layer was extracted twice with ethyl acetate (20 mL). The combined organic layers were washed with brine then dried (magnesium sulfate) and concentrated in vacuo to obtain a semi-solid. The semi-solid was crystallized by trituration with hexane to obtain 0.5 g (42%) of title compound as a solid.

(6) 7,7-Dimethyl-1-octanamine

To a solution of 0.45 g (2.62 mmol) of Part A(5) compound in 50 mL of dry diethyl ether stirred under argon at 0° C. was added 0.11 g (2.9 mmol) of lithium aluminum hydride. Gas was evolved. The reaction mixture was stirred at room temperature for 4 days. While stirring vigorously, the reaction was cautiously quenched by sequential addition of 0.02 mL of $H_2O$, 0.02 mL of 15% aqueous NaOH, 0.072 mL of $H_2O$, and 1 mL of diethyl ether. A white precipitate formed. After stirring for 0.5 hours the mixture was filtered and the filtrate was concentrated in vacuo to obtain 0.4 g (89%) of a yellow oil. This was crystallized by trituration with hexane and $CHCl_3$ to give title amine.

B.
[1S-(1α,2α,3α,4α)]-2-[[3-[4-[[(7,7-Dimethyloctyl)amino]carbonyl]-2-oxazolyl]-7-oxabicyclo[2.2.1]hept-2-yl]methyl]benzenepropanoic acid, methyl ester To a solution of 140 mg (0.36 mmol), of [1S-(1α,2α,3α,4α)]-2-[[3-[4-(carboxy)-2-oxazolyl]-7-oxabicyclo[2.2.1]hept-2-yl]methyl]benzenepropanoic acid, methyl ester prepared as described in Example 2, Part J, first paragraph, in 4 mL dry $CH_2Cl_2$ (distilled from $P_2O_5$) was added 1 small drop of dimethylformamide, followed by 40 μL (0.46 mmol, Aldrich) of oxalyl chloride. The reaction was stirred until gas evolution ceased (about 20 minutes), then the mixture was concentrated in vacuo to give the crude acid chloride as a pale yellow solid.

To a solution of crude acid chloride in 3 mL dry $CH_2Cl_2$ (distilled from $P_2O_5$), cooled to 0° C., was added 63 mg (80% pure, equivalent to 51 mg pure amine, 0.32 mmol) of Part A amine, then a solution of 65 μL (0.46 mmol, distilled from $CaH_2$) triethylamine in 1 mL dry $CH_2Cl_2$ was added to the reaction mixture. After 30 minutes the reaction mixture was partitioned between 15 mL CH$_2$Cl$_2$ and 15 mL H$_2$O; the organic layer was separated and the aqueous layer was extracted with an additional 15 mL CH$_2$Cl$_2$. The combined organic layers were dried (MgSO$_4$) and concentrated in vacuo to give a crude solid. The crude solid was flash chromatographed (Merck silica, 12×2.5 cm, 1:1 ethyl acetate:hexane) to give 135 mg 0.26 mmol, 81%) of title amine as a white solid.

C.

[1S-(1α,2α,3α,4α)]-2-[[3-[4-[[(7,7-Dimethyloctyl)amino]carbonyl]-2-oxazolyl]-7-oxabicyclo[2.2.1]hept-2-yl]methyl]benzenepropanoic acid To a mixture of 134 mg 0.26 mmol) of Part B amide in 4 mL THF/1 mL H$_2$O was added 22 mg (0.51 mmol, Aldrich) of lithium hydroxide monohydrate. The reaction was stirred at room temperature for 2.5 hours, then quenched by the addition of 1 mL 1M HCl. The mixture was partitioned between 20 mL H$_2$O and 20 mL ethyl acetate; the organic layer was separated, dried (MgSO$_4$) and concentrated in vacuo to give a crude white solid. The crude solid was recrystallized (hot ethyl acetate/hexane) to give 100 mg (0.20 mmol, 77%) of title acid as a white solid, mp 151°–153° C.

IR (KBr): 3409, 2950, 2932, 1726, 1649, 1603, 1520 cm$^{-1}$

270 MHz $^1$H NMR (CDCl$_3$) δ: 8.15 (s, 1H), 7.27 (s, 1H), 7.10 (m, 4H), 4.98 (d, 1H), 4.39 (d, 1H), 3.38 (m, 3H), 2.90 (t, 2H), 2.55 (t, 3H), 2.34 (t, 1H), 2.20 (dd, 1H), 1.90–1.00 (m, 14H), 0.81 (s, 9H)

67.5 MHz $^{13}$C NMR (CDCl$_3$) δ: 176.2, 163.9, 160.8, 141.0, 138.5, 137.8, 136.0, 129.7, 129.0, 126.7, 126.5, 79.7, 78.7, 50.0, 47.0, 44.2, 39.2, 34.7, 32.5, 30.3, 29.9, 29.6, 29.4, 28.9, 27.4, 27.0, 24.5

MS (CI): 511 (M+H)+

TLC: R$_f$ (silica gel, 1:9 methanol/methylene chloride)=0.20, ammonium molybdate/ceric sulfate and UV, homogeneous.

Analysis Calc'd for C$_{30}$H$_{42}$N$_2$O$_5$: C, 70.56; H, 8.29; N, 5.50 Found: C, 70.44; H, 8.42; N, 5.50

Examples of additional compounds in accordance with the present invention which may be prepared following the procedures outlined in the specification and working Examples include, but are not limited to the following:

| Example No. | (CH$_2$)$_m$ m | (CH$_2$)$_n$ n | X | Y(position) | R$^1$ | R$^2$ | R |
|---|---|---|---|---|---|---|---|
| 11 | 1 | 2 | O | -(2) | —C$_6$H$_{13}$ | CH$_3$ | CO$_2$H |
| 12 | 2 | 2 | O | -(2) | —(CH$_2$)$_4$-(2-thienyl) | CH$_3$ | CO$_2$H |
| 13 | 2 | 1 | NH | -(3) | -(2-thienyl) | H | CONHSO$_2$CH$_3$ |
| 14 | 1 | 2 | S | -(4) | —C$_2$H$_4$-(4-chlorophenyl) | H | —CH$_2$-5-tetrazolyl |
| 15 | 2 | 3 | O | -(2) | C$_6$H$_5$ | C$_6$H$_5$ | CO$_2$H |
| 16 | 1 | 2 | NH | -(3) | —CH$_2$C$_6$H$_5$ | H | —CH$_2$-5-tetrazolyl |
| 17 | 1 | 2 | O | -(2) | i-C$_3$H$_7$ | H | CONHSO$_2$C$_6$H$_5$ |
| 18 | 1 | 3 | O | -(2) | —CH$_2$-(2-thienyl) | n-C$_4$H$_9$ | CONHSO$_2$CH$_2$C$_6$H$_5$ |
| 19 | 1 | 2 | NH | -(3) | —(CH$_2$)$_3$-cyclopropyl | H | CO$_2$H |

-continued

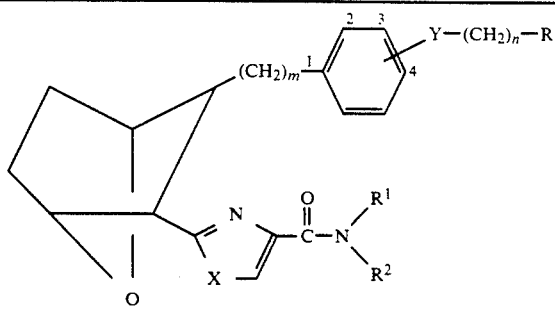

| Example No. | (CH₂)ₘ m | (CH₂)ₙ n | X | Y(position) | R¹ | R² | R |
|---|---|---|---|---|---|---|---|
| 20 | 2 | 2 | O | -(3) | cyclobutyl | CH₂C₆H₅ | CO₂CH₃ |
| 21 | 1 | 2 | S | -(3) | C₂H₅ | H | CO₂Li |
| 22 | 1 | 2 | O | -(2) | 4-Cl-C₆H₄- | H | CO₂C₂H₅ |
| 23 | 1 | 2 | O | -(2) | (CH₂)₂C₆H₅ | CH₃ | CO₂H |
| 24 | 1 | 3 | O | -(4) | n-C₃H₇ | CH₂C₆H₅ | —CH₂-5-tetrazolyl |
| 25 | 1 | 2 | NH | -(3) | n-C₅H₁₁ | H | CO₂H |
| 26 | 2 | 3 | O | -(2) | tetrahydrothiopyranyl | CH₃ | CONHC₆H₅ |
| 27 | 1 | 2 | O | -(2) | —(CH₂)₆— (R¹ and R² joined) | | CONH₂ |
| 28 | 2 | 0 | O | -(3) | n-C₄H₉ | n-C₄H₉ | CO₂H |
| 29 | 1 | 0 | NH | -(2) | C₆H₅ | H | CONHCH₃ |
| 30 | 1 | 2 | O | -(2) | —(CH₂)₄—N(imidazolyl) | H | CO₂H |
| 31 | 2 | 2 | O | -(3) | —(CH₂)₅-(2-pyridyl) | H | CO₂H |
| 32 | 1 | 1 | NH | -(2) | —(CH₂)₆—N(pyrrolidinyl) | H | CONHCH₂C₆H₅ |
| 33 | 1 | 2 | O | -(2) | —(CH₂)₄-(tetrahydropyranyl) | H | CO₂H |

EXAMPLE 34

[1S-(1α,2α,3α,4α)]-2-[[3-[4-[[(1-Piperidinylbutyl)amino]carbonyl]-2-oxazolyl]-7-oxabicyclo[2.2.1]hept-2-yl]methyl]benzenepropanoic acid, methyl ester

A. 1-Piperidinebutanenitrile

To a solution of 5.0 g (58.7 mMol, Aldrich) of piperidine an 8.2 mL (59 mMol) of sieve-dried triethylamine, stirring at room temperature, was added 5.8 mL (59 mMol, Aldrich) of 4-bromobutyronitrile. After stirring 1 minute, a white precipitate formed; the reaction became very exothermic and an orange solid formed. The solid was slurried in 5 mL dichloromethane, cooled to 0° for 2 hours, then stirred at room temperature for 56 hours. The mixture was partitioned between 20 mL water and 50 mL chloroform. The organic layer was separated and the aqueous layer was extracted with two 50 mL portions of chloroform. The chloroform layers were combined, washed with saturated NaCl solution, dried (MgSO₄) and concentrated in vacuo to give a red slush. The slush was slurried in 10 mL hexane and minimal amounts of ethyl acetate and dichloromethane until a white precipitate formed. The mixture was filtered to give 430 mg (2.8 mMol, 6%) of title nitrile as a white solid; the filtrate was concentrated in vacuo to give an additional 6.57 g (43.1 mMol, 72%) of title nitrile as a reddish oil; total yield of title nitrile 7.0 g (45.9 mMol, 78%).

B. 1-Piperidinebutanamine

To a solution of 2.0 g 13.1 mMol) of crude Part A nitrile in 30 mL diethyl ether, stirring at 0°, was added 550 mg (14.4 mMol) of lithium aluminum hydride in 100 mg portions. The reaction mixture was warmed to room temperature and stirred for 3 hours, then quenched by the slow, dropwise addition of 0.6 mL H₂O, 0.6 mL 15% NaOH and 1.8 mL H₂O. After stirring 30 minutes, the reaction mixture was filtered; the filtrate was concentrated in vacuo to give a yellow oil. The yellow oil was azeotroped with toluene and with dichloromethane to give 2.0 g (12.8 mMol, 100%) of title amine as a yellow oil.

C. [1S-(1α,2α,3α,4α)]-2-[3-[4-[[(1-Piperidinylbutyl)amino]carbonyl]-2-oxazolyl]-7-oxabicyclo[2.2.1]hept-2-yl]methyl]-benzenepropanoic acid, methyl ester To a solution of 300 mg 0.78 mMol) of the intermediate acid prepared in Example 2, Part J in 5 mL dry CH₂Cl₂ (distilled from P₂O₅) was added 1 small drop of DMF, followed by 82 μL (0.94 mMol, Aldrich) of oxalyl chloride. The reaction was stirred until gas evolution ceased (about 30 minutes), then the mixture was concentrated in vacuo to give the crude acid chloride as a pale yellow solid.

To a solution of crude acid chloride in 5 mL dry CH₂Cl₂ (distilled from P₂O₅), cooled to 0°, was added 330 μL (2.34 mMol, distilled from CaH₂) triethylamine, followed by the dropwise addition of a solution of 365 mg (2.34 mMol) of Part B amine in 5 mL CH₂Cl₂. The reaction was stirred at 0° for 16 hours, then partitioned between 40 mL ethyl acetate/40 mL saturated NaHCO₃ solution. The water layer was washed with three 20 mL portions of ethyl acetate. The combined ethyl acetate layers were dried (Na₂SO₄) and concentrated in vacuo to give a crude yellow solid. The crude solid was flash chromatographed (Merck silica, 3% (C₂H₅)₃N/EtOAc) to give 300 mg (0.57 mmol, 74%) of title ester as a pale yellow solid.

EXAMPLE 35

[1S-(1α,2α,3α,4α)]-2-[[3-[4-[[(1-Piperidinylbutyl)amino]carbonyl]-2-oxazolyl]-7-oxabicyclo[2.2.1]hept-2-yl]methyl]benzenepropanoic acid, monolithium salt To a mixture of 300 mg (0.57 mMol) of Example 34 ester in 6 mL distilled THF/1.5 mL water was added 48 mg (1.15 mMol, Aldrich) of lithium hydroxide monohydrate. The reaction was stirred vigorously for 16 hours, then concentrated in vacuo to give a crude yellow oil. The crude oil was flash chromatographed (MCI HP-20 resin, H₂O then 1:1 H₂O/CH₃CN) to give 280 mg (0.54 mMol, 95%) of title lithium salt as a white lyophylate.
IR (KBr): 3418, 2945, 1653, 1575, 1538, 1521 cm⁻¹.
MS(CI): 510 (M+H)⁺
OR: [α]_D= +23.2° (c=1.0 in CHCl₃)

TLC: R_f (silica gel, 2:1 EtOAc/(20:6:11 pyridine/CH₃COOH/H₂O ))=0.10, ammonium molybdate/ceric sulfate and UV, homogeneous.
Analysis Calc'd for C₂₉G₃₈N₃O₅Li+2.05 H₂O: C, 63.03; H, 7.68; N, 7.61 Found: C, 63.13; H, 7.42; N, 7.51

EXAMPLE 36

[1S-(1α,2α,3α,4α)]-2-[[3-[4-[[[4-(4-Phenylmethoxyphenyl)butyl]amino]carbonyl]-2-oxazolyl]-7-oxabicyclo[2.2.1]hept-2-yl]methyl]benzenepropanoic acid

A. 4-(Phenylmethoxy)benzenepropanol

The oil was removed from 2.6 g (60% in oil, 65 mmol, Aldrich) of sodium hydride dispersion with 3 hexane washes, then 25 mL of sieve-dried DMF (Burdick & Jackson) was added. The slurry was heated to 50° (hot water bath) and a solution of 5.00 g (30.1 mmol, Aldrich) of 3-(4-hydroxyphenyl)propionic acid in 20 mL of DMF was added dropwise over 15 minutes. The mixture was stirred until gas evolution ceased (a precipitate formed). An additional 20 mL DMF was added and the reaction was stirred for 1 hour. To the resulting slurry was added dropwise over 5 minutes 10.3 g (60.2 mmol, Aldrich) of benzyl bromide. After stirring for 20 hours, the slurry was partitioned between 200 mL H₂O/200 mL 1:1 EtOAc/hexane. The organic layer was separated, washed 3 times with 200 mL H₂O, dried (MgSO₄) and concentrated in vacuo to give 8.75 g of crude dibenzylated product as an oily solid.

To a solution of the crude material in 75 mL dry diethyl ether (distilled from Na/C₆H₅)₂CO), stirring at 0°, was added 1.00 g (26.3 mmol, Aldrich) of lithium aluminum hydride in 200 mg portions. The reaction was stirred for 2 hours, then quenched by the slow, dropwise addition of H₂O, followed by addition of 100 mL of 1M HCl. The mixture was stirred for 15 minutes, then the organic layer was separated, washed with 25 mL of brine, dried (MgSO₄) and concentrated in vacuo to give a crude solid. The crude solid was flash chromatographed (Merck silica, 1:1 EtOAc/hexane), then recrystallized (EtOAc/hexane) to give 4.50 g (18.6 mmol, 73%) of title alcohol as a white crystalline solid, mp 58°-61°.

B. 4-(Phenylmethoxy)benzenebutanenitrile

To a solution of 4.00 g (16.5 mmol) of Part A alcohol, 3.2 mL (23 mmol, distilled from CaH₂) of triethylamine and 25 mL of dry CH₂Cl₂ (distilled from P₂O₅), stirring at −20°, was added dropwise 2.27 g (19.8 mmol, Aldrich) of mesyl chloride. The reaction was stirred for 15 minutes, then diluted with 50 mL of hexane. The resulting slurry was washed 2 times with 50 mL 1M HCl, 50 mL 1:1 saturated aqueous NaHCO₃/H₂O, then 25 mL brine, dried (MgSO₄) and concentrated in vacuo to give 5.30 g (16.5 mmol, 100%) of crude mesylate as a white solid.

To a solution of 5.30 g (16.5 mmol) of crude mesylate in 25 mL DMSO (Burdick & Jackson, sieve-dried) was added 1.62 g (33.1 mmol, Aldrich) of sodium cyanide. The reaction was heated to 50° for 24 hours, cooled, added to 100 mL H₂O and extracted with 100 mL of 4:1 hexane/ether. The organic layer was separated, washed 3 times with 100 mL H₂O, dried (MgSO₄) and concentrated in vacuo to give a crude white solid. The crude solid was recrystallized (ether/hexane) to give 2.90 g (11.6 mmol, 70%) of title nitrile as a white crystalline solid, mp 47°-48°.

C. 4-(Phenylmethoxy)benzenebutanamine, monohydrochloride

To a slurry of 500 mg (13.2 mmol, Aldrich) of lithium aluminum hydride in 40 mL dry diethyl ether (distilled from Na/C$_6$H$_5$)$_2$CO), stirring at 0°, was added dropwise over 15 minutes a solution of 2.70 g (10.8 mmol) of Part B nitrile in 20 mL of dry diethyl ether. The reaction mixture was stirred for 3 hours at room temperature, cooled to 0° and quenched by the successive, slow addition of 0.5 mL H$_2$O, 0.5 mL 15% aqueous NaOH solution and 1.5 mL H$_2$O. The mixture was warmed to room temperature and filtered; the filtrate was concentrated in vacuo to give a crude white solid. To a solution of the crude solid in 25 mL CH$_3$OH, stirring at 0°, was added 50 mL of cold methanolic HCl (prepared by addition of 3 mL CH$_3$COCl to 50 mL CH$_3$OH at 0°). To the resulting homogeneous solution was added 200 mL of diethyl ether; a white precipitate formed, collected on a Buchner funnel, and dried under vacuum (100°/2 hours) to give 1.90 g (6.53 mmol, 60%) of title amine hydrochloride as a white powder, mp 225°–227°.

D.
[1S(1α,2α,3α,4α)]-2-[[3-[4-[[[4-(4-Phenylmethoxyphenyl)butyl]amino]carbonyl]-2-oxazolyl]-7-oxabicyclo[2.2.1]hept-2-yl]-methyl]benzenepropanoic acid, methyl ester To a solution of 200 mg (0.52 mmol), of the intermediate acid prepared in Example 2, Part J in 20 mL dry CH$_2$Cl$_2$ (distilled from P$_2$O$_5$) was added 1 small drop of DMF, followed by 310 μL (0.63 mmol, 2M/CH$_2$Cl$_2$, Aldrich) of oxalyl chloride solution. The reaction was stirred until gas evolution ceased (about 30 minutes), then the mixture was concentrated in vacuo to give the crude acid chloride as a pale yellow solid.

To a solution of crude acid chloride in 10 mL dry CH$_2$Cl$_2$ (distilled from P$_2$O$_5$), cooled to 0°, was added 170 μL (1.25 mmol, distilled from CaH$_2$) of triethylamine, followed by the portionwise addition of 181 mg (0.62 mmol, Aldrich) of Part C amine hydrochloride. The reaction was stirred at 0° for 2 hours, then partitioned between 100 mL ethyl acetate/75 mL 1M HCl. The ethyl acetate layer was separated, dried (MgSO$_4$) and concentrated in vacuo to give a crude orange solid. The crude solid was flash chromatographed (Merck silica, 1:1 ethyl acetate/hexane) to give 320 mg (0.53 mmol, of title ester as a white solid.

E.
[1S(1α,2α,3α,4α)]-2-[[3-[4-[[[4-(4-Phenylmethoxyphenyl)butyl]amino]carbonyl]-2-oxazolyl]-7-oxabicyclo[2.2.1]hept-2-yl]-methyl]benzenepropanoic acid, To a mixture of 250 mg (0.41 mmol) of Part D ester in 8 mL distilled THF/2 mL water was added 34 mg (0.82 mmol, Aldrich) of lithium hydroxide monohydrate. The reaction was stirred vigorously for 3 hours, then quenched by the addition of 1.6 mL (1.60 mmol) 1M HCl solution. The mixture was partitioned between 30 mL ethyl acetate/30 mL water. The ethyl acetate layer was dried (MgSO$_4$) and concentrated in vacuo to give 239 mg (0.39 mmol, 96%) of title acid as a crude white solid.

EXAMPLE 37

[1S-(1α,2α,3α,4α)]-2-[[3-[4-[[[4-(4-Hydroxyphenyl)-butyl]amino]carbonyl]-2-oxazolyl]-7-oxabicyclo[2.2.1-]hept-2-yl]methyl]benzenepropanoic acid To a solution of 238 mg (0.39 mmol) of Example 36 acid in 10 mL sieve-dried CH$_3$OH/5 mL EtOAc, stirring under argon for 15 minutes, was added 238 mg 10% Pd/C catalyst (Aldrich). The reaction atmosphere was evacuated and filled 3 times with hydrogen; the reaction was stirred under hydrogen (balloon) for 16 hours, then filtered through a polycarbonate filter. The filtrate was concentrated in vacuo to give a crude foam. The crude foam was flash chromatographed (Merck silica, 0.25% CH$_3$COOH/EtOAc) to give 110 mg (0.21 mmol, 54%) of title acid as a white solid, mp decomp. at 212° (decomp.).

IR (KBr): 3402, 2929, 2849, 1717, 1652, 1646, 1603, 1515 cm$^{-1}$.

MS(CI): 519 (M+H)$^+$.

OR: $[\alpha]_D = +12.7°$ (c=1.0 in methanol)

TLC: R$_f$ (silica gel, 1:9 methanol/methylene chloride)=0.31, ammonium molybdate/ceric sulfate and UV, homogeneous.

Analysis Calc'd for C$_{30}$H$_{34}$N$_2$O$_6$: C, 69.48; H, 6.61; N, 5.40 Found: C, 69.84; H, 7.06; N, 5.04

EXAMPLE 38

[1S-(1α,2α,3α,4α)]-2-[[3-[4-[(Propylamino)carbonyl]-2-oxazolyl]-7-oxabicyclo[2.2.1]hept-2-yl]methyl]benzenepropanoic acid, methyl ester To a solution of 200 mg (0.52 mMol), of the intermediate acid prepared in Example 2, Part J in 20 mL dry CH$_2$Cl$_2$ (distilled from P$_2$O$_5$) was added 1 small drop of DMF, followed by 310 μL (0.63 mMol, 2M/CH$_2$Cl$_2$, Aldrich) of oxalyl chloride solution. The reaction was stirred until gas evolution ceased (about 30 minutes), then the mixture was concentrated in vacuo to give the crude acid chloride as a pale yellow solid.

To a solution of crude acid chloride in 10 mL dry CH$_2$Cl$_2$ (distilled from P$_2$O$_5$), cooled to 0°, was added 120 μL (0.83 mMol, distilled from CaH$_2$) of triethylamine, followed by the dropwise addition of a solution of 50 μL (0.62 mMol, Aldrich) of propylamine in 5 mL CH$_2$Cl$_2$. The reaction was stirred at 0° for 16 hours, then partitioned between 100 mL ethyl acetate/75 mL 1M HCl. The ethyl acetate layer was separated, dried (MgSO$_4$) and concentrated in vacuo to give a crude yellow solid. The crude solid was flash chromatographed (Merck silica, 2:1 ethyl acetate/hexane) to give 190 mg (0.45 mMol, 86%) of title ester as a white solid.

EXAMPLE 39

[1S-(1α,2α,3α,4α)-2-[[3-[4-[(Propylamino)carbonyl]-2-oxazolyl]-7-oxabicyclo[2.2.1]hept-2-yl]methyl]benzenepropanoic acid To a mixture of 190 mg (0.45 mMol) of Example 38 ester in 16 mL distilled THF/4 mL water was added 37 mg (0.89 mMol, Aldrich) of lithium hydroxide monohydrate. The reaction was stirred vigorously for 4 hours, then quenched by the addition of 1.8 mL (1.8 mMol) 1M HCL. The mixture was partitioned between 80 mL ethyl acetate/60 mL water. The ethyl acetate layer was separated, dried (MgSO$_4$) and concentrated in vacuo to give a crude white solid. The crude solid was recrystallized (hot ethyl acetate/hexane) to give 155 mg (0.38 mMol, 84%) of title acid as a white solid, mp 165°–168°.

IR (KBr): 3409, 3403, 2961, 2876, 1726, 1707, 1646, 1603 cm$^{-1}$.

MS(CI): 413 (M+H)$^+$.

OR: $[\alpha]_D = +5.4°$ (c=1.0 in methanol)

TLC: $R_f$ (silica gel, 1:9 methanol/methylene chloride)=0.20, ammonium molybdate/ceric sulfate and UV, homogeneous.

Analysis Calc'd for $C_{23}H_{28}N_2O_5$: C, 66.97; H, 6.84; N, 6.79 Found: C, 66.66; H, 6.92; N, 6.68

EXAMPLE 40

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid, methyl ester To a solution of 200 mg (0.52 mMol) of oxazole acid intermediate prepared in Example 2, Part J in 3 mL of dry methylene chloride (distilled from phosphorous pentoxide) was added a small drop of dimethylformamide then 55 μL (0.63 mMol, Aldrich) of oxalyl chloride. The reaction mixture was stirred until gas evolution ceased, about 15 minutes, then concentrated in vacuo to give a solid. The solid was dissolved in 2 mL of sieve-dried benzene (Burdick and Jackson) then concentrated in vacuo to give the crude acid chloride as a solid. The crude acid chloride was dissolved in 5 mL of dry methylene chloride then cooled to 0° and added was 110 μL, (0.75 mMol, distilled from calcium hydride) of triethylamine followed by 72 μL (0.62 mMol, Aldrich) of n-amylamine. The reaction mixture was stirred for 30 minutes then partitioned between 20 mL of ethyl acetate and 10 mL of 1M aqueous HCl solution. The organic layer was separated, dried (magnesium sulfate) and concentrated in vacuo to give a solid. The crude solid was purified by flash chromatography (Merck silica, 12×3.0 cm, 2:1 ethyl acetate/hexane) to give 171 mg (0.38 mMol, 72%) of title ester as a white solid.

EXAMPLE 41

[1S-(1α,2α,3α,4α)]-2-[[3-[4-[(Pentylamino)carbonyl]-2-oxazolyl]-7-oxabicyclo[2.2.1]hept-2-yl]methyl]benzenepropanoic acid A solution of 165 mg (0.36 mMol) of Part A ester and 30 mg (0.71 mMol, Aldrich) of lithium hydroxide monohydrate in 6 mL of 2:1 THF/water was stirred rapidly at room temperature for 1.5 hours. The reaction mixture was acidified by addition of 1 mL of 1M aqueous HCl solution, added to 20 mL of water then extracted with two 15 mL portions of ethyl acetate. The organic extracts were combined, dried (magnesium sulfate) and concentrated in vacuo to give 155 mg (0.35 mMol, 98%) of title acid as a white solid, mp 136°–139°.

IR(KBr): 3414 (broad), 2956, 1709, 1649, 1604, 1520 cm$^{-1}$.

MS(CI): 441 (M+H)$^+$.

OR: $[\alpha]_D = +21.5°$ (c=0.5 in chloroform)

TLC: $R_f$ (silica gel, 1:9 methanol/methylene chloride)=0.50, ammonium molybdate/ceric sulfate and UV, homogeneous. Analysis Calc'd for $C_{25}H_{32}N_2O_5$: C, 68.16; H, 7.32; N, 6.36 Found: C, 68.18; H, 7.28; N, 6.11

EXAMPLE 42

[1S-(1α,2α,3α,4α)]-2-[[3-[4-[[(2-Cyclohexylethyl)amino]carbonyl]-2-oxazolyl]-7-oxabicyclo[2.2.1]hept-2-yl]methyl]benzenepropanoic acid, methyl ester

A. 2-Cyclohexylethylamine hydrochloride

To a solution of 50.0 g (389 mmol, Aldrich) of 2-cyclohexylethanol, 127.9 g (487 mmol, Aldrich) of triphenylphosphine and 77.4 g (526 mmol, Aldrich) of phthalamide in 500 mL of dichloromethane were added dropwise 100 mL (508 mmol, Aldrich) of diisopropyl azodicarboxylate. The reaction was stirred at room temperature for 16 hours, then concentrated in vacuo; the crude product was dissolved in 250 mL methanol/150 mL dichloromethane and cooled in an ice bath, followed by the dropwise addition of 49.5 mL (1559 mmol, Aldrich) of anhydrous hydrazine. The reaction was monitored by tlc until complete, then azeotroped 2 times with toluene and concentrated in vacuo to give a solid. The crude solid was dissolved in hot methanol, cooled to 0° and filtered to give product as a solid; the filtrate was concentrated in vacuo to give more crude product. The combined crude solids were partitioned between 400 mL water/400 mL chloroform; the chloroform layer was concentrated in vacuo to give a yellow solid. The crude solid was flash chromatographed (Merck silica, gradient 2%–30% $CH_3OH/CH_2Cl_2$ in 5% $NH_4OH$) to give 9.6 g (75.5 mmol, 20%) of title amine as a yellow solid. $^1H$ NMR ($D_2O$) showed product was the amine hydrochloride.

B.

[1S-(1α,2α,3α,4α)]-2-[[3-[4-[[(2-Cyclohexylethyl)amino]carbonyl]-2-oxazolyl]-7-oxabicyclo[2.2.1]hept-2-yl]methyl]benzenepropanoic acid, methyl ester To a solution of 200 mg (0.52 mmol) of intermediate oxazole acid prepared in Example 2, Part J in 20 mL dry $CH_2Cl_2$ (distilled from $P_2O_5$) was added 1 small drop of DMF, followed by 310 μL (0.63 mmol, 2M/$CH_2Cl_2$, Aldrich) of oxalyl chloride solution. The reaction was stirred until gas evolution ceased (about 30 minutes), then the mixture was concentrated in vacuo to give the crude acid chloride a pale yellow solid.

To a solution of the crude acid chloride in 10 mL dry $CH_2Cl_2$ (distilled form $P_2O_5$), cooled to 0°, was added 170 μL (1.25 mmol, distilled from $CaH_2$) of triethylamine, followed by the dropwise addition of a solution of 102 mg (0.62 mmol) of Part A amine hydrochloride in 5 mL $CH_2Cl_2$. The reaction was stirred at 0° for 3 hours, then partitioned between 100 mL ethyl acetate/75 mL 1M HCl. The ethyl acetate layer was separated, dried (MgSO$_4$) and concentrated in vacuo to give a crude orange solid. The crude solid was flash chromatographed (Merck silica, 2:1 ethyl acetate/hexane) to give 100 mg (0.20 mmol, 39%) of title ester as a white solid.

EXAMPLE 43

[1S-(1α,2α,3α,4α)]-2-[[3-[4-[[(2-Cyclohexylethyl)amino]carbonyl]-2-oxazolyl]-7-oxabicyclo[2.2.1]hept-2-yl]methyl]benzenepropanoic acid To a mixture of 100 mg (0.20 mmol) of Part B ester in 8 ml distilled THF/2 mL water was added 17 mg (0.40 mmol, Aldrich) of lithium hydroxide monohydrate. The reaction was stirred vigorously for 3 hours, then quenched by the addition of 810 μL (0.81 mmol) 1M HCl. The mixture was partitioned between 40 mL ethyl acetate/30 mL water. The ethyl acetate layer was dried (MgSO$_4$) and concentrated in vacuo to give a crude white solid. The crude solid was recrystallized (hot ethyl acetate/hexane) to give 94 mg (0.19 mmol, 97%) of title acid as a white solid, mp 158°–161°.

IR (KBr): 3409, 2921, 2849, 1723, 1711, 1646, 1602 cm$^{-1}$.

Ms(CI): 481 (M+H)$^+$.

OR: $[\alpha]_D = +13.9°$ (c=1.0 in methanol).

TLC: R$_f$ (silica gel, 1:9 methanol/methylene chloride)=0.46, ammonium molybdate/ceric sulfate and UV, homogeneous.

Analysis Calc'd for C$_{28}$H$_{36}$N$_2$O$_5$: C, 69.97; H, 7.55; N, 5.83 Found: C, 69.74; H, 7.65; N, 5.93

EXAMPLE 44

[1S-(1α,2α,3α,4α)]-2-[[3-[4-[[(5,5-Dimethylhexyl)amino]carbonyl]-2-oxazolyl]-7-oxabicyclo[2.2.1]hept-2-yl]methyl]benzenepropanoic acid, methyl ester

A. 3,3-Dimethylbutanal

To a stirred slurry of 64.5 g (30 mmol) of pyridinium chlorochromate (PCC) and 80.5 g of Celite in 350 mL of CH$_2$Cl$_2$ at 0° was added rapidly a solution of 20.4 g (20 mmol, Aldrich) of 3,3-dimethylbutanol in 50 mL of CH$_2$Cl$_2$. This was stirred vigorously for 1.75 hours at which time the reaction was judged incomplete by TLC. An additional 10.4 g (48 mmol) of PCC was added and the reaction was allowed to proceed for an additional 1.75 hours. The reaction mixture was diluted with 500 mL of diethyl ether (ether) and then filtered through a 2 inch pad of Florisil. The filter cake was rinsed with 200 mL of ether. The combined filtrates was concentrated in vacuo at 0° C. to minimize product loss. When the filtrate was concentrated to approximately 50 mL, it was diluted with 200 mL of ether and filtered through Florisil again. The filtrate was concentrated in vacuo at 0° C. to afford 13.0 g (130 mmol, 65%) of title compound.

B. (E)-5,5-Dimethyl-2-hexenoic acid, methyl ester

To a stirred solution of 6.5 g (65 mmol) of Part A compound in 55 mL of CH$_2$Cl$_2$ was added 24.0 g (71.8 mmol) of methyl triphenylphosphorylideneacetate. The reaction mixture was stirred for 16 hours at room temperature and then concentrated in vacuo. The residue was slowly diluted with 20 mL of ether followed by 40 mL of hexane. The solid was removed by filtration and the filtrate was concentrated in vacuo. The residue was diluted with hexane and refrigerated. The additional precipitate was removed by filtration and the filtrate was concentrated in vacuo. The residue was dissolved in 1:1 hexane:ether and filtered through a short plug of silica gel. The silica gel was rinsed with 50 mL of 1:1 hexane:ether. The combined filtrates was concentrated in vacuo to afford 7.5 g (48.1 mmol, 74%) of title compound.

C. (E)-5,5-Dimethyl-2-hexenoic acid

To a stirred solution of 7.5 g (48.1 mmol) of Part B compound in 50 mL of THF and 10 mL of CH$_3$OH was added 50 mL of 2N KOH solution. This was stirred for 72 hours and then concentrated in vacuo. The residue was diluted with 50 mL of water and acidified to pH=2 with 6N HCl solution. This was then extracted with two 50 mL portions of ether. The combined ether layers was washed with 20 mL of water, dried over MgSO$_4$, filtered and concentrated in vacuo to afford to 6.2 g (43.6 mmol, 91%) of title unsaturated acid.

D. 5,5-Dimethylhexanoic acid

A solution of 3.0 g (21.1 mmol) of Part C acid in 50 mL of toluene was degassed by several vacuum-fill cycles with argon. To this solution was then added 0.60 g of 10% Pd/C and the atmosphere was exchanged for hydrogen. The reaction was allowed to proceed for 48 hours and then the catalyst was removed by filtration through a short pad of Celite. The pad was rinsed with ether and the combined filtrates were concentrated in vacuo to afford 3.00 g (20.80 mmol, 98%) of title acid.

E. 5,5-Dimethylhexanamide

To a solution of 2.95 g (20.5 mmol) of Part D acid in 30 mL dry methylene chloride (distilled from P$_2$O$_5$) was added one drop of sieve-dried DMF, followed by the dropwise addition of 12.3 mL (2M/CH$_2$Cl$_2$, 24.6 mmol, Aldrich) oxalyl chloride solution. The reaction was stirred until gas evolution ceased (approximately 30 minutes), then the mixture was concentrated in vacuo and azeotroped three times with toluene to give the crude acid chloride as a pale yellow solid.

To a solution of 7.5 mL (61.4 mmol, 8.2M) methanolic ammonia in 20 mL dry methylene chloride, stirring at 0°, was added dropwise over 30 minutes a solution of crude acid chloride in 20 mL dry chloroform. The reaction was warmed to room temperature and stirred for 18 hours, then the reaction mixture was partitioned between 75 mL 1M HCl and 75 mL ethyl acetate. The water layer was separated and washed with 2×50 mL portions of ethyl acetate; the combined ethyl acetate layers were washed with 100 mL 1M NaOH, 75 mL saturated NaCl solution, dried (MgSO$_4$) and concentrated in vacuo to give 2.93 g (20.5 mmol, 100%) of title amide as a white solid.

F. 5,5-Dimethylhexanamine, monohydrochloride

To a slurry of 1.74 g (40.9 mmol, Aldrich) of lithium aluminum hydride in 70 mL dry ether (distilled from Na, (C$_6$H$_5$)$_2$CO), stirred at 0°, was added dropwise over 20 minutes a solution of 2.93 g (20.5 mmol) of Part E amide in 50 mL dry ether. The reaction was warmed to room temperature and stirred for 32 hours, then cooled to 0° and quenched by the slow dropwise addition of 1.74 mL H$_2$O, 1.74 mL 15% NaOH and 5.24 mL H$_2$O. The mixture was stirred at 0° for 1 hour, then filtered; the filtrate was concentrated in vacuo to give the crude amine as a clear liquid. The crude amine in 20 mL sieve-dried methanol was added over 20 minutes to 100 mL acidic methanol (prepared by addition of 1.6 mL of acetyl chloride to 100 mL methanol) at 0°. The reaction was stirred at 0° for 1 hour, concentrated in vacuo and diluted with 200 mL ether. The mixture was cooled to 0° for 2 hours. The solid which formed was then filtered to give 880 mg (5.3 mmol, 26%) of title amine hydrochloride as a white solid, mp 144°–147°.

G.

[1S-(1α,2α,3α,4α)]-2-[[3-[4-[[(5,5-Dimethylhexyl)amino]carbonyl]-2-oxazolyl]-7-oxabicyclo[2.2.1]hept-2-yl]methyl]benzenepropanoic acid, methyl ester To a solution of 200 mg (0.52 mmol) of intermediate oxazole acid prepared in Example 2, Part J in 20 mL dry methylene chloride (distilled from P$_2$O$_5$) was added one drop of sieve-dried DMF, then dropwise over 10 minutes was added a solution of 0.31 mL (2M/CH$_2$Cl$_2$, 0.62 mmol, Aldrich) oxalyl chloride in 5 mL dry methylene chloride. The reaction was stirred until gas evolution ceased (approximately 30 minutes), then concentrated in vacuo to give the crude acid chloride as a yellow solid. To a solution of crude acid chloride in 10 mL dry methylene chloride, stirred at 0°, was added 0.17 mL (1.2 mmol) of sieve-dried triethylamine, followed by a solution of 126 mg (0.62 mmol), Part F amine hydrochloride in 7 mL dry methylene chloride over 10 minutes. The reaction was stirred at 0° for 2 hours, partitioned between 100 mL ethyl acetate and 75 mL 1M HCl. The ethyl acetate layer was separated, dried ($MgSO_4$) and concentrated in vacuo to give a crude orange solid. The crude solid was recrystallized (hot hexane) to give 199 mg (0.40 mmol, 77%) of title ester as a white solid.

EXAMPLE 45

[1S-(1α,2α,3α,4α)]-2-[[3-[4-[[(5,5-Dimethylhexyl)amino]carbonyl]-2-oxazolyl]-7-oxabicyclo[2.2.1]hept-2-yl]methyl]benzenepropanoic acid To a mixture of 199 mg (0.40 mmol) of Example 44 ester in 8 mL dry THF/2 mL water was added 34 mg (0.80 mmol, Aldrich) lithium hydroxide monohydrate. The mixture was stirred at room temperature for 2 hours, then quenched by the addition of 1.61 mL (1.61 mmol) 1M HCl. The mixture was partitioned between 30 mL ethyl acetate and 30 mL water; the ethyl acetate layer was separated, dried ($MgSO_4$) and concentrated in vacuo to give a crude solid. The crude solid was recrystallized from hot ethyl acetate/hexane to give 150 mg (0.31 mmol, 78%) of title acid as a white solid, mp 147°–149°.

IR (KBr): 3412, 2952, 1725, 1652, 1602, 1522 $cm^{-1}$.
MS (CI): 483 $(M+H)^+$.
OR: $[\alpha]_D = +15.8$ (c=1.0 in chloroform)
TLC: $R_f$(silica gel, 1:9 methanol:methylene chloride)=0.20; ammonium molybdate/ceric sulfate and UV, homogeneous.

Analysis calc'd for $C_{28}H_{38}N_2O_5$: C, 69.03; H, 7.97; N, 5.75 Found: C, 69.10; H, 7.98; N, 5.63

EXAMPLE 46

[1S-(1α,2α,3α,4α)]-2-[[3-[4-[[[4-(4-Methoxyphenyl)-butyl]amino]carbonyl]-2-oxazolyl]-7-oxabicyclo[2.2.1-]hept-2-yl]methyl]benzenepropanoic acid, methyl ester

A. 4-Methoxybenzenepropenoic acid, methyl ester

To a slurry of 25.78 g (77.1 mmol, Aldrich) of methyl (triphenylphosphoranylidene)acetate in 150 mL dry THF [distilled from K,)$C_6H_5)_2CO$] was added dropwise over 20 minutes 10.00 g (73.5 mmol, Aldrich) of p-anisaldehyde. The mixture was stirred at room temperature for 16 hours, then heated to reflux for 16 hours. TLC showed that the reaction had not gone to completion. A second portion of 1.22 g (3.7 mmol) of methyl (triphenylphosphoranylidene)acetate was added; after stirring 3 hours, the reaction was complete. The reaction mixture was concentrated in vacuo to give a white solid, which was triturated with 200 mL hexane, cooled to 0° and filtered. The filtrate was concentrated in vacuo to give a crude beige solid, which was flash chromatographed (Merck silica, 4:1 hexane:ethyl acetate) to give 12.05 g (62.7 mmol, 85%) of title alkene as a white solid.

B 4-Methoxybenzenepropanoic acid, methyl ester

To a portion of 50 mL glacial acetic acid, purged with argon, was added 12.05 g of 10% Pd/C (Aldrich) followed by a solution of 12.05 g (62.7 mmol) of Part A alkene in 40 mL glacial $CH_3COOH$. The reaction vessel was evacuated and purged with $H_2$ three times, then the reaction mixture was stirred under $H_2$ (1 atm) for 48 hours. The mixture was filtered through a polycarbonate filter; the filtrate was concentrated in vacuo and azeotroped three times with toluene to give a crude liquid. The crude liquid was flash chromatographed (Merck silica, 6:1 hexane/ethyl acetate) to give 9.05 g (46.6 mmol, 74%) of title ester as a clear liquid.

C. 4-Methoxybenzenepropanol

To a slurry of 3.15 g (83.0 mmol, Aldrich) of lithium aluminum hydride in 100 mL dry ether (distilled from Na, $(C_6H_5)_2CO$), stirred at 0°, was added dropwise over 30 minutes a solution of 8.96 g (46.1 mmol) of Part B ester in 75 mL dry ether. The mixture was stirred at room temperature for 16 hours, cooled to 0°, then quenched by successive dropwise addition of 3.1 mL $H_2O$, 3.1 mL 15% NaOH and 9.4 mL $H_2O$. The reaction mixture was stirred at 0° for 1 hour, then filtered; the filtrate was concentrated in vacuo to give 6.90 g (41.5 mmol, 90%) of crude title alcohol as a clear liquid.

D. 4-Methoxybenzenepropanol, methanesulfonate ester

To a solution of 6.90 g (41.5 mmol) of Part C alcohol and 8.7 mL (62.3 mmol, Aldrich) of triethylamine in 150 mL dry $CH_2Cl_2$ (distilled from $P_2O_5$), stirring at −20°, was added dropwise over 15 minutes a solution of 3.9 mL (49.8 mmol, Aldrich) of methanesulfonyl chloride in 20 mL dry $CH_2Cl_2$. The reaction mixture was stirred at 0° for 15 minutes, then washed with 300 mL 1M HCl. The water layer was separated and extracted 2 times with 100 mL CH&hd 2Cl2; the combined $CH_2Cl_2$ layers were washed with 200 mL saturated $NaHCO_3$, dried ($MgSO_4$) and concentrated in vacuo to give 7.48 g (41.5 mmol, 100%) of title mesylate as a clear liquid.

E 4-Methoxybenzenebutanenitrile

To a solution of 7.48 g (41.5 mmol) of Part D mesylate in 100 mL dry DMSO (Burdick & Jackson) was added 4.05 g (62.3 mmol, Aldrich) of potassium cyanide in four portions. The reaction mixture was stirred at 80° for 2 hours, then added to 600 mL water/600 mL ether. The ether layer was separated, washed 3 times with 200 mL water, then 200 mL saturated NaCl solution, dried ($MgSO_4$) and concentrated in vacuo to give a crude liquid. The crude liquid was flash chromatographed (Merck silica, 1:4 ethyl acetate/hexane) then distilled (150°, ~/mm) to give 6.26 g (35.7 mmol, 86%) of title nitrile as a pale yellow liquid.

F. 4-Methoxybenzenebutanamine

To a slurry of 1.63 g (43.0 mmol, Aldrich) of lithium aluminum hydride in 50 mL dry ether (distilled from Na $(C_6H_5)_2CO$), stirring at 0°, was added dropwise over 20 minutes a solution of Part E nitrile in 10 mL dry ether. The reaction mixture was stirred at room temperature for 2 hours, during which it separated into two layers, then quenched by the dropwise addition of 1.6 mL $H_2O$, 1.6 mL 15% NaOH and 4.9 mL $H_2O$. The reaction mixture was stirred at 0° for 1 hour to give a white paste; the paste was extracted 4 times with 100 mL ether. The combined ether layers were concentrated in vacuo to give a clear oil, which was triturated with 200 mL ether to give a white precipitate. The mixture was filtered to give 580 mg of product; the mother liquor was concentrated in vacuo to give 2.86 g of product giving a total of 3.44 g (19.2 mmol, 80%) of title amine as a white solid.

G.

[1S-(1α,2α,3α,4α)]-2-[[3-[4-[[[4-(4-Methoxyphenyl)-butyl]amino]carbonyl]-2-oxazolyl]-7-oxabicyclo[2.2.1-]hept-2-yl]-methyl]benzenepropanoic acid, methyl ester To a solution of 200 mg (0.52 mmol) of acid prepared in Example 2, Part J in 20 mL dry $CH_2Cl_2$ (distilled from $P_2O_5$) was added 1 small drop of DMF, followed by 310 μL (2M/$CH_2Cl_2$, 0.63 mmol, Aldrich) of oxalyl chloride in 5 mL dry $CH_2Cl_2$. The reaction was stirred until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$), cooled to 0°, was added 120 μL (0.83 mmol, distilled from $CaH_2$) of triethylamine, followed by the dropwise addition of a solution of 112 mg (0.62 mmol) of Part F amine in 5 mL $CH_2Cl_2$. The reaction was stirred at 0° for hours, then partitioned between 150 mL ethyl acetate/75 mL 1M HCl. The organic layer was separated, dried ($MgSO_4$) and concentrated in vacuo to give a crude orange solid. The crude solid was flash chromatographed (Merck silica, 1:1 ethyl acetate/hexane) to give 230 mg (0.42 mmol, 81%) of title ester as a white solid.

EXAMPLE 47

[1S-(1α,2α,3α,4α)]-2-[[3-[4-[[[4-(4-Methoxyphenyl)-butyl]amino]carbonyl]-2-oxazolyl]-7-oxabicyclo[2.2.1-]hept-2-yl]methyl]benzenepropanoic acid To a mixture of 210 mg (0.38 mmol) of Example 46 ester in 8 mL distilled THF/2 mL water was added 32 mg (0.77 mmol, Aldrich) of lithium hydroxide monohydrate. The reaction was stirred vigorously for 3 hours, then quenched by the addition of 1.54 mL (1.54 mmol) 1M HCl. The mixture was partitioned between 40 mL ethyl acetate/30 mL water. The early acetate layer was dried ($MgSO_4$) and concentrated in vacuo to give a crude white solid. The crude solid was recrystallized from hot ethyl acetate/hexane to give 165 mg (0.31 mmol, 81%) of title acid as a white solid, mp 125°–127°.

IR (KBr): 3406, 2936, 1724, 1644, 1603, 1512 cm$^{-1}$.
MS(CI): 533 (M+H)$^+$.
OR: $[\alpha]_D = +14.3°$ (c=1.0 in methanol)
TLC: $R_f$ (silica gel, 1:9 methanol/methylene chloride)=0.31, ammonium molybdate/ceric sulfate and UV, homogeneous.
Analysis Calc'd for $C_{31}H_{36}N_2O_6$: C, 69.90; H, 6.81; N, 5.26 Found: C, 69.61; H, 6.71; N, 5.25

EXAMPLE 48

[1S-(1α,2α,3α,4α)]-2-[[3-[4-[[(4-Cyclohexyl-2-butenyl)amino]carbonyl]-2-oxazolyl]-7-oxabicyclo[2.2.1]hept-2-yl]methyl]benzenepropanoic acid, methyl ester To stirred mixture of acid prepared as described in Example 2, Part J (520 mg, 1.35 mmol) in 50 mL of dry $CH_2Cl_2$ under argon was added 2 drops of DMF and 2 M solution of oxalyl chloride in $CH_2Cl_2$ (0.82 mL, 1.62 mmol). This mixture was stirred at 0° C. for 15 minutes and 1 hour at room temperature. The mixture was concentrated in vacuo and diluted with 20 mL of dry $CH_2Cl_2$. To this stirred mixture at 0° C. under argon was added a solution of 4-cyclohexyl-2-butenylamine hydrochloride salt (307 mg, 1.62 mmol, preparation was completed by: 1. oxidation of 2-cyclohexylethyl alcohol to 2-cyclohexylacetaldehyde with PCC; 2. condensation of 2-cyclohexylacetaldehyde with methyl (triphenylphosphoranylidene)acetate; 3. DIBAL-H reduction of the ester at −78° C. to give the alcohol; 4. conversion of the alcohol to amine with diisopropylazodicarboxylate (DIAD) and phthalimide, followed by the treatment of anhydrous hydrazine at room temperature overnight and refluxing in $CH_3OH$) and $(C_2H_5)_3N$ (0.75 mL, 5.40 mmol) in 10 mL of dry $CH_2Cl_2$ over 10 minutes. The mixture was stirred at 0° C. for 30 minutes and at room temperature for 1 hour. The mixture was diluted with 300 mL of EtOAc and washed with 1N HCl solution (1×100 mL). The aqueous layer was extracted with EtOAc (2×100 mL). The combined EtOAc extracts were dried ($MgSO_4$), filtered and concentrated in vacuo. Purification was effected by flash chromatography on 45 g of Merck silica gel 60 using 1:1 hexane-EtOAc as eluant to give 520 mg (74%) of title ester.

TLC: silica gel, EtOAc, $R_f$ 0.90, Ce(SO$_4$)$_2$.
$^{13}$C of title ester (CDCl$_3$, 67.5 MHz): δ 173.7, 163.7, 160.2, 140.6, 138.4, 137.7, 136.0, 132.4, 129.6, 128.9, 126.6, 126.4, 126.2, 79.6, 78.5, 51.5, 49.9, 46.9, 40.9, 40.1, 37.7, 34.8, 33.0, 33.0, 32.3, 29.8, 28.8, 27.5, 26.4, 26.2, 26.2.

EXAMPLE 49

[1S-(1α,2α,3α(E),4α)]-2-[[3-[4-[[(4-Cyclohexyl-2-butenyl)amino]carbonyl]-2-oxazolyl]-7-oxabicyclo[2.2.1]hept-2-yl]methyl]benzenepropanoic acid To a stirred mixture of Example 48 ester (510 mg, 0.98 mmol) in 20 mL of freshly distilled THF and 5 mL of water was added LiOH monohydrate (123 mg, 2.94 mmol). The mixture was stirred at room temperature for 2 hours at which time additional LiOH monohydrate (41 mg, 0.98 mmol) was added. The mixture was stirred at room temperature for 1.5 hours and acidified to pH 2 by the addition of 1N HCl solution. The mixture was diluted with 20 mL of water and extracted with EtOAc (4×60 mL). The combined EtOAc extracts were dried ($MgSO_4$), filtered and concentrated in vacuo. This was recrystallized in 300 mL of 3:2 hexane-EtOAc at room temperature to give 410 mg (81%) of pure title acid.

TLC: silica gel, 6% $CH_3OH/CH_2Cl_2$, $R_f$ 0.50, Ce(SO$_4$)$_2$.
$^{13}$C of title acid (CDCl$_3$—CD$_3$OD, 67.5 MHz): δ 174.3, 163.8, 160.5, 140.1, 137.9, 136.7, 135.0, 131.3, 128.5, 129.1, 125.7, 125.5, 125.3, 79.5, 78.4, 40.0, 39.4, 37.0, 34.0, 32.2, 32.2, 31.5, 28.5, 27.9, 26.8, 25.6, 25.4, 25.4.

EXAMPLE 50

[1S-(1α,2α,3α,4α)]-2-[[3-[4-[[(4-Cyclohexylidenebutyl)amino]carbonyl]-2-oxazolyl]-7-oxabicyclo[2.2.1]hept-2-yl]methyl]benzenepropanoic acid, methyl ester To a stirred solution of acid prepared as described in Example 2, Part J (500 mg, 1.30 mmol) in 50 mL of dry $CH_2Cl_2$ under argon at 0° was added one drop of DMF and then added 2M solution of oxalyl chloride in $CH_2Cl_2$ (0.78 mL, 1.56 mmol). The mixture was stirred at 0° C. for 30 minutes and at room temperature for one hour. The mixture was concentrated in vacuo and diluted with 30 mL of dry $CH_2Cl_2$. To this stirred mixture was added a solution of 4-cyclohexylidenebutanamine (238 mg, 1.56 mmol) (preparation of the above amine completed by 1. condensation of cyclohexanone with 4-carboxylbutyltriphenyl phosphonium bromide. 2. conversion of acid to amide through acid chloride and ammonium hydroxide. 3. reduction of amide to amine with lithium aluminum hydride) and $(C_2H_5)_3N$ (0.36 mL, 2.6 mmol) in 10 mL of dry $CH_2Cl_2$. This mixture was stirred at 0° C. for one hour and poured into a mixture of 100 mL of EtOAc and 70 mL of 1N (aq) HCl solution. The aqueous layer was separated and extracted with EtOAc (1×50 mL). The combined organic extracts were dried ($MgSO_4$), filtered and concentrated in vacuo. Purification was effected by flash chromatography on 50 g of Merck silica gel 60 using 1:1 hexane:EtOAc as eluant to give 540 mg (80%) of title ester TLC: silica gel, EtOAc, $R_f$ 0.90, $Ce(SO_4)_2$.

$^{13}C$ NMR title ester (67.5 MHz, $CDCL_3$): δ 173.0, 163.7, 160.5, 140.5, 138.5, 137.8, 136.1, 129.5, 128.9, 126.6, 126.4, 120.0, 79.6, 78.6, 51.5, 50.0, 46.9, 38.6, 37.1, 34.8, 32.3, 29.9, 28.8, 28.6, 28.6, 27.7, 27.6, 26.8, 24.4.

EXAMPLE 51

[1S-(1α,2α,3α,4α)]-2-[[3-[4-[[(4-Cyclohexylidenebutyl)amino]carbonyl]-2-oxazolyl]-7-oxabicyclo[2.2.1]hept-2-yl]methyl]benzenepropanoic acid To a stirred solution of Example 50 ester (530 mg, 1.02 mmol) in 20 mL of freshly distilled THF and 5.0 mL of $H_2O$ under argon was added $LiOH.H_2O$ (68 mg, 2.04 mmol). The mixture was stirred at room temperature for 1.5 hours at which time $LiOH.H_2O$ (43 mg, 1.02 mmol) was added. The reaction mixture was stirred at room temperature for 3 hours and acidified at 0° C. to pH 2 by the addition of 1N HCl solution. The mixture was diluted with 15 mL of $H_2O$ and extracted with EtOAc (4×50 mL). The combined EtOAc extracts were washed once with 30 mL of brine, dried ($MgSO_4$), filtered and concentrated in vacuo. This was recrystallized in 120 mL of 3:2 hexane:EtOAc at room temperature to give 399 mg (77%) of pure title acid, mp 144°–147°.

TLC: silica gel, 6% $CH_3OH/CH_2Cl_2$, $R_f$ 0.50, $Ce(SO_4)_2$. $^{13}C$ NMR title acid (67.5 MHz, $CD_3OD$): δ 176.6, 166.4, 142.4, 141.8, 140.4, 139.2, 137.5, 130.4, 127.9, 127.8, 121.7, 81.9, 80.8, 51.1, 50.3, 40.2, 38.5, 36.2, 33.7, 31.1, 30.7, 30.1, 29.9, 29.2, 29.1, 28.3, 25.8.

EXAMPLE 51a

[1S-(1α,2α,3α,4α)]-3-[4-[[(4-Cyclohexylbutyl)amino]carbonyl]-2-oxazolyl]-7-oxabicyclo[2.2.1]-heptane-2-hexanoic acid A solution of 130 mg of Example 1 acid in 10 mL of ethyl acetate and 1.0 mL of acetic acid was degassed via a vacuum-fill cycle with argon. To this solution was added 34 mg of 10% Pd/C and the atmosphere was exchanged for hydrogen by two vacuum-fill cycles. A slight positive pressure was maintained through use of a hydrogen balloon. The mixture was stirred at room temperature for 22.5 hours, diluted with $CH_2Cl_2$ and filtered through a polycarbonate filter to remove the catalyst. The filtrate was concentrated in vacuo. The residue was diluted with toluene and reconcentrated. Upon addition of ethyl acetate to the residue, a small amount of gel-like material did not dissolve. The solution was decanted off and concentrated in vacuo. The crude product was dissolved in minimal hot ethyl acetate and diluted with ca. three volumes of hexane. On cooling no solid appeared, however, after standing at 5° C. overnight a white gel-like solid formed. This was removed by filtration and dried in vacuo. The resulting white powder was triturated in hexane, filtered and dried in vacuo to afford 61 mg of pure title acid; m.p. 97(softens), 122°–3° C.

Analysis Calc'd for $C_{26}H_{40}N_2O_5$: C, 67.79; H, 8.75; N, 6.08 Found: C, 67.58; H, 8.79; N, 5.97

TLC: silica gel, 4% $CH_3OH/CH_2Cl_2$, $R_f$=0.35, $Ce(SO_4)_2$.

$[\alpha]_D$= +23 (c=0.68, $CHCl_3$).

$^{13}C$ NMR ($CDCl_3$, 67.5 MHz): δ 164.2, 160.8, 140.7, 135.9, 79.5, 79.4, 49.8, 47.2, 39.2, 37.5, 37.1, 33.7, 33.4, 29.9, 29.7, 29.2, 29.0, 28.1, 26.7, 26.4, 24.5, 24.2.

EXAMPLE 52

[1S-(1α,2α,3α,4α)]-2-[[3-[4-[(Heptylamino)carbonyl]-2-oxazolyl]-7-oxabicyclo[2.2.1]hept-2-yl]methyl]benzenepropanoic acid, methyl ester To a solution of 200 mg (0.52 mmol) of acid prepared in Example 2, Part J in 20 mL dry $CH_2Cl_2$ (distilled from $P_2O_5$) was added 1 small drop of DMF, followed by 310 μL (0.63 mmol, 2M/$CH_2Cl_2$, Aldrich) of oxalyl chloride. The reaction was stirred until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$), cooled to 0°, was added 120 μL (0.83 mmol, distilled from $CaH_2$) of triethylamine, followed by the dropwise addition of a solution of 92 μL (0.62 mmol, Aldrich) of heptylamine in 5 mL $CH_2Cl_2$. The reaction was stirred at 0° for 1.5 hours, then partitioned between 150 mL ethyl acetate/75 mL 1M HCl. The ethyl acetate layer was separated, dried ($MgSO_4$) and concentrated in vacuo to give a crude orange solid. The crude solid was flash chromatographed (Merck silica, 2:1 ethyl acetate:hexane) to give 190 mg (0.39 mmol, 76%) of title ester as a white solid.

EXAMPLE 53

[1S-(1α,2α,3α,4α)]-2-[[3-[4-[(Heptylamino)carbonyl]-2-oxazolyl]-7-oxabicyclo[2.2.1]hept-2-yl]methyl]benzenepropanoic acid To a mixture of 180 mg (0.37 mmol) of Example 52 ester in 8 mL distilled THF/2mL water was added 31 mg (0.75 mmol, Aldrich) of lithium hydroxide monohydrate. The reaction was stirred vigorously for 3 hours, then quenched by the addition of 1.49 mL (1.49 mmol) 1M HCl. The mixture was partitioned between 40 mL ethyl acetate/30 mL water. The ethyl acetate layer was separated, dried ($MgSO_4$) and concentrated in vacuo to give a crude white solid. The crude solid was recrystallized from hot ethyl acetate/hexane to give 146 mg (0.31 mmol, 84%) of title acid as a white solid, mp 134°–137°.

IR (KBr): 3390, 3301, 2927, 1708, 1647, 1606, 1517 $cm^{-1}$.

MS(CI): 469 $(M+H)^+$.

OR: $[\alpha]_D$= +16.7° (c=1.0 in methanol)

TLC: $R_f$(silica gel, 1:9 methanol/methylene chloride)=0.34, ammonium molybdate/ceric sulfate and UV, homogeneous.

Analysis Calc'd for $C_{27}H_{36}N_2O_5$: C, 69.20; H, 7.74; N, 5.98 Found: C, 68.87; H, 7.72; N, 5.93

EXAMPLE 54

]1S-(1α,2α,3α,4α)]-2-[2-[3-[4-[[(4-Cyclohexylbutyl)amino]carbonyl]-2-oxazolyl]-7-oxabicyclo[2.2.1]hept-2-yl]ethyl]benzeneacetic acid, methyl ester

A.
2-[2-[[Dimethyl(1,1,2-trimethylpropyl)silyl]oxy]ethyl]benzene bromide

2-Bromophenethyl alcohol (43.80 g, 217.9 mmol) was dissolved in anhydrous $CH_2Cl_2$ (200 mL) and imidazole (16.32 g, 239.6 mmol) was added and stirred under argon 0° C. Dimethylthexylsilyl chloride (42.83 g, 239.6 mmol) was added dropwise and the reaction mixture was stirred for three days at room temperature. It was diluted with $H_2O$ (50 mL) and ether (100 mL) and partitioned. The aqueous layer was extracted with ether (2×100 mL). The combined organic layers were washed with 5% aqueous HCl (1 time), $H_2O$ (1 time), aqueous $NaHCO_3$ (1 time), $H_2O$ (1 time), and brine, then dried ($MgSO_4$) and concentrated in vacuo to obtain a yellow oil. The crude product was Kugelrohr distilled (55°–80°) under oil pump vacuum to give the purified title compound.

B.
[1S-(1α,2α,3α,4α)]-α-[2-[2-[[Dimethyl(1,1,2-trimethylpropyl)silyl]oxy]ethyl]phenyl]-3-(hydroxymethyl)-7-oxabicyclo[2.2.1]heptane-2-ethanol To a solution of Part A compound (6.05 g, 17.6 mmol) under argon in anhydrous ether (25 mL) at −78° was added t-butyllithium (18.6 mL, 1.70 M solution in pentane) over fifteen minutes at −78° C., then 30 minutes at 0° C. The reaction solution was cooled to −78° C. and anhydrous THF (20 mL) was added. [4aR-(4aα,5β,8β,8aβ)]-Octahydro-5,8-epoxy-1H-2-benzopyran-3-ol (1.18 g, 6.93 mmol) dissolved in anhydrous THF (10 mL) was added dropwise and stirred for fifteen minutes at −78° C. A white precipitate formed. The reaction mixture was then warmed to 0° C. for one hour and quenched with water (100 mL). The aqueous mixture was extracted with EtOAc (2 times) and the combined extracts were dried ($MgSO_4$), filtered and concentrated in vacuo to give a yellow oil. The crude product was chromatographed on a silica gel column and eluted with 30-60% EtOAc in hexane to obtain title compound (2.35 g, 78%) as a viscous, pale, yellow oil.

C.
[1S-(1α,2α,3α,4α)]-2-[1-(Acetyloxy)-2-[3-[(acetyloxy)methyl]-7-oxabicyclo[2.2.1]hept-2-yl]ethyl]benezeneacetic acid, methyl ester To Part B compound (2.35 g, 5.41 mmol) in pyridine (2.4 mL) under argon at 0° C. was added acetic anhydride (1.66 g, 16.2 mmol) over ten minutes. The mixture was stirred at 0° C. for one hour, then at room temperature for sixteen hours. The reaction mixture was diluted with ether (125 mL) and washed with 1N aqueous HCl (3×50 mL). The ether layer was dried ($MgSO_4$), filtered and concentrated in vacuo. The residue which contained [1S-(1α,2α,3α,4α)]-α-[2-[2-[[dimethyl(1,1,2-trimethylpropyl)silyl]oxy]ethyl]phenyl]-3-[(acetyloxy)methyl]-7-oxabicyclo[2.2.1]heptane-2-ethanol, acetate ester, was dissolved in acetone (40 mL) and treated with Jones Reagent until the orange color persisted. The reaction mixture was stirred for four hours at room temperature, then quenched with excess isopropyl alcohol (IPA), concentrated in vacuo and partitioned between water (50 mL) and EtOAc (4×20 mL). The combined organic layers were washed with $H_2O$, dried ($MgSO_4$), filtered and concentrated in vacuo. The residue was dissolved in ether (50 mL) and treated with excess ethereal diazomethane at room temperature for one hour. A white precipitate was removed by filtration and the filtrate was concentrated in vacuo and chromatographed on a silica gel column and eluted with 20–30% EtOAc-hexane to give title compound (1.79 g, 82%) as a viscous, colorless oil.

D.
[1S-(1α,2α,3α,4α)]-2-[2-[3-[(Acetyloxy)methyl]-7-oxabicyclo[2.2.1]hept-2-yl]ethyl]benzeneacetic acid, methyl ester To a stirred solution of Part C compound (1.79 g, 4.43 mmol) in methyl acetate (35 mL) under argon was added 70% aqueous $HClO_4$ (0.83 mL) and 10% Pd/C (0.18 g). The atmosphere was replaced with $H_2$ using an $H_2$ filled balloon by several vacuumfill cycles. The reaction mixture was stirred vigorously for eight hours before the catalyst was filtered off through a bed of anhydrous $MgSO_4$. The solids were rinsed well with EtOAc. The filtrate was washed with dilute aqueous HCl. The aqueous layer was extracted with EtOAc (3 times) and the combined organic layers were dried ($MgSO_4$), filtered and concentrated in vacuo. The crude oil was chromatographed on a silica gel column and eluted with 20–25% EtOAc in hexane to obtain title compound (1.06 g, 69%) as a viscous, colorless oil.

E.
[1S-(1α,2α,3α,4α)]-2-[2-[3-(Hydroxymethyl)-7-oxabicyclo[2.2.1]hept-2-yl]ethyl]benzeneacetic acid, methyl ester To a stirred solution of Part D compound (1.05 g, 3.03 mmol) in $CH_3OH$ (30 mL) under argon at 0° C. was added potassium t-butoxide (0.37 g, 3.33 mmol). The mixture was stirred at 0° C. for fifteen minutes then at room temperature for two hours. The reaction mixture was then concentrated and partitioned between 0.1 N aqueous HCl and ether (4×50 mL). The combined extracts were dried ($MgSO_4$), filtered and concentrated. The crude oil was dissolved in ether treated with excess diazomethane (to re-esterify any hydrolyzed ester), concentrated and chromatographed on a silica gel column and eluted with 50% EtOAc in hexane to obtain title compound (0.77 g, 84%) as a viscous, colorless oil.

F.
[1S-(1α,2α,3α,4α)]-2-[2-[3-Carboxy-7-oxabicyclo[2.2.1]hept-2-yl]ethyl]benzeneacetic acid, methyl ester To Part E compound (0.73 g, 2.40 mmol) in acetone (20 mL) at 0° C. under argon was treated with Jones Reagent until the orange color persisted. The reaction mixture was stirred while warming to room temperature. Forty minutes after the ice bath was removed the excess Jones Reagent was destroyed by the addition of IPA. After concentration the reaction mixture was partitioned between 3M aqueous $NaHSO_3$ and EtOAc (3 times). The combined organic layers were dried ($MgSO_4$), filtered and concentrated to obtain title compound (0.75 g, 99%) as a viscous colorless liquid.

G.

[1S-(1α,2α,3α,4α]-2-[2-[3-[[[2-[(4-Cyclohexylbutyl)amino]-1-(hydroxymethyl)-2-oxoethyl]amino]carbonyl]-7-oxabicyclo[2.2.1]hept-2-yl]ethyl]benzeneacetic acid, methyl ester Part F compound (0.37 g, 1.16 mmol), 1-hydroxybenzotriazole hydrate (0.20 g, 1.16 mmol), the hydrochloride salt of N-(4-cyclohexylbutyl)-L-serinamide (0.32 g, 1.16 mmol) and DMF were combined under argon at 0° C. Triethylamine (0.25 g, 34.9 mmol) was added and stirred for five minutes. 1-(3-Dimethylaminopropyl)-3-ethylcarbodiimide hydrochloride (0.23 g, 1.16 mmol) was added and the reaction mixture was stirred for sixteen hours while warming to room temperature. The DMF was removed under reduced pressure and the residue was dissolved in EtOAc, washed with 1N aqueous HCl (2 times), dilute aqueous NaOH (2 times) and saturated aqueous KHCO$_3$. The organic layer was dried (MgSO$_4$), filtered and concentrated. The crude white solid was chromatographed on a silica gel column and eluted with 2-4% CH$_3$OH in CH$_2$Cl$_2$ to obtain title compound (0.52 g, 83%) as a white solid.

H.

[1S-(1α,2α,3α,4α)]-2-[2-[3-[4-[[(4-Cyclohexylbutyl)amino]carbonyl]-4,5-dihydro-2-oxazolyl]-7-oxabicyclo[2.2.1]hept-2-yl]ethyl]benzeneacetic acid, methyl ester To a stirred solution of Part G compound (0.52 g, 0.96 mmol) and N,N-diisopropylethylamine (0.37 g, 2.87 mmol) in CH$_2$Cl$_2$ (25 mL) at 0° C. under argon was added methanesulfonyl chloride (0.11 g, 0.96 mmol) and stirred for one hour while warming to room temperature. Additional methanesulfonyl chloride (0.03 g, 0.26 mmol) was added and stirring was continued for an additional one hour. The reaction solution was concentrated and the residue was diluted with acetone (25 mL). Finely powdered K$_2$CO$_3$ (0.40, 2.28 mmol) was added and the reaction mixture was cooled to room temperature, filtered and concentrated. The crude yellow solid was chromatographed on a silica gel column and eluted with 50-100% EtOAc in hexane to obtain title compound (0.41 g, 82%) as a white solid.

I.

[1S-(1α,2α,3α,4α)]-2-[2-[3-[4-[[(4-Cyclohexylbutyl)amino]carbonyl]-2-oxazolyl]-7-oxabicyclo[2.2.1]hept-2-yl]ethyl]benzeneacetic acid To copper (II) bromide (0.27 g, 1.20 mmol) in EtOAc (3 mL) was added DBU (0.35 g, 2.29 mmol) and stirred for 30 minutes at room temperature. Part H compound (0.30 g, 0.57 mmol) dissolved in CHCl$_3$ (3 mL) was added dropwise and stirred for 48 hours at room temperature. The reaction solution was then poured into a 1:1 aqueous NH$_4$Cl:NH$_4$OH mixture and extracted with EtOAc (2 times). The combined organic extracts were dried (MgSO$_4$), filtered and concentrated. The crude oil was chromatographed on silica gel column and eluted with 20-60% EtOAc in hexane to obtain title ester (0.21 g, 70%) as a white foam.

EXAMPLE 55

[1S-(1α,2α,3α,4α)]-2-[2-[3-[4-[[(4-Cyclohexylbutyl)amino]carbonyl]-2-oxazolyl]-7-oxabicyclo[2.2.1]hept-2-yl]ethyl]benzeneacetic acid To Example 54 (0.21 g, 0.40 mmol) in H$_2$O (2 mL) and THF (8 mL) was added lithium hydroxide monohydrate (0.051 g, 1.21 mmol) and stirred vigorously for six hours at room temperature. The reaction was cooled to 0° C. and acidified to pH 2.0 with 1N aqueous HCl. The acidified reaction mixture was extracted with EtOAc (4 times) and the combined organic layers were washed with brine, dried (MgSO$_4$), filtered and concentrated. The crude white solid was chromatographed on a silica gel column and eluted with 50-60% EtOAc in hexane with 0.25% CH$_3$COOH added to obtain title acid (0.18 g, 90%) as a white solid.

EXAMPLE 56

[1S-(1α,2α,3α,4α)]-3-[2-[3-[4-[[(4-Cyclohexylbutyl)amino]carbonyl]-2-oxazolyl]-7-oxabicyclo[2.2.1]hept-2-yl]ethyl]benzeneacetic acid, methyl ester

A.

3-[2-[[Dimethyl(1,1,2-trimethylpropyl)silyl]oxy]ethyl]benzene bromide

3-Bromophenethyl alcohol (46.0 g, 228.78 mmol) was combined with dimethylaminopyridine (6.99 g, 57.19 mmol) and triethylamine (34.73 g, 343.17 mmol) in anhydrous CH$_2$Cl$_2$ (200 mL) and cooled to 0° C. Dimethylhexylsilyl chloride (44.18 g, 247.08 mmol) was added dropwise over ten minutes, then the reaction mixture was warmed to room temperature and stirred for sixteen hours. The reaction mixture was diluted with hexane (800 mL) and filtered. The filtrate was concentrated and the residue was partitioned between ether (800 mL) and 0.3N aqueous HCl (2 times with 400 mL), saturated aqueous NaHCO$_3$ (400 mL), dried (MgSO$_4$) and concentrated. The crude liquid was chromatographed on a silica gel column and eluted with 20% ether in hexane to give title compound (74.45 g, 95%) as a clear liquid.

B.

[1S-(1α,2α,3α,4α)]-α-[3-[2-[[Dimethyl(1,1,2-trimethylpropyl)silyl]oxy]ethyl]phenyl]-3-(hydroxymethyl)-7-oxabicyclo[2.2.1]heptane-2-ethanol To a solution of Part A compound (4.84 g, 14.1 mmol) under argon in anhydrous ether (30 mL) at −78° was added t-butyllithium (14.9 mL, 1.70 M solution in pentane) over fifteen minutes at −78° C., then 30 minutes at 0° C. The reaction solution was cooled to −78° C. and anhydrous THF (20 mL) was added. (endo)-Octahydro-5,8-epoxy-1H-benzopyran-3-ol (1.0 g, 5.88 mmol) dissolved in anhydrous THF (10 mL) was added dropwise and stirred for fifteen minutes at −78° C. A white precipitate formed. The reaction mixture was then warmed to 0° C. for one hour and quenched with water (100 mL). The aqueous mixture was extracted with EtOAc (2 times) and the combined extracts were dried (MgSO$_4$), filtered and concentrated to give a yellow oil. The crude product was chromatographed on a silica gel column and eluted with 50-80% EtOAc in hexane to obtain title compound (2.11 g 82%) as a viscous, pale, yellow oil.

C.

[1S-(1α,2α,3α,4α)]-3-[1-(Acetyloxy)-2-[3l-[(acetyloxy)methyl]-7-oxabicyclo[2.2.1]hept-2-yl]ethyl]benzeneacetic acid, methyl ester To Part B compound (3.65 g, 8.40 mmol) in pyridine (4.07 mL) under argon at 0° C. was added acetic anhydride (2.57 g, 25.2 mmol) over ten minutes. The mixture was stirred at 0° C. for one hour, then at room temperature for sixteen hours. The reaction mixture was diluted with ether (200 ml) and washed with 1N aqueous HCl (3 times with 50 mL). The ether layer was dried (MgSO$_4$), filtered and concentrated. The residue was dissolved in acetone (60 mL) and treated with Jones Reagent until the orange color persisted. The reaction mixture was stirred for four hours at room temperature, then quenched with excess IPA, concentrated and partitioned between water (70 mL) and EtOAc (4 times with 50 mL). The combined organic layers were washed with H$_2$O, dried (MgSO$_4$), filtered and concentrated. The residue was dissolved in ether (70 mL) and treated with excess ethereal diazomethane at room temperature for one hour. A white precipitate was removed by filtration and the filtrate was concentrated and chromatographed on a silica gel column and eluted with 20–30% EtOAc-hexane to give title compound (2.99 g, 88%) as a viscous, colorless oil.

D.
[1S-(1α,2α,3α,4α)]-3-[2-[3-[(Acetyloxy)methyl]-7-oxabicyclo[2.2.1]hept-2-yl]ethyl]benzeneacetic acid, methyl ester To a stirred solution of Part C compound (2.99 g, 7.39 mmol) in methyl acetate (55 mL) under argon was added 70% aqueous HClO$_4$ (1.40 mL) and 10% Pd/C (0.30 g). The atmosphere was replaced with H$_2$ using an H$_2$ filled balloon by several vacuum-fill cycles. The reaction mixture was stirred vigorously for four hours before the catalyst was filtered off through a bed of anhydrous MgSO$_4$. The solids were rinsed well with EtOAc. The filtrate was washed with aqueous KHCO$_3$. The aqueous layer was extracted with EtOAc (2 times) and the combined organic layers were dried (MgSO$_4$), filtered and concentrated. The crude oil was chromatographed on a silica gel column and eluted with 10–20% EtOAc in hexane to obtain title compound (1.83 g, 72%) as a viscous, colorless oil.

E.
[1S-(1α,2α,3α,4α)]-3-[2-[3-(Hydroxymethyl)-7-oxabicyclo[2.2.1]hept-2-yl]ethyl]benzeneacetic acid, methyl ester To a stirred solution of Part D compound (1.83 g, 5.31 mmol) in CH$_3$OH (50 mL) under argon at 0° C. was added potassium t-butoxide (0.66 g, 5.84 mmol). The mixture was stirred at 0° C. for fifteen minutes then at room temperature for two hours. The reaction mixture was then concentrated and partitioned between 0.1N aqueous HCl and ether (4 times with 50 mL). The combined extracts were dried (MgSO$_4$), filtered and concentrated. The crude oil was dissolved in ether treated with excess diazomethane (to re-esterify any hydrolyzed ester), concentrated and chromatographed on a silica gel column and eluted with 50% EtOAc in hexane to obtain title compound (1.16 g, 72%) as a viscous, colorless oil.

F.
[1S-(1α,2α,3α,4α)]-3-[2-[3-Carboxy-7-oxabicyclo[2.2.1]hept-2-yl]ethyl]benzeneacetic acid, methyl ester Part E compound (0.51 g, 1.68 mmol) in acetate (20 mL) at 0° C. under argon was treated with Jones Reagent until the orange color persisted. The reaction mixture was stirred while warming to room temperature. Forty minutes after the ice bath was removed the excess Jones Reagent was destroyed by the addition of IPA. After concentration, the reaction mixture was partitioned between 3M aqueous NaHSO$_3$ and EtOAc (3 times). The combined organic layers were dried (MgSO$_4$), filtered and concentrated to obtain title compound (0.54 g, 100%) as a viscous, colorless liquid.

G.
[1S-(1α,2α,3α,4α)]-3-[2-[3-[[[2-[(4-Cyclohexylbutyl)amino]-1-(hydroxymethyl)-2-oxoethyl]amino]carbonyl]-7-oxabicyclo[2.2.1]hept-2-yl]ethyl]benzeneacetic acid, methyl ester Part F compound (0.30 g, 0.94 mmol), 1-hydroxybenzotriazole hydrate (0.13 g, 0.94 mmol) the hydrochloride salt of N-(4-cyclohexylbutyl)-L-serinamide (0.26 g, 0.94 mmol) and DMF were combined under argon at 0° C. Triethylamine (0.29 g, 2.83 mmol) was added and stirred for five minutes. 1-(3-Dimethylaminopropyl)-3-ethylcarbodiimide hydrochloride (0.18 g, 0.94 mmol) was added and the reaction mixture was stirred for sixteen hours while warming to room temperature. The DMF was removed under reduced pressure and the residue was dissolved in EtOAc, washed with 1N aqueous HCl (2 times), dilute aqueous NaOH (2 times) and saturated aqueous KHCO$_3$. The organic layer was dried (MgSO$_4$), filtered and concentrated. The crude white solid was chromatographed on a silica gel column and eluted with 2–4% CH$_3$OH in CH$_2$Cl$_2$ to obtain title compound (0.46 g, 86%) as a white solid.

H.
[1S-(1α,2α,3α,4α)]-3-[2-[3-[4-[[(4-Cyclohexylbutyl)amino]carbonyl]-4,5-dihydro-2-oxazolyl]-7-oxabicyclo[2.2.1]hept-2-yl]ethyl]benzeneacetic acid, methyl ester To a stirred solution of Part G compound (0.44 g, 0.81 mmol) and N,N-diisopropylethylamine (0.31 g, 2.43 mmol) in CH$_2$Cl$_2$ (25 mL) at 0° C. under argon was added methanesulfonyl chloride (0.093 g, 0.81 mmol) and stirred for one hour while warming to room temperature. The reaction solution was concentrated and the residue was diluted with acetone (25 mL). Finely powdered K$_2$CO$_3$ (0.34 g, 2.43 mmol) was added and the reaction mixture was cooled at room temperature, filtered and concentrated. The crude yellow solid was chromatographed on silica gel column and eluted with 50–100% EtOAc in hexane to obtain title compound (0.41 g, 95%) as a white solid.

I.
[1S-(1α,2α,3α,4α)]-3-[2-[3-[4-[[(4-Cyclohexylbutyl)amino]carbonyl]-2-oxazolyl]-7-oxabicyclo[2.2.1]hept-2-yl]ethyl]benzeneacetic acid, methyl ester To copper (II) bromide (0.34 g, 1.52 mmol) in EtOAc (3 mL) was added DBU (0.44 g, 2.90 mmol) and stirred for 30 minutes at room temperature. Part H compound (0.38 g, 0.72 mmol) dissolved in CHCl$_3$ (3 mL) was added dropwise and stirred for 48 hours at room temperature. The reaction solution was then poured into a 1:1 aqueous NH$_4$Cl:NH$_4$OH mixture and extracted with EtOAc (2 times). The combined organic extracts were dried (MgSO$_4$), filtered and concentrated. The crude oil was chromatographed on a silica gel column and eluted with 20–50% EtOAc in hexane to obtain title ester (0.21 g, 55%) as a white foam.

EXAMPLE 57

[1S-(1α,2α,3α,4α)]-3-[2-[3-[4-[[(4-Cyclohexylbutyl)amino]carbonyl]-2-oxazolyl]-7-oxabicyclo[2.2.1]hept-2-yl]ethyl]benzeneacetic acid To Example 56 ester (0.21 g, 0.40 mmol) in H$_2$O (2 mL) and THF (8 mL) was added lithium hydroxide monohydrate (0.051 g, 1.20 mmol) and stirred vigorously for six hours at room temperature. The reaction mixture was cooled to 0° C. and acidified to pH 2.0 with 1N aqueous HCl. The acidified reaction mixture was extracted with EtOAc (4 times) and the combined organic layers were washed with brine, dried (MgSO$_4$), filtered and concentrated. The crude white solid was chromatographed on a silica gel column and eluted with 50% EtOAc in hexane with 0.25% CH$_3$COOH added to obtain title acid (0.20 g, 99%) as a white solid.

EXAMPLE 58

[1S-(1α,2α,3α,4α)]-2-[2-[3-[4-[[(4-Cyclohexylbutyl)amino]carbonyl]-2-oxazolyl]-7-oxabicyclo[2.2.1]hept-2-yl]ethyl]benzenepropanoic acid, methyl ester

A.

[1S-(1α,2α,3α,4α)]-2-[2-[2-[3-[[Dimethyl(1,1,2-trimethylpropyl)silyl]oxy]propyl]phenyl]ethanol]-7-oxabicyclo[2.2.1]heptane-3-methanol To a solution of [3-(2-bromophenyl)propyl]dimethyl(1,1,2-trimethylpropyl)silyl ether (6.61 g, 17.8 mmol) in 40 mL dry diethyl ether (Et$_2$O) maintained at −78° C. was added 18.4 mL of a 1.7M solution of t-C$_4$H$_9$Li in pentane over a 25 minute period; the reaction was then stirred for an additional 15 minutes at −78° C. and then allowed to come to 0° C. and stirred for 3 minutes. The reaction mixture was then cooled to −78° C. and 25 mL of dry THF was added followed by a solution of octahydro 5,8-epoxy-1H-2-benzopyran-3-ol (1.25 g, 7.3 mmol) in 15 mL of dry THF; the mixture was allowed to stir at −78° C. for an additional 15 minutes and then warmed to 0° C. for 1 hour. The reaction was quenched with 3 mL of H$_2$O, and then poured into H$_2$O and extracted twice with EtOAc. The organic layers were combined, dried over anhydrous MgSO$_4$, filtered, and concentrated in vacuo to leave an oil. The crude product was purified by flash chromatography on 800 mL of LPS-1 silica gel using 1:1 hexane/EtOAc and then EtOAc as the eluent. Isolation of product afforded 2.98 g (90%) of title compound in the form of a clear oil.

[α]$_D$= +0.27° (c=22.3, CHCl$_3$)

TLC system 1:1 hexane/EtOAc (UV and Ce(SO$_4$)$_2$ detection) R$_f$ title compound: 0.12.

B.

[1S-(1α,2α,3α,4α)]-2-[2-[2-[3-[[Dimethyl(1,1,2-trimethylpropyl)silyl]oxy]propyl]phenyl]ethyl]-7-oxabicyclo[2.2.1]heptane-3-methanol A solution of Part A compound (2.8 g, 6.3 mmol) and 20% Pd(OH)$_2$ on carbon (moist <50% H$_2$O; 0.91 g, 33 wt %) in 70 mL of glacial acetic acid was stirred vigorously under an atmosphere of hydrogen (balloon) at room temperature. After 24 hours reaction was still not complete, and an additional 15 weight percent of catalyst was added. After an additional 24 hours the reaction was complete, and the mixture was filtered and concentrated in vacuo. The residue was taken up in EtOAc and washed twice with 1N NaOH followed by brine, dried over anhydrous MgSO$_4$, filtered, and concentrated in vacuo to yield 2.74 g of a colorless liquid.

The crude product was flash chromatographed on 400 mL of LPS-1 silica gel using 3:1 hexane/EtOAc for 3 L and then 1:1 hexane/EtOAc for 1 L. Removal of solvents afforded 2.00 g of title compound (77%).

[α]$_D$= +9.28 (c=1.94, CHCl$_3$)

TLC system: 2:1 EtOAc/Hexane, R$_f$ title compound: 0.4 (UV and Ce(SO$_4$)$_2$ detection).

C.

[1S-(1α,2α,3α,4α)]-2-[2-[3-(Hydroxymethyl)-7-oxabicyclo[2.2.1]hept-2-yl]ethyl]benzenepropanoic acid, methyl ester A solution of the Part B compound (2.21 g, 5.11 mmol) in 13 mL of 1:1 pyridine-acetic anhydride was treated with N,N-dimethylamino pyridine (DMAP) (0.12 g, 0.98 mmol) and then stirred at room temperature for 3 hours. The reaction mixture was then concentrated in vacuo and the residue partitioned between EtOAc and 1N HCl. The organic layer was separated and washed with 1N NaOH followed by brine, dried over anhydrous MgSO$_4$, filtered, and concentrated in vacuo to yield a yellow liquid.

A solution of the crude acetate in 35 mL of reagent grade acetone was chilled to 0° C. and treated with Jones Reagent (2.6M in Cr$^{+6}$, 7 mL). The solution was stirred at room temperature for 2 hours, then 3 mL of isopropyl alcohol (IPA) was added and the solution was allowed to stir for 30 minutes. The green slurry was filtered through a Celite pad and concentrated in vacuo. The residue was partitioned between H$_2$O and Et$_2$O. The organic layer was separated and dried over anhydrous MgSO$_4$, filtered, and concentrated in vacuo to yield 3.0 g of a colorless oil.

The crude acid-acetate was stirred at room temperature in 60 mL of a 1:2 solution of THF-1N NaOH for 3 hours. The reaction was cooled to 0° C. and quenched with 30 mL of 1N HCL, and then extracted four times with Et$_2$O. The ethereal layers were combined and dried over anhydrous MgSO$_4$, filtered, and concentrated in vacuo to yield 2.47 g of a yellowish liquid.

The crude acid-alcohol was stirred at 0° C. in 23 mL of acidic methanol (prepared by the addition of 1.1 mL of acetyl chloride to dry methanol at 0° C.), for 2 hours. The solution was concentrated in vacuo to yield 1.47 g of a brown oil. The crude alcohol-ester was flash chromatographed on 200 mL of LPS-1 silica gel using EtOAc as the eluent. Removal of solvents in vacuo left 1.1 g (67%) of title compound in the form of a tannish oil.

[α]$_D$= +17.0 (c=2.00, CHCl$_3$)

TLC system EtOAc R$_f$ title compound: 0.45 (UV and Ce(SO$_4$)$_2$ detection)

D.

[1S-(1α,2α,3α,4α)]-2-[2-[3-(Carboxy)-7-oxabicyclo[2.2.1]hept-2-yl]ethyl]benzenepropanoic acid, methyl ester A solution of Part C compound (1.21 g, 3.8 mmol) in 12 mL of reagent acetone was chilled to 0° C. and treated with Jones Reagent (2.6M in Cr$^{+6}$, 4.7 mL), and then stirred at room temperature for 2 hours. Then 2.5 mL of IPA was added and the reaction was left to stir for an additional 15 minutes. The resulting green slurry was filtered through a Celite pad and then partitioned between H$_2$O and Et$_2$O. The aqueous layer was separated and then washed with another portion of Et$_2$O. The organic layers were combined, dried over anhydrous MgSO$_4$, filtered, and concentrated in vacuo to yield 1.2 g (95%) of title compound in the form of a greenish-yellow liquid.

$[\alpha]_D = +153.6$ (c=7.26, CHCl$_3$)

TLC system EtOAc; R$_f$ title compound: 0.39 (UV and Ce(SO$_4$)$_2$ detection).

E.

[1S-(1α,2α,3α,4α)]-2-[2-[3-[[[1-(Hydroxymethyl)-2-(amino-4-cyclohexylbutyl)-2-oxoethyl]amino]carbonyl]-7-oxabicyclo[2.2.1]hept-2-yl]ethyl]benzenepropanoic acid, methyl ester A solution of Part D ester (0.85 g, 2.56 mmol), 1-hydroxybenzotriazole hydrate (HOBt.H$_2$O) (0.43 g, 2.55 mmol) and [1-aminoethane-2-ol][4-cyclohexylamino]carbonyl hydrochloride (0.71 g, 2.55 mmol) in 18 mL of dry DMF (stirred over 4 A sieves) was cooled to 0° C. and triethylamine (0.80 g, 7.89 mmol) was added. The solution was stirred at 0° C. until dissolution was complete and then WSC (0.49 g, 2.55 mmol) was added, and the solution was warmed to room temperature and stirred overnight. The DMF was removed in vacuo and the residue was dissolved in EtOAc. The solution was washed twice with 1N HCl, once with 1N NaOH and once with brine, dried over anhydrous MgSO$_4$, filtered, and concentrated in vacuo to yield 1.21 g of an off-white solid. The crude product was chromatographed on 250 mL of LPS-1 silica gel using EtOAc as the mobile phase. Removal of solvents in vacuo left 0.34 g of title compound in the form of a white solid.

$[\alpha]_D = -0.16$ (c=0.69, CHCl$_3$)

TLC system: 4% CH$_3$OH/CH$_2$Cl$_2$ R$_f$ title compound: 0.21 (UV and Ce(SO$_4$)$_2$ detection).

F.

[1S-(1α,2α,3α,4α)]-2-[2-[3-[4,5-Dihydro-4-[(4-cyclohexylbutyl)amino]carbonyl]-2-oxazolin]-7-oxabicyclo[2.2.1]hept-2-yl]ethyl]benzenepropanoic acid, methyl ester To a stirred solution of Part E compound (0.38 g, 0.68 mmol) and N,N-diisopropyl ethyl amine (0.36 mL, 2.1 mmol) in 18 mL of dry CH$_2$Cl$_2$ (distilled over P$_2$O$_5$) was added methanesulfonyl chloride (0.053 mL, 0.68 mmol). After one hour the solution was concentrated in vacuo and the residue was dissolved in 8 mL of reagent acetone; the solution was then treated with K$_2$CO$_3$ (0.28 g, 2.0 mmol), and the solution was then heated to reflux. After four hours the solution was filtered, the solids washed with reagent acetone and solvents removed in vacuo to yield a colorless oil. The oil was purified by flash chromatography on 100 mL of LPS-1 silica gel using 1% CH$_3$OH in CH$_2$Cl$_2$; removal of solvents in vacuo left 0.34 g (92%) of title compound in the form of a yellowish oil.

$[\alpha]_D = 167.4$ (c=0.95, CHCl$_3$)

TLC system 4% CH$_3$OH/CH$_2$Cl$_2$ R$_f$ title compound: 0.40 (UV and Ce(SO$_4$)$_2$ detection).

G.

[1S-(1α,2α,3α,4α)]-2-[2-[3-[4-[[(4-Cyclohexylbutyl)amino]carbonyl]-2-oxazolyl]-7-oxabicyclo[2.2.1]hept-2-yl]ethyl]benzenepropanoic acid, methyl ester A solution of CuBr$_2$ (0.23 g, 1.03 mmol) in 3 mL of EtOAc was treated with DBU (0.29 mL, 1.93 mmol) and let stir at room temperature for 45 minutes. Next a solution of Part F compound (0.26 g, 0.48 mmol) in 3 mL of CHCl$_3$ was added and the reaction mixture was stirred at room temperature. After 24 hours additional DBU (0.29 mL, 1.93 mmol) and CuBr$_2$ (0.23 g, 1.03 mmol) was added and the solution allowed to stir at room temperature for an additional 48 hours. The reaction mixture was diluted with CHCl$_3$ and washed twice with a 1:1 NH$_4$OH/NH$_4$Cl solution; the organic layer was dried over anhydrous MgSO$_4$, filtered, and concentrated in vacuo to leave a reddish residue. The residue was purified by flash chromatography on 100 mL of LPS-1 silica gel using 2:1 hexane/EtOAc as the mobile phase. Removal of solvents in vacuo left 0.101 g (40%) of title compound in the form of a colorless oil.

$[\alpha]_D = +36.8$ (c=0.19, CHCl$_3$)

TLC system 2:1 Hexane/EtOAc R$_f$ title compound: 0.10 (UV and Ce(SO$_4$)$_2$ detection).

EXAMPLE 59

[1S-(1α,2α,3α,4α)]-2-[-2-[3-[4-[[(4-Cyclohexylbutyl)amino]carbonyl]-2-oxazolyl]-7-oxabicyclo[2.2.1]hept-2-yl]ethyl]benzenepropanoic acid A solution of Example 58 ester (0.0971 g, 0.18 mmol) in 5 mL of 4:1 THF/H$_2$O was treated with LiOH.H$_2$O (0.0234 g, 0.56 mmol) and then stirred at room temperature for 3.5 hours. The reaction mixture was then cooled to 0° C. and acidified to pH=2 with 1N HCl, and then poured on to H$_2$O and extracted four times with EtOAc. The organic layers were combined, washed with brine, dried over anhydrous MgSO$_4$, filtered, and concentrated in vacuo to yield 0.0844 g (89%) of title acid as a clear oil.

$^{13}$C NMR; CDCl$_3$: 24.2, 26.4, 26.7, 27.3, 29.2, 29.6, 29.8, 31.3, 33.3, 35.1, 37.0, 37.5, 39.2, 47.2, 49.4, 79.5, 79.6, 126.4, 126.6, 128.8, 129.3, 135.9, 137.8, 139.0, 141.0, 160.7, 164.0, 177.1.

TLC system: 0.25% CH$_3$COOH in EtOAc R$_f$ title acid: 0.32 (UV and Ce(SO$_4$)$_2$ detection).

EXAMPLE 60

[1S-(1α,2α,3α,4α)-2-[[3-[4-[[(4-Cyclohexylbutyl)amino]carbonyl]-2-oxazolyl]-7-oxabicyclo[2.2.1]hept-2-yl]methyl]benzoic acid, methyl ester

A.

[1S-(1α,2α,3α,4α)]-α-[2-(4,5-Dihydro-4,4-dimethyl-2-oxazolyl)phenyl]-7-oxabicyclo[2.2.1]heptane-2,3-dimethanol (Product A) and

[1S-(1α,2α,3α,4α)]-2-[4',4'-Dimethylspiro[isobenzofuran-1(3H),2'-oxazolidin-2-yl]]-7-oxabicyclo[2.2.1]heptane-3-methanol (Product B)

To a stirred solution of 4,5-dihydro-4,4-dimethyl-2-phenyloxazole in 70 mL of dry THF (7.22 g, 41.3 mmol, preparation is described by A. I. Meyers et al, in J. Org. Chem., 39, 2787 (1974)) at −45° C. under argon was added 2.5M n-C$_4$H$_9$Li/hexane (15.4 mL, 38.5 mmol) dropwise over 10 minutes. The mixture was stirred at −45° C. for 3.5 hours at which time (endo)octahydro-4,7-epoxyisobenzofuran-1-ol (2.15 g, 13.8 mmol) was added in one portion. This mixture was stirred at −45° C. for 1 hour and at room temperature for 15.5 hours. To a stirred saturated NH$_4$Cl solution (40 mL) was added slowly 25 mL of the above reaction mixture, which was then extracted with EtOAc (4×50 mL). The EtOAc extracts were dried (MgSO$_4$), filtered and concentrated in vacuo to give crude product A. The remaining reaction mixture was quenched by the addition of saturated NaHCO$_3$ solution and partitioned between 100 mL of saturated NaHCO$_3$ solution and EtOAc (4×120 mL). The combined EtOAc extracts were dried (MgSO$_4$), filtered and concentrated in vacuo to give crude product B. The products A and B have an identical TLC. These two products were combined and chromatographed on 180 g of Merck silica gel 60 using 1.5 L of each of 1% and 2% CH$_3$OH in CH$_2$Cl$_2$ as eluant to give title Product A (2.26 g, 45%) and (secondary Product B) (2.19 g, 44%).

TLC: silica gel, 4% CH$_3$OH in CH$_2$Cl$_2$, R$_f$ title Product A, 0.38; Product B, 0.44; (Ce(SO$_4$)$_2$).

$^{13}$C NMR title Product A (67.5 MHz, CDCl$_3$) δ 161.5, 145.4, 131.3, 130.4, 126.9, 126.4, 124.9, 79.5, 78.1, 77.9, 68.2, 61.9, 50.7, 49.9, 30.0, 29.3, 28.5, 28.1.

$^{13}$C NMR secondary Product B (67.5 MHz, CDCl$_3$): δ 143.2, 131.7, 127.6 80.7, 79.5, 79.1, 68.0, 62.8, 51.5, 29.8, 29.6, 28.1.

B.

[1S-(1α,2α,3α,4α)]-2-[1,3-Dihydro-3-oxo-1-isobenzofuranyl]-7-oxabicyclo[2.2.1]heptane-3-methanol To a stirred mixture of Part A diol (1.26 g, 3.81 mmol) in 5 mL of THF was added 25 mL of 5% (aqueous) oxalic acid solution. This homogeneous mixture was stirred vigorously at room temperature for 75 hours and diluted with 200 mL of saturated NaHCO$_3$ solution. This mixture was extracted with EtOAc (4×250 mL). The combined EtOAc extracts were dried (MgSO$_4$), filtered and concentrated in vacuo to give 0.91 g (98%) of title lactone.

TLC: silica gel, 4% CH$_3$OH in CH$_2$Cl$_2$, R$_f$ 0.40, Ce(-SO$_4$)$_2$.

$^{13}$C NMR title lactone (67.5 MHz, CDCl$_3$): δ 170.4, 149.8, 134.3, 129.2, 126.3, 125.6, 121.9, 79.3, 78.7, 75.6, 62.2, 49.9, 49.8, 30.4, 28.7.

C.

[1S-(1α,2α,3α,4α)]-2-[[3-(Hydroxymethyl)-7-oxabicyclo[2.2.1]hept-2-yl]methyl]benzoic acid, methyl ester To a stirred solution of Part B lactone (980 mg, 4.02 mmol) in 18 mL of glacial acetic acid under argon was added 1.00 g of 20% Pd(OH)$_2$ on carbon. The atmosphere was replaced with hydrogen by several vacuum-fill cycles. The reaction mixture was stirred vigorously for 4 days. The mixture was filtered through a 2" pad of Celite and the pad was rinsed with acetic acid (HOAc) (3×30 mL). The filtrate was concentrated in vacuo. This crude acid was dissolved in 100 mL of CH$_3$OH. To this stirred mixture was then added 1 mL of acetyl chloride (AcCl). The mixture was stirred at room temperature for 16 hours and concentrated in vacuo. This was chromatographed on 45 g of Merck silica gel 60 using hexane-EtOAc 2:3 as eluant to give 490 mg of title ester and 200 mg of acid. The acid was again dissolved in 60 mL of CH$_3$OH and treated with 0.5 mL of acetyl chloride. The mixture was stirred at room temperature for 16 hours and concentrated in vacuo. The crude product was chromatographed on 25 g of Merck silica gel 60 using hexane-EtOAc 2:3 as eluant to give 80 mg of title ester. The total yield was 570 mg (51%).

TLC: silica gel, 4% CH$_3$OH in CH$_2$Cl$_2$, R$_f$ 0.50, Ce(-SO$_4$)$_2$.

NOTE: The azaorthoester Part A secondary product was also hydrolyzed to lactone in 89% yield. But this lactone failed to react under the hydrogenation conditions.

$^{13}$C NMR title ester (67.5 MHz, CDCl$_3$): δ 167.7, 143.8, 132.0, 131.7, 131.2, 128.9, 126.1, 79.3, 79.1, 61.8, 51.9, 49.5, 47.9, 33.0, 29.7, 29.2.

D.

[1S-(1α,2α,3α,4α)]-2-[[3-[[[2-[(4-Cyclohexylbutyl)amino]-1-(hydroxymethyl)-2-oxoethyl]amino]carbonyl]-7-oxabicyclo[2.2.1]hept-2-yl]methyl]benzoic acid methyl ester To a stirred solution of Part C ester (560 mg, 2.03 mmol) in 50 mL of acetone at 0° C. under argon was added MnSO$_4$ treated Jones reagent (about 100 mg MnSO$_4$ dissolved in 100 mL of Jones reagent) until an orange red color persisted. The mixture was stirred at 0° C. for 20 minutes and at room temperature for 30 minutes. The mixture was quenched with isopropyl alcohol (IPA) and concentrated in vacuo. The crude acid was partitioned between 50 mL of 3M (aqueous) NaHSO$_3$ solution and EtOAc (4×70 mL). The combined EtOAc extracts were dried (MgSO$_4$), filtered and concentrated in vacuo to give 577 mg (98%) of the desired acid. To a stirred mixture of acid (490 mg, 1.69 mmol), 1-hydroxybenzotriazole.H$_2$O (290 mg, 1.69 mmol) and N-(4-cyclohexylbutyl)serinamide (4.09 mg, 1.69 mmol) in 15 mL of DMF at 0° C. under argon was added (C$_2$H$_5$)$_3$N (0.47 mL, 3.38 mmol). To this mixture was then added ethyl-3(3-dimethylamino)propyl carbodiimide (324 mg, 1.69 mmol). The reaction mixture was stirred at room temperature for 10 hours and concentrated in vacuo. The crude product was dissolved in 300 mL of EtOAc and washed with 0.2N NaOH solution (2×60 mL), 1N HCl solution (2×60 mL) and saturated NaHCO$_3$ solution (1×60 mL). The EtOAc layer was dried (MgSO$_4$), filtered and concentrated in vacuo. Purification was effected by flash chromatography on 60 g of Merck silica gel 60 using 2% CH$_3$OH in CH$_2$Cl$_2$ as eluant to give 0.73 g (84%) of title alcohol.

TLC: silica gel, 4% CH$_3$OH in CH$_2$Cl$_2$, R$_f$ 0.44, Ce(-SO$_4$)$_2$.

$^{13}$C NMR title alcohol (67.5 MHz, CDCl$_3$): δ 172.9, 170.8, 167.7, 142 6, 132.2, 131.9, 131.3, 129.0, 126.5, 79.1, 78.0 62.8, 54.6, 53.6, 52.1, 49.5, 39.5, 37.4, 36.9, 34.6, 33.2, 33.2, 29.7, 29.3, 28.9, 26.6, 26.3, 26.3, 24.1.

E.

[1S-(1α,2α,3α,4α)]-2-[[3-[4-[[(4-Cyclohexylbutyl)amino]carbonyl]-4,5-dihydro-2-oxazolyl]-7-oxabicyclo[2.2.1]hept-2-yl]methyl]benzoic acid, methyl ester To a stirred solution of Part D alcohol (730 mg, 1.42 mmol) and diisopropyl ethyl amine (0.74 mL, 4.26 mmol) in 30 mL of dry CH$_2$Cl$_2$ under argon at 0° C. was added methanesulfonyl chloride (MsCl) (0.13 mL, 1.70 mmol). This mixture was stirred at 0° C. for 30 minutes and at room temperature for 1 hour. The mixture was concentrated in vacuo and diluted with 30 mL of acetone. To this mixture was added K$_2$CO$_3$ (589 mg, 4.26 mmol). The reaction mixture was refluxed for 4 hours and cooled to room temperature. The precipitate was filtered off and rinsed with acetone (4×30 mL). The filtrate was concentrated in vacuo and chromatographed on 35 g of Merck silica gel 60 using hexane-EtOAc 1:2 as eluant to give 680 mg (97%) of title oxazoline.

TLC: silica gel, EtOAc, R$_f$ 0.31, Ce(SO$_4$)$_2$.

$^{13}$C NMR title oxazoline (22.5 MHz, CDCl$_3$): δ 171,6, 169.7, 142.7, 132.2, 132.2, 131.4, 126.5, 78.8, 77.8, 70.5, 68.3, 51.9, 49.7, 47.1, 39.1, 37.3, 37.0, 34.5, 33.2, 33.2, 29.7, 28.6, 26.6, 26.2, 26.2, 24.0.

F.
[1S-(1α,2α,3α,4α)-2-[[3-[4-[[(4-Cyclohexylbutyl)amino]carbonyl]-2-oxazolyl]-7-oxabicyclo[2.2.1]hept-2-yl]methyl]benzoic acid, methyl ester To a stirred solution of Part E oxazoline (680 mg, 1.37 mmol) in 15 mL of dry $CH_2Cl_2$ was added 1.32 g of $NiO_2$. The reaction mixture was stirred vigorously at room temperature for 1 hour at which time 680 mg of $NiO_2$ was added. The reaction mixture was stirred at room temperature for 2 hours and again 680 mg of $NiO_2$ was added. The mixture was stirred at room temperature for 2.5 hours and one more portion of 340 mg of $NiO_2$ was added. The mixture was stirred at room temperature for one more hour and then diluted with 120 mL of EtOAc, 30 mL of 3M $NaHSO_3$ solution and 40 mL of 1M sodium citrate solution. The mixture was stirred vigorously until all solids dissolved. The mixture was extracted with EtOAc (4×100 mL). The combined EtOAc extracts were dried ($MgSO_4$), filtered and concentrated in vacuo. This was chromatographed on 24 g of Merck silica gel 60 using hexane-EtOAc 2:1 as eluant to give 380 mg (56%) of title oxazole.

TLC: silica gel, EtOAc, $R_f$ 0.82, $Ce(SO_4)_2$.

$^{13}C$ NMR title oxazole (67.5 MHz, $CDCL_3$): δ 167.6, 164.0, 160.6, 142.1, 140.6, 136.1, 132.0, 131.9, 131.3, 129.3, 126.4, 79.7, 78.4, 51.9, 50.4, 47.2, 39.1, 37.5, 37.1, 35.0, 33.3, 33.3, 29.9, 29.8, 28.9, 26.7, 26.3, 26.3, 24.2.

EXAMPLE 61

[1S-(1α,2α,3α,4α)-2-[[3-[4-[[(Cyclohexylbutyl)amino]carbonyl]-2-oxazolyl]-7-oxabicyclo[2.2.1]hept-2-yl]methyl]benzoic acid To a stirred solution of Example 60 oxazole (103 mg, 0.21 mmol) in 2 mL of $CH_3OH$ and 2 mL of THF was added 0.5 mL of 1N NaOH solution. The mixture was stirred at room temperature for 3 hours at which time 0.5 mL of 1N NaOH solution was added. This mixture was stirred at room temperature for 2 hours. To this mixture was added 83 mg of solid NaOH. The mixture was stirred at room temperature for 2.5 hours at which time 70 mg of solid NaOH was added. The reaction mixture was stirred at room temperature for 15 hours and concentrated in vacuo. The crude acid was partitioned between 30 mL of 1N HCl solution (saturated with KCl) and EtOAc (4×40 mL). The combined EtOAc extracts were dried ($MgSO_4$), filtered and concentrated in vacuo. Purification was effected by flash chromatography on 12 g of Merck silica gel 60 using 4% $CH_3OH/CH_2Cl_2$ as eluant to give 62.5 mg (62%) of pure title acid.

TLC: silica gel, 6% $CH_3OH/CH_2Cl_2$, $R_f$ 0.50, $Ce(SO_4)_2$).

$^{13}C$ NMR title acid (67.5 MHz, $CDCl_3$): δ 164.5, 161.6, 145.3, 142.9, 142.5, 140.9, 135.6, 131.9, 131.9, 126.5, 79.7, 78.4, 50.9, 47.3, 39.4, 37.5, 37.1, 35.6, 33.3, 33.3, 29.8, 28.7, 26.7, 26.4, 26.4, 24.2.

EXAMPLE 62

[1S-(1α,2α,3α,4α)]-2-[[3-[4-[(Decylamino)carbonyl]-2-oxazolyl]-7-oxabicyclo[2.2.1]hept-2-yl]methyl]benzenepropanoic acid, methyl ester To a solution of 200 mg (0.52 mMol) of acid prepared in Example 2, Part J in 20 mL dry $CH_2Cl_2$ (distilled from $P_2O_5$) was added 1 small drop of DMF, followed by 310 μL (0.63 mMol, 2M/$CH_2Cl_2$, Aldrich) of oxalyl chloride solution. The reaction was stirred until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$ cooled to 0°, was added 120 μL (0.83 mMol, distilled from $CaH_2$) of triethylamine, followed by the dropwise addition of a solution of 98 mg (0.62 mMol, Aldrich) of n-decylamine in 5 mL $CH_2Cl_2$. The reaction was stirred at 0° for 16 hours, then partitioned between 80 mL ethyl acetate/60 mL 1M HCl. The ethyl acetate layer was separated, dried ($MgSO_4$) and concentrated in vacuo to give a crude yellow solid. The crude solid was flash chromatographed (Merck silica gel, 2:1 ethyl acetate/hexane) to give 210 mg (0.40 mMol, 77%) of title ester as a white solid.

EXAMPLE 63

[1S-(1α,2α,3α,4α)]-2-[[3-4-[(Decaylamino)carbonyl]-2-oxazolyl]-7-oxabicyclo[2.2.1]hept-2-yl]methyl]benzenepropanoic acid To a mixture of 210 mg (0.40 mMol) of Example 62 ester in 8 mL distilled THF/2 mL water was added 34 mg (0.80 mMol, Aldrich) of lithium hydroxide monohydrate. The reaction was stirred vigorously for 4 hours, then quenched by the addition of 1.6 mL (1.6 mMol) 1M HCl. The mixture was partitioned between 40 mL ethyl acetate/40 mL water. The ethyl acetate layer was separated, dried ($MgSO_4$) and concentrated in vacuo to give 196 mg (0.38 mMol, 96%) of title acid, SQ 34,607, as a white solid, mp 145°-147°.

IR (KBr): 3413, 3130, 2926, 2854, 1709, 1649, 1604, 1518 $cm^{-1}$.

MS(CI): 511 (M-H)+.

OR: $[\alpha]_D = +16.1°$ (c=1.0 in chloroform).

TLC: $R_f$ (silica gel, ethyl acetate)=0.15, ammonium molybdate/ceric sulfate and UV, homogeneous.

Analysis Calc'd for $C_{30}H_{42}N_2O_5 + 0.10\ H_2O$: C, 70.31; H, 8.30; N, 5.47
Found: C, 70.46; H, 8.48; N, 5.38

EXAMPLE 64

[1S-(1α,2α,3α,4α)]-2-[[3-[[(4-Cyclohexylbutyl)amino]carbonyl]-2-oxazolyl]-7-oxabicyclo[2.2.1]hept-2-yl]methyl]benzeneacetic acid A.
[1S-(1α,2α,3α,4α)]-α-2-[2-[[Dimethyl(1,1,2-trimethylpropyl)silyl]oxy]ethyl]phenyl]-7-oxabicyclo[2.2.1]heptane-2,3-dimethanol To a stirred mixture of Mg turning (4.67 g, 192 mmol) and few crystals of iodine in 50 mL of dry THF at 65° C. under argon was added about 5% of a solution of Example 54, Part A bromide (16.5 g, 48.1 mmol) in 30 mL of dry THF. This mixture was heated at 65° C. for 20 minutes at which time the iodine color had dispersed. The remaining 95% of the bromide solution was added dropwise over 20 minutes. The mixture was heated at 65° C. for 1 hour and cooled to 0° C. To a stirred mixture of (endo)-octahydro-4,7-epoxyisobenzofuran-1-ol hemiacetal (5.00 g, 32.1 mmol) in 40 mL of dry THF under argon at 0° C. was added 2.0 M solution of $C_2H_5MgBr$ in THF (14.4 mL, 28.8 mmol). This mixture was stirred at 0° C. for 10 mintues at which time the above precooled (0° C.) Grignard solution was added dropwise over 10 minutes. The reaction mixture was stirred at room temperature for 22 hours and was quenched by the addition of a solution of 10 g of $NH_4Cl$ in 35 mL of H$_2$O. This mixture was then combined with 250 g of anhydrous Na$_2$SO$_4$ and diluted with 300 mL of CH$_2$Cl$_2$. The solid was filtered off and rinsed with CH$_2$Cl$_2$ (4×60 mL). The filtrate was concentrated in vacuo and partitioned between 300 mL of saturated NH$_4$Cl solution and EtOAc (4×400 mL). The EtOAc extracts were dried (MgSO$_4$), filtered and concentrated in vacuo. Purification was effected by flash chromatography on 240 g of Merck silica gel 60 using 1.2 L each of 1%, 2%, and 3% CH$_3$OH in CH$_2$Cl$_2$ as eluant to give 11.9 g (91%) of the title diol.

TLC: silica gel, 4% CH$_3$OH/CH$_2$Cl$_2$, R$_f$ 0.42, Ce(SO$_4$)$_2$.

B.
[1S-(1α,2α,3α,4α)]-2-[[3-[(Acetyloxy)methyl]-7-oxabicyclo[2.2.1]hept-2-yl]methyl]benzeneethanol To a stirred mixture of Part A diol (11.8 g, 28.1 mmol) in 180 mL of acetic acid under argon was added 20% Pd(OH)$_2$/C (2.4 g, 20% based on the weight of Part A diol). The atmosphere was replaced with hydrogen and the mixture was stirred at room temperature for 24 hours. The catalyst was filtered off and rinsed with EtOAc (4×100 mL). The filtrate was diluted with 0.5 L of benzene and concentrated in vacuo to give the crude alcohol. To a stirred mixture of this alcohol in 9.3 mL of pyridine at 0° C. under argon was added acetic anhydride (4.08 mL, 43.2 mmol) over 5 minutes. The mixture was stirred at room temperature for 16 hours and diluted with 700 mL of ether. The mixture was washed with 1N HCl solution (2×175 mL), saturated NaHCO$_3$ solution (2×150 mL) and brine (1×120 mL). The organic layer was dried (MgSO$_4$), filtered and concentrated in vacuo to give crude acetate. To a stirred mixture of this acetate in 11 mL of dry THF under argon at room temperature was added 1M solution of (n-C$_4$H$_9$)$_4$NF in THF (25 mL, 25 mmol) over 10 minutes. This mixture was stirred at room temperature for 17 hours and diluted with 400 mL of EtOAc. The mixture was then washed with 1N HCl solution (3×60 mL), saturated NaHCO$_3$ solution (1×60 mL) and brine (1×100 mL). The organic layer was dried (MgSO$_4$), filtered and concentrated in vacuo. Purification was effected by flash chromatography on 160 g of Merck silica gel 60 using 2% CH$_3$OH in CH$_2$Cl$_2$ as eluant to give 5.5 g (68%) of the title acetate alcohol.

TLC: silica gel, 4% CH$_3$OH/CH$_2$Cl$_2$, R$_f$ 0.48, Ce(SO$_4$)$_2$.

C.
(1S-(1α,2α,3α,4α)]-2-[[3-[(Acetyloxy)methyl]-7-oxabicyclo2.2.1]hept-2-yl]methyl]-benzeneacetic acid, methyl ester To a stirred mixture of Part B acetate alcohol (3.80 g, 13.2 mmol) in 60 mL of dry CH$_2$Cl$_2$ was added Dess-Martin oxidant (6.48 g, 14.5 mmol). This heterogeneous mixture was stirred at room temperature for 3 hours and diluted with a solution of 100 mL of ether and 60 mL of saturated NaHCO$_3$ solution. To this mixture was added 5 g of sodium thiosulfate. The mixture was stirred at room temperature for 5 minutes. The aqueous layer was separated and extracted with ether (4×100 mL). The combined organic extracts were washed once with 60 mL of brine, dried (MgSO$_4$), filtered and concentrated in vacuo. The crude product was loaded on a 4" pad of Merck silica gel 60 in a 600 mL of fritted glass funnel and eluted with 250 mL of 4% CH$_3$OH in CH$_2$Cl$_2$ to give 3.69 g (98%) of pure aldehyde.

TLC: silica gel, 4% CH$_3$OH in CH$_2$Cl$_2$, R$_f$ 0.74, Ce(SO$_4$)$_2$.

To a stirred mixture of aldehyde (3.68 g 12.9 mmol) in 129 mL of B & J CH$_3$OH was added N-iodosuccinimide (7.24 g, 32.2 mmol), followed by the immediate addition of K$_2$CO$_3$ (4.45 g, 32.2 mmol). This mixture was stirred in the dark at room temperature for 70 minutes and filtered through a 2" pad of Celite. The Celite pad was rinsed with CH$_3$OH (3×40 mL). The filtrate was concentrated in vacuo and diluted with 400 mL of EtOAc. The resulting EtOAc solution was washed in 1N HCl solution (2×30 mL), saturated sodium thiosulfate solution (2×50 mL) and brine (1×50 mL). The organic layer was dried (MgSO$_4$), filtered and concentrated in vacuo. This was chromatographed on 120 g of Merck silica gel 60 using 1.4 L each of 2:1 and 1:1 hexane-ether as eluants to give 2.30 g (57%) of title ester.

TLC: silic gel, 1:1 hexane-ether, R$_f$ 0.44, Ce(SO$_4$)$_2$.

D.
[1S-(1α,2α,3α,4α)]-2-[[3-(Carboxymethyl)-7-oxabicyclo[2.2.1]hept-2-yl]methyl]benzeneacetic acid, methyl ester To a stirred mixture of Part C ester (2.27 g, 6.83 mmol) in 60 mL of B & J CH$_3$OH under argon was added anhydrous K$_2$CO$_3$ (0.199 g, 1.37 mmol). This mixture was stirred vigorously at room temperature for 2 hours at which time 0.03 g of anhydrous K$_2$CO$_3$ was added. The mixture was stirred at room temperature for 1.5 hours and concentrated in vacuo to about 5 mL. This mixture was partitioned between 80 mL of saturated NaHCO$_3$ solution and EtOAc (4×100 mL). The combined EtOAc extracts were dried (MgSO$_4$), filtered and concentrated in vacuo to give the crude alcohol. To a stirred mixture of this alcohol in 140 mL of acetone in a cold water bath was added MnSO$_4$ treated Jones reagent (about 5 mL) until an orange-red color persisted. This mixture was stirred at room temperature for 2 hours and quenched with IPA. The mixture was concentrated in vacuo and partitioned between 100 mL of 3M NaHSO$_3$ solution and EtOAc (4×120 mL). The combined EtOAc extracts were washed with brine (2×50 mL), dried (MgSO$_4$), filtered and concentrated in vacuo to give 2.08 g of title acid in a quantitative yield.

TLC: silica gel, 10% CH$_3$OH/CH$_2$Cl$_2$, R$_f$ 0.36, Ce(SO$_4$)$_2$.

E.
[1S-(1α,2α,3α,4α)-2-[[3-[[[2[(4-Cyclohexylbutyl)amino]-1-(hydroxymethyl)-2-oxoethyl]amino]carbonyl]-7-oxabicyclo[2.2.1]hept-2-yl]methyl]benzeneacetic acid, methyl ester To a stirred mixture of Part D acid (100 g, 3.29 mmol), 1-hydroxybenzotriazole monohydrate (0.56 g, 3.29 mmol) and Example 1A, Part B amine.HCl (1.10 g, 3.95 mmol) in 30 mL of DMF under argon was added sequentially (C$_2$H$_5$)$_3$N (1.38 mL, 9.87 mmol) and ethyl-3-(3-dimethylamino) propyl carbodiimide hydrochloride salt (30.69 g, 3.62 mmol). This mixture was stirred at room temperature for 17 hours and concentrated in vacuo. The crude product was diluted with 400 mL of EtOAc and washed with 1N HCl solution (2×70 mL), 0.2 N NaOH solution (1×50 mL), saturated NaHCO$_3$. solution (1×50 mL), and brine (1×100 mL). The organic layer was dried (MgSO$_4$), filtered and concentrated in vacuo. This was chromatographed on 140 g of Merck silica gel 60 using 4% CH₃OH in CH₂Cl₂ as eluant to give 1.35 g (78%) of title amide.

TLC: silica gel, 4% CH₃OH/CH₂Cl₂, $R_f$ 0.24, Ce(SO₄)₂.

F. [1S-(1α,2α,3α,4α)]-2-[[3-[4-[[(4-Cyclohexylbutyl)amino]carbonyl]-4,5-dihydro-2-oxazolyl]-7-oxabicyclo[2.2.1]hept-2-yl]methyl]benzeneacetic acid, methyl ester To a stirred mixture of Part E amide (1.35 g, 2.56 mmol) in 30 ML of CHCl₃ under argon at 0° C. was added sequentially diisopropylethyl amine (0.58 mL, 3.32 mmol) and methanesulfonyl chloride (0.24 mL, 3.07 mmol). The reaction mixture was stirred at 0° C. for 1 hours and at room temperature for 1 hour. This mixture was concentrated in vacuo and diluted with 100 mL of acetone. To this mixture was added K₂CO₃ (1.00 g, 7.24 mmol). The mixture was refluxed gently under argon for 3 hours and cooled to room temperature. The solid was filtered off and rinsed with acetone (3×3 mL). The filtrate was concentrated in vacuo and chromatographed on 60 g of Merck silica gel 60 using 2% CH₃OH in CH₂Cl₂ as eluant to give 1.23 g (94%) of title oxazoline.

TLC: silica gel, 4% CH₃OH in CH₂Cl₂, $R_f$ 0.44, Ce(SO₄)₂.

G. [1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzeneacetic acid, methyl ester To a stirred mixture of CuBr₂ (1.06 g, 4.74 mmol) in 12 mL of EtOAc was added DBU (1.42 mL, 9.47 mmol). This mixture was stirred at room temperature for 30 minutes at which time a solution of Part F oxazoline (1.15 g, 2.25 mmol) in 12 mL of CHCl₃ was added. This mixture was stirred at room temperature for 17 hours. To this mixture was added CuBr₂ (0.53 g, 2.37 mmol) and DBU (0.70 mL, 4.73 mmol). This mixture was stirred vigorously at room temperature for 8 hours at which time again CuBr₂ (0.53 g, 2.37 mmol) and DBU (0.34 mL, 2.36 mmol) was added. The reaction mixture was stirred at room temperature for another 18 hours and poured into a solution of 200 mL of EtOAc and 200 mL of 1:1 concentrated NH₄OH solution and saturated NH₄Cl solution. The aqueous layer was separated and extracted with EtOAc (2×250 mL). The combined organic extracts were washed once with 100 mL of brine, dried (MgSO₄), filtered and concentrated in vacuo. Purification was effected by flash chromatography on 65 g of Merck silica gel 60 using 2% CH₃OH as eluant to give 370 mg (32%) of title oxazole.

TLC: silica gel, 4% CH₃OH in CH₂Cl₂, $R_f$ 0.52, Ce(SO₄)₂.

EXAMPLE 65

[1S-(1α,2α,3α,4α)]-2-[[3-[[(4-Cyclohexylbutyl)amino]carbonyl]-2-oxazolyl]-7-oxabicyclo2.2.1]hept-2-yl]methyl]benzeneacetic acid To a stirred mixture of Example 64 oxazole (360 mg, 0.71 mmol) in 15 mL of freshly distilled THF and 3.50 mL of H₂O was added LiOH.H₂O (89.2 mg, 2.13 mmol). This mixture was stirred at room temperature vigorously for 6.5 hours and acidified tp pH 2 by the addition of 1N HCl solution. This mixture was diluted with 15 mL of H₂O and extracted with EtOAc (4×30 mL). The combined EtOAc extracts were washed with brine (2×15 mL), dried (MgSO₄), filtered and concentrated in vacuo. This was recrystallized in 30 mL of 8:1 hexane-EtOAc at room temperature to give 280 mg (80%) of title pure acid as a solid, m.p. 130°–132° C.

TLC: silica gel, 4% CH₃OH/CH₂Cl₂, $R_f$ 0.10, Ce(SO₄)₂.

¹³C NMR (67.5 MHz, CDCl₃): δ 174.9, 163,9, 160.8, 141.1, 138.5, 135.8, 132.6, 130.9, 129.7, 127.5, 127.5, 126.6, 79.6, 78.6, 49.6, 46.9, 39.2, 38.3, 37.5, 37.0, 33.3, 33.3, 32.8, 29.8, 29.7, 28.8, 26.7, 26.3, 26.3, 24.2.

EXAMPLE 66

[1S-(1α,2α,3α,4α)]-2-[[3-[4-[(Cyclohexylamino)carbonyl]-2-oxazolyl]-7-oxabicyclo[2.2.1]hept-2-yl]methyl]benzenepropanoic acid, methyl ester To a solution of 200 mg (0.52 mMol, L223-88-23) of Example 2, Part J acid in 20 mL dry CH₂Cl₂ (distilled from P₂O₅) was added 1 small drop of DMF, followed by 310 μL (0.63 mMol, 2M/CH₂Cl₂, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry CH₂Cl₂ (distilled from P₂O₅), cooled to 0°, was added 120 μL (0.83 mMol, distilled from CaH₂) of triethylamine, followed by the dropwise addition of a solution of 62 mg (0.62 mMol, Aldrich) of cyclohexylamine in 5 mL CH₂Cl₂. The reaction was stirred at 0° for 16 hours, then partitioned between 80 mL ethyl acetate/60 mL 1M HCl. The ethyl acetate layer was separated, dried (MgSO₄) and concentrated in vacuo to give a crude yellow solid. The crude solid was flash chromatographed (Merck silica, 1:2 ethyl acetate/hexane) to give 220 mg (0.47 mMol, 91%) of title ester as a white solid.

EXAMPLE 67

[1S-(1α,2α,3α,4α)]-2-[[3-[4-[(Cyclohexylamino)carbonyl]-2-oxazolyl]-7-oxabicyclo[2.2.1]hept-2-yl]-methyl]benzenepropanoic acid To a mixture of 220 mg (0.47 mMol) of Example 66 ester in 8 mL distilled THF/2 mL water was added 40 mg (0.94 mMol, Aldrich) of lithium hydroxide monohydrate. The reaction was stirred vigorously for 4 hours at room temperature, then quenched by the addition of 1.8 mL (1.8 mMol) 1M HCl. The mixture was partitioned between 40 mL ethyl acetate/40 mL water. The ethyl acetate layer was separated, dried (MgSO₄) and concentrated in vacuo to give 210 mg (0.46 mMol, 98%) of title acid, SQ 34,614, as a white form m.p. 58°–62°.

IR (KBr): 3400, 3121, 2933, 2854, 1728, 1645, 1601 cm⁻¹.

MS(CI): 453 (M+H)⁺.

OR: $[\alpha]_D$ = +14.9° (c=1.0 in chloroform)

TLC: $R_f$ (silica gel, 1:9 methanol/methylene chloride)=0.37, ammonium molybdate/ceric sulfate and UV, homogeneous.

Analysis Calc'd for C₂₃H₂₈N₂O₅0.45 mol H₂O: C, 67.78; H, 7.20; N, 6.08

Found: C, 67.82; H, 7.27; N, 6.04

EXAMPLE 68

[1S-(1α,2α,3α,4α)]-2-[[3-[4-[[(1-Methylethyl)amino]-carbonyl]-2-oxazolyl]-7-oxabicyclo[2.2.1]hept-2-yl]-methyl]benzenepropanoic acid, methyl ester To a solution of 200 mg (0.52 mMol) of Example 2, Part J acid in 20 mL dry $CH_2Cl_2$ (distilled from $P_2O_5$) was added 1 small drop of DMF, followed by 310 μL (0.63 mMol, 2M/$CH_2Cl_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$) cooled to 0°, was added 120 μL (0.83 mMol, distilled from $CaH_2$) of triethylamine, followed by the dropwise addition of a solution of 37 mg (0.62 mMol, Aldrich) of isopropylamine in 5 mL $CH_2Cl_2$. The reaction was stirred at 0° for 16 hours, then partitioned between 80 mL ethyl acetate/60 mL 1M HCl. The ethyl acetate layer was separated, dried ($MgSO_4$) and concentrated in vacuo to give a crude yellow solid. The crude solid was flash chromatographed (Merck silica gel, 2:1 ethyl acetate/hexane) to give 112 mg (0.26 mMol, 51% of title ester as a white solid.

EXAMPLE 69

[1S-(1α,2α,3α,4α)]-2-[[3-[4-[[(1-Methylethyl)amino]carbonyl]-2-oxazolyl]-7-oxabicyclo[2.2.1]hept-2-yl]-methyl]benzenepropanoic acid To a mixture of 112 mg (0.26 mMol) of Example 68 ester in 8 mL distilled THF/2 mL water was added 22 mg (0.53 mMol, Aldrich) of lithium hydroxide monohydrate. The reaction was stirred vigorously for 3 hours at room temperature, then quenched by the addition of 1.1 mL (1.1 mMol) 1M HCl. The mixture was partitioned between 40 mL ethyl acetate/40 mL water. The ethyl acetate layer was separated, dried ($MgSO_4$) and concentrated in vacuo to give 100 mg (0.24 mMol, 92%) of title acid as a white foam, mp 57°-63°.

IR (KBr): 3431, 3416, 2972, 1716, 1651, 1602 $cm^{-1}$.
MS(CI): 413 $(M+H)^+$.
OR: $[\alpha]_D = +16.8°$ (c=1.0 in chloroform).
TLC: $R_f$ (silica gel, 1:9 methanol/methylene chloride)=0.32, ammonium molybdate/ceric sulfate and UV, homogeneous.

Analysis Calc'd for $C_{23}H_{28}N_2O_5 + 0.59\ H_2O$: C, 65.29; H, 6.95; N, 6.62
Found: C, 65.49; H, 7.05; N, 6.42

EXAMPLE 70

[1S-(1α,2α,3α,4α)]-2-[[3-[4-[[(8-Cyclohexyloctyl)-amino]carbonyl]-2-oxazolyl]-7-oxabicyclo[2.2.1]hept-2-yl]methyl]benzenepropanoic acid, methyl ester

A. 4-Cyclohexane-1-butanal

A solution of 3.06 mL (4.45 g, 35.0 mmol) of oxalyl chloride in 150 mL of dry methylene chloride was stirred under argon at −60° C. in an acetone and dry ice bath. A solution of 5.0 mL (5.99 g, 76.7 mmol) of methylene chloride was added slowly and the resulting mixture was stirred at −60° C. for ten minutes before 5.0 g (31.9 mmol) of 4-cyclohexyl-1-butanol was added slowly. After 20 minutes 22.23 mmol (16.13 g 159.5 mmol) of triethylamine was added slowly at −60° C. The cooling bath was then removed and the reaction was warmed up to room temperature. 17 mL of water was added and after stirring, the two layers were separated. The aqueous layer was extracted twice more with methylene chloride (50 mL). The organic layers were combined, washed with brine, dried over $MgSO_4$, and concentrated to obtain title aldehyde in the form of a yellow semisolid 4.63 g (94%).

B. (3-Carboxypropyl)triphenylphosphonium bromide

A solid mixture of 4-bromobutyric acid (100 g, 0.60 mol) and triphenylphosphine (157.1 g, 0.60 mol) was reacted at 140° C. (oil bath temperature) under argon for 3 hours. When heat was first applied, both solid starting materials melted to form a homogeneous solution. After a few minutes of heating, extensive precipitation occurred. After cooling to room temperature, a rock-hard solid was broken up, suspended in 250 mL of refluxing chloroform under argon, and diluted with 800 mL of ether. Stirring at room temperature was carried out for 30 minutes. The suspension was cooled to 0° C. (ice bath temperature), and the product was collected by filtration and washed with ether. Yield: 218.12 g.

C. (Z)-8-Cyclohexyl-4-octenoic acid

To a stirred solution of 17.77 g (41.49 mmol) of Part B acid in 75 mL THF at 0° C. under argon, was added slowly 42 mL (75.2 mmol) of K-t-amyl-alcoholate. After the reaction mixture was stirred for ½ hour, 4.0 g (25.9 mmol) of Part A aldehyde was added as a solution in 2.5 mL of $CHCl_3$. The reaction mixture was stirred for 24 hours at room temperature. The reaction was quenched by the addition of 18 mL of $CH_3CO_2H$ and concentrated on a roto evaporator. Residual $CH_3CO_2H$ was removed by twice adding toluene and concentrating. The residue was extracted with 100 mL ethyl acetate, the organic layers separated and the aqueous layer extracted twice more (100 mL each). The organic layers were combined, washed with brine, dried over $MgSO_4$, and concentrated to obtain an oil. The oil was chromatographed eluting with a gradient of hexane and ethyl acetate (80:20-70:30) containing 0.5% $CH_3CO_2H$ to obtain 5.8 g (100%) of title acid in the form of an orange oil.

$R_f$=0.6 in 1:1 hexane-EtOAc with 0.5% AcOH.
$^{13}C$ NMR (67.8 MHz, $CDCl_3$): δ 179.7, 131.9, 126.9, 37.6, 37.1, 34.2, 33.3, 27.4, 26.9, 26.7, 26.4, 22.5.

D. Cyclohexaneoctanoic acid

A solution of 5.50 g (25.8 mmol) of Part C acid in 30 mL of $CH_3CO_2H$ was stirred at room temperture under argon. A hydrogen balloon was attached, and the reaction mixture was stirred at room temperature for two days. The reaction mixture was filtered through a celite pad and the filter cake was washed with methylene chloride. The filtrate was concentrated to obtain 5.20 g (90%) of title acid in the form of a brownish oil.

$^{13}C$ NMR (67.8 MHz, $CDCl_3$): δ 171.0, 37.6, 37.6, 37.4, 34.1, 33.4, 29.7, 29.2, 29.0, 26.7, 26.4, 26.0, 24.7.

E. Cyclohexaneoctanamide

To a solution of 5.1 g (22.5 mmol) of Part D acid in 20 mL of dry $CH_2Cl_2$ at 0° C. under argon was added dropwise 9.8 mL (14.3 g, 113 mmol) of oxalyl chloride. The ice bath was removed, and the reaction mixture was warmed to room temperature and stirred for 18 hours. The reaction mixture was concentrated, toluene (100 mL) was added, and the mixture was concentrated again. This process was repeated once more. To the residue, 5 mL of 9M methanolic ammonia was added and this was stirred at room temperature for 2½ days. To this 100 mL ethyl acetate and 20 mL water were added and the two layers were separated. The aqueous layer was extracted twice more with ethyl acetate (100 mL each). The organic layers were combined, washed with brine, dried over MgSO₄, and concentrated to obtain a brown oil. This was crystallized by the addition of hexane. A small amount, 0.46 g (9%) of title amide in the form of a tan solid was obtained.

$R_f$=0.48 in 0.5% NH₄OH/EtOAc.

$^{13}$C NMR (67.8 MHz, CDCl₃): δ 176.0, 37.4, 37.2, 35.6, 33.2, 29.6, 29.1, 29.0, 26.6, 26.2, 25.3.

F. Cyclohexaneoctanamine

To a solution of 0.46 g (2.04 mmol) of Part E amide in 50 mL of ether at 0° C. under argon was added slowly 0.09 g (2.24 mmol) of lithium aluminum hydride, and the reaction was warmed to room temperature. After two hours the reaction mixture was quenched with 0.09 mL of water, then 0.09 mL of 15% aqueous NaOH, followed by 0.27 mL of water. After stirring for 15 minutes, the precipitate was filtered, and the filtrate was concentrated to obtain a semi-solid. This was chromatographed using 0.5% concentrated aqueous NH₃ in ethyl acetate to obtain 0.21 g (49%) of title amine in the form of a yellow oil.

$R_f$=0.41 in 0.5% NH₄OH/EtOAc.

$^{13}$C NMR (67.8 MHz, CDCl₃): δ 42.1, 37.6, 37.5, 33.7, 33.4, 29.9, 29.6, 29.4, 26.8, 26.7, 26.4.

G.
[1S-(1α,2α,3α,4α)]-2-[[3-[4-[[(8-Cyclohexyloctyl-)amino]carbonyl]-2-oxazolyl]-7-oxabicyclo[2.2.1]hept-2-yl]methyl]benzenepropanoic acid, methyl ester To a solution of (0.21 g, 0.99 mmol) Part F amine in 5 mL of chloroform under argon at 0° C., was added (0.14 mL, 0.10 g, 0.99 mmol) triethylamine and (0.20 g, 0.49 mmol) Example 2, Part J acid. The mixture was stirred at room temperature for 18 hours, then diluted with 20 mL of chloroform and 5 mL of water. The organic layer was separated, and the aqueous layer was extracted with 20 mL of chloroform twice. The organic layers were combined, washed with brine over MgSO₄, and concentrated to obtain title compound in the form of a white solid 0.22 g (77%).

$R_f$=0.8 in EtOAc.

$^{13}$C NMR (67.8 MHz, CDCl₃): δ 173.0, 163.7, 160.4, 140.4, 138.4, 137.8, 136.1, 129.6, 128.9, 126.6, 126.4, 79.6, 78.6, 51.5, 49.9, 46.9, 39.0, 37.6, 37.4, 34.8, 33.3, 32.3, 29.8, 29.6, 29.5, 29.2, 28.8, 27.6, 26.8, 26.4.

EXAMPLE 71
[1S-(1α,2α,3α,4α)]-2-[[3-[4-[[(8-Cyclohexyloctyl-)amino]carbonyl]-2-oxazolyl]-7-oxabicyclo[2.2.1]hept-2-yl]methyl]benzenepropanoic acid A solution of (0.22 g, 0.38 mmol) of Example 70 ester in 1 mL of 1N aqueous NaOH, 3 mL of THF, and 2 mL water was stirred for 18 hours. After acidification to pH 1.5 with 10% HCl, 25 mL of EtOAc was added, and the organic layer was separated. The aqueous layer was extracted twice with 25 mL EtOAc. The organic layers were combined, washed with brine, dried over MgSO₄, and concentrated in vacuo to obtain 0.18 g of solid. This was crystallized from chloroform and hexane to obtain 0.18 g (86%) of title acid in the form of a solid.

$R_f$=0.59 in (0.5% acetic acid in ethyl acetate; UV, Ce(SO₄)₂, m.p. 148°-149°.

$[α]°_D$= +38.4 in CH₃OH at c 0.50 g/100 mL.

EXAMPLE 72
[1S-(1α,2α,3α,4α)]-3-[2-[3-[4-[[(4-Cyclohexylbutyl-)amino]carbonyl]-2-oxazolyl]-7-oxabicyclo[2.2.1]hept-2-yl]ethyl]benzoic acid, methyl ester

A.
3-[[Dimethyl(1,1,2-trimethylpropyl)silyl]oxy]benzene bromide

To a stirred solution of 3-bromophenyl alcohol (5.0 g, 26.7 mmol) and triethylamine (3.25 g, 32.1 mmol) in anhydrous CH₂Cl₂ (125 mL) at room temperature under argon was added dropwise dimethylthexylsilylchloride (5.26 g, 29.4 mmol). After 1.5 hours, 4-dimethylaminopyridine (0.50 g) was added and the stirring was continued for an additional 3 hours. The reaction mixture was diluted with hexane (200 mL) and the precipitate was filtered off. The filtrate was concentrated, partitioned between hexane (200 mL) and 1N aqueous HCl (3×40 mL), and the organic layer was washed with saturated aqueous NaHCO₃ (2×40 mL). The organic layer was dried (MgSO₄), filtered and concentrated to yield title bromide (8.01 g, 91%).

B.
[1S-(1α,2α,3α,4α)]-α-[3-[[Dimethyl(1,1,2-trimethylpropyl)silyl]oxy]phenyl]-3-(hydroxymethyl)-7-oxabicyclo[2.2.1]-heptane-2-ethanol To a solution of Part A bromide (5.88 g, 16.9 mmol) under argon in anhydrous ether (40 mL) at −78° C. was added t-butyllithium (17.8 mL, 1.70M solution in pentane) over fifteen minutes, and the the mixture was stirred for an additional 30 minutes at 0° C. The reaction solution was cooled to −78° C. and anhydrous THF (40 mL) was added. (endo)-Octahydro-5,8-epoxy-1H-benzopyran-3-ol (1.20 g, 7.10 mmol) dissolved in anhydrous THF (50 mL) was added dropwise and stirred for fifteen minutes at −78° C. A white precipitate formed. The reaction mixture was then warmed to 0° C. for one hour and quenched with water (3.0 mL). The aqueous mixture was extracted with EtOAc (2 times) and the combined extracts were dried (MgSO₄), filtered and concentrated to give a yellow oil. The crude product was chromatographed on a silica gel column and eluted with 50–100% EtOAc in hexane to obtain title compound (1.47 g, 49%) as a white foam.

C.
[1S-(1α,2α,3α,4α)]-3-[1-(Acetyloxy)-2[3-[(acetyloxy)-methyl]-7-oxabicyclo2.2.1]hept-2-yl]ethyl]benzoic acid, methyl ester To Part B compound (1.47 g, 3.49 mmol) in pyridine (1.70 mL) under argon at 0° C. was added acetic anhydride (1.07 g, 10.5 mmol) over ten minutes. The mixture was stirred at 0° C. for one hour, then at room temperature for sixteen hours. The reaction mixture was diluted with ether (10 mL) and washed with 1N aqueous HCl (3×25 mL). The ether layer was dried (MgSO₄), filtered and concentrated. The residue was dissolved in acetone (25 mL) and treated with Jones Reagent until the orange color persisted. The reaction mixture was stirred for four hours at room temperature, then quenched with excess IPA, concentrated and partitioned between water (30 mL) and EtOAc (3×30 mL).

The combined organic layers were washed with H₂O, dried (MgSO₄), filtered and concentrated. The residue was dissolved in ether (30 mL) and treated with excess ethereal diazomethane at 0° C. for ten minutes. The reaction mixture was concentrated and chromatographed on a silica gel column and eluted with 10–25% EtOAc-hexane to give title compound (1.22 g, 76%) as a viscous, colorless oil.

D.
[1S-(1α,2α,3α,4α)]-3-[2-[3-[(Acetyloxy)methyl]-7-oxabicyclo[2.2.1hept-2-yl]-ethyl]benzoic acid, methyl ester To a stirred solution of Part C compound (1.22 g, 3.12 mmol) in methyl acetate (25 mL) under argon was added 70% aqueous HClO₄ (0.60 mL) and 10% Pd/C (0.13 g). The atmosphere was replaced with H₂ from a H₂ filled balloon by several vacuum-fill cycles. The reaction mixture was stirred vigorously for 4 hours before the catalyst was filtered off through a bed of anhydrous MgSO₄. The solids were rinsed well with EtOAc. The filtrate was concentrated to ½ its original volume and then was washed with saturated aqueous NH₄Cl, saturated aqueous KHCO₃, and brine. The organic layer was dried (MgSO₄), filtered and concentrated to give title compound (0.84 g, 81%) as a viscous, colorless oil.

E. [1S-(1α,260,3α,4α)]-3-[2-[3-(Hydroxymethyl)-7-oxabicyclo[2.2.1-]hept-2-yl]ethyl]benzoic acid, methyl ester To Part C compound (0.80 g, 2.40 mL) in methanol (10 mL) and acetone (30 mL) was added finely crushed K₂CO₃ and stirred for 4 hours at 0° C. H₂O was added to the reaction mixture before the organic solvents were removed under reduced pressure. The aqueous layer was extracted with EtOAc (3 times), dried (MgSO₄), filtered and concentrated to give crude title compound (1.01 g) as a viscous oil. The alcohol was taken on to the next step without further purification.

F.
[1S-(1α,2α,3α,4α)]-3-[2-[3-Carboxy-7-oxabicyclo[2.2.1-]hept-2-yl]ethyl]benzoic acid, methyl ester Part E compound (0.73 g, 2.52 mmol) in acetone (20 mL) at 0° C. under argon was treated with Jones Reagent until the orange color persisted. The reaction mixture was stirred while warming to room temperature. One hour after the ice bath was removed the excess Jones Reagent was destroyed by the addition of IPA. After concentration the reaction mixture was partitioned between 3M aqueous NaHSO₃ and EtOAc (3 times). The combined organic layers were dried (MgSO₄), filtered and concentrate to obtain title compound (0.40 g, 80%) as a white crystalline solid.

G.
[1S-(1α,2α,3α,4α)]-3-2-[3-[[[2-[(4-Cyclohexylbutyl)amino]-1-(hydroxymethyl)-2-oxoethyl]amino]carbonyl]-7-oxabicyclo-[2.2.1]hept-2-yl]ethyl]benzoic acid, methyl ester Part F compound (0.40 g, 1.45 mmol), 1-hydroxybenzotriazole hydrate (0.25 g, 1.45 mmol), Example 1A, Part B amine HCl (0.40 g, 1.45 mmol) and DMF (10 mL) were combined under argon at 0° C. Triethylamine (0.44 g, 4.34 mmol) was added and stirred for 25 minutes. 1-(3-Dimethylaminopropyl)-3-ethylcarbodiimide hydrochloride (0.28 g, 1.45 mmol) was added and the reaction mixture was stirred for sixteen hours while warming to room temperature. The reaction mixture was diluted with EtOAc, washed with 1N aqueous HCl (2 times), diluted aqueous NaOH (2 times) and saturated aqueous KHCO₃. The organic layer was dried (MgSO₄), filtered and concentrated to obtain title compound (0.50 g, 65%) as a white solid.

H.
[1S-(1α,2α,3α,4α)]-3-[2-[3-[4-[[(4-Cyclohexylbutyl)amino]carbonyl]-4,5-dihydro-2-oxazolyl]-7-oxabicyclo-[2.2.1]hept-2-yl]ethyl]benzoic acid, methyl ester To a stirred solution of Part G compound (0.50 g, 0.95 mmol) and N,N-diisopropylethylamine (0.37 g, 2.84 mmol) in C₂Cl₂ (25 mL) at 0° C. under argon was added methanesulfonyl chloride (0.11 g, 0.96 mmol) and stirred for one hour while warming to room temperture. The reaction solution was concentrated and the residue was diluted with acetone (25 mL). Finely powdered K₂CO₃ (0.39 g, 2.84 mL) was added and the reaction mixture was refluxed for 2½ hours. The reaction mixture was cooled to room temperature, filtered and concentrated. The crude product was chromatographed on a silica gel column and eluted with 50% EtOAc in hexane to obtain title compound (0.48 g, 100%) as a white solid.

I.
[1S-(1α,2α,3α,4α)]-3-[2-[3-[4-[[(4-Cyclohexylbutyl)amino]carbonyl-2-oxazolyl]-7-oxabicyclo[2.2.1]hept-2-yl]ethyl]benzoic acid, methyl ester To copper (II) bromide (0.44 g, 1.97 mmol) in EtOAc (3 mL) was added DBU (0.57 g, 3.76 mmol) and stirred for 30 mintues at room temperature. Part H compound (0.48 g, 0.94 mmol) dissolved in CHCl₃ (3 mL) was added dropwise and stirred for 22 hours at room temperature. The reaction solution was poured into a 1:1 aqueous NH₄Cl:NH₄OH mixture and extracted with EtOAc (2 times). The combined organic extracts were dried (MgSO₄), filtered and concentrated. The crude product was chromatographed on a silica gel column and eluted with 20–50% EtOAc in hexane to obtain title ester (0.23 g 48%) as a white solid.

EXAMPLE 73

[1S-(1α,2α,3α,4α)]-3-[2-[3-[4-[[(4-Cyclohexylbutyl)-amino]carbonyl]-2-oxazolyl]-7-oxabicyclo[2.2.1]hept-2-yl]ethyl]benzoic acid To Example 72 ester (0.23 g 0.45 mmol) in H₂O (2 mL) and THF (8 mL) was added lithium hydroxide monohydrate (0.06 g, 1.36 mmol) and stirred vigorously for 18 hours at room temperature. The reaction mixture was cooled to 0° C. and acidified to pH 2.0 with 1N aqueous HCl. The acidified reaction mixture was extracted with EtOAc (4 times) and the combined organic layers were washed with brine, dried (MgSO₄), filtered and eluted with 50% EtOAc in hexane with 0.25% acetic acid added to obtain title acid (0.20 g, 91%) as a white solid.

$^1$H (270 MHz, CDCl₃): δ 8.96 (br s, 1H), 8.20 (s, 1H), 7.91 (d, 1H), 7.82 (s, 1H), 7.41–7.21 (m, H), 7.09 (t, 1H), 4.90 (s, 1H), 4.55 (s, 1H), 3.48–3.23 (m, 3H), 2.73–2.42 (m, 2H), 2.30–2.18 (m, 1H), 1.93–0.71 (m, 23H).

$^{13}$C (67.8 MHz, CDCl₃): δ 170.5, 164.0, 160.7, 141.6, 141.0, 135.9, 133.4, 130.0, 129.9, 128.5, 127.9, 79.5, 48.9, 47.1, 39.2, 37.5, 37.0, 34.3, 33.3, 31.7, 29.8, 29.5, 29.2, 26.6, 26.3, 24.2.

EXAMPLE 74

1S-(1α,2α,3α,4α)]-[2-[[3-[4-[[[4-[4-(Methylthiophenyl)-butyl]amino]carbonyl]-2-oxazolyl]-7-oxabicyclo[2.2.1-]hept-2-yl]methyl]benzenepropanoic acid, methyl ester

A. (E)-3-[4-(Methylthio)phenyl]-2-propenoic acid, methyl ester

A slurry of 6.00 g (39.5 mMol, Aldrich) of p-(methylthio)benzaldehyde, and 13.8 g (41.3 mMol, Aldrich) of methyl (triphenylphosphoranylidene)acetate in 60 mL of dry THF (distilled from sodium/benzophenone ketyl) was stirred at room temperature for 18 hours. The resulting homogeneous solution was concentrated in vacuo to give a solid. The crude material was purified by flash chromatography (Merck silica, 22×5.0 cm, methylene chloride load then 1:5 ethyl acetate/hexane elution) to afford 6.53 g (31.4 mMol, 79%) of title acrylate as a white solid, mp 89°–91°.

B. 4-(Methylthio)benzenepropanoic acid, methyl ester

A mixture of 1.00 g (4.81 mMol) of Part A acrylate and 2.00 g of 10% palladium on activated carbon catalyst (Aldrich) in 75 mL of reagent ethyl acetate was shaken under an atmosphere of hydrogen (50 psi) on a Parr apparatus for 18 hours. The reaction was filtered on a Buchner funnel then passed through a 4 μM polycarbonate membrane. The filtrate was concentrated in vacuo to give 1.00 g (4.76 mMol, 99%) of title ester as a colorless oil.

C. 4-(Methylthio)benzenepropanol

To a solution of 3.05 g (14.5 mMol) of Part B ester in 25 mL of dry THF (distilled from sodium/benzophenone ketyl) cooled in an ice bath was added 650 mg (29.5 mMol, Alfa) of lithium borohydride. The reaction mixture was warmed to room temperature, stirred for 16 hours then cooled in an ice bath and quenched by slow addition of 100 mL of 1M aqueous HCl solution. The resulting mixture was stirred for 10 minutes then extracted with two-50 mL portions of ethyl acetate. The organic extracts were combined, washed with 100 mL of 1M aqueous NaOH solution, 25 mL of brine, dried (magnesium sulfate) and concentrated in vacuo to give an oil. The crude material was purified by flash chromatography (Merck silica, 12×5.0 cm, 2:1 ethyl acetate/hexane) to yield 2.31 g (12.7 mMol, 88%) of title alcohol as a colorless oil.

D. 4-(Methylthio)benzenebutanenitrile

To a solution of 2.26 g (12.4 mMol) of Part C alcohol in 15 mL of dry methylene chloride (distilled from phosphorous pentoxide) was added at room temperature 1.56 g (13.6 mMol, Aldrich) of methanesulfonyl chloride then 1.3 mL (16 mMol, Burdick and Jackson) of pyridine. The reaction mixture was stirred for 18 hours (TLC analysis showed about 20% unreacted starting material) then an additional 0.50 g (4.4 mMol) of methanesulfonyl chloride and 0.40 mL (5.0 mMol) of pyridine were added. After 4 hours 60 mL of ethyl acetate was added to the reaction and the resulting slurry washed successively with two-25 mL portions of 1M aqueous HCl solution, 25 mL of saturated sodium bicarbonate solution then 25 mL of brine, dried (magnesium sulfate) and concentrated in vacuo to give the crude mesylate as an oil.

A mixture of the crude mesylate and 1.62 g (24.9 mMol, Mallinckrodt) of potassium cyanide in 20 mL of DMSO (Burdick and Jackson) was heated to 75° for 2 hours. The resulting orange-brown semisolid was cooled to room temperature and partitioned between 100 mL of water and 75 mL of ethyl acetate. The organic layer was separated, washed with two-100 mL portions of water, 25 mL of brine, dried (magnesium sulfate) and concentrated in vacuo to give an oil. The crude oil was purified by flash chromatography (Merck silica gel, 12×5.0 cm, 1:4 ethyl acetate/hexane) to afford 1.30 g (6.80 mMol, 55%) of title nitrile as a colorless oil.

E. 4-(Methylthio)benzenebutanamine, monohydrochloride

To a solution of 1.18 g (6.18 mMol) of Part D nitrile in 10 mL of dry ether (distilled from sodium/benzophenone ketyl) cooled in an ice bath was added 260 mg (6.84 mMol, Aldrich) of lithium aluminum hydride. The reaction mixture was stirred at 0° for 15 minutes then at room temperature for 2.5 hours. The resulting solution was re-cooled in an ice bath then quenched by slow, successive addition of 0.25 mL of water, 0.25 mL of 1M aqueous NaOH solution then 0.75 mL of water. The reaction was warmed to room temperature, stirred for 15 minutes then the resulting slurry was filtered. The filtrate ws concentrated in vacuo to give the crude amine as an oil. The hydrochloride was obtained by addition of 20 mL of ice-cold acidic methanol (prepared from 1 mL of acetyl chloride to 20 mL of cold methanol) to the crude amine. The resulting solution was concentrated in vacuo to give 1.13 g of crude amine hydrochloride. The crude material was purified by recrystallization (methanol/ether) to afford 689 mg (48%) of title amine hydrochloride as a white solid, mp 165° (softens).

F. [1S-(α,2α,3α,4α)-2-[[3-[4-[[[4-[4-Methylthiophenyl]-butyl]amino]carbonyl]-2-oxazolyl]-7-oxabicyclo[2.2.1-]hept-2-yl]-methyl]benzenepropanoic acid, methyl ester To a solution of 500 mg (1.30 mMol) of acid prepared as described in Example 2, Part J in 6 mL of dry methylene chloride (distilled from phosphorous pentoxide) was added at room temperature a small drop of DMF then 135 μL (1.54 mMol, Aldrich) of oxalyl chloride. The reaction mixture was stirred until gas evolution ceased, 30 minutes, then the solution was concentrated in vacuo to give the crude acid chloride as a pale yellow solid.

To a solution of the crude acid chloride in 5 mL of dry methylene chloride, cooled in an ice bath, was added 362 mg (1.56 mMol) of Part E amine hydrochloride then 400 μL (2.9 mMol, distilled from calcium hydride) of triethylamine. The reaction mixture was stirred for 30 minutes then partitioned between 20 mL of ethyl acetate and 20 mL of 1M aqueous HCl solution. The organic layer was separated, dried (magnesium sulfate) and concentrated in vacuo to give a solid. The crude solid was purified by flash chromatography (Merck silica, 12×3.0 cm, methylene chloride load then 2:1 ethyl acetate/hexane elution) to afford 600 mg (1.07 mMol, 82%) of title ester as a white solid.

EXAMPLE 75

[1S-(1α,2α,3α,4α)]-2-[[3-[4-[[[4-[4-Methylthiophenyl]-butyl]amino]carbonyl]-2-oxazolyl]-7-oxabicyclo[2.2.1-]hept-2-yl]methyl]benzenepropanoic acid A mixture of 200 mg (0.36 mMol) of Example 74 ester and 30 mg (0.71 mmol, Aldrich) of lithium hydroxide monohydrate in 3 mL of 2:1 THF/water was stirred rapidly at room temperature for 2 hours then acidified by addition of 1.5 mL of 1M aqueous HCl solution. The mixture was partitioned between 15 mL of ethyl acetate and 15 mL of water. The organic layer was separated, dried (magnesium sulfate) and concentrated in vacuo to give a solid. The crude material was purified by recrystallization (acetonitrile/ethyl acetate) to afford 158 mg (0.29 mMol, 80%) of title acid as a white solid, mp 155°-158°.

IR(KBr): 3441 (broad), 1723, 1643, 1602, 1523, 1105 cm$^{-1}$.

MS(CI): 549 (M+H)$^+$.

OR: $[α]_D = +17°$ (c=0.5 in chloroform).

TLC: R$_f$(silica gel, 1:9 methanol/methylene chloride)=0.51, ammonium molybdate/ceric sulfate and UV, homogeneous.

Analysis Calc'd for $C_{31}H_{36}N_2O_5S$: C, 67.86; H, 6.61; N, 5.11; S, 5.84

Found: C, 68.13; H, 6.80; N, 5.05; S, 5.87.

EXAMPLE 76

[1S-(1α,2α,3α,4α)]-2-[[3-[4-[[[4-[4-(Methylsulfonyl-phenyl]butyl]amino]carbonyl]-2-oxazolyl]-7-oxabicyclo[2.2.1]hept-2-yl]methyl]benzenepropanoic acid, methyl ester To a solution of 1.08 g (1.76 mMol, MW 615, Alfa) of oxone monopersulfate in 4 mL of water was added rapidly a solution of 330 mg (0.59 mMol) of Example 74 ester in 8 mL of 1:1 methanol/THF (mildly exothermic). The reaction mixture was stirred for 30 minutes then partitioned between 40 mL of water and 25 mL of ethyl acetate. The organic layer was separated and the aqueous layer was extracted with an additional 25 mL of ethyl acetate. The organic extracts were combined, dried (magnesium sulfate) and concentrated in vacuo to give an oil. The crude oil was purified by flash chromatography (Merck silica, 15×3.0 cm, methylene chloride load the ethyl acetate elution) to afford 313 mg (0.54 mMol, 91%) of title sulfone as a white foam.

EXAMPLE 77

[1S-(1α,2α,3α,4α)]-2-[[3-[4-[[[4-[4-(Methylsulfonyl-phenyl]butyl ]amino]carbonyl]-2-oxazolyl]-7-oxabicyclo[2.2.1]hept-2-yl]methyl]benzenepropanoic acid A solution of 305 mg (0.51 mMol) of Example 76 ester and 45 mg (1.1 mMol, Aldrich) of lithium hydroxide monohydrate in 6 mL of 2:1 THF/water was stirred rapidly at room temperature for 1.5 hours. The reaction mixture was acidified with 2.2 mL of 1M HCl solution then partitioned between 20 mL of ethyl acetate and 20 mL of water. The organic layer was separated, washed with 20 mL of brine, dried (magnesium sulfate) and concentrated in vacuo to give a solid. The crude solid was purified by recrystallization (ethyl acetate) to afford 230 mg (0.40 mMol, 78%) of title acid as a white solid, mp 159°-161°.

IR(KBr): 3432 (broad), 2945, 1719, 1642, 1601, 1521, 1302, 1148 cm$^{-1}$.

MS(CI): 598 (M+NH)$^+$.

OR: $[α]_D = +9.0°$ (c=0.5 in chloroform).

TLC: R$_f$(silica gel, 1:9 methanol/methylene chloride)=0.41, ammonium molybdate/ceric sulfate and UV, homogeneous.

Analysis Calc'd for $C_{31}H_{36}N_2O_7S$: C, 64.21; H, 6.25; N, 4.83; S, 5.52

Found: C, 64.32; H, 6.19; N, 4.79; S, 5.35

EXAMPLE 78

[1S-(1α,2α,3α,4α)]-2-[[3-[4-[[(Cyclohexylbutyl)amino]-carbonyl]-2-oxazolyl]-7-oxabicyclo[2.2.1]hept-2-yl]methyl]-N-ethylbenzenepropanamide To a stirred solution of 0.11 g (0.58 mmol) of WSC and 0.08 g (0.58 mmol) of HOBT.H$_2$O in 30 mL of DMF at room temperature under argon was added 0.05 g (0.58 mmol) of ethylamine hydrochloride, 0.12 g (1.17 mmol) of triethylamine and 0.30 g (0.58 mmol) of Example 1 compound. The resulting yellow solution was stirred for 2.5 days. 15 mL of water was added, and the mixture was extracted with three 50 mL portions of EtOAc. The organic layers were combined, washed with brine, dried over MgSO$_4$, and concentrated to obtain a yellow solid. This was crystallized from chloroform and hexane, and 0.13 g (40%) of a title amide in the form of a white solid was obtained.

R$_f$=0.4; 50% (0.5% AcOH/EtOAc)/Hexane, m.p. 155°-156° C.

$[α]_D = +3.6$ at c=0.90 g/100 mL in CH$_3$OH at room temperature.

EXAMPLE 79

[1S-(1α,2α,3α,4α)]-2-[[3-[4-[[(4-Cyclohexylbutyl)amino]carbonyl]-2-oxazolyl]-7-oxabicyclo2 2.1]hept-2-yl]methyl]benzenepropanamide To a stirred solution of 0.11 g (0.58 mmol) of WSC and 0.08 g (0.58 mmol) of HOBT.H$_2$O in 30 mL of DMF at room temperature under argon was added 0.032 g (0.58 mmol) of ammonium chloride, 0.12 g (1.17 mmol) of triethylamine and 0.30 g (0.58 mmol) of Example 1 compound. The resulting yellow solution was stirred for 2.5 days. 15 mL of water was added, and the mixture was extracted with three 50 mL portions of ethyl acetate. The organic layers were combined, washed with brine, dried over MgSO$_4$, and concentrated to obtain a yellow solid. This was crystallized from chloroform and hexane, and 0.29 g (100%) of a title amide in the form of a white solid was obtained.

R$_f$=0.20, EtOAc (silica gel) m.p. 173°-174° C.

$[α]_D = +15$ at c=0.14 g/100 mL in CH$_3$OH at room temperture.

EXAMPLE 80

[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzenepropanoic acid, ethyl ester To a flask containing 20 mL of dry ethanol (distilled from Mg(OC$_2$H$_5$)$_2$) was added 0.25 mL of acetyl chloride. This solution was stirred for 90 minutes at which time 353 mg of Example 1 acid product (0.69 mmol) was added. This solution was stirred at 23° C. for 90 minutes at which time TLC analysis showed the reaction to be essentially complete. The reaction mixture was diluted with CH$_2$Cl$_2$ and concentrated in vacuo. The residue was dissolved in $CH_2Cl_2$ and stored in the refrigerator overnight. The solution was diluted to ca. 40 mL with $CH_2Cl_2$ and washed with 20 mL of saturated aqueous $NaHCO_3$ solution. The organic layer was dried over $MgSO_4$, filtered, and concentrated in vacuo to afford a white solid. This was triturated with ether and then diluted with an equal volume of hexane. The slurry was chilled and the solid was collected to afford 280 mg (76%) of title ester, m.p. 130°-1° C.

Analysis Calc'd for $C_{32}H_{44}N_2O_5.0.35\ H_2O$: C, 70.78; H, 8.17; N, 5.16

Found: C, 70.75; H, 7.85; N, 4.79

TLC: silica gel, 3% $CH_3OH/CH_2Cl_2$, $R_f=0.65$, EtOAc, vanillin.

$[\alpha]_D = +3.68$ (c=1.44, $CH_3OH$)

$^{13}C$ NMR ($CDCl_3$ 67.5 MHz): δ 163.7, 160.5, 140.5, 138.5, 137.8, 136.2, 129.7, 128.9, 126.6, 126.4, 79.7, 78.6, 60.4, 50.0, 39.1, 37.5, 37.1, 35.1, 33.3, 33.2, 32.5, 29.9, 28.8, 27.6, 26.7, 26.4, 26.4, 24.2, 14.2.

EXAMPLE 81

1S-(1α,2α,3α,4α)]-N-[4-(Cyclohexylbutyl)-2-[2-[[2-(3-hydroxypropyl)]phenyl]methyl]-7-oxabicyclo[2.2.1-]hept-3-yl]-4-oxazolecarboxamide To a slurry of 420 mg of impure Example 80 ester in 20 mL of ether was added 56.3 mg of $LiBH_4$ (2.56 mmol). After the reaction mixture was stirred for 5 minutes, it appeared that additional solid had formed so 5.0 mL of distilled THF was added. The reaction mixture was stirred at 23° C. for 24 hours and then quenched by the addition of 1N HCl solution until the gas evolution ceased and the pH=1. This was then concentrated in vacuo to remove most of the THF, diluted with 20 mL of water, and extracted with 25 mL of ether. The aqueous layer was extracted with two 25 mL portions of $CH_2Cl_2$. The combined organic layers was dried ($MgSO_4$), filtered, and concentrated in vacuo. The crude product was chromatographed on 40 g of silica gel using 3% $CH_3OH/CH_2Cl_2$ as eluent to afford 280 mg of impure alcohol. This was then dissolved in 1-2 mL of $CH_2Cl_2$, diluted with ether, warmed and diluted with a near equal volume of hexane. On standing in the refrigerator, very fine white crystals formed. These were collected and dried in vacuo to afford 120.5 mg of pure title alcohol, m.p. 119°-121° C.

Analysis Calc'd for $C_{30}H_{42}N_2O_4$: C, 72.84; H, 8.56; N, 5.66

Found: C, 73.07; H, 8.68; N, 5.61

TLC: silica gel, 3% $CH_3OH/CH_2Cl_2$, $R_f=0.35$, vanillin.

$[\alpha]_D = +3.97$ (c=0.94, $CH_3OH$).

$^{13}C$ NMR ($CDCl_3$, 67.5 MHz): δ 163.9, 160.6, 140.5, 140.3, 137.8, 136.3, 129.6, 129.4, 126.5, 126.1, 79.8, 78.6, 62.1, 50.1, 47.0, 39.2, 37.5, 37.1, 34.1, 33.4, 32.1, 29.9, 28.8, 26.7, 26.4, 24.2.

EXAMPLE 82

[1S-(1α,2α,3α,4α)]-2-[[3-[4-[(Phenylamino)carbonyl]-2-oxazolyl]-7-oxabicyclo2.2.1]hept-2-yl]methyl]-benzenepropanic acid, methyl ester To a solution of 200 mg (0.52 mMol) of Example 2, Part J acid in 20 mL dry $CH_2Cl_2$ (distilled from $P_2O_5$) was added 1 small drop of DMF, followed by 310 μL (0.62 mMol, 2M/$CH_2Cl_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$), cooled to 0°, was added 120 μL (0.83 mMol, distilled from $CaH_2$) of triethylamine, followed by the dropwise addition of a solution of 58 mg (0.62 mMol, Aldrich) of aniline in 5 mL $CH_2Cl_2$. The reaction was stirred at 0° for 16 hours, then partitioned between 80 mL ethyl acetate/60 mL 1M HCl. The ethyl acetate layer was separated, dried ($MgSO_4$) and concentrated in vacuo to give a crude yellow solid. The crude solid was flash chromatographed (Merck silica, 1:2 ethyl acetate/hexane) to give 180 mg (0.39 mMol, 78%) of title ester as a white solid, mp 177°-178°.

EXAMPLE 83

[1S-(1α,2α,3α,4α)]-2-[[3-[4-[(Phenylamino)carbonyl]-2-oxazolyl]-7-oxabicyclo[2.2.1]hept-2-yl]methyl]benzenepropanic acid To a mixture of 180 mg (0.39 mMol) of Example 82 ester in 8 mL distilled THF/2 mL water was added 33 mg (0.78 mMol, Aldrich) of lithium hydroxide monohydrate. The reaction was stirred vigorously for 4 hours at room temperature, then quenched by the addition of 1.6 mL (1.6 mMol) 1M HCl. The mixture was partitioned between 60 mL ethyl acetate/60 mL water. The ethyl acetate layer was separated, dried ($MgSO_4$) and concentrated in vacuo to give 170 mg (0.38 mMol, 98%) of title acid, as a white foam, mp 170°-172°.

IR (KBr): 2953, 2931, 2872, 1728, 1622, 1601, 1577 $cm^{-1}$.

MS(CI): 447 $(M+H)^+$.

OR: $[\alpha]_D = +4°$ (c=1.0 in chloroform).

TLC: $R_f$ (silica gel, 1:9 methanol/methylene chloride)=0.43, ammonium molybdate/ceric sulfate and UV, homogeneous.

Analysis Calc'd for $C_{26}H_{26}N_2O_5$: C, 69.94; H, 5.87; N, 6.28

Found: C, 69.70; H, 5.88; N, 6.17

EXAMPLE 84

[1S-(1α,2α,3α,4α)]-2-[[3-[4-[(Pentylmethylamino)carbonyl]-2-oxazolyl]-7-oxabicyclo[2.2.1]hept-2-yl]methyl]benzenepropanoic acid, methyl ester To a solution of 200 mg (0.52 mMol, L223-88-23) of Example 2, Part J acid in 20 mL dry $CH_2Cl_2$ (distilled from $P_2O_5$) was added 1 small drop of DMF, followed by 310 μL (0.62 mMol, 2M/$CH_2Cl_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$), cooled to 0°, was added 170 μL (1.25 mMol, distilled from $CaH_2$) of triethylamine, followed by the dropwise addition of a solution of 86 mg (0.62 mMol) of methyl(5-n-pentyl)amine hydrochloride in 5 mL $CH_2Cl_2$. The reaction was stirred at 0° for 16 hours, then partitioned between 80 mL ethyl acetate/60 mL 1M HCl. The ethyl acetate layer was separated, dried ($MgSO_4$) and concentrated in vacuo to give a crude yellow solid. The crude solid was flash chromatographed (Merck silica, 1:2 ethyl acetate/hexane) to give 160 mg (0.34 mMol, 66%) of title ester as a yellow oil.

EXAMPLE 85

[1S-(1α,2α,3α,4α)]-2-[[3-[4-[Pentylmethylamino)carbonyl]-2-oxazolyl]-7-oxabicyclo[2.2.1]hept-2-yl]methyl]benzenepropanoic acid To a mixture of 160 mg (0.34 mMol) of Example 84 ester in 8 mL distilled THF/2 mL water was added 29 mg (0.68 mMol, Aldrich) of lithium hydroxide monohydrate. The reaction was stirred vigorously for 4 hours at room temperature, then quenched by the addition of 1.4 mL (1.4 mMol) 1M HCl. The mixture was partitioned between 60 mL ethyl acetate/60 mL water. The ethyl acetate layer was separated, dried (MgSO$_4$) and concentrated in vacuo to give 150 mg (0.33 mMol, 97%) of title acid as a yellow oil.

IR (KBr): 2980, 2951, 2941, 1726, 1703, 1672, 1624 cm$^{-1}$.

MS(CI): 455 (M+H)$^+$.

OR: [α]$_D$= +27° (c=1.0 in chloroform).

TLC: R$_f$ (silica gel, 1:9 methanol/methylene chloride)=0.38, ammonium molybdate/ceric sulfate and UV, homogeneous.

Analysis Calc'd for C$_{26}$H$_{34}$N$_2$O$_5$: C, 68.70; H, 7.54; N, 6.16

Found: C, 69.08; H, 7.82; N, 5.82

EXAMPLE 86

[1S-(1α,2α,3α,4α)]-2-[[3-[4-[[Amino[1,1'biphenyl]4-yl]carbonyl]-2-oxazolyl]-7-oxabicyclo[2.2.1]hept-2-yl]methyl]benzenepropanoic acid, methyl ester To a solution of 200 mg (0.52 mMol) of oxazole acid prepared in Example 2, Part J in 2 mL of dry methylene chloride (distilled from phosporous pentoxide) was added at room temperature a small drop of DMF then 55 μL (0.63 mMol, Aldrich) of oxalyl chloride. The solution was stirred until gas evolution ceased, about 30 minutes, then concentrated in vacuo to give the acid chloride as a pale yellow solid.

To a solution of the crude acid chloride (about 0.52 mMol) in 4 mL of dry methylene chloride cooled in an ice-bath was added 105 mg (0.62 mMol, Aldrich) of 4-aminobiphenyl followed by 110 μL (0.78 mMol, distilled from calcium hydride) of triethylamine. The reaction mixture was warmed to room temperature and stirred for 1 hour. The resulting yellow solution was partitioned between 20 mL 1M aqueous HCl solution and 20 mL of hot ethyl acetate. The organic layer was separated, dried (magnesium sulfate) and concentrated in vacuo to give a yellow solid. The crude material was recrystallized (ethyl acetate/hexane) to afford 212 mg (0.40 mMol, 76%) of title ester as a white solid, mp 174°–175°.

EXAMPLE 87

[1S-(1α,2α,3α,4α)]-2-[[3-[4-[[Amino[1,1'biphenyl]4-yl]carbonyl]-2-oxazolyl]-7-oxabicyclo[2.2.1]hept-2-yl]methyl-]benzenepropanoic acid A mixture of 160 mg (0.93 mMol) of Example 86 ester and 4 mL of THF was warmed until homogeneous then 1 mL of water was added followed by 25 mg (0.60 mMol, Aldrich) of lithium hydroxide monohydrate. The reaction mixture was stirred at room temperature for 4 hours then acidified by addition of 1.2 mL of 1M HCl solution. The resulting solution was partitioned between 20 mL of 1M aqueous HCl solution and 20 mL of ethyl acetate. The organic layer was separated, dried (magnesium sulfate) and then concentrated in vacuo to give a solid. The crude material was recrystallized (acetonitrile) to afford 138 mg (0.26 mMol, 88%) of title acid as white crystals, mp 204°–206°.

IR(KBr): 3444 (broad), 1688, 1597, 1526, 1489, 1406, 1103 cm$^{-1}$.

MS(CI): 523 (M+H)$^+$.

OR: [α]$_D$= −2° (c=0.5 in chloroform).

TLC: R$_f$ (silica gel, 1:9 methanol/methylene chloride)=0.47, ammonium molybdate/ceric sulfate and UV, homogeneous.

Analysis Calc'd for C$_{32}$H$_{30}$N$_2$O$_5$: C, 73.54; H, 5.79; N, 5.36

Found: C, 73.41; H, 5.68; N, 5.22

EXAMPLE 88

1S-(1α,2α,3α,4α)]-2-[[3-[4-[[(4-Cyclohexylbutyl)methylamino]carbonyl]-2-oxazolyl]-7-oxabicyclo[2.2.1]hept-2-yl]methyl]benzenepropanoic acid, methyl ester To a solution of 200 mg (0.52 mMol, L223-88-23) of acid prepared in Example 2, Part J in 20 mL dry CH$_2$Cl$_2$ (distilled from P$_2$O$_5$) was added 1 small drop of DMF, followed by 310 μL (0.62 mMol, 2M/CH$_2$Cl$_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry CH$_2$Cl$_2$ (distilled from P$_2$O$_5$), cooled to 0°, was added 170 μL (1.25 mMol, distilled from CaH$_2$) of triethylamine, followed by the dropwise addition of a solution of 160 mg (80% pure, 128 mg, 0.62 mMol) of 4-cyclohexylbutyl(methyl) amine hydrochloride in 5 mL CH$_2$Cl$_2$. The reaction was stirred at 0° for 16 hours, then partitioned between 80 mL ethyl acetate/60 mL 1M HCl. The ethyl acetate layer was separated, dried (MgSO$_4$) and concentrated in vacuo to give a crude yellow solid. The crude solid was flash chromatographed (Merck siilca, 1:2 ethyl acetate/hexane) to give 200 mg (0.37 mMol, 72%) of title ester as a white solid.

EXAMPLE 89

[1S-(1α,2α,3α,4α)]-2-[[3-[4-[[(4-Cyclohexylbutyl)methylamino]carbonyl]-2-oxazolyl]-7-oxabicyclo2.2.1-]hept-2-yl]methyl]benzenepropanoic acid To a mixture of 130 mg (0.25 mMol) of Example 88 ester in 8 mL distilled THF/2 mL water was added 20 mg (0.48 mMol, Aldrich) of lithium hydroxide monohydrate. The reaction was stirred vigorously for 4 hours at room temperature, then quenched by the addition of 1.0 mL (1.0 mMol) 1M HCl. The mixture was partitioned between 80 mL ethyl acetate/80 mL water. The ethyl acetate layer was separated and the water layer was extracted with 2×50 mL of ethyl acetate. The combined ethyl acetate layers were dried (MgSO$_4$) and concentrated in vacuo to give 100 mg (0.19 mMol, 79%) of title acid as a white foam, mp 60°–65°.

IR (KBr): 3439, 3431, 2922, 2850, 1716, 1697, 1612, 1585 cm$^{-1}$.

MS(CI): 523 (M+H)$^+$.

OR: [α]$_D$= +20° (c=1.0 in chloroform).

TLC: R$_f$ (silica gel, 1:9 methanol/methylene chloride)=0.31, ammonium molybdate/ceric sulfate and UV, homogeneous.

Analysis Calc'd for C$_{31}$H$_{42}$N$_2$O$_5$+0.25 mol H$_2$O: C, 70.61; H, 8.13, N, 5.31

Found: C, 70.52; H, 8.12, N, 5.04

EXAMPLE 90

[1S-(1α,2α,3α,4α)]-2-[[3-[4-[[(4-Phenylbutyl)amino]carbonyl-2-oxazolyl]-7-oxabicyclo[2.2.1]hept-2-yl]methyl]benzenepropanoic acid, methyl ester To a solution of 200 mg (0.52 mMol) of acid prepared in Example 2, Part J in 20 mL dry $CH_2Cl_2$ (distilled from $P_2O_5$) was added 1 small drop of DMF, followed by 310 µL (0.62 mMol, 2M/$CH_2Cl_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry $CH_2Cl_2$ (distilled from $P_2O_5$), cooled to 0°, was added 120 µL (0.83 mMol, distilled from $CaH_2$) of triethylamine, followed by the dropwise addition of a solution of 93 mg (0.62 mMol, Aldrich) of 4-phenylbutylamine in 5 mL $CH_2Cl_2$. The reaction was stirred at 0° for 16 hours, then partitioned between 80 mL ethyl acetate/60 mL 1M HCl. The ethyl acetate layer was separated, dried ($MgSO_4$) and concentrated in vacuo to give a crude yellow solid. The crude solid was flash chromatographed (Merck silica, 1:2 ethyl acetate/hexane) to give 250 mg (0.48 mMol, 93%) of title ester as a white solid, mp 132°-134°.

EXAMPLE 91

[1S-(1α,2α,3α,4α)]-2-[[3-[4-[[(4-Phenylbutyl)amino]carbonyl]-2-oxazolyl]-7-oxabicyclo[2.2.1]hept-2-yl]methyl]benzenepropanoic acid To a solution of 237 mg (0.46 mMol) of Example 90 ester in 8 mL distilled THF/2 mL water was added 39 mg (0.92 mMol, Aldrich) of lithium hydroxide monohydrate. The reaction was stirred vigorously for 4 hours at room temperature, then quenched by the addition of 1.9 mL (1.9 mMol) 1M HCl. The mixture was partitioned between 60 mL ethyl acetate/60 mL water. The ethyl acetate layer was separated, dried ($MgSO_4$) and concentrated in vacuo to give crude yellow foam. The crude foam was flash chromatographed (Merck silica, ethyl acetate then 1:9 methanol:methylene chloride) to give 170 mg (0.34 mMol, 74%) of title acid as a white solid, mp 148°-150°.

IR (KBr): 3423, 2935, 1716, 1653, 1602, 1523 cm$^{-1}$.

MS(CI): 503 (M+H)$^+$.

OR: $[\alpha]_D = +7°$ (c=1.0 in chloroform).

TLC: $R_f$ (silica gel, 1:9 methanol/methylene chloride)=0.51, ammonium molybdate/ceric sulfate and UV, homogeneous.

Analysis Calc'd for $C_{30}H_{34}N_2O_5 + 0.4$ mol $H_2O$: C, 70.69; H, 6.88; N, 5.50

Found: C, 70.95; H, 6.79; N, 5.17

EXAMPLE 92

[1S-(1α,2α,3α,4α)]-2-[[3-[4-[[[4-(Phenylmethoxy)-phenyl]amino]carbonyl]-2-oxazolyl]-7-oxabicyclo[2.2.1]hept-2-yl]methyl]benzenepropanoic acid, methyl ester To a solution of 500 mg (1.30 mMol) of oxazole acid prepared in Example 2, Part J in 5 mL of dry methylene chloride (distilled from phosphorous pentoxide) was added at room temperature a small drop of DMF then 135 µL (1.54 mMol, Aldrich) of oxalyl chloride. The solution was stirred until gas evolution ceased, about 30 minutes, then concentrated in vacuo to give the acid chloride as a pale yellow solid.

To a solution of the crude acid chloride (about 1.30 mMol) in 6 mL of dry methylene chloride cooled in an ice-bath was added 400 µL (1.85 mMol, distilled from calcium hydride) of triethylamine followed by 368 mg (1.56 mMol, Aldrich) of 4-benzyloxyaniline hydrochloride. The reaction mixture was stirred at 0° for 10 minutes then at room temperature for 1 hour. The resulting yellow solution was partitioned between 20 mL 1M aqueous HCl solution and 20 mL of ethyl acetate. The organic layer was separated, dried (magnesium sulfate) and concentrated in vacuo to give a yellow solid. The crude material was recrystallized (ethyl acetate/hexane) to afford 560 mg (0.99 mMol, 76%) of title ester as a white solid, mp 154°-155°.

EXAMPLE 93

[1S-(1α,2α,3α,4α)]-2-[[3-[4-[[4-(Phenylmethoxy)-phenyl]amino]carbonyl]-2-oxazolyl]-7-oxabicyclo[2.2.1]hept-2-yl]methyl]benzenepropanoic acid A solution of 515 mg (0.92 mMol) of Example 92 ester and 78 mg (1.9 mMol, Aldrich) of lithium hydroxide monohydrate in 9 mL of 2:1 THF/water was stirred at room temperature for 4 hours. The resulting solution was partitioned between 20 mL of 1M aqueous HCl solution and 20 mL of ethyl acetate. The organic layer was separated, dried (magnesium sulfate) and then concentrated in vacuo to give a solid. The crude material was recrystallized (ethyl acetate/hexane) to afford 380 mg (0.69 mMol, 75%) of title acid as white crystals, mp 192°-193°.

IR(KBr): 3434 (broad), 1711, 1682, 1640, 1603, 1510, 1229 cm$^{-1}$.

MS(CI): 553 (M+H)$^+$.

OR: $[\alpha]_D = +4.4°$ (c=0.5 in chloroform).

TLC: $R_f$ (silica gel, 1:9 methanol/methylene chloride)=0.53, ammonium molybdate/ceric sulfate and UV, homogeneous.

Analysis Calc'd for $C_{33}H_{32}N_2O_6$: C, 71.72; H, 5.84; N, 5.07

Found: C, 71.68; H, 5.74; N, 4.95.

EXAMPLE 94

[1S-(1α,2α,3α,4α)]-2-[[3-[4-[[(Hydroxyphenyl)amino]-carbonyl]-2-oxazolyl]-7-oxabicyclo[2.2.1]hept-2yl]methyl]benzenepropanoic acid A mixture of 200 mg (0.36 mMol) of Example 93 acid and 40 mg of 20% palladium hydroxide on carbon catalyst (Aldrich) in 20 mL of sieve-dried methanol was stirred rapidly under an atmosphere of hydrogen (balloon) at room temperature for 2 hours. The reaction mixture was passed through a 4 µM polycarbonate membrane then the filtrate was concentrated in vacuo to give a foam. The foam was crystallized (ethyl acetate/hexane) to afford 142 mg (0.31 mMol, 86%) of title acid as small white crystals, mp 185°-186°.

IR(KBr): 3426, 1713, 1636, 1514, 1435, 1215 cm$^{-1}$.

MS(CI): 463 (M+H)$^+$.

OR: $[\alpha]_D = -17°$ (c=0.5 in methanol).

TLC: $R_f$ (silica gel, 1:9 methanol/methylene chloride)=0.31, ammonium molybdate/ceric sulfate and UV, homogeneous.

Analysis Calc'd for $C_{26}N_2O_6$: C, 67.52; H, 5.67; N, 6.06

Found: C, 67.35; H, 5.51; N, 5.74.

EXAMPLE 95

[1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]-N-methylsulfonylbenzenepropanamide Into an over-dried flask under argon was placed 0.25 g Example 1 acid (0.49 mmol), 0.07 g N,N-dimethylaminopyridine (0.6 mmol), 0.13 g methanesulfonamide (1.4 mmol), and 0.13 g WSC (0.7 mmol). To this was added by syringe 2 mL of DMF (Burdick & Jackson, new bottle, assayed 0.010% water). Upon stirring at room temperature, all of the solid components dissolved. TLC indicated nearly complete reaction after 2.5 hours. After 1 day (TLC showed starting material consumed), the reaction mixture was diluted with EtOAc, washed with 1.0M aqueous HCl three times, dried over Na$_2$SO$_4$, and evaporated. The residue was flash chromatographed (35% to 50% [5% AcOH in EtOAc] in hexane gradient) to obtain, after azeotroping away AcOH with toluene and crystallizing by addition and evaporation of Et$_2$O, 0.26 g of pure title amide, a white solid (mp 154°–156°). The yield of product was 91%.

$[\alpha]°_D = +20.1°$ in CHCl$_3$ at c=1.71 g/100 mL.

TLC (50% [5% AcOH in EtOAc] in hexane - anisaldehyde):

| Example 1 acid | 0.36 |
|---|---|
| Title amide | 0.33 |

EXAMPLE 96

[1S-[1α,2α,3α(E),4α]]-2-[[3-[4-[[(2-Propynyl)amino]carbonyl]-2-oxazolyl]-7-oxabicyclo-[2.2.1]hept-2-yl]methyl]benzenepropanoic acid, methyl ester To a stirring mixture of 137 mg (C$_2$H$_5$)$_3$N (1.36 mmol, 1.6 equiv) and 92 mg propargylamine hydrochloride (1.00 mmol, 1.2 equiv) in 6 mL CHCl$_3$ under argon at room temperature, was added 340 mg of Example 2, Part J acid chloride (0.84 mmol) in 6 mL CHCl$_3$. After stirring overnight, TLC indicated incomplete reaction. Therefore, 109 mg (C$_2$H$_5$)$_3$N (1.08 mmol, 1.3 equiv) and 92 mg propargylamine hydrochloride (1.00 mmol, 1.2 equiv) were added. TLC indicated complete reaction after 5 minutes. The reaction mixture was evaporated and flash chromatographed (silica, 50% EtOAc in hexane) to obtain 350 mg of pure title amide as a white solid. The yield of product was quantitative.

TLC (1% F$_3$CCO$_2$H, 1% CH$_3$OH, 98% EtOAc - anisaldehyde):

| Acid of Example 2 Part J | 0.86 |
|---|---|
| title ester | 0.76 |

$^{13}$C NMR (67.8 MHz in CDCl$_3$): δ 173.0, 163.9, 160.1, 140.8, 138.4, 137.7, 135.5, 129.6, 128.9, 126.5, 126.5, 79.6, 79.2, 78.5, 71.4, 51.5, 49.9, 46.8, 34.8, 32.3, 29.8, 28.7, 28.5, 27.5.

EXAMPLE 97

[1S-[1α,2α,3α(E),4α]]-2-[[3-[4-[[(2-Propynyl)amino]carbonyl]-2-oxazolyl]-7-oxabicyclo[2.2.1]hept-2-yl]methyl]benzenepropanoic acid To 350 mg of pure Example 96 amide in 10 mL CH$_3$OH at room temperature, was added 10 mL of 1.0M aqueous NaOH solution and 10 mL THF. After stirring the mixture for 2 hours, 14 mL of 1M aqueous HCl solution was added to lower the pH to 1. Extraction with CH$_2$Cl$_2$ (3 time) followed. The extracts were dried over Na$_2$SO$_4$, and solvent evaporation gave 360 mg of title acid as a white solid in quantitative yield.

TLC (50% [5% AcOH in EtOAc]in hexane - anisaldehyde):

| Example 98 amide | 0.30 |
|---|---|
| title acid | 0.17 |

EXAMPLE 98

[1S-[1α,2α,3α(E),4α]]-2-[[3-[4-[[(3-Iodo-2-propenyl)amino]carbonyl]-2-oxazolyl]-7-oxabicyclo[2.2.1]hept-2-yl]methyl]benzenepropanoic acid

A.

[1S-[1α,2α,3α(E),4α]]-2-[[3-[4-[[(3-Tributylstannane-2-propenyl)amino]carbonyl]-2-oxazolyl]-7-oxabicyclo[2.2.1]hept-2-yl]methyl]benzenepropanoic acid Under argon a mixture of 120.9 mg (0.296 mmol)of Example 97 acid, 6.3 mg azobisisobutyronitrile (AIBN) (0.038 mmol, 0.13 equiv), and 332 mg C$_4$H$_9$)$_3$SnH (1.14 mmol, 3.8 equiv) in 0.4 mL freshly distilled THF was heated to reflux for 10 minutes. The reaction solution was evaporated and directly flash chromatographed (silica, 25% to 47%[5% AcOH in EtOAc] in hexane gradient). Evaporation of the chromatography solvent was quickly followed by coevaporation with toluene to remove residual AcOH. After exposure to high vacuum, 130 mg of nearly pure title vinyl stannane, an oil, was obtained. Title vinyl stannane was contaminated with a trace of the unsubstituted allyl analogue. The yield of title compound was 63%.

TLC (50% [5% AcOH in EtOAc]in hexane - anisaldehyde):

| Example 99 acid | 0.20 |
|---|---|
| title vinylstannane | 0.45 |

$^{13}$C NMR (67.8 MHz in CDCl$_3$): δ 176.8, 163.9, 160.6, 142.9, 141.2, 138.5, 137.7, 135.8, 130.7, 129.7, 129.0, 126.6, 126.6, 79.7, 78.6, 49.9, 46.9, 44.5, 34.8, 32.5, 29.8, 29.0, 28.8, 27.4, 27.2, 13.6, 9.4.

B.

[1S-[1α,2α,3α(E),4α]]-2-[[3-[4-[[(3-Iodo-2-propenyl)amino]carbonyl]-2-oxazolyl]-7-oxabicyclo[2.2.1]hept-2-yl]methyl]benzenepropanoic acid This chemistry is described in J. L. Musachio and J. R. Lever, *Tetrahedron Letters*, 1989, 30, 3613.

To a solution of 121 mg Part A compound (0.17 mmol) in 34 mL CH$_3$OH, 10 mL pH 7.7 buffer (preparation: 2.72 g KH$_2$PO$_4$ (20 mmol) and 20.9 g K$_2$HPO$_4$ (120 mmol) dissolved to 1.0L with Millipore purified water), and 10 mL water stirring at room temperature, was added 52 m9 NaI (0.41 mmol), then 47 mg Chloramine-T hydrate (<0.21 mmol). The solids dissolved, and an iodine color formed. After 1 hour (solution still colored), 2 mL 3M aqueous NaHSO$_3$ and 2 mL 1M aqueous HCl were added. The mixture was extracted three times with CH$_2$Cl$_2$, and the extracts were dried over Na$_2$SO$_4$ and evaporated. Flash chromatography (silica gel, 30% to 40% [5% AcOH in EtOAc] in hexane gradient), collecting only the pure fractions, gave 41 mg (45% yield) of title compound, a white solid (mp 142°-145°).

$[\alpha]°_D = +11.1°$ in $CHCl_3$ at $c=1.29$ g/100 mL.

TLC (50% [5% AcOH in EtOAc] in hexane - anisaldehyde):

| Part A compound | 0.59 |
|---|---|
| Example 96 ester | 0.39 |

EXAMPLE 99

[1S-(1α,2α,3α,4α)]-2-[[3-[4-[[[4-(4-Hydroxy-3-iodophenyl)butyl]amino]carbonyl]-2-oxazolyl]-7-oxabicyclo2.2.1]hept-2-yl]methyl]benzenepropanoic acid To a solution of 209 mg Example 37 acid (0.40 mmol) in 8 mL $CH_3OH$ and 8 mL pH 7.7 buffer (preparation: 2.72 g $KH_2PO_4$ (20 mmol) and 20.9 g $K_2HPO_4$ (120 mmol) dissolved to 1.0L with Millipore purified water) stirring at room temperature, was added 79 mg NaI (0.53 mmol), then 128 mg Chloramine-T hydrate (<0.56 mmol). The solids dissolved, an iodine color formed, and the mixture then decolorized. After 1 hour, 2 mL 3M aqueous $NaHSO_3$ and 2 mL 1M aqueous HCl were added. The mixture was extracted three times with $CH_2Cl_2$, and the extracts were dried over $Na_2SO_4$ and evaporated. Flash chromatography (silica gel, 30% to 50% [5% AcOH in EtOAc] in hexane gradient) separated about 125 mg of impure undesired diiodo product from the desired product and remaining starting material. The latter two were separated by flash chromatography using a different solvent system (10% to 15% [10% AcOH in acetone in toluene gradient). This gave 53 mg (21% yield) of pure title compound, which solidified upon addition and evaporation of $Et_2O$ (mp 84°-91°).

$[\alpha]°_D = +11.7°$ in $CHCl_3$ at $c=0.76$ g/100 mL.

TLC (50% [5% AcOH in EtOAc] in hexane - anisaldehyde):

| Example 37 acid | 0.20 |
|---|---|
| title compound | 0.24 |
| diiodo product | 0.36 |

TLC (5% AcOH in [20% acetone in toluene] - anisaldehyde):

| Example 37 acid | 0.32 |
|---|---|
| title compound | 0.38 |
| diiodo product | 0.46 |

EXAMPLE 100

1S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzenepropanoic acid, monopotassium salt To a slurry of 262 mg Example 1 acid (0.516 mmol) in 10 mL $CH_3OH$ stirring at room temperature, was added 473 μL of 1.09M aqueous KOH solution (0.516 mmol). (The KOH solution was prepared by dissolving in 50.0 mL of house line purified water 3.51 g of 86.8% pure KOH, new bottle, Mallinckrodt, 3.05 g net, 54.3 mmol). The starting material slowly dissolved. The resulting solution was evaporated to a glass on a rotoevaporator. Addition and evaporation of $CH_3CN$ caused the glass to solidify. After addition of more $CH_3CN$, the solid was filtered, washing with $CH_3CN$, and exposed to high vacuum. This gave 224 mg (80% yield) of title salt (mp 90°-110°).

$[\alpha]°_D = +0.2°$ in $CH_3OH$ at $c=1.41$ g/100 mL.

TLC (50% [5% AcOH in EtOAc] in hexane - anisaldehyde):

| Example 1 acid | 0.36 |
|---|---|
| title salt | 0.36 |

EXAMPLE 101

[S-(1α,2α,3α,4α)]-2-[[3-[4-[[(4-Cyclohexylbutyl)amino]carbonyl]-2-oxazolyl]-7-oxabicyclo[2.2.1]hept-2-yl]methyl]benzenepropanoic acid, monosodium salt To a slurry of 324 mg of Example 1 acid (0.638 mmol) in 20 mL $CH_3OH$ stirring at room temperature, was added 638 μL of 1.00M aqueous NaOH solution (Mallinckrodt). The starting material slowly dissolved. The resulting solution was evaporated to a glass on a rotoevaporator. Addition and evaporation of $CH_3CN$ caused the glass to solidify. After addition of more $CH_3CN$, the solid was filtered and dried under high vacuum. This gave 290 mg (86% yield) of title salt (mp 274°-275°).

$[\alpha]°_D = -0.3°$ in $CH_3OH$ at $c=1.50$ g/100 mL.

TLC (50% [5% AcOH in EtOAc] in hexane - anisaldehyde):

| Example 1 acid | 0.36 |
|---|---|
| title salt | 0.36 |

EXAMPLE 102

[1S-(1α,2α,3α,4α)]-2-[[3-[4-[[(4-Methoxyphenyl)amino]carbonyl]-2-oxazolyl]-7-oxabicyclo[2.2.1]hept-2-yl]methyl]benzenepropanoic acid, methyl ester To a solution of 200 mg (0.52 mMol) of acid prepared as described in Example 2, Part J in 20 mL dry $CH_2Cl_2$ (distilled from P was added 1 small drop of DMF, followed by 310 μL (0.62 mMol, 2M/$CH_2Cl_2$, Aldrich) of oxalyl chloride solution. The reaction was stirred at room temperature until gas evolution ceased (about 30 minutes), then the reaction mixture was concentrated in vacuo to give the crude acid chloride as a pale yellow solid.

To a solution of the crude acid chloride in 10 mL dry $CH_2Cl_2$ (distilled from $P_2O_5$), cooled to 0°, was added 120 μL 0.83 mMol, distilled from $CaH_2$) of triethylamine, followed by the dropwise addition of a solution of 77 mg (0.62 mMol, Aldrich) of p-anisidine in 5 mL $CH_2Cl_2$. The reaction was stirred at 0° for 16 hours, then partitioned between 80 mL ethyl acetate and 80 mL 1M HCl. The ethyl acetate layer was separated, dried ($MgSO_4$) and concentrated in vacuo to give a yellow solid. The crude solid was flash chromatographed (Merck silica, 1:2 ethyl acetate/hexane) then recrystallized (hexane/ethyl acetate) to give 210 mg (0.43 mMol, 82%) of title ester as a white solid, mp 153°-155°.

EXAMPLE 103

[1S-(1α,2α,3α,4α)]-2-[[3-[4-[[(4-Methoxyphenyl)amino]carbonyl]-2-oxazolyl]-7-oxabicyclo[2.2.1]hept-2-yl]methyl]benzenepropanoic acid To a solution of 210 mg (0.43 mMol) of Example 102 ester in 8 mL distilled THF and 2 mL water was added 36 mg (0.86 mMol, Aldrich) of lithium hydroxide monohydrate. The reaction was stirred vigorously for 4 hours at room temperature, quenched by the addition of 1.7 mL (1.7 mMol) 1M HCl then partitioned between 60 mL ethyl acetate and 60 mL water. The ethyl acetate layer was separated, dried (MgSO$_4$) and concentrated in vacuo to give 200 mg (0.42 mMol, 98%) of title acid, as a solid white foam.

IR (KBr): 3437, 3144, 2987, 1710, 1637, 1604, 1525 cm$^{-1}$.

MS(CI): 477 (M+H)$^+$.

OR: [α]$_D$ = +0° (c=1.0 in chloroform).

TLC: R$_f$(silica gel, 1:9 methanol/methylene chloride)=0.54, ammonium molybdate/ceric sulfate and UV, homogeneous.

Analysis Calc'd for C$_{27}$H$_{28}$N$_2$O$_6$+0.39 H$_2$O: C, 67.06; H, 6.00; N, 5.79

Found: C, 67.46; H, 6.02; N, 5.39

EXAMPLE 104

[1S-(1α,2α,3α,4α)]-2-[[3-[4-[[(4-Chlorophenyl)amino]carbonyl]-2-oxazolyl]-7-oxabicyclo[2.2.1]hept-2-yl]methyl]benzenepropanoic acid, methyl ester To a solution of 200 mg (0.52 mMol) of acid prepared in Example 2, Part J in 20 mL dry CH$_2$Cl$_2$ (distilled from P$_2$O$_5$) was added 1 small drop of DMF, followed by 310 μL (0.62 mMol, 2M/CH$_2$Cl$_2$, Aldrich) of oxalyl chloride solution. The reaction was stirred at room temperature until gas evolution ceased (about 30 minutes), then the reaction mixture was concentrated in vacuo to give the crude acid chloride as a pale yellow solid.

To a solution of the crude acid chloride in 10 mL dry CH$_2$Cl$_2$ (distilled from P$_2$O$_5$), cooled to 0°, was added 120 μL (0.83 mMol, distilled from CaH$_2$) of triethylamine, followed by the dropwise addition of a solution of 79 mg (0.62 mMol, Aldrich) of p-chloroaniline in 5 mL CH$_2$Cl$_2$. The reaction was stirred at 0° for 16 hours, then partitioned between 80 mL ethyl acetate and 80 mL 1M HCl. The ethyl acetate layer was separated, dried (MgSO$_4$) and concentrated in vacuo to give a crude yellow solid. The crude solid was flash chromatographed (Merck silica, 1:4 ethyl acetate/hexane) to give a yellow solid. The crude solid was recrystallized (hexane/ethyl acetate) to give 170 mg (0.34 mMol, 66%) of title ester as a white solid, mp 179°–181°.

EXAMPLE 105

[1S-(1α,2α,3α,4α)]-2-[[3-[4-[[(4-Chlorophenyl)amino]carbonyl]-2-oxazolyl]-7-oxabicyclo[2.2.1]hept-2-yl]methyl]benzenepropanoic acid To a solution of 170 mg (0.34 mMol) of Example 104 ester in 8 mL distilled THF/2 mL water was added 29 mg (0.92 mMol, Aldrich) of lithium hydroxide monohydrate. The reaction was stirred vigorously for 4 hours at room temperature, then quenched by the addition of 1.4 mL (1.4 mMol) 1M HCl and partitioned between 60 mL ethyl acetate and 60 mL water. The ethyl acetate layer was separated, dried (MgSO$_4$) and concentrated in vacuo to give 160 mg (0.33 mMol, 98%) of title acid as a white solid, mp 220°–221°.

IR KBr : 3435, 3107, 1709, 1687, 1597, 1581 cm$^{-1}$.

MS(CI): 498 (M+NH$_4$)$^+$.

OR:[α]$_D$ = −3° (c=1.0 in chloroform).

TLC: R$_f$(silica gel, 1:9 methanol/methylene chloride)=0.56, ammonium molybdate/ceric sulfate and UV, homogeneous.

Analysis Calc'd for C$_{26}$H$_{25}$N$_2$O$_5$Cl: C, 64.93; H, 5.24; N, 5.83; Cl, 7.37

Found: C, 64.83; H, 5.19; N, 5.56; Cl, 7.32

EXAMPLE 106

[1S-(1α,2α,3α,4α)]-2-[[3-[4-[[[3-(1H-Imidazol-1-yl)propyl]amino]carbonyl]-2-oxazolyl]-7-oxabicyclo[2.2.1]hept-2-yl]methyl]benzenepropanoic acid, methyl ester To a solution of 0.21 g (0.52 mmol) Example 2, Part J acid chloride in 5 mL of chloroform, was added 0.071 g (0.58 mmol) of 1-(3-aminopropyl)imidazole and 0.07 g (0.7 mmol) triethylamine. The mixture was stirred at room temperature for 20 hours then concentrated on a rotoevaporator. The residue was diluted with 50 mL EtOAc and 10 mL water. The organic layer was separated, and the aqueous layer was extracted with 20 mL of EtOAc twice. The organic layers were combined, washed with brine, dried over MgSO$_4$, and concentrated to obtain 0.25 g (98%) of an oil.

R$_f$=0.6 in 10% CH$_3$OH in CH$_2$Cl$_2$, UV, Ce(SO$_4$)$_2$.

$^{13}$C NMR (67.8 MHz, CDCl$_3$): δ 173.2, 163.9, 161.0, 140.7, 138.4, 138.0, 137.7, 136.0, 135.8, 129.6, 128.9, 127.0, 126.7, 126.5, 79.8, 78.7, 51.6, 49.9, 46.9, 46.9, 36.1, 34.9, 32.4, 31.3, 29.8, 28.9, 27.6.

EXAMPLE 107

[1S-(1α,2α,3α,4α)]-2-[[3-[4-[[[3-(1H-Imidazol-1-yl)propyl]amino]carbonyl]-2-oxazolyl]-7-oxabicyclo[2.2.1]hept-2-yl]methyl]benzenepropanoic acid A solution of 0.25 g (0.51 mmol) of Example 106 ester in 1 mL of 1N NaOH, 2 mL of methanol, and 2 mL of THF was stirred for 2.5 days. The reaction mixture was washed with 20 mL of EtOAc (3 times) to remove unreacted ester. The aqueous layer was acidified with 10% aqueous HCl to pH 1 and extracted with CHCl$_3$ (3 times, 50 mL). The organic layers were combined, washed with brine, dried over MgSO$_4$, and concentrated in vacuo. Flash chromatography (silica, 30% PAW [20 parts pyridine:6 parts AcOH:11 parts water] in EtOAc) was followed by coevaporation with CH$_3$OH and toluene to remove residual pyridine and AcOH. Any silica gel was removed by filtration through a Millipore/Fluropore membrane filter (0.5 μm FH) with a prefilter pad as a solution in 15% CH$_3$OH in EtOAc. The solvent was evaporated, the residue was dissolved in hot water, and the water was evaporated to produce title compound in the form of a dry white solid (mp 215°–216°).

R$_f$=0.16 in 30% PAW [20 parts pyridine:6 parts AcOH: 11 parts water] in EtOAc, anisaldehyde. ROTATION.

EXAMPLE 108

[1S-(1α,2α,3α,4α)]-2-[[3-[4-[[(4-Cyclohexylbutyl)amino]carbonyl]-1H-imidazol-2-yl]-7-oxabicyclo[2.2.1]hept-2-yl]methyl]benzenepropanoic acid, methyl ester

A.
3-Amino-2-[[(1,1-dimethylethoxy)carbonyl]amino]-propanoic acid, benzyl ester To a stirred mixture of [bis(trifluoroacetoxy)iodosyl]benzene (2.00 g, 4.66 mmol) in 24 mL of 1:1 DMF-water was added N-α-Boc-asparagine benzyl ester (1.00 g, 3.11 mmol, preparation was described by Wang, G. et al, in J. Org. Chem., Vol, 42, p 1286-1290, 1977). This mixture was stirred in a cold water bath for 15 minutes at which time dry pyridine (0.50 mL, 6.21 mmol) was added. The mixture was stirred at room temperature for 4 hours and concentrated in vacuo. The crude product was partitioned between 10 mL of 1N HCl solution and ether (4×15 mL). The aqueous layer was neutralized with NaHCO$_3$, saturated with NaCl and extracted with EtOAc (4×15 mL). The combined EtOAc extracts were dried (MgSO$_4$), filtered and concentrated in vacuo to give 0.53 g (58%) of title amine.

TLC: silica gel, 6% CH$_3$OH/CH$_2$Cl$_2$, R$_f$ 0.44, Ce(SO$_4$)$_2$.

B.
[1S-[1α,2α,3α,4α]]-2-[[3-[[[2-[[(1,1-Dimethylethoxy)carbonyl]amino]-3-oxo-3-(phenylmethoxy)propyl]amino]oxomethyl]-7-oxabicyclo[2.2.1]hept-2-yl]methyl]-benzenepropanoic acid, methyl ester To a stirred mixture of Example 2, Part E acid (3.75 g, 11.8 mmol), 1-hydroxybenzotriazole monohydrate (1.97 g, 11.8 mmol) and Part A amine (3.30 g, 11.8 mmol) in 80 mL of dry DMF under argon at 0° C. was added sequentially (C$_2$H$_5$)$_3$N (3.28 mL, 23.6 mmol) and ethyl-3-(3-dimethylamino)propyl carbodiimide hydrochloride salt (2.26 g, 11.8 mmol). The mixture was stirred at room temperature for 12 hours and concentrated in vacuo. The crude product was diluted with 400 mL of EtOAc and washed with 0.1N NaOH solution (3×40 mL), 1N HCl solution (2×40 mL), saturated NaHCO$_3$ solution (1×40 mL) and brine (1×80 mL). The EtOAc layer was dried (MgSO$_4$), filtered and concentrated in vacuo. This was chromatographed on Merck silica gel 60 using 2% CH$_3$OH/CH$_2$Cl$_2$ as eluant to give 1.87 g 27%) of title amide.

TLC: silica gel, 6% CH$_3$OH/CH$_2$Cl$_2$, R$_f$ 0.76, Ce(SO$_4$)$_2$.

C.
[1S-[1α,2α,3α,4α]]-2-[[3-[[[2-[[(1,1-Dimethylethoxy)carbonyl]amino]-3-oxo-3-(phenylmethoxy)propyl]amino]thioxomethyl]-7-oxabicyclo[2.2.1]hept-2-yl]methyl]benzenepropanoic acid, methyl ester To a stirred mixture of Part B amide (650 mg, 1.12 mmol) in 14 mL benzene under argon was added Lawesson's reagent (2.93 g, 0.72 mmol). The mixture was heated at 65° C. under argon for 2 hours and cooled to room temperature. The mixture was diluted with 200 mL of ether and washed with saturated NaHCO$_3$ solution (1×30 mL) and brine (1×40 mL). The organic layer was dried (MgSO$_4$), filtered and concentrated in vacuo. Purification was effected by flash chromatography on 24 g of Merck silica gel 60 using 1:1 ether-hexane as eluant to give 350 mg (52%) of title thioamide.

TLC: silica gel, 3:1 ether-hexane, R$_f$ 0.58, Ce(SO$_4$)$_2$.

D.
[1S-[1α,2α,3α,4α]]-2-[[3-[1-[(1,1-Dimethylethoxy)carbonyl-4,5-dihydro-5-[(phenylmethoxy)carbonyl]-1H-imidazol-2-yl]-7-oxabicyclo[2.2.1]hept-2-yl]methyl]benzenepropanoic acid, methyl ester To a stirred mixture of Part E thioamide (340 mg, 0.57 mmol), (C$_6$H$_5$)$_3$P (448 mg, 1.71 mmol) and (C$_2$H$_5$)$_3$N (0.24 mL, 1.71 mmol) in 6 mL of acetonitrile was added CCl$_4$ (0.62 mL, 6.27 mmol). The mixture was stirred at room temperature for 4 hours and diluted with 100 mL of ether and 10 mL of water. The resulting mixture was saturated with NaCl and extracted with ether (4×40 mL). The combined ether extracts were dried (MgSO$_4$), filtered and concentrated in vacuo. This was chromatographed on 20 g of Merck silica gel 60 using 200 mL of each of 2:1, 1:1, and 1:3 hexane-ether as eluant to give 180 mg (56%) of title Boc (or BOC)-imidazoline.

TLC: silica gel, ether, R$_f$ 0.24, Ce(SO$_4$)$_2$.

E.
[1S-[1α,2α,3α,4α]]-2-[[3-[5-[[(4-Cyclohexylbutyl)amino]carbonyl]-1-[(1,1-dimethylethoxy)carbonyl]-4,5-dihydro-1H-imidazol-2-yl]-7-oxabicyclo-[2.2.1]hept-2-yl]methyl]benzenepropanoic acid, methyl ester To a stirred mixture of Part D Boc-imidazoline (180 mg, 0.32 mmol) in 10 mL of methanol under argon was added 20% Pd/C (36 mg, 20% based on the weight of Part D compound). The atmosphere was replaced with hydrogen by several vacuum-fill cycles. The mixture was stirred at room temperature for 4.5 hours and the catalyst was filtered off through a 4 μm polycarbonate film. The catalyst was rinsed with DMF (4×20 mL). The filtrate was concentrated in vacuo to give crude acid [1S-[1α,2α,3α,4α]]-2-[[3-[5-carboxy-1-[(1,1-dimethylethoxy)carbonyl]-4,5-dihydro-1H-imidazol-2-yl]-7-oxabicyclo[2.2.1]hept-2-yl]methyl]benzenepropanoic acid, methyl ester. To a stirred mixture of this acid, 1-hydroxybenzotriazole monohydrate (54 mg, 0.32 mmol) and 4-cyclohexylbutyl amine hydrochloride salt (74 mg, 0.38 mmol) in 3 mL of DMF under argon at 0° C. was added sequentially (C$_2$H$_5$)$_3$N (0.11 mL, 0.79 mmol) and ethyl-3-(3-dimethylamino)propyl carbodiimide hydrochloride salt (61 mg, 0.32 mmol). The mixture was stirred at room temperature for 18 hours and concentrated in vacuo. The crude product was partitioned between 150 mL of EtOAc and 0.1N NaOH solution (2×25 mL), 1N HCl solution (2×25 mL) and saturated NaHCO$_3$ solution (1×25 mL). The organic layer was dried (MgSO$_4$), filtered and concentrated in vacuo. This was chromatographed on 10 g of Merck silica gel 60 using 2% CH$_3$OH/CH$_2$Cl$_2$ as eluant to give 42.1 mg (22%) of title amide.

TLC: silica gel, 6% CH$_3$OH/CH$_2$Cl$_2$ , R$_f$ 0.58, Ce(SO$_4$)$_2$.

F.
[1S-(1α,2α,3α,4α)]-2-[[3-[4-[[(4-Cyclohexylbutyl)amino]carbonyl]-1H-imidazol-2-yl]-7-oxabicyclo[2.2.1]hept-2-yl]methyl]-benzenepropanoic acid, methyl ester To a stirred mixture of Part E amide (555 mg, 0.94 mmol) in 3 mL of dry CH$_2$Cl$_2$ at 0° C. was added 6 mL of trifluoroacetic acid (TFA). The mixture was stirred at room temperature for 3 hours. The mixture was diluted with 40 mL of toluene and concentrated in vacuo to give [1S-[1α,2α,3α,4α]]-2-[[3-[5-[[(4-cyclohexylbutyl)amino]carbonyl]-4,5-dihydro-1H-imidazol-2-yl]-

7-oxabicyclo[2.2.1]hept-2-yl]methyl]-benzenepropanoic acid, methyl ester. The crude imidazole-TFA salt was diluted with 150 mL of EtOAc and washed once with 40 mL of saturated NaHCO$_3$ solution. The aqueous layer was extracted with EtOAc (1×100 mL). The combined EtOAc extracts were dried (MgSO$_4$), filtered and concentrated in vacuo. To this crude imidazoline in 15 mL of CHCl$_3$ was added MnO$_2$ (570 mg, 6.55 mmol). The mixture was stirred at room temperature for 64 hours at which time MnO$_2$ (570 mg, 6.55 mmol) was added. The mixture was stirred at room temperature for 1 day and another amount of MnO$_2$ (290 mg, 3.28 mmol) was added. The mixture was stirred at room temperature for one more day and again MnO$_2$ (190 mg, 2.18 mmol) was added. The mixture was stirred at room temperature for 1 day and MnO$_2$ was filtered off through a pad of Celite and the pad was rinsed with CHCl$_3$ (6×30 mL). The filtrate was concentrated in vacuo and chromatographed on 40 g of Merck silica gel 60 (the silica gel was pretreated with 0.1% Et$_3$N in CH$_2$Cl$_2$ and then washed with CH$_2$Cl$_2$) using 150 mL of CH$_2$Cl$_2$ and 150 mL of 2% CH$_3$OH/CH$_2$Cl$_2$ as eluant to give 370 mg (76%) of imidazole.

TLC: silica gel, 6% CH$_3$OH/CH$_2$Cl$_2$, R$_f$ 0.66, Ce(-SO$_4$)$_2$.

EXAMPLE 109

[1S-(1α,2α,3α,4α)]-2-[[3-[4-[[(4-Cyclohexylbutyl)amino]carbonyl]-1H-imidazol-2-yl]-7-oxabicyclo[2.2.1]hept-2-yl]methyl]benzenepropanoic acid, hydrochloride salt To a stirred mixture of Example 108 imidazole (25 mg, 0.05 mmol) in 1 mL of methanol was added 0.4 mL of 2N KOH solution. The mixture was stirred at room temperature for 4 hours and concentrated in vacuo to remove methanol. The residue was diluted with 2 mL of CH$_2$Cl$_2$ and acidified to pH 2 by the addition of 1N HCl solution. The aqueous layer was separated and extracted with CH$_2$Cl$_2$ (4×4 mL). The combined CH$_2$Cl$_2$ extracts were dried (Na$_2$SO$_4$), filtered and concentrated in vacuo. The crude product was dissolved in 4 mL of CH$_2$Cl$_2$ and combined with 0.25 mL of 4N HCl in ether. The resulting mixture was concentrated in vacuo and triturated in hot EtOAc (2 mL). The mixture was cooled to room temperature and the solid was collected by filtration to give 12.6 mg (48%) of title hydrochloride salt, m.p. 229°–232° C.

TLC: silica gel, 6% CH$_3$OH/CH$_2$Cl$_2$, R$_f$ 0.29, Ce(-SO$_4$)$_2$, UV-active.

EXAMPLE 110

[1S-(1α,2α,3α,4α)]-2-[[3-[4-[[[2-(4-Chlorophenyl)ethyl]amino]carbonyl]-2-oxazolyl]-7-oxabicyclo[2.2.1]hept-2-yl]methyl]benzenepropanoic acid

A.
[1S-(1α,2α,3α,4α)]-2-[[3-[4-[[[2-(4-Chlorophenyl)ethyl]amino]carbonyl]-2-oxazolyl]-7-oxabicyclo[2.2.1]hept-2-yl]methyl]-benzenepropanoic acid, methyl ester To a solution of 150 mg (0.39 mmol) of oxazole acid prepared in Example 2, Part J in 3 mL of dry methylene chloride (distilled from phosphorous pentoxide) was added at room temperature a small drop of DMF then 45 μL (0.51 mmol, Aldrich) of oxalyl chloride. The solution was stirred until gas evolution ceased, about 30 minutes, then concentrated in vacuo to give the acid chloride as a pale yellow solid.

To a solution of the crude acid chloride (about 0.39 mmol) in 3 mL of dry methylene chloride cooled in an ice-bath was added 82 μL (0.58 mmol, distilled from calcium hydride) of triethylamine followed by 66 μL (0.47 mmol, Aldrich) of 2-(4-chlorophenyl)ethylamine. The reaction mixture was stirred for 15 minutes then partitioned between 20 mL of 1M aqueous HCl solution and 20 mL of ethyl acetate. The organic layer was separated, dried (magnesium sulfate) and concentrated in vacuo to give a solid. The crude material was recrystallized (ethyl acetate/hexane) to afford 163 mg (0.31 mmol, 80%) of title ester as white needles, mp 188°–189° C.,

B.
[1S-(1α,2α,3α,4α)]-2-[[3-[4-[[[2-(4-Chlorophenyl)ethyl]amino]carbonyl]-2-oxazolyl]-7-oxabicyclo[2.2.1]hept-2-yl]methyl]-benzenepropanoic acid A mixture of 150 mg (0.29 mmol) of Part A ester and 50 mg (1.2 mmol, Aldrich) of lithium hydroxide monohydrate in 6 mL of 2:1 THF/water was stirred rapidly at room temperature for 5 hours then acidified by addition of 2.4 mL of 1M aqueous HCl solution. The resulting solution was partitioned between 20 mL of water and 20 mL of ethyl acetate. The organic layer was separated, dried (magnesium sulfate) and then concentrated in vacuo to give a solid. The crude material was recrystallized (ethyl acetate) to afford 134 mg (0.26 mmol, 91%) of title compound as white crystals, mp 187°–188° C.

IR(KBr): 3437, 1715, 1642, 1605, 1521, 1493, 1094 cm$^{-1}$.

MS(CI): 509/511 (M+H)$^+$.

OR: [α]$_D$ = +51° (c=0.25 in chloroform).

TLC: R$_f$ (silica gel, 1:9 methanol/methylene chloride) = 0.51, ammonium molybdate/ceric sulfate and UV, homogeneous.

Analysis Calc'd for C$_{28}$H$_{29}$ClN$_2$O$_5$: C, 66.07; H, 5.74; N, 5.50; Cl, 6.97

Found: C, 66.12; H, 5.76; N, 5.43; Cl, 7.16.

EXAMPLE 111

[1S-(1α,2α,3α,4α)]-2-[[3-[4-[[(1,1-Dimethylethyl)amino]carbonyl]-2-oxazolyl]-7-oxabicyclo[2.2.1]-hept-2-yl]methyl]benzenepropanoic acid

A.
[1S-(1α,2α,3α,4α)]-2-[[3-[4-[[(1,1-Dimethylethyl)amino]carbonyl]-2-oxazolyl]-7-oxabicyclo[2.2.1]hept-2-yl]methyl]benzenepropanoic acid, methyl ester To a solution of 200 mg (0.52 mmol) of oxazole acid prepared in Example 2, Part J in 2 mL of dry methylene chloride (distilled from phosphorous pentoxide) was added at room temperature a small drop of DMF then 55 μL (0.63 mmol, Aldrich) of oxalyl chloride. The solution was stirred until gas evolution ceased, about 30 minutes, then concentrated in vacuo to give the acid chloride as a pale yellow solid.

To a solution of the crude acid chloride (about 0.52 mmol) in 4 mL of dry methylene chloride cooled in an ice-bath was added 110 μL (0.78 mmol, distilled from calcium hydride) of triethylamine followed by 65 μL (0.70 mmol, Aldrich) of t-butylamine. The reaction mixture was stirred for 30 minutes. The resulting solution was partitioned between 20 mL 1M aqueous HCl solution and 20 mL of ethyl acetate. The organic layer was separated, dried (magnesium sulfate) and concentrated in vacuo to give an oil. The crude material was purified by flash chromatography (Merck silica, 12×3.0 cm, 2:1 ethyl acetate/hexane) to afford 210 mg (0.48 mmol, 92%) of title ester as a colorless oil.

B.

[1S-(1α,2α,3α,4α)]-2-[[3-[4-[[(1,1-Dimethylethyl)amino]carbonyl]-2-oxazolyl]-7-oxabicyclo[2.2.1]hept-2-yl]methyl]benzenepropanoic acid A mixture of 202 mg (0.46 mmol) of Part A ester and 39 mg (0.93 mmol, Aldrich) of lithium hydroxide monohydrate in 3 mL of 2:1 THF/water was stirred rapidly at room temperature for 2 hours then acidified by addition of 2.0 mL of 1M HCl solution. The resulting solution was added to 20 mL of 1M aqueous HCl solution then extracted with two-20 mL portions of ethyl acetate. The combined organic layers were dried (magnesium sulfate) and then concentrated in vacuo to give an oil. The crude material was crystallized (ethyl acetate/hexane) to afford 162 mg 0.38 mmol, 83%) of title compound as white crystals, mp 155°–156°.

IR(KBr): 3403, 2967, 1715, 1674, 1599, 1520, 1219 cm$^{-1}$.

MS(CI): 427 (M+H)$^+$.

OR: $[\alpha]_D = 16°$ (c=0.5 in chloroform).

TLC: R$_f$(silica gel, 1:9 methanol/methylene chloride)=0.43, ammonium molybdate/ceric sulfate and UV, homogeneous.

Analysis Calc'd for $C_{24}H_{30}N_2O_5$: C, 67.58; H, 7.09; N, 6.57

Found: C, 67.51; H, 7.01; N, 6.56.

EXAMPLE 112

[1S-(1α,2α,3α,4α)]-2-[[3-[4-[[(1,1-Dimethylpropyl)amino]carbonyl]-2-oxazolyl]-7-oxabicyclo[2.2.1]-hept-2-yl]methyl]benzenepropanoic acid

A.

[1S-(1α,2α,3α,4α)]-2-[[3-[4-[[(1,1-Dimethylpropyl)amino]carbonyl]-2-oxazolyl]-7-oxabicyclo[2.2.1]hept-2-yl]methyl]benzenepropanoic acid, methyl ester To a solution of 200 mg (0.52 mmol) of oxazole acid prepared in Example 2, Part J in 2 mL of dry methylene chloride (distilled from phosphorous pentoxide) was added at room temperature a small drop of DMF then 55 μL (0.63 mmol, Aldrich) of oxalyl chloride. The solution was stirred until gas evolution ceased, about 30 minutes, then concentrated in vacuo to give the acid chloride as a pale yellow solid.

To a solution of the crude acid chloride (about 0.52 mmol) in 3 mL of dry methylene chloride cooled in an ice-bath was added 110 μL (0.78 mmol, distilled from calcium hydride) of triethylamine followed by 81 μL (0.69 mmol, Aldrich) of t-amylamine. The reaction mixture was stirred for 15 minutes. The resulting solution was added to 15 mL of 1M aqueous HCl solution and extracted with two-15 mL portions of ethyl acetate. The organic layers were combined, dried (magnesium sulfate) and concentrated in vacuo to give an oil. The crude material was purified by flash chromatography (Merck silica, 10×3.0 cm, 2:1 ethyl acetate/hexane) to afford 201 mg (0.44 mmol, 85%) of title ester as a colorless oil.

B.

[1S-(1α,2α,3α,4α)]-2-[[3-[4-[[(1,1-Dimethylpropyl)amino]carbonyl]-2-oxazolyl]-7-oxabicyclo[2.2.1]hept-2-yl]methyl]benzenepropanoic acid A mixture of 195 mg (0.43 mmol) of Part A ester and 36 mg (0.86 mmol, Aldrich) of lithium hydroxide monohydrate in 3 mL of 2:1 THF/water was stirred rapidly at room temperature for 2 hours then acidified by addition of 2.0 mL of 1M HCL solution. The resulting solution was added to 15 mL of 1M aqueous HCl solution then extracted with two-15 mL portions of ethyl acetate. The combined organic layers were dried (magnesium sulfate) and then concentrated in vacuo to give a solid. The crude material was recrystallized (ethyl acetate/hexane) to afford 160 mg (0.36 mmol, 85%) of title compound (SQ 34,805) as white crystals, mp 128–132° C.

IR(KBr): 3437, 1715, 1655, 1599, 1522, 1202 cm$^{-1}$.

MS(CI): 441 (M+H)$^+$.

OR: $[\alpha]_D = +27°$ (c=0.5 in chloroform).

TLC: R$_f$(silica gel, 1:9 methanol/methylene chloride)=0.49, ammonium molybdate/ceric sulfate and UV, homogeneous.

Analysis Calc'd for $C_{25}H_{32}N_2O_5$: C, 68.16; H, 7.32; N, 6.36

Found: C, 68.10; H, 7.36; N, 6.41.

EXAMPLE 113

[1S-(1α,2α,3α,4α)]-2-[[3-[4-[(Octadecylamino)carbonyl]-2-oxazolyl]-7-oxabicyclo[2.2.1]hept-2-yl]methyl]benzenepropanoic acid

A.

[1S-(1α,2α,3α(Z),4α)]-2-[[3-[4-[(Octadec-9-enylamino)carbonyl]-2-oxazolyl]-7-oxabicyclo[2.2.1]hept-2-yl]methyl]benzenepropanoic acid, methyl ester To a solution of 100 mg (0.26 mmol) of oxazole acid prepared in Example 2, Part J in 3 mL of dry methylene chloride (distilled from phosphorous pentoxide) was added at room temperature a small drop of DMF then 30 μL (0.34 mmol, Aldrich) of oxalyl chloride. The solution was stirred until gas evolution ceased, about 15 minutes, then concentrated in vacuo to give the acid chloride as a pale yellow solid.

To a solution of the crude acid chloride (about 0.26 mmol) in 3 mL of dry methylene chloride cooled in an ice-bath was added 50 μL (0.36 mmol, distilled from calcium hydride) of triethylamine followed by a solution of 83 mg (0.31 mmol, Fluka, practical grade) of oleylamine in 1 mL of methylene chloride. The reaction mixture was stirred for 15 minutes. The resulting solution was partitioned between 15 mL of 1M aqueous HCl solution and 20 mL of ethyl acetate. The aqueous layer was separated and extracted with an additional 10 mL of ethyl acetate. The organic layers were combined, washed with 15 mL of brine, dried (magnesium sulfate) and concentrated in vacuo to give a solid. The crude material was purified by flash chromatography (Merck silica, 15×1.5 cm, 2:1 ethyl acetate/hexane) to afford 146 mg (0.23 mmol, 88%) of title ester as a wax.

B.

[1S-(1α,2α,3α(Z),4α)]-2-[[3-[4-[Octadec-9-enylamino)carbonyl-2-oxazolyl]-7-oxabicyclo[2.2.1]hept-2-yl]methyl]benzenepropanoic acid A mixture of 142 mg (0.22 mmol) of Part A ester and 20 mg (0.48 mmol, Aldrich) of lithium hydroxide monohydrate in 2.5 mL of 4:1 THF/water was stirred rapidly at room temperature for 16 hours then acidified by addition of 2.0 mL of 1M HCl solution. The resulting solution was partitioned between 15 mL of 1M aqueous HCl solution and 15 mL of ethyl acetate. The organic layer was separated, washed with 15 mL of brine, dried (magnesium sulfate) and then concentrated in vacuo to give 137 mg (0.22 mmol, 100%) of title acid as a white solid, mp 122°-123° C.

C.
[1S-(1α,2α,3α,4α)]-2-[[3-[4-[(Octadecylamino)carbonyl]-2-oxazolyl]-7-oxabicyclo[2.2.1]hept-2-yl]methyl]benzenepropanoic acid A mixture of 132 mg (0.21 mmol) of Part B olefin and 25 mg of 10% palladium on activated carbon catalyst (Aldrich) in 6 mL of 2:1 ethyl acetate/methanol was stirred under an atmosphere of hydrogen (balloon) for 3 hours. The reaction mixture was then passed through a 0.4 μM polycarbonate membrane and the filtrate concentrated in vacuo to give a solid. The crude solid was recrystallized (ethyl acetate/hexane) to afford 105 mg (0.17 mmol, 81%) of title compound as a white solid, mp 135°-136° C.

IR(KBr): 3413, 2923, 2851, 1708, 1648, 1604, 1516, 1218 cm$^{-1}$.

MS(CI): 623 (M+H)$^+$.

OR: $[\alpha]_D = +21°$ (c=0.5 in chloroform).

TLC: R$_f$(silica gel, 1:9 methanol/methylene chloride)=0.57, ammonium molybdate/ceric sulfate and UV, homogeneous.

Analysis Calc'd for $C_{38}H_{58}N_2O_5$: C, 73.27; H, 9.39; N, 4.50
Found: C, 73.08; H, 9.49; N, 4.38.

EXAMPLE 114

[1S-(1α,2α,3α,4α)]-2-[[3-[4-[[[5-(Cyclohexylamino)-5-oxopentyl]amino]carbonyl]-2-oxazolyl]-7-oxabicyclo2.2.1]hept-2-yl]methyl]benzenepropanoic acid A. 5-[[(1,1-Dimethylethoxy)carbonyl]amino]pentanoic acid The title compound was prepared employing the procedure described by R. Houssin, J. -L. Bernier, and J. -P. Henichart, *Synth.*, 1988, 259.

B.
N-Cyclohexyl-5-[[(1,1-dimethylethoxy)carbonyl]amino]pentanamide

To a solution of 2.74 g (12.6 mmol) of Part A acid in 50 mL of THF at 0° under argon, was added 2.66 g (16.3 mmol) of carbonyldiimidazole. The reaction mixture was stirred for 30 minutes and then warmed to room temperature for 10 minutes. After recooling to 0°, 1.88 mL (1.63 g, 16.4 mmol) of cyclohexylamine and 2.29 mL (1.66 g, 16.4 mmol) of triethylamine were added. After warming to room temperature, stirring was continued for 2 days. 10 mL of water was added, and the mixture was extracted three times with ethyl acetate (10 mL). The organic layers were combined and dried over MgSO$_4$, filtered, and concentrated on a rotoevaporator to obtain a white solid. This was chromatographed eluting first with 70-30 EtOAc-hexane, then EtOAc, to obtain 1.41 g (37%) of a pure title product. R$_f$ is 0.8 in EtOAc. (UV, Ce(SO$_4$)$_2$).

$^{13}$C NMR (68.7 MHz, CDCl$_3$): δ 171.7, 156.0, 79.0, 48.0, 39.8, 36.1, 33.1, 29.4, 28.3, 25.5, 24.8, 22.7.

C. 5-Amino-N-cyclohexylpentanamide, monohydrochloride

To a solution of 0.50 g (1.67 mmol) of Part B compound in 3 mL CH$_2$Cl$_2$ at 0° under argon, was added 0.26 mL of trifluoroacetic acid (TFA). After stirring for 2 hours, the reaction mixture was concentrated on a rotoevaporator. The residue was twice coevaporated with 5 mL CHCl$_3$ to remove excess TFA. The residue was treated with 1 mL of CH$_3$OH and 0.18 mL concentrated aqueous HCl and concentrated on a rotoevaporater. The residue was crystallized from ether to obtain 0.10 g (26%) of a solid as title product. R$_f$ is 0.17 in EtOAc. (UV, Ce(SO$_4$)$_2$).

$^{13}$C NMR (67.8 MHz, CDCl$_3$): δ 172.9, 38.5, 34.0, 31.7, 25.9, 24.7, 24.4, 24.2, 21.9.

D.
[1S-(1α,2α,3α,4α)]-2-[[3-[4-[[[5-(Cyclohexylamino)-5-oxopentyl]amino]-carbonyl]-2-oxazolyl]-7-oxabicyclo[2.2.1]hept-2-yl]methyl]benzenepropanoic acid, methyl ester To a solution of 0.10 g (0.42 mmol) of Part C amine in 5 mL of chloroform at 0° C. under argon, was added 0.14 mL (0.10 g, 1.0 mmol) of triethylamine and 0.51 mmol of acid chloride prepared in Example 2, Part J. The mixture was refluxed for 6 hours and stirred at room temperature for 15 hours, then diluted with EtOAc and water. The organic layer was separated, and the aqueous layer was extracted with 20 mL of EtOAc twice. The organic layers were combined, washed with brine, dried over MgSO$_4$, and concentrated. Flash chromatography (0% to 100% EtOAc in hexane gradient, then 5% CH$_3$OH in EtOAc) gave 0.17 g of title product as a clear oil in 59% yield. R$_f$ is 0.5 in EtOAc (UV, Ce(SO$_4$)$_2$).

$^{13}$C NMR (67.8 MHz, CDCl$_3$): 67 173.0, 171.7, 163.8, 160.6, 140.4, 138.4, 137.7, 135.7, 129.6, 128.8, 126.5, 126.4, 79.6, 78.5, 51.5, 49.9, 47.9, 46.8, 38.1, 36.0, 34.8, 33.0, 32.3, 29.8, 29.0, 28.8, 27.5, 25.5, 24.7, 22.9.

E.
1S-(1α,2α,3α,4α)]-2-[[3-[4-[[[5-(Cyclohexylamino)-5-oxopentyl]amino]carbonyl]-2-oxazolyl]-7-oxabicyclo[2.2.1]hept-2-yl]methyl]benzenepropanoic acid A solution of 0.17 g (0.30 mmol) of Part D ester in 1 mL of 1N NaOH, 2 mL of methanol, 2 mL of THF, and 1 mL water was stirred for 18 hours, then acidified to pH 1.5 with 10% HCl. This was extracted three times with 50 mL chloroform. The organic layers were combined, washed with brine, dried over MgSO$_4$, and concentrated in vacuo. A clear oil was obtained. This was crystallized from chloroform and hexane to obtain title compound in the form of a white solid (0.11 g, 69%). R$_f$=0.21 in 0.5% acetic acid in ethyl acetate (UV, Ce(SO$_4$)$_2$). m.p. 168°-169°. $[\alpha]_D = +4.07$ in CH$_3$OH at c 0.50 g/100 mL.

EXAMPLE 115

[1S-(1α,2α,3α,4α)]-2-[[3-[4-[[(5-Hydroxy-5-methylhexyl)amino]carbonyl]-2-oxazolyl]-7-oxabicyclo[2.2.1]hept-2-yl]methyl]benzenepropanoic acid A. 5-Methyl-1,5-hexanediol To 67 mL of a 3.0M solution of methylmagnesium bromide (201 mmol in ether) stirring at 0° C. under argon, was added dropwise a solution of valerolactone (5.0 g, 50 mmol) in 25 mL dry THF. A white precipitate was formed. After 30 minutes the reaction mixture was warmed up to room temperature. After 4.5 hours, the reaction was quenched with 12 mL of water and concentrated on a rotoevaporator. The residue was stirred with 50 mL EtOAc and 20 mL saturated aqueous NH$_4$Cl. The 2 layers were separated. The aqueous layer was extracted twice more with EtOAc (50 mL each).

The organic layers were combined and washed with brine, dried over MgSO$_4$, and concentrated on a rotoevaporator to obtain 5.57 g (84%) of the title product. R$_f$ is 0.35 in EtOAc; UV, Ce(SO$_4$)$_2$.

$^{13}$C NMR (67.8 MHz, CDCl$_3$): δ 70.8, 62.2, 43.2, 32.9, 29.2, 20.3.

B.
1,3-Dihydro-α,α-dimethyl-1,3-dioxo-2H-indole-2-pentanol

To a stirred solution of 1.50 g (11.3 mmol) of Part A compound, 2.08 g (14.2 mmol) of phthalimide and 3.93 g (15.0 mmol) of triphenylphosphine in 30 mL of dry CH$_2$Cl$_2$ at 0° C. under argon, was added slowly 2.93 mL (3.0 g, 15.0 mmol) of DIAD. After the addition, the reaction mixture was warmed up to room temperature. The reaction mixture was concentrated on a rotoevaporator. The residue was chromatographed eluting with 60:40 hexane-EtOAc to obtain 2.47 g (83%) of the title product. R$_f$=0.2 in 1:1 hexane-EtOAc; UV, Ce(SO$_4$)$_2$.

$^{13}$C NMR (67.8 MHz, CDCl$_3$): δ 168.0, 133.5, 131.3, 122.5, 69.7, 42.4, 37.2, 28.4, 27.9, 21.0.

C. 6-Amino-2-methyl-2-hexanol, monohydrochloride

A solution of 3.24 g (12.4 mmol) of Part B compound in 100 mL of dry CH$_2$Cl$_2$ under argon was cooled in an ice bath and stirred at 0° C. 1.57 mL (1.59 g, 49.6 mmol) of anhydrous hydrazine was added dropwise, and the mixture was stirred for 16 hours. A white precipitate was formed. The reaction mixture was concentrated on a rotoevaporator. The excess of hydrazine was removed by concentrating the residue with 50 mL of toluene twice. The residue (white precipitate) was dissolved in 180 mL of CH$_3$OH and refluxed for 16 hours. A solution of 2 mL concentrated HCl in 8 mL of CH$_3$OH was added as the reaction mixture was slowly cooled to room temperature. A white precipitate was formed. This was filtered off, and the filtrate was concentrated to a yellow solid of 1.80 g (79%).

$^{13}$C NMR (67.8 MHz, CDCl$_3$): δ 69.0, 43.1, 29.3, 27.7, 22.1, 21.1.

D.
[1S-(1α,2α,3α,4α)]-2-[[3-[4-[[(5-Hydroxy-5-methylhexyl)amino]carbonyl]-2-oxazolyl]-7-oxabicyclo[2.2.1-]hept-2-yl]methyl]benzenepropanoic acid, methyl ester To a stirred solution of Part C compound (0.11 g, 0.66 mmol) in 3 mL of methylene chloride at 0° C. under argon, was added first (C$_2$H$_5$)$_3$N (0.10 g, 1.0 mmol), then 0.51 mmol of acid chloride prepared as in Example 2, Part J as a solution in 2 mL of methylene chloride. The reaction mixture was slowly warmed to room temperature. After stirring for 5 hours at room temperature, water was added, and the reaction mixture was extracted with methylene chloride (25 mL) 3 times. The organic layers were combined and washed with brine, dried over MgSO$_4$, and concentrated to obtain an oil. This oil was crystallized from EtOAc/hexane to obtain 0.25 g (100%) of a white solid.

$^{13}$C NMR (CDCl$_3$): δ 172.9, 163.6, 160.4, 140.4, 138.2, 137.5, 135.9, 129.4, 128.7, 126.4, 126.2, 79.5, 78.4, 69.3, 51.4, 49.7 46.6, 43.0, 38.6, 34.6, 32.1, 29.8, 29.6, 29.0, 28.6, 27.3, 21.3.

E.
[1S-(1α,2α,3α,4α)]-2-[[3-[4-[[(5-Hydroxy-5-methylhexyl)amino]carbonyl]-2-oxazolyl]-7-oxabicyclo[2.2.1-]hept-2-yl]methyl]benzenepropanoic acid A solution of Part D ester (0.25 g, 0.50 mmol) in 3 mL of CH$_3$OH, 1 mL of 1N NaOH, and 3 mL of THF at room temperature was stirred for 16 hours. The reaction mixture was acidified with 10% aqueous HCl to pH 1 and extracted with EtOAc (three times, 50 mL each). The organic layers were combined, washed with brine, dried over MgSO$_4$, and concentrated to obtain a white solid. This was crystallized from EtOAc/hexane to obtain 0.21 g (88%) of a solid. m.p. 149°-150° C. R$_f$ is 0.16 in 0.5% CH$_3$COOH, 5% CH$_3$OH, 94.5% EtOAc; UV, Ce(SO$_4$)$_2$. [α]$_D$= +1.49° at c 0.67 g/100 mL of CH$_3$OH at room temperature.

EXAMPLE 116
[1S-(1α,2α,3α,4α)]-2-[[3-[4-[[(5-Carboxy-5-methylhexyl)amino]carbonyl]-2-oxazolyl]-7-oxabicyclo[2.2.1-]hept-2-yl]methyl]benzenepropanoic acid

A. 2,2-Dimethylpentanedioic acid, 5-methyl ester

A solution of 5.0 g (35.1 mmol) of 2,2-dimethyl glutaric anhydride in 10 mL of CH$_3$OH was stirred under argon. This reaction mixture was heated slowly to 100° C. and stirred for 1 hour. The reaction mixture was then cooled and concentrated on the rotoevaporator to obtain 6.13 g (100%) of title compound in the form of a yellow oil. R$_f$ is 0.7 in EtOAc; UV, Ce(SO$_4$)$_2$.

$^{13}$C NMR (67.8 MHz, CDCl$_3$): δ 175.0, 167.0, 51.5, 41.5, 38.8, 35.2, 25.5.

B. Tetrahydro-3,3-dimethyl-2H-pyran-2-one

To a solution of 6.13 g (35.2 mmol) of Part A compound in 50 mL THF and 25 mL 2-propanol at 0° C. under argon, was added slowly 1.92 g (88.0 mmol) of LiBH$_4$. This was then warmed to room temperature and stirred for 18 hours. The reaction mixture was cooled in an ice bath and quenched slowly with 25 mL of water and concentrated HCl until the pH was 1.5. This mixture was concentrated on the rotoevaporator to remove the organic solvent. The remaining aqueous mixture was stirred with 50 mL CHCl$_3$, a white precipitate was filtered, and the organic layer was separated. The aqueous layer was extracted twice more with (25 mL each) CHCl$_3$. The organic layers were combined, washed with brine, dried over MgSO$_4$, and concentrated on the rotoevaporator to obtain 4.08 g of a clear oil. This was flash chromatographed eluting with gradient 0%-50% EtOAc in hexane to obtain 1.05 g of title compound and 3.0 g of the alcohol acid (seco-title compound).

$^{13}$C NMR (67.8 MHz, CDCl$_3$): δ 177.0, 70.4, 38.6, 34.9, 27.6, 20.5.

C. 5-Bromo-2,2-dimethylpentanoic acid

To a solution of 1.05 g (8.2 mmol) of Part B compound in 13 mL of 48% HBr was added 0.33 mL of concentrated H$_2$SO$_4$. The reaction mixture was refluxed at 120° C. for 3 hours, then cooled and extracted three times with CHCl$_3$ (25 mL each). The organic layers were combined, washed with brine, dried over MgSO$_4$ and concentrated to obtain 1.44 g (84%) of a yellow oil.

$^{13}$C NMR (67.8 MHz, CDCl$_3$): δ 184.4, 41.7, 38.9, 33.6, 28.4, 24.9.

D. 5-Bromo-2,2-dimethylpentanoic acid, methyl ester

To a solution of 1.44 g (6.89 mmol) of Part C compound in 5 mL of $CH_3OH$, was added (0.73 mL, 0.81 g, 10.3 mmol) acetyl chloride, and the reaction mixture was stirred for 18 hours at room temperature. The reaction mixture was neutralized to pH 7 with triethylamine and concentrated on a rotoevaporator to obtain a semisolid. The solid was filtered, washed with ether, and the filtrate was concentrated to obtain 1.5 g (98%) of title compound in the form of an orange oil. $R_f$ is 0.98 in 1:1 hexane-EtOAc; UV, $Ce(SO_4)_2$.

E. 5-Cyano-2,2-dimethylpentanoic acid, methyl ester

A solution of 1.50 g (6.72 mmol) of Part D compound in 10 mL of ethanol was added to a solution of 2.18 g (33.6 mmol) of KCN in 3 mL of water. The resulting homogeneous reaction mixture was stirred for 2178 days at room temperature. To the reaction mixture was added 50 mL of EtOAc and 8 mL of $H_2O$ to form two layers. The organic layer was separated, and the aqueous layer was extracted twice more with EtOAc (50 mL each). The organic layers were combined, washed with brine, dried over $MgSO_4$, and concentrated on the rotoevaporator to obtain 0.88 g (78%) of title compound in the form of a yellow oil.

F. 6-Amino-2,2-dimethylhexanoic acid, methyl ester, monohydrochloride

To a solution of 0.44 g (2.60 mmol) of Part E compound in 3 mL of $CH_3OH$, at room temperature was added 1 mL of acetyl chloride, and the reaction mixture was stirred for 15 minutes. To the above mixture, 0.09 g of $PtO_2$ was added, and a hydrogen balloon was attached. The reaction mixture was stirred at room temperature for 16 hours, then filtered through a Celite pad. The filter cake was washed three times with $CH_3OH$, and the filtrate was concentrated to obtain title compound in the form of a yellow oil of 0.46 g (84%), which solidified in the freezer.

$^{13}C$ NMR (67.8 MHz, $CDCl_3$): δ 177.9, 51.6, 41.9, 39.7, 27.7, 24.9, 22.0.

G.
[1S-(1α,2α,3α,4α)]-2-[[3-[4-[[(5-Carboxy-5-methylhexyl)amino]carbonyl]-2-oxazolyl]-7-oxabicyclo[2.2.1]hept-2-yl]methyl]benzenepropanoic acid, methyl ester To a stirred solution of Part F compound (0.12 g, 0.57 mmol) in 3 mL of methylene chloride at 0° C. under argon, was added first triethylamine (0.10 g, 1.0 mmol), then 0.51 mmol of acid chloride prepared as in Example 2, Part J as a solution in 2 mL of $CH_2Cl_2$. The reaction mixture was slowly warmed to room temperature. After stirring for 18 hours at room temperature, water was added, and the reaction mixture was extracted with methylene chloride (25 mL). The aqueous layer was extracted twice more with $CH_2Cl_2$ (25 mL). The organic layers were combined, washed with brine, dried over $MgSO_4$, and concentrated to obtain title compound in the form of a yellow solid of 0.20 g (71%). $R_f$=0.8 in 5% $CH_3OH$/95% EtOAc; UV, $Ce(SO_4)_2$.

H.
[1S-(1α,2α,3α,4α)]-2-[[3-[4-[[(5-Carboxy-5-methylhexyl)amino]carbonyl]-2-oxazolyl]-7-oxabicyclo[2.2.1]hept-2-yl]methyl]benzenepropanoic acid A solution of Part G ester (0.20 g, 0.37 mmol) in 2 mL of $CH_3OH$, 1 mL of 1N NaOH, and 2 mL of THF at room temperature was stirred for 2.5 days. The reaction mixture was acidified with 10% HCl to pH 1, and extracted three times with EtOAc (25 mL each). The organic layers were combined, washed with brine, dried over $MgSO_4$, and concentrated to obtain a white solid. This was crystallized from EtOAc/hexane to obtain 0.10 g (53%) of title compound in the form of a solid. m.p. 123°-125° C. $R_f$ is 0.7 in 0.5% $CH_3CO_2H$, 10% $CH_3OH$, 89.5% EtOAc; UV, $Ce(SO_4)_2$. $[α]°_D = +5.4°$ at c 0.26 g/100 mL of $CH_3OH$ at room temperature.

EXAMPLE 117

[1S-(1α,2α,3α,4α)]-2-[[3-[4-(Aminocarbonyl)-2-oxazolyl]-7-oxabicyclo[2.2.1]hept-2-yl]methyl]benzenepropanoic acid

A.
[1S-(1α,2α,3α,4α)]-2-[[3-[4-(Aminocarbonyl)-2-oxazolyl]-7-oxabicyclo[2.2.1]hept-2-yl]methyl]benzenepropanoic acid, methyl ester To a solution of 200 mg (0.52 mmol) of acid prepared as in Example 2, Part J in 10 mL dry $CH_2Cl_2$ (distilled from $P_2O_5$) was added 1 small drop of DMF, followed by 310 μL (0.62 mmol, 2M/$CH_2Cl_2$, Aldrich) of oxalyl chloride solution. The reaction was stirred at room temperature until gas evolution ceased (about 30 minutes), then the mixture was concentrated in vacuo and azeotroped with two-5 mL portions of toluene to give the crude acid chloride as a pale yellow solid.

To a solution of 0.14 mL (1.6 mmol, 11M) methanolic ammonia, stirred at −30° C., was added dropwise over 10 minutes a solution of crude acid chloride in 10 mL dry $CH_2Cl_2$ (distilled from $P_2O_5$). The reaction was stirred at room temperature for 1 hour, then the mixture was partitioned between 40 mL ethyl acetate and 40 mL 1M HCl. The organic layer was separated; the water layer was extracted with two-15 mL portions of ethyl acetate. The combined ethyl acetate layers were dried ($MgSO_4$) and concentrated in vacuo to give 120 mg (0.32 mmol, 62%) of title amide as a white solid.

B.
[1S-(1α,2α,3α,4α)]-2-[[3-[4-(Aminocarbonyl)-2-oxazolyl]-7-oxabicyclo[2.2.1]hept-2-yl]methyl]benzenepropanoic acid To a solution of 120 mg (0.32 mmol) of Part A ester in 4 mL distilled THF/1 mL water was added 27 mg (0.65 mmol, Aldrich) of lithium hydroxide monohydrate. The reaction was stirred vigorously for 3.5 hours at room temperature, then quenched by the addition of 1.3 mL (1.3 mmol) 1M HCl. The mixture was partitioned between 30 mL ethyl acetate and 30 mL water; the water layer was separated and extracted with two-15 mL portions of ethyl acetate. The combined ethyl acetate layers were dried ($MgSO_4$) and concentrated in vacuo to give a crude white solid. The crude solid was recrystallized from hot methanol to give 70 mg (0.19 mMol, 61%) of title acid as a white solid, mp >200° C.

IR (KBr): 3443, 3288, 3107, 2982, 2953, 1709, 1664, 1608 $cm^{-1}$.

MS(CI): 371 $(M+H)^+$.

OR: $[α]_D = +11°$ (c=0.25 in DMSO).

TLC: $R_f$ (silica gel, 1:9 methanol/methylene chloride)=0.20, ammonium molybdate/ceric sulfate and UV, homogeneous.

Analysis Calc'd for $C_{20}H_{22}N_2O_5$: C, 64.85; H, 5.99; N, 7.56

Found: C, 64.74; H, 6.16; N, 7.34.

EXAMPLE 118

[1S-(1α,2α(E),3α,4α)]-3-[2-[[3-[[(4-Cyclohexylbutyl)amino]carbonyl]-2-oxazolyl]-7-oxabicyclo2.2.1]hept-2-yl]methyl]phenyl]-2-propenoic acid

A.

[1S-(1α,2α,3α,4α)]-2-[[3-[[[Dimethyl(1,1,2-trimethylpropyl)silyl]oxy]methyl]7-oxabicyclo[2.2.1]hept-2-yl]methyl]benzenepropanoic acid methyl ester To a stirred mixture of alcohol prepared in Example 1, Part J (1.32 g, 4.34 mmol) in 20 mL of dry CH$_2$Cl$_2$ under argon was added sequentially triethylamine (0.91 mL, 6.51 mmol) and chlorodimethylthexyl silane (1.02 mL, 5.21 mmol). This mixture was stirred at room temperature for 22 hours at which time 100 mg of N,N-dimethylaminopyridine was added. The mixture was stirred at room temperature for 2.5 hours and diluted with 400 mL of EtOAc. The resulting mixture was washed with 1N HCl solution (3×40 mL), saturated NaHCO$_3$ solution (1×40 mL) and brine (1×40 mL). The organic layer was dried (MgSO$_4$), filtered and concentrated in vacuo. This was chromatographed on 100 g of Merck silica gel 60 using 4:1 hexane-ether as eluant to give 1.54 g (87%) of title silyl ether.

TLC: silica gel, 4:1 hexane-ether, R$_f$ 0.52, Ce(SO$_4$)$_2$.

B.

[1S-(1α,2α,3α,4α)]-2-[[3-[[[Dimethyl(1,1,2-trimethylpropyl)silyl]oxy]methyl]-7-oxabicyclo[2.2.1]hept-2-yl]methyl]-α-(phenylseleno)benzenepropanoic acid, methyl ester To a stirred mixture of dry diisopropylamine (1.80 mL, 12.8 mmol) in 30 mL of dry THF under argon at −78° C. was added 2.5M solution of n-butylLi in hexane (4.67 mL, 11.7 mmol) over 2 minutes. This mixture was stirred at −78° C. under argon for 50 minutes at which time a solution of Part A silyl ether (2.82 g, 6.32 mmol) in 20 mL of dry THF was added dropwise over 10 minutes. This mixture was stirred at −78° C. under argon for 30 minutes. To this mixture was added a solution of diphenyl diselenide (3.64 g, 11.7 mmol) in 10 mL of dry THF over 5 minutes. This mixture was stirred at −78° C. for 30 minutes and at room temperature for 30 minutes. The mixture was quenched slowly by the addition of 60 mL of saturated NH$_4$Cl solution. The aqueous layer was separated and extracted with ether (4×100 mL). The combined organic extracts were dried (MgSO$_4$), filtered and concentrated in vacuo. Purification was effected by flash chromatography on 170 g of Merck silica gel 60 using 4:1 hexane-ether as eluant to give 2.81 g (74%) of title selenide. TLC: silica gel, 4:1 hexane-ether, R$_f$ 0.54, Ce(SO$_4$)$_2$.

$^{13}$C of title compound (67.5 Mz, CDCl$_3$): δ 172.8, 139.7, 139.7, 136.6, 135.8, 129.8, 129.3, 129.0, 128.6, 128.0, 126.9, 126.1, 79.2, 61.6, 52.0, 49.5, 46.8, 46.4, 43.7, 43.2, 35.1, 34.3, 34.2, 31.6, 30.2, 29.6, 29.4, 25.1, 22.6, 20.4, 20.4, 20.1, 18.6, 14.1, −1.5, −3.4.

C.

[1S-[1α,2α(E),3α,4α]]-3-[2-[[3-[[[Dimethyl(1,1,2-trimethylpropyl)silyl]oxy]methyl]-7-oxabicyclo[2.2.1]hept-2-yl]methyl]phenyl]-2-propenoic acid, methyl ester To a stirred mixture of Part B selenide (2.81 g, 4.67 mmol) in 28 mL of EtOAc and 18 mL of CH$_3$OH was added 4 mL of 30% H$_2$O$_2$. The mixture was stirred at room temperature for 1 hour and diluted with 400 mL of EtOAc. The resulting mixture was washed once with 50 mL of brine, dried (MgSO$_4$), filtered and concentrated in vacuo. This was chromatographed on 120 g of Merck silica gel 60 using 4:1 hexane-ether as eluant to give 1.13 g (55%) of title cinnamate. TLC: silica gel, 4:1 hexane-ether. R$_f$ 0.54, vanillin.

$^{13}$C of title compound (67.5 Mz, CDCl$_3$): δ 167.2, 142.2, 141.3, 133.2, 130.8, 130.0, 126.9, 126.6, 119.4, 79.3, 79.0, 61.8, 51.7, 49.5, 47.3, 34.2, 31.2, 29.6, 29.3, 25.1, 20.1, 18.6, −3.4.

D. [1S-[1α,2α(E),3α,460

]]-3-[2-[[3-(Hydroxymethyl)-7-oxabicyclo[2.2.1]hept-2-yl]methyl]phenyl]-2-propenoic acid, methyl ester To a stirred mixture of Part C cinnamate (1.12 g, 2.52 mmol) in 70 mL of CH$_3$OH was added 0.5 mL of acetyl chloride. This mixture was stirred at room temperature for 2 hours and concentrated in vacuo. This was chromatographed on 24 g of Merck silica gel 60 using 2% CH$_3$OH in CH$_2$Cl$_2$ as eluant to give 510 mg (67%) of title alcohol. TLC: silica gel, 2% CH$_3$OH/CH$_2$Cl$_2$, R$_f$ 0.24, Ce(SO$_4$)$_2$.

$^{13}$C of title compound (67.5 Mz, CDCl$_3$): δ 167.4, 142.2, 141.2, 133.0, 130.6, 126.7, 126.6, 119.0, 79.3, 79.1, 61.6, 51.7, 49.2, 47.5, 31.4, 29.5, 29.3.

E.

[1S-[1α,2α(E),3α,4α]]-3-[2-[(3-Carboxy7-oxabicyclo[2.2.1]hept-2-yl)methyl]phenyl]2-propenoic acid, methyl ester To a stirred mixture of Part D alcohol (500 mg, 1.66 mmol) in 50 mL of acetone was added MnSO$_4$ treated Jones Reagent (about 4 mL) until an orange-red color persisted. The mixture was stirred at room temperature for 2 hours and quenched with isopropyl alcohol (IPA). The mixture was concentrated in vacuo and partitioned between 80 mL of 3M NaHSO$_3$ solution and EtOAc (4×100 mL). The combined EtOAc extracts were washed with brine (2×80 mL), dried (MgSO$_4$), filtered and concentrated in vacuo to give 490 mg (94%) of title acid. TLC: silica gel, 4% CH$_3$OH in CH$_2$Cl$_2$, R$_f$ 0.11, Ce(SO$_4$)$_2$.

$^{13}$C of title compound (67.5 Mz, CDCl$_3$): δ 176.7, 167.3, 141.8, 139.7, 133.0, 131.1, 130.0, 126.9, 126.8, 119.4, 78.5, 52.1, 51.7, 48.8, 32.9, 29.2, 28.6.

F.

[1S-[1α,2α(E),3α,4α]]-3-[2-[[3-[[[2-(4-Cyclohexylbutyl)-1-(hydroxymethyl)-2-oxoethyl]amino]carbonyl]-7-oxabicyclo[2.2.1]hept-2-yl]methyl]phenyl-2-propenoic acid, methyl ester To a stirred mixture of Part E acid (490 mg, 1.55 mmol), 1-hydroxybenzotriazole monohydrate (262 mg, 1.55 mmol) and 2-amino-n-(4-cyclohexylbutyl)-3-hydroxypropanamide (500 mg, 2.07 mmol) in 30 mL of DMF under argon was added sequentially triethylamine (0.43 mL, 3.10 mmol) and ethyl-3-(3-dimethyamino)propyl carbodiimide hydrochloride salt (287 mg, 1.55 mmol). This mixture was stirred at room temperature for 16 hours and concentrated in vacuo. The crude product was diluted with 400 mL EtOAc and washed with 0.2N NaOH solution (1×60 mL), 1N HCl solution (1×40 mL), saturated NaHCO$_3$ solution (1×20 mL) and brine (1×40 mL). The organic layer was dried (MgSO$_4$), filtered and concentrated in vacuo. Purification was effected by flash chromatography on 50 g of Merck silica gel 60 using 0.35 L of each of 2% and 4% CH$_3$OH in CH$_2$Cl$_2$ as eluants to give 630 mg (75%) of title amide. TLC: silica gel, 4% CH$_3$OH in CH$_2$Cl$_2$, R$_f$ 0.44, Ce(SO$_4$)$_2$.

$^{13}$C of title compound (67.5 Mz, CDCl$_3$): 67 172.7, 170.6, 167.5, 141.9, 140.1, 133.0, 130.9, 126.9, 119.2, 79.1, 62.8, 54.1, 51.8, 49.0, 39.6, 37.4, 36.9, 33.2, 33.2, 29.7, 26.6, 26.3, 26.3.

G.
[1S-[1α,2α(E),3α,4α]]-3-[2-[[3-[4-[[(4-Cyclohexylbutyl)amino]carbonyl]-4,5-dihydro-2-oxazolyl]-7-oxabicyclo[2.2.1]hept-2-yl]methyl]phenyl]-2-propenoic acid, methyl ester To a stirred mixture of Part F amide (630 mg, 1.17 mmol) in 15 mL of CHCl$_3$ under argon at 0° C. was added in order triethylamine (0.32 mL, 2.30 mmol) and mesyl chloride (0.11 mL, 1.42 mmol). This mixture was stirred at 0° C. for 10 minutes and at room temperature for 20 minutes. The mixture was concentrated in vacuo and diluted with 60 mL of acetone. To this mixture was added K$_2$CO$_3$ (323 mg, 2.34 mmol). The mixture was refluxed under argon for 2 hours and cooled to room temperature. The solid was filtered off and rinsed with acetone (5×30 mL). The filtrate was concentrated in vacuo and chromatographed on 40 g of Merck silica gel 60 using 0.3 L of each of 2% and 4% CH$_3$OH in CH$_2$Cl$_2$ as eluants to give 610 mg of title oxazoline in a quantitative yield. TLC: silica gel, 4% CH$_3$OH in CH$_2$Cl$_2$, R$_f$ 0.54, Ce(SO$_4$)$_2$.

$^{13}$C of title compound (67.5 Mz, CDCl$_3$): δ 171.4 169.0, 167.3, 141.8, 140.1, 132.7, 130.8, 130.2, 127.0, 126.8, 119.1 79.0, 78.0, 70.1, 68.4, 51.7, 49.6, 46.8, 39.2, 37.4, 37.0, 33.2, 33.2, 29.8, 28.5, 26.6, 26.3, 26.3, 24.0.

H.
[1S-(1α,2α(E),3α,4α)]-3-[2-[[3-[[(4-Cyclohexylbutyl)amino]carbonyl]-2-oxazolyl]-7-oxabicyclo[2.2.1]hept-2-yl]methyl]phenyl]-2-propenoic acid, methyl ester To a stirred mixture of CuBr$_2$ (557 mg, 2.49 mmol) in 6 mL of EtOAc under argon was added DBU (0.75 mL, 4.99 mmol). The mixture was stirred at room temperature for 20 minutes. To this dark brown mixture was then added a solution of Part G oxazoline (610 mg, 1.20 mmol) in 6 mL of CHCl$_3$. The reaction mixture was stirred at room temperature for hours at which time CuBr$_2$ (560 mg, 2.49 mmol) and DBU (0.38 mL, 2.50 mmol) were added. The mixture was stirred for 8 hours. To this mixture was again added CuBr$_2$ (280 mg, 1.25 mmol) and DBU (0.38 mL, 2.50 mmol). The mixture was stirred at room temperature for 16 hours at which time once more CuBr$_2$ (280 mg, 1.25 mmol) and DBU (0.38 mL, 2.50 mmol) were added. The reaction mixture was stirred at room temperature for another 7 hours and poured into a solution of 100 mL of EtOAc and 100 mL of 1:1 concentrated NH$_4$OH solution and saturated NH$_4$OH solution. The aqueous layer was separated and extracted with EtOAc (3×100 mL). The combined EtOAc extracts were dried (MgSO$_4$), filtered and concentrated in vacuo. This was chromatographed on 40 g of Merck silica gel 60 using 2% CH$_3$OH in CH$_2$Cl$_2$ as eluant to give 381 mg (63%) of title oxazole. TLC: silica gel, 6% CH$_3$OH in CH$_2$Cl$_2$, R$_f$ 0.74, Ce(SO$_4$)$_2$.

$^{13}$C of title compound (67.5 Mz, CDCl$_3$): δ 167.3, 163.5, 160.5, 141.9, 140.5, 139.7, 136.3, 133.0, 130.6, 130.0, 126.9, 119.3, 79.5, 78.4, 51.7, 50.6, 46.9, 39.1, 37.5, 37.0, 33.3, 33.3, 29.9, 28.6, 26.6, 26.3, 26.3, 24.2.

I.
[1S-(1α,2α(E),3α,4α)]-3-[2-[[3-[[(4-Cyclohexylbutyl)amino]carbonyl]-2-oxazolyl]-7-oxabicyclo[2.2.1]hept-2-yl]methyl]phenyl]-2-propenoic acid To a stirred mixture of Part H oxazole (375 mg, 0.72 mmol) in 10 mL of THF and 12 mL of CH$_3$OH was added 5 mL of 1N NaOH solution. This mixture was stirred vigorously at room temperature for 5 hours and concentrated in vacuo to remove the organic solvents. The mixture was acidified to pH 2 by the addition of 1N HCl solution, saturated with NaCl and extracted with EtOAc (4×40 mL). The combined EtOAc extracts were dried (MgSO$_4$), filtered and concentrated in vacuo. The crude acid was recrystallized in 1% CH$_3$OH/EtOAc and hexane at −5° C. to give 280 mg (77%) of pure title acid, m.p. 210°–211° C. TLC: silica gel, 4% CH$_3$OH in CH$_2$Cl$_2$, R$_f$ 0.13, Ce(SO$_4$)$_2$.

$^{13}$C NMR title compound (CDCl$_3$+CD$_3$OD, 67.5 MHz): δ 170.9, 168.6, 163.8, 141.9, 140.7, 139.1, 135.7, 132.9, 130.3, 129.8, 126.8, 119.9, 79.8, 78.6, 50.0, 46.6, 39.2, 39.0, 37.3, 36.9, 33.2, 33.1, 33.1, 29.4, 28.6, 26.4, 26.1, 26.1, 24.0.

EXAMPLE 119
[1S-(1α,2α,3α,4α)]-2-[[3-[4-[[[2-(4-Fluorophenyl)-1,1-dimethylethyl]amino]carbonyl]-2-oxazolyl]-7-oxabicyclo[2.2.1]hept-2-yl]methyl]benzenepropanoic acid

A. 3-(4-Fluorophenyl)propionic acid, methyl ester

To 35 mL of methanol (Burdick and Jackson) cooled in an ice-bath was added dropwise over several minutes 3.5 mL of acetyl chloride (Mallinckrodt). The solution was stirred for 10 minutes then 3.00 g (17.9 mmol, Trans World Chemicals) of 3-(4-fluorophenyl)propionic acid, was added. The reaction mixture was stirred at 0° C. for 6 hours then concentrated in vacuo. The residue was dissolved in 25 mL of ether, dried (magnesium sulfate) and concentrated in vacuo to give 3.08 g (16.9 mmol, 95%) of title ester as a colorless liquid.

B. 4-Fluoro-α,α-dimethylbenzenepropanoic acid, methyl ester

To a solution of 3.2 mL (23 mmol, distilled from calcium hydride) of diisopropylamine in 30 mL of dry THF (distilled from sodium/benzophenone) cooled to −78° C. was added dropwise 8.5 mL (2.5M in hexane, 21 mmol, Aldrich) of n-butyllithium solution over 10 minutes. The resulting solution was stirred for 20 minutes then a solution of 3.1 mL (18 mmol, Aldrich) of sieve-dried hexamethylphosphoramide (HMPA) in 3 mL of THF was added rapidly followed by the dropwise addition over 10 minutes of a solution of 3.00 g (16.5 mmol) of Part A ester in 10 mL of dry THF. The reaction mixture was stirred for 20 minutes then added dropwise was 1.6 mL (26 mmol, filtered through basic alumina) of iodomethane over about 2 minutes. The reaction was stirred at −78° C. for 30 minutes then warmed to 0° C., quenched with 5 mL of 1M aqueous HCl solution and partitioned between 200 mL of 1M aqueous HCl and 60 mL of 1:1 ethyl acetate/hexane. The organic layer was separated, washed with 200 mL of 1M aqueous HCl, 200 mL of water, 100 mL of 1:1 3M aqueous sodium bisulfite/brine solution, dried (magnesium sulfate) and concentrated in vacuo to give the crude monoalkylation product as an oil. The alkylation procedure was repeated as described above and the crude dialkylation product was purified by flash chromatography (Merck silica, 20×5.0 cm, 1:20 ethyl acetate/hexane) to afford 2.15 g (10.2 mmol, 62%) of title ester as a colorless oil.

C. 4-Fluoro-α,α-dimethylbenzenepropanoic acid

A mixture of 2.10 g (10.0 mmol) of Part B ester and 4.2 g (100 mmol, Aldrich) of lithium hydroxide monohydrate in 30 mL of 3:2:1 of p-dioxane/methanol/water was stirred rapidly at 65° C. for 4 hours. The reaction was cooled then concentrated in vacuo to give an oil. To the oil was added 50 mL of 1M aqueous HCl solution then concentrated HCl (about 5 mL) was added until pH<1. The resulting mixture was extracted with two-50 mL portions of ether. The ether extracts were combined, dried (magnesium sulfate) and concentrated in vacuo to give 1.85 g (9.44 mmol, 94%) of crude acid as an oil.

D. 1-Fluoro-4-(2-isocyanato-2-methylpropyl)benzene

To a solution of 1.80 g (9.18 mmol) of Part C acid in 20 mL of t-butanol (distilled from sodium) was added at room temperature 1.02 g (10.1 mmol, distilled from calcium hydride) of triethylamine then 2.78 g (10.1 mmol, Aldrich) of diphenylphosphoryl azide. The resulting solution was heated to reflux (about 90° C.) for 20 hours. The reaction mixture was cooled then concentrated in vacuo to give an oil. The crude oil was purified by flash chromatography (Merck silica, 10×5.0 cm, 1:10 ethyl acetate/hexane) to afford 1.31 g (6.79 mmol, 74%) of title isocyanate as a colorless oil.

E. [2-(4-Fluorophenyl)-1,1-dimethylethyl]carbamic acid, phenylmethyl ester

A solution of 1.30 g (6.74 mmol) of Part D isocyanate and 2.0 mL (19 mmol, Aldrich) of benzyl alcohol was heated to 100° C. for 20 hours. The reaction mixture was cooled and purified by flash chromatography (Merck silica, 12×5.0 cm, 1:8 ethyl acetate/hexane) to afford 1.62 g (5.38 mmol, 80%) of title compound as a colorless oil.

F. 4-Fluoro-α,α-dimethylbenzeneethanamine, monohydrochloride

A mixture of 1.60 g (5.32 mmol) of Part E carbamate and 160 mg of 10% palladium on activated carbon catalyst (Aldrich) in 15 mL of methanol (Burdick and Jackson) was stirred rapidly under an atmosphere of hydrogen (balloon) for 1.5 hours. The reaction mixture was passed through a 0.4 μM polycarbonate membrane then the filtrate was cooled in an ice-bath and 10 mL of acidic methanol was added (prepared by addition of 1 mL of acetyl chloride to 10 mL of methanol at 0° C.). The resulting solution was concentrated in vivo to give a solid. The crude solid was dissolved in several milliliters of methanol then ether was added. The solid which precipitated was collected on a Buchner funnel, washed with additional ether then dried under oil pump vacuum to give 945 mg (4.64 mmol, 87%) of title amine hydrochloride as small white flakes, mp 189°-190° C.

G. [1S-(1α,2α,3α,4α)]-2-[[3-[4-[[[2-(4-Fluorophenyl)-1,1-dimethylethyl]amino]carbonyl]-2-oxazolyl]-7-oxabicyclo[2.2.1]hept-2-yl]methyl]benzenepropanoic acid, methyl ester To a solution of of 200 mg (0.52 mmol) of oxazole acid prepared as in Example 2, Part J in 3 mL of dry methylene chloride (distilled from phosphorous pentoxide) was added at room temperature a small drop of DMF then 55 μL (0.63 mmol, Aldrich) of oxalyl chloride. The solution was stirred until gas evolution ceased, about 20 minutes, then concentrated in vacuo to give the acid chloride as a pale yellow solid.

To a solution of the crude acid chloride (about 0.52 mmol) in 4 mL of dry methylene chloride cooled in an ice-bath was added 210 μL (1.5 mmol, distilled from calcium hydride) of triethylamine followed by 136 mg (0.67 mmol) of Part F amine hydrochloride. The reaction mixture was stirred for 30 minutes. The resulting solution was partitioned between 20 mL of 1M aqueous HCl solution and 20 mL of ethyl acetate. The organic layer was separated, dried (magnesium sulfate) and concentrated in vacuo to give an oil. The crude material was purified by flash chromatography (Merck silica, 10×3.0 cm, ethyl acetate) to afford 275 mg (0.51 mmol, 98%) of title ester as a colorless oil.

H. 1S-(1α,2α,3α,4α)]-2-[[3-[4-[[[2-(4-Fluorophenyl)-1,1-dimethylethyl]amino]carbonyl]-2-oxazolyl]-7-oxabicyclo[2.2.1]hept-2-yl]methyl]benzenepropanoic acid A mixture of 270 mg (0.51 mmol) of Part G ester and 84 mg (2.0 mmol, Aldrich) of lithium hydroxide monohydrate in 3 mL of 2:1 THF/water was stirred rapidly at room temperature for 3 hours then partitioned between 20 mL of 1M aqueous HCl solution and 20 mL of ethyl acetate. The organic layer was separated, dried (magnesium sulfate) and then concentrated in vacuo to give an oil. The crude material was purified by flash chromatography (Merck silica, 12×1.5 cm, 1:9 methanol/methylene chloride) to afford 233 mg (0.45 mmol, 88%) of title acid as a solid white foam, mp 68° C. (softens).

IR(KBr): 3435, 2978, 1719, 1657, 1599, 1508, 1219, 1159 cm$^{-1}$.

MS(CI): 521 (M+H)$^+$.

OR: $[\alpha]_D = +22°$ (c=0.5 in chloroform)

TLC: $R_f$ (silica gel, 1:9 methanol/methylene chloride)=0.53, ammonium molybdate/ceric sulfate and UV, homogeneous.

Analysis Calc'd for $C_{30}H_{33}FN_2O_5$: C, 69.21; H, 6.39; N, 5.38; F, 3.65

Found: C, 68.80; H, 6.25; N, 5.18; F, 3.63.

EXAMPLE 120

[1S-(1α,2α,3α,4α)]-2-[[3-4-[[[4-(4-Fluorophenyl)butyl]amino]carbonyl]-2-oxazolyl]-7-oxabicyclo[2.2.1]hept-2-yl]methyl]benzenepropanoic acid

A. 4-Fluorobenzenepropanol

To a solution of 5.00 g (29.8 mmol, Trans World Chemicals) of 3-(4-fluorophenyl)propionic acid in 20 mL of dry THF (distilled from Na/benzophenone) cooled in an ice-bath was added dropwise 40 mL (1.0M in THF, 40 mmol, Aldrich) of borane-tetrahydrofuran solution over 30 minutes. The solution was allowed to warm to room temperature then stirred for 18 hours. The reaction mixture was quenched by slow addition of about 5 mL of water then concentrated in vacuo. The oily residue was partitioned between 50 mL of 1M aqueous NaOH solution and 50 mL of ethyl acetate. The organic layer was separated, washed with 50 mL of water, dried (magnesium sulfate) and concentrated in vacuo to afford 4.50 g (29.2 mmol, 98%) of crude title alcohol as a pale yellow liquid.

B. 4-Fluorobenzenebutanenitrile

To a solution of 4.45 g (28.9 mmol) of Part A alcohol and 4.2 mL (42 mmol, distilled from calcium hydride) of triethylamine in 30 mL of dry methylene chloride (distilled from phosphorous pentoxide) cooled to −20° C. was added dropwise over 5 minutes a solution of 2.7 mL (35 mmol, Aldrich) of methanesulfonyl chloride in 5 mL of methylene chloride. The reaction mixture was stirred for 15 minutes then partitioned between 30 mL of methylene chloride and 50 mL of 1M aqueous HCl solution. The organic layer was separated then washed with 50 mL of 1M aqueous HCl solution, 50 mL of saturated aqueous sodium bicarbonate solution, dried (magnesium sulfate) and concentrated in vacuo to give the crude mesylate as an oil. A mixture of the crude mesylate and 3.76 g (57.8 mmol, Mallinckrodt) of potassium cyanide in 50 mL of DMSO (Burdick and Johnson) was heated to 80° C. for 1.5 hours. The resulting gel was cooled to room temperature then partitioned between 200 mL of water and 100 mL of 1:1 ethyl acetate/hexane. The organic layer was separated, washed with two-200 mL portions of water, 100 mL of brine, dried (magnesium sulfate) and concentrated in vacuo to give a liquid. The crude material was purified by flash chromatography (Merck silica, 10×5.0 cm, 1:4 ethyl acetate/hexane) to afford 4.17 g (25.6 mmol, 89%) of title nitrile as a colorless liquid.

C. 4-Fluorobenzenebutanamine, monohydrochloride

To a solution of 4.10 g (25.2 mmol) of Part B nitrile in 40 mL of dry ether (distilled from Na/benzophenone) cooled to 0° C. was added a total 1.00 g (26 mmol, Aldrich) of lithium aluminum hydride in several portions. The reaction mixture was stirred at 0° C. for 2 hours then at room temperature for 24 hours. The resulting mixture was cooled in an ice-bath then quenched by slow, successive addition of 1.0 mL of water, 1.0 mL of 15% of aqueous NaOH solution, then 3.0 mL of water. After 30 minutes the slurry was filtered to remove precipitated aluminum salts. The salts were washed with additional ether. The filtrate was collected and acidified by addition of 50 mL of methanolic HCl (prepared by addition of 3.5 mL of acetyl chloride to 50 mL of methanol at 0° C.). The solution was concentrated in vacuo to give a gummy white solid. The crude material was recrystallized (ether/methanol) to afford 2.95 g (14.5 mmol, 58%) of title amine hydrochloride as a white solid.

D.
[1S-(1α,2α,3α,4α)]-2-[[3-[4-[[[4-(4-Fluorophenyl)butyl]amino]carbonyl]-2-oxazolyl]-7-oxabicyclo[2.2.1]hept-2-yl]methyl]benzenepropanoic acid, methyl ester To a solution of 200 mg (0.52 mmol) of oxazole acid prepared as in Example 2, Part J in 3 mL of dry methylene chloride (distilled from phosphorous pentoxide) was added at room temperature a small drop of DMF then 55 μL (0.63 mmol, Aldrich) of oxalyl chloride. The solution was stirred until gas evolution ceased, about 20 minutes, then concentrated in vacuo to give the acid chloride as a pale yellow solid.

To a solution of the crude acid chloride (about 0.52 mmol) in 5 mL of dry methylene chloride cooled in an ice-bath was added 200 μL (1.4 mmol, distilled from calcium hydride) of triethylamine followed by 142 mg (0.70 mmol) of Part C compound. The reaction mixture was stirred for 15 minutes. The resulting solution was added to 20 mL of 1M aqueous HCl solution and extracted with two-15 mL portions of ethyl acetate. The organic layers were combined, dried (magnesium sulfate) and concentrated in vacuo to give a solid. The crude material was purified by flash chromatography (Merck silica, 12×1.5 cm, 4:2:1 ethyl acetate/hexane/methylene chloride) followed by recrystallization (ethyl acetate/hexane) to afford 201 mg (0.38 mmol, 73%) of title ester as a white solid, mp 165°-166° C.

E.
[1S-(1α,2α,3α,4α)]-2-[[3-[4-[[[4-(4-Fluorophenyl)butyl]amino]carbonyl]-2-oxazolyl]-7-oxabicyclo[2.2.1]hept-2-yl]methyl]benzenepropanoic acid A mixture of 175 mg (0.33 mmol) of Part D ester and 28 mg (0.67 mmol, Aldrich) of lithium hydroxide monohydrate in 6 mL of 2:1 THF/water was stirred rapidly at room temperature for 2.5 hours then acidified by addition of 1.5 mL of 1M HCl solution. The resulting solution was added to 20 mL of water then extracted with two-15 mL portions of ethyl acetate. The combined organic layers were dried (magnesium sulfate) and then concentrated in vacuo to give a solid. The crude material was recrystallized (ethyl acetate/hexane) to afford 140 mg (0.27 mmol, 82%) of title acid as small white crystals, mp 141°-143° C.

IR(KBr): 3408, 2940, 1709, 1651, 1601, 1510, 1219 cm$^{-1}$.

MS(CI): 521 (M+H)$^+$.

OR: $[\alpha]_D$ = +20° (c=0.5 in chloroform).

TLC: $R_f$ (silica gel, 1:9 methanol/methylene chloride)=0.51, ammonium molybdate/ceric sulfate and UV, homogeneous.

Analysis Calc'd for $C_{30}H_{33}FN_2O_5$: C, 69.21; H, 6.39; N, 5.38; F, 3.65

Found: C, 69.12; H, 6.33; N, 5.35; F, 3.72.

EXAMPLE 121

[1S-(1α,2α,3α,4α)]-2-[[3-[4-[[(2,2-Dimethylbutyl)amino]carbonyl]-2-oxazolyl]-7-oxabicyclo[2.2.1]hept-2-yl]methyl]benzenepropanoic acid

A.
[1S-(1α,2α,3α,4α)]-2-[[3-[4-[[(2,2-Dimethylbutyl)amino]carbonyl]-2-oxazolyl]-7-oxabicyclo[2.2.1]hept-2-yl]methyl]benzenepropanoic acid, methyl ester To a stirred mixture of oxazole acid prepared in Example 2, Part J (92.1 mg, 0.24 mmol) in 4 mL of dry CH$_2$Cl$_2$ under argon at 0° C. was added one drop of DMF and then added dropwise 2M solution of oxalyl chloride in CH$_2$Cl$_2$ (0.14 mL, 0.29 mmol). The mixture was stirred at 0° C. for 10 minutes and stirred at room temperature for 1 hour. The mixture was cooled to 0° C. Excess oxalyl chloride was removed. To this mixture was added a solution of Et$_3$N (0.13 mL, 0.96 mmol) and 2,2-dimethylbutyl amine hydrochloride salt (39.4 mg, 0.29 mmol, prepared by 1) treatment of 2,2-dimethylbutyric acid chloride with concentrated NH$_4$OH 2) amide was reduced with LAH and worked up directly as a hydrochloride salt to prevent the loss of this volatile amine). The mixture was stirred at 0° C. for 20 minutes and at room temperature for 1 hour. The mixture was diluted with 100 mL of EtOAc and washed once with 20 mL of 1N HCl solution. The organic layer was dried (MgSO$_4$), filtered and concentrated in vacuo. This was chromatographed on 8 g of Merck silica gel 60 using 1:1 EtOAc-hexane as eluant to give 50 mg (45%) of title ester.

TLC: silica gel, EtOAc, R$_f$ 0.84, Ce(SO$_4$)$_2$.

$^{13}$C NMR of title compound (67.5 MHz, CDCl$_3$) δ: 173.0, 163.7, 160.7, 140.7, 138.5, 137.8, 136.1, 129.7, 128.9, 126.6, 126.4, 79.6, 78.6, 51.6, 50.0, 48.4, 47.0, 34.8, 34.7, 32.4, 32.1, 29.9, 28.9, 27.6, 24.4, 8.3.

B. 1S-(1α,2α,3α,4α)]-2-[3-4-[[(2,2-Dimethylbutyl)amino]carbonyl]-2-oxazolyl]7-oxabicyclo[2.2.1]hept-2-yl]methyl]benzenepropanoic acid To a stirred mixture of Part A ester (45 mg, 0.10 mmol) in 3 mL of freshly distilled THF was added 0.75 mL of water and LiOH monohydrate (12 mg, 0.29 mmol). The mixture was stirred at room temperature for 5 hours and acidified to pH 2 by the addition of 1N HCl solution. The mixture was diluted with 10 mL of EtOAc and 5 mL of water, saturated with KCl and extracted with EtOAc (3×10 mL). The EtOAc extracts were dried (MgSO$_4$), filtered and concentrated in vacuo. Purification was effected by flash chromatography on 6 g of Merck silica gel 60 using 0.2% HOAc in 6% CH$_3$OH/CH$_2$Cl$_2$ as eluant to give 37 mg of acid. This acid was recrystallized in 3 mL of 1:5 EtOAc-hexane at −5° C. to give 28.2 mg (65%) of pure title acid. m.p. 117°–119° C., TLC: silica gel, 0.2% HOAc in 6% CH$_3$OH/CH$_2$Cl$_2$, R$_f$ 0.60, Ce(SO$_4$)$_2$.

$^{13}$C NMR of title compound (67.5 MHz, CDCl$_3$) δ: 177.0, 163.9, 161.0, 141.2, 138.5, 137.8, 135.8, 129.6, 129.0, 126.7, 126.5, 79.6, 78.6, 50.0, 48.5, 47.0, 34.8, 34.6, 32.4, 32.2, 29.9, 28.9, 27.4, 24.4, 8.2.

EXAMPLE 122

[1S-(1α,2α,3α,4α)]-2-[[3-[4-[[(2,2-Dimethylpropyl)amino]carbonyl]-2-oxazolyl]-7-oxabicyclo[2.2.1]hept-2-yl]methyl]benzenepropanoic acid

A. t-Butylamide

To a solution of 20 mL of concentrated ammonium hydroxide and 40 mL of THF (distilled from sodium/benzophenone) cooled in an ice-bath was added dropwise 12 mL (98 mmol, Aldrich) of trimethylacetyl chloride over ~15 minutes. The reaction mixture was stirred for 30 minutes then partitioned between 200 mL of water and 100 mL of ethyl acetate. The organic layer was separated, washed with 200 mL of saturated aqueous sodium bicarbonate solution, 100 mL of brine, dried (magnesium sulfate) and concentrated in vacuo to give a solid. The crude solid was recrystallized (ethyl acetate/hexane) to afford 2.20 g (21.8 mmol, 22%) of title amide as white flakes.

B. 2-(Trimethyl)ethylamine hydrochloride

To a solution of 2.00 g (19.8 mmol) of Part A amide in 20 mL of ether (distilled from sodium/benzophenone) and 10 mL of THF (distilled from sodium/benzophenone) cooled in an ice-bath was added in small portions a total of 1.5 g (39 mmol, Aldrich) of lithium aluminum hydride. The reaction mixture was stirred at 0° C. for 1 hour then at room temperature for 48 hours. The resulting mixture was cooled in an ice-bath then quenched by slow, successive addition of 1.5 mL of water, 1.5 mL of 15% aqueous sodium hydroxide solution and 4.5 mL of water and stirred for 30 minutes. The slurry which formed was filtered. The aluminum salts were washed with additional ether then the filtrate was added to 40 mL of acidic methanol (prepared by addition of 4 mL of acetyl chloride to 40 mL of methanol). The solution was concentrated in vacuo to give a solid. The crude solid was purified by recrystallization (ether/methanol) to afford 950 mg (7.69 mmol, 39%) of title amine hydrochloride as white needles, m.p. >270°.

C. [1S-(1α,2α,3α,4α)]-2-[[3-[4-[[(2,2-Dimethylpropyl)amino]carbonyl]-2-oxazolyl]-7-oxabicyclo[2.2.1]hept-2-yl]methyl]benzenepropanoic acid, methyl ester To a solution of 150 mg (0.39 mmol), of oxazole acid prepared as described in Example 2, Part J in 3 mL of dry methylene chloride (distilled from phosphorous pentoxide) was added at room temperature a small drop of DMF then 45 μL (0.51 mmol, Aldrich) of oxalyl chloride. The solution was stirred until gas evolution ceased, ~30 minutes, then concentrated in vacuo to give the acid chloride as a pale yellow solid.

To a solution of the crude acid chloride (~0.39 mmol) in 3 mL of dry methylene chloride cooled in an ice-bath was added 140 μL (1.0 mmol, distilled from calcium hydride) of triethylamine followed by 58 mg (0.47 mmol, Aldrich) of Part B amine hydrochloride. The reaction mixture was stirred for 30 minutes then partitioned between 25 mL of 1M aqueous HCl solution and 25 mL of ethyl acetate. The organic layer was separated, dried (magnesium sulfate) and concentrated in vacuo to give a solid. The crude material was recrystallized (ethyl acetate/hexane) to afford 138 mg (0.30 mmol, 78%) of title ester as white crystals, m.p. 113°–115°.

D. [1S-(1α,2α,3α,4α)]-2-[[3-[4-[[(2,2-Dimethylpropyl)amino]carbonyl]-2-oxazolyl]-7-oxabicyclo[2.2.1]hept-2-yl]methyl]benzenepropanoic acid A mixture of 132 mg (0.29 mmol) of Part C ester and 50 mg (1.2 mmol, Aldrich) of lithium hydroxide monohydrate in 4.5 mL of 2:1 THF/water was stirred rapidly at room temperature for 3 hours then acidified by addition of 2.4 mL of 1M aqueous HCl solution. The resulting solution was partitioned between 20 mL of water and 25 mL of ethyl acetate. The organic layer was separated, dried (magnesium sulfate) and then concentrated in vacuo to give a solid foam. The crude material was recrystallized (ethyl acetate/hexane) to afford 116 mg (0.26 mmol, 91%) of title compound as white crystals, mp 172°–173°.

IR(KBr): 3418, 2956, 1720, 1602, 1527, 1205, 1104 cm$^{-1}$.

MS(CI): 441 (M+H)$^+$.

OR: [α]$_D$ = +39° (c=0.25 in chloroform).

TLC: R$_f$ (silica gel, 1:9 methanol/methylene chloride)=0.48, ammonium molybdate/ceric sulfate and UV, homogeneous.

Anal. Calc'd for C$_{25}$H$_{32}$N$_2$O$_5$+0.25 EtOAc: C, 67.51; H, 7.41; N, 6.06 Found: C, 67.25; H, 7.44; N, 5.96.

EXAMPLE 123

[1S-(1α,2α,3α,4α)]-2-[[3-[4-[[(3,3-Dimethylbutyl)aminocarbonyl]-2-oxazolyl]-7-oxabicyclo[2.2.1]-hept-2-yl]methyl]benzenepropanoic acid

A. [1S-(1α,2α,3α,4α)]-2-[[3-4-[[(3,3-Dimethylbutyl)amino]carbonyl]-2-oxazolyl]-7-oxabicyclo[2.2.1]hept-2-yl]methyl]benzenepropanoic acid, methyl ester To a solution of 200 mg (0.52 mmol) of oxazole acid prepared as described in Example 2, Part J in 3 mL of dry methylene chloride (distilled from phosphorous pentoxide) was added at room temperature a small drop of DMF then 55 μL (0.63 mmol, Aldrich) of oxalyl chloride. The solution was stirred until gas evolution ceased, ~20 minutes, then concentrated in vacuo to give the acid chloride as a pale yellow solid.

To a solution of the crude acid chloride (~0.52 mmol) in 3 mL of dry methylene chloride cooled in an ice-bath was added 180 μL (1.3 mmol, distilled from calcium hydride) of triethylamine followed by 83 μL (0.62 mmol, Aldrich) of 3,3-dimethylbutylamine. The reaction mixture was stirred for 15 minutes. The resulting solution was partitioned between 20 mL 1M aqueous HCl solution and 20 mL of ethyl acetate. The organic layer was separated, dried (magnesium sulfate) and concentrated in vacuo to give an oil. The crude material was purified by flash chromatography (Merck silica, 12×1.5 cm, 2:1 ethyl acetate/hexane) to afford 205 mg (0.44 mmol, 84%) of title ester as a white solid, mp 156°–158°.

B. [1S-(1α,2α,3α,4α)[-2-[[3-[[4-[[(3,3-Dimethylbutyl)amino]carbonyl]-2-oxazolyl]-7-oxabicyclo-2.2.1]hept-2-yl]methyl]benzenepropanoic acid A mixture of 195 mg (0.42 mmol) of Part A ester and 70 mg (1.7 mmol, Aldrich) of lithium hydroxide monohydrate in 6 mL of 2:1 THF/water was stirred rapidly at room temperature for 3 hours then acidified by addition of 3.0 mL of 1M HCl solution. The resulting solution was partitioned between 20 mL of water and 20 mL of ethyl acetate. The organic layer was separated, dried (magnesium sulfate) and then concentrated in vacuo to give a solid. The crude material was recrystallized (ethyl acetate/hexane) to afford 155 mg (0.34 mmol, 81%) of title compound as white crystals, mp 160°–162°.

IR(KBr): 3427, 2956, 1716, 1653, 1605, 1524, 1208 cm$^{-1}$.

MS(CI) 455 (M+H)+.

OR: [α]$_D$= +27° (c=0.5 in chloroform)

TLC: R$_f$ (silica gel, 1:9 methanol/methylene chloride)=0.49, ammonium molybdate/ceric sulfate and UV, homogeneous.

Anal Calc'd for C$_{26}$H$_{34}$N$_2$O$_5$: C, 68.70; H, 7.54; N, 6.16 Found: C, 68.70; H, 7.37; N, 6.23.

EXAMPLE 124

[1S-(1α,2α,3α,4α)]-2-[[3-[4-[[[2-(4-Fluorophenyl)ethyl]aminocarbonyl]-2-oxazolyl]-7-oxabicyclo-2.2.1]hept-2-yl]methyl]benzenepropanoic acid A. [S-(1α,2α,3α,4α)]-2-[[3-[4-[[[2-(4-Fluorophenyl)ethyl]amino]carbonyl]-2-oxazolyl]-7-oxabicyclo[2.2.1-]hept-2-yl]methyl]benzenepropanoic acid, methyl ester To a solution of 200 mg (0.519 mmol) of oxazole acid prepared as described in Example 2, Part J in 10 mL dry CH$_2$Cl$_2$ (distilled from P$_2$O$_5$) was added 1 small drop of DMF, followed by 310 μL (0.62 mmol, 2M/CH$_2$Cl$_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry CH$_2$Cl$_2$ (distilled from PO$_2$O$_5$), cooled to 0°, was added 170 μL (1.3 mmol, distilled from CaH$_2$) of triethylamine, followed by the dropwise addition of 109 mg (0.62 mmol, Aldrich) of 4-fluorophenethylamine hydrochloride. The reaction was stirred at 0° for 16 hours then partitioned between 80 mL ethyl acetate/80 mL 1M HCl. The ethyl acetate layer was separated; the water layer was extracted with two-30 mL portions of ethyl acetate. The combined ethyl acetate layers were dried (MgSO$_4$) and concentrated in vacuo to give a crude yellow solid. The crude solid was flash chromatographed (Merck silica, 1:1 ethyl acetate/hexane) to give 108 mg (0.21 mmol, 41%) of title ester as a white solid, mp 199°–200°.

B. 1S-(1α, 2α, 3α, 4α)]-2-[[3-[4-[[[2-(4-Fluorophenyl)ethyl]amino]carbonyl-2-oxazolyl]-7-oxabicyclo[2.2.-1hept-2-yl]benzenepropanoic acid To a solution of 108 mg (0.21 mmol) of Part A ester in 8 mL distilled THF/2 mL water was added 18 mg (0.42 mmol, Aldrich) of lithium hydroxide monohydrate. The reaction was stirred vigorously for 2 hours at room temperature, then quenched by the addition of 0.9 mL (0.9 mmol) 1M HCl. The mixture was partitioned between 50 mL ethyl acetate/50 mL water; the water layer was separated and extracted with two-25 mL portions of ethyl acetate. The combined ethyl acetate layers were dried (MgSO$_4$) and concentrated in vacuo to give a crude white solid. The crude solid was recrystallized from hot ethyl acetate/hexane to give 94 mg (0.19 mmol, 86%) of title acid as a white solid, mp 187°–189°.

IR (KBr): 3443, 3425, 3109, 2954, 1713, 1645, 1605 cm$^{-1}$.

MS(CI): 493 (M+H)+.

OR: [α]$_D$= −0.9° (c=0.25 in MeOH)

TLC: R$_f$ (silica gel, 1:9 methanol/methylene chloride)=0.60, ammonium molybdate/ceric sulfate and UV, homogeneous.

Anal Calc'd for C$_{28}$H$_{29}$N$_2$O$_5$F: C, 68.28; H, 5.93; N, 5.69; F, 3.86 Found: C, 68.12; H, 5.98; N, 5.80; F, 3.82.

EXAMPLE 125

[1S(1α, 2α, 3α, 4α)]-2-[[3-[4-[[(2-Phenylethyl)amino]carbonyl]-2-oxazolyl]-7-oxabicyclo[2.2.1]hept-2-yl]methylbenzenepropanoic acid A. [1S-(1α,2α,3α,4α)]-2-[[3-[4-[[(2-Phenylethyl)aminocarbony]-2-oxazolyl]-7-oxabicyclo[2.2.1]hept-2-yl]methyl]benzenepropanoic acid To a solution of 200 mg (0.519 mmol) of acid prepared in Example 2, Part J in 10 mL dry CH$_2$Cl$_2$ (distilled from P$_2$O$_5$) was added 1 small drop of DMF, followed by 310 μL (0.62 mmol, 2M/CH$_2$Cl$_2$, Aldrich) of oxalyl chloride solution. The reaction was stirred at room temperature until gas evolution ceased (about 30 minutes), then the mixture was concentrated in vacuo to give the crude acid chloride as a pale yellow solid.

To a solution of crude acid chloride in 10 mL dry CH$_2$Cl$_2$ (distilled from P ), cooled to 0°, was added 120 μL (0.83 mmol, distilled from CaH$_2$) of triethylamine, followed by the dropwise addition of 80 μL (0.62 mmol, Matheson Co.) of phenethylamine. The reaction was stirred at 0° for 16 hours, then partitioned between 80 mL ethyl acetate/80 mL 1M HCl. The ethyl acetate layer was separated; the water layer was extracted with two-30 mL portions of ethyl acetate. The combined ethyl acetate layers were dried (MgSO$_4$) and concentrated in vacuo to give a crude yellow solid. The crude solid was flash chromatographed (Merck silica, 1:1 ethyl acetate/hexane) to give 229 mg (0.47 mmol, 90%) of title ester as a white solid, mp 173°–175°.

B. [1S-(1α,2α,3α,4α)]-2-[[3-[4-[[(2-Phenylethyl)amino]carbonyl]-2-oxazolyl]-7-oxabicyclo[2.2.1]hept-2-yl]methyl]benzenepropanoic acid To a solution of 227 mg (0.464 mmol) of Part A ester in 8 mL distilled THF/2 mL water was added 39 mg (0.93 mmol, Aldrich) of lithium hydroxide monohydrate. The reaction was stirred vigorously for 1.5 hours at room temperature, then quenched by the addition of 1.9 mL (1.9 mmol) 1M HCl. The mixture was partitioned between 50 mL ethyl acetate/50 mL water; the water layer was separated and extracted with two-25 mL portions of ethyl acetate. The combined ethyl acetate layers were dried (MgSO$_4$) and concentrated in vacuo to give a crude white solid. The crude solid was recrystallized from hot ethyl acetate to give 180 mg (0.38 mmol, 82%) of title acid as a white solid, mp 181°–183°.

IR (KBr): 3412, 3104, 2979, 2952, 1712, 1698, 1656, 1601 cm$^{-1}$.

MS(CI): 475 (M+H)hu +.

OR: $[\alpha]_D = +1.5°$ (c=0.5 in MeOH)

TLC: R$_f$ (silica gel, 1:9 methanol/methylene chloride)=0.58, ammonium molybdate/ceric sulfate and UV, homogeneous.

Anal. Calc'd for C$_{28}$H$_{30}$N$_2$O$_5$: C, 70.86; H, 6.37; N, 5.90 Found: C, 70.43; H, 6.39; N, 5.84

EXAMPLE 126

1S-(1α,2α,3α,4α)]-2-[[3-[4-[(6-Heptynylamino)carbonyl-2-oxazolyl] TM 7-oxabicyclo-[2.2.1]hept-2-yl]methyl]benzenepropanoic acid

A. [1S-(1α,2α,3α,4α)]-2-[[3-[4-[(6-Heptynylamino)carbonyl-2-oxazolyl]-7-oxabicyclo-[2.2.1]hept-2-yl]methylbenzenepropanoic acid, methyl ester To a stirred mixture of oxazole acid prepared in Example 2, Part J (151 mg, 0.39 mmol) in 10 mL of dry CH$_2$Cl$_2$ under argon at 0° C was added one drop of DMF and then added dropwise 1M solution of oxalyl chloride in CH$_2$Cl$_2$ (0.47 mL, 0.47 mmol). The mixture was stirred at 0° C for 30 minutes and stirred at room temperature for 30 minutes. The mixture was concentrated in vacuo and dissolved in 10 mL of dry CH$_2$Cl$_2$. The mixture was concentrated in vacuo again and then redissolved in 8 mL of CH$_2$Cl$_2$ To this mixture at 0° C under argon was added a solution of triethylamine (Et$_3$N) (0.16 mL, 1.18 mmol) and 6-heptynylamine hydrochloride salt (69.0 mg, 0.47 mmol) in 3 mL of CH$_2$Cl$_2$ The mixture was stirred at room temperature for 4 hours. The mixture was diluted with 200 mL of EtOAc and washed with 1N HCl solution (2×60 mL) and saturated NaHCO$_3$ solution (1×60 mL). The organic layer was dried (MgSO$_4$), filtered and concentrated in vacuo. This was chromatographed on 30 g of Merck silica gel 60 using 2% CH$_{30}$H/CH$_2$Cl$_2$ as eluant to give 154 mg (82%) of title ester.

TLC: silica gel, 6% CH$_3$OH/CH$_2$Cl$_2$, R$_f$ 0.70, Ce(SO$_4$)$_2$.

$^{13}$C NMR of title compound (67.5 MHz, CDCl$_3$): δ 173.0, 163.7, 160.5, 140.5, 138.4, 137.7, 136.1, 129.6, 128.9, 126.6, 126.4, 84.2, 79.6, 78.6, 68.4, 51.5, 50.0, 46.9, 38.8, 34.8, 32.3, 29.8, 29.0, 28.8, 27.9, 27.5, 25.9, 18.2.

B. [1S-(1α,2α,3α,4α)]-2-[3-[4-[(6-Heptynylamino]carbonyl]-2-oxazolyl]-7-oxabicyclo-[2.2.1]hept-2-yl]methyl]benzenepropanoic acid To a stirred mixture of Part A ester (150 mg, 0.31 mmol) in 6 mL of freshly distilled THF was added 1.5 mL of water and LiOH monohydrate (39.5 mg, 0.94 mmol). The mixture was stirred at room temperture for 19 hours and acidified to pH 2 by the addition of 1N HCl solution. The mixture was diluted with 10 mL of water, saturated with KCl and extracted with EtOAc (4x30 mL). The EtOAc extracts were dried (MgSO$_4$), filtered and concentrated in vacuo. Recrystallization in 4 mL of acetonitrile at −5° C. gave 78 mg (54%) of title acid, m.p. 143°-144° C.

TLC: silica gel, 4% CH$_3$OH/CH$_2$Cl$_2$, R$_f$ 0.28, Ce(SO$_4$)$_2$.

$^{-}$C NMR of title compound (67.5 MHz, CDCl$_3$): δ 6.5, 163.9, 160.8, 141.0, 138.5, 137.7, 135.8, 9.7, 128.9, 126.6, 126.4, 84.3, 79.6, 78.6, 68.4, 49.9, 46.9, 38.9, 34.8, 32.4, 29.8, 28.9, 28.8, 27.9, 27.4, 25.9, 18.2

EXAMPLE 127

1S-(1α,2α,3α,4α)]-2-[[3-[4-[[(4-Cyclohexylbutyl)oxy]carbonyl]-2-oxazolyl-7-oxabicyclo[2.2.1]hept-yl]methyl]benzenepropanoic acid

A. [1S-(1α,2α,3α,4α)]-2-[3-[4-[[(4-Cyclohexylbutyl)amino]carbonyl-2-oxazolyl]-7-oxabicyclo[2.2.1hept-2-yl]methyl]benzenepropanoic acid, benzyl ester To a mixture of 200 mg (0.39 mol) of Example 1 acid and 80 mg (0.58 mmol, Mallinckrodt) of anhydrous granular potassium carbonate in 4 mL of sieve-dried dimethylformamide (DMF) (Burdick and Jackson) was added 60 μL (0.50 mmol, Aldrich) of benzyl bromide at room temperature. The reaction was stirred for 3 hours, then partitioned between 5 mL of water and 25 mL of ethyl acetate. The organic layer was separated, washed with three-25 mL portions of water, dried (magnesium sulfate) and concentrated in vacuo to give a solid. The crude solid was recrystallized (ethyl acetate/hexane) to afford 198 mg (0.33 mmol, 85%) of title benzyl ester as a white solid, mp 114°–116°.

B. [1S-(1α,2α,3α,4α)]-2-[[3-[4-[(4-Cyclohexylbutyl)oxy]carbonyl]-2-oxazolyl-7-oxabicyclo2.2.1hept-2-yl]methyl]benzenepropanoic acid, benzyl ester A mixture of 190 mg (0.32 mmol) of Part A benzyl ester in 5 mL of 1:4 glacial acetic acid/acetic anhydride was warmed until homogeneous then cooled in an ice-bath. To the resulting solution was added in one portion 480 mg (6.96 mmol, Mallinckrodt) of sodium nitrite. The reaction was stirred for 45 minutes during which time a precipitate formed. The mixture was warmed to room temperature, an additional 480 mg (6.96 mmol) of sodium nitrite was added and stirring continued for 2.5 hours. The resulting mixture was diluted with 25 mL of ethyl acetate then added to 50 mL of water. The organic layer was separated, washed with two-50 mL portions of ice-cold 1M aqueous NaOH solution, 20 mL of brine, dried (magnesium sulfate) and concentrated in vacuo to afford the crude N-nitrosoamide as a yellow oil.

A solution of the crude N-nitrosoamide in 3 mL of dioxane (Burdick and Jackson) was heated to 95° for 2 hours then cooled to room temperature. The solution color changed from yellow to colorless during this time. The resulting solution was concentrated in vacuo to give an oil. The crude oil was purified by flash chromatography (Merck silica, 12×3.0 cm, 1:2 ethyl acetate/hexane) to afford 105 mg (0.18 mmol, 56%) of title diester as a colorless glass.

C.
[1S-(1α,2α,3α,4α)]-2-[[3-[4-[[(4-Cyclohexylbutyl)oxycarbonyl-2-oxazolyl]-7-oxabicyclo[2.2.1]hept-2-yl]methyl]benzenepropanoic acid A mixture 100 mg (0.17 mmol) of Part B benzyl ester and 20 mg of 10% palladium on activated carbon catalyst (Aldrich) in 5 mL of reagent ethyl acetate was stirred rapidly under an atmosphere of hydrogen (balloon) for 5 hours then passed through a 0.4 μM polycarbonate membrane. The filtrate was concentrated in vacuo to give a solid. The crude solid was recrystallized (ethyl acetate/hexane) to afford 68 mg (0.13 mmol, 79%) of title acid as a white solid, mp 135°–137°.

IR(KBr): 3438, 2922, 1721, 1633, 1581, 1215, 1151, 1110 cm$^{-1}$.

MS(CI): 510 (M+H)$^+$. OR: $[\alpha]_D = +44°$ (c=0.27 in chloroform).

TLC: $R_f$ (silica gel, 1:9 methanol/methylene chloride)=0.54, ammonium molybdate/ceric sulfate and UV, homogeneous.

Anal. Calc'd for $C_{30}H_{39}NO_6$: C, 70.70; H, 7.71; N, 2.75 Found: C, 70.79; H, 7.79; N, 2.70.

EXAMPLE 1A
[1S-[1α,2α,3α,4α]]-6-[3-[4-[[(4-Cyclohexylbutyl)amino]carbonyl]-2-oxazolyl]-7-oxabicyclo[2.2.1]hept-2-yl]-4-hexenoic acid

A. [(1,1-Dimethylethoxy)carbonyl]-N-(4-cyclohexylbutyl-)-L-serinamide

To a solution of 575 mg of 4-cyclohexylbutyl amine hydrochloride (3.0 mmol), 615 mg t-butyloxy carbonyl-L-serine (3.0 mmol, 1.0 equiv), 405 mg 1-hydroxybenzotriazole hydrate (3.0 mmol, 1.0 equiv), and 387 mg diisopropylethylamine (3.0 mmol, 1.0 equiv) in 10 mL dry tetrahydrofuran (THF) stirring under argon at 0°, was added 618 mg 1,3-dicyclohexylcarbodiimide (3.0 mmol, 1.0 equiv) in a single portion. A precipitate slowly formed. After 1 hour the mixture was warmed to room temperature and stirred for 4 hours. After dilution with ethyl acetate, the mixture was filtered, and the filtrate was washed with a pH 1 salt solution (formed by mixing water, brine, and 1 M aqueous HCl solution). Further washing (twice) with 1 M NaHCl$_3$ was followed by drying over Na$_2$SO$_4$ and evaporation to give 1.1 g of crude title amide.

TLC (10% [10% conc. aqueous NH in CH$_3$OH] in CH$_2$Cl$_2$ - anisaldehyde):

| cyclohexylbutylamine HCl | 0.27 |
|---|---|
| title amide | 0.47 |

B. N-(4-Cyclohexylbutyl)-L-serinamide

To a solution of 1.1 g crude Part A amide in 4 mL CH$_2$Cl$_2$ at room temperature was added 4 mL trifluoroacetic acid. The mixture was stirred for hours. After solvent evaporation, residual trifluoroacetic acid was azeotropically removed by rotoevaporation with CHCl$_3$. Flash chromatography (150 g silica, 10% [10% concentrated aqueous NH$_3$ in CH$_3$OH] in C$_2$Cl$_2$) gave, after azeotroping with toluene and exposure to high vacuum, 495 mg of pure title amine as a white solid. The yield of title amine was 68% overall from 4-cyclohexylbutyl amine hydrochloride.

TLC (10% [10% conc. aqueous NH3 in CH$_3$OH] in CH$_2$Cl$_2$-anisaldehyde):

| Part A amide | 0.47 |
|---|---|
| title amine | 0.17 |

$^{13}$C NMR (67.8 MHz in CDCl$_3$): 173.4, 64.6, 56.3, 39.1, 37.3, 36.9, 33.1, 29.6, 26.5, 26.2, 24.0

C.
1S-[1α,2α,(Z),3α,4α]]-6-[3-(Hydroxymethyl)-7-oxabicyclo[2.2.1]hept-2-yl]-4-hexenoic acid, methyl ester To a partial solution of 36.27 g of [4aR-(4αa,5β,8β,-8aβ)]-octahydro-5, 8-epoxy-1H-2-benzopyran- 3-ol (prepared as described in U.S. Pat. No. 4,143,054) (0.23 mol) and 3-carboxypropyltriphenylphosphonium bromide (127.34 g, 0.37 mol) in 600 mL of dry THF under argon at 3° C. was added dropwise over 1 hour a solution of 370.6 mL of potassium t-amylate (0.68 mol of a 1.8M toluene solution) with mechanical stirring. Initially the reaction temperature reached a maximum of 8° C. and subsequently leveled off to 4° C. for the remainder of the base addition. The reaction was then run at room temperature for 90 minutes. A 0° C. ice bath was introduced and the reaction was quenched by the addition of 152 mL of glacial acetic acid, over 30 minutes. Solvents were removed in vacuo (azeotroped with toluene). Water (640 mL) and 50 mL of concentrated HCl were added (pH 2.6). Dilution with 640 mL of ethyl acetate, the addition of 149 g of NaCl and a few seed crystals of 3-carboxypropyltriphenylphosphonium bromide was followed by vigorous stirring for 15 minutes. The precipitate was collected by filtration and washed with 2 portions each of 320 mL of ethyl acetate. The ethyl acetate layer was separated, the aqueous layer was extracted with ethyl acetate (2×200 mL each), the combined ethyl acetate layers were dried over MgSO$_4$ and concentrated. Aqueous 5% K$_2$CO$_3$ was added (507 mL) followed by vigorous stirring for 1 hour. No precipitation occurred. The reaction mixture was concentrated to a paste and suspended in 508 mL of water. Several hours of vigorous stirring produced no precipitate. The water was decanted off and the residue was suspended in 200 mL of aqueous 5% K$_2$CO$_3$ solution. After vigorous stirring, a light tan solid was collected by filtration and rinsed several times with water. The combined aqueous layers were extracted 5× with 1:1 toluene/ether (230 mL each). After cooling the combined aqueous layers with a 0° C. ice bath, concentrated HCl was added to pH 2.5, followed by extraction 1× with 460 mL then 2× with 230 mL each of ethyl acetate. The combined ethyl acetate layers were dried over MgSO$_4$ and evaporated in vacuo to yield 49.74 of an amber oil. Trituration from 330 mL of ether (room temperature, overnight) oiled out phosphorous by-products. The ether solution was decanted away from the dark red oil into a separatory funnel, and the oil which was carried over by the decantation was drained off (1.56 g). Evaporation of the ether solution in vacuo yielded 43.08 g of [1S-[1α, 2α,(Z),3α,4α]]-6-[3-hydroxymethyl)-7-oxabicyclo[2.2.1]hept-2-yl]-4-hexenoic acid in the form of a viscous yellow oil.

$^1$H NMR indicated a product: triphenylphosphine oxide: ether molar ratio of 23:1:1.8 (mass % 93:4.7:2.2). Yield exclusive of triphenylphosphine oxide/ether, 40.06 g (72.5%).

Acetyl chloride (5.20 mL, 0.073 mol) was added dropwise to 80 mL of methanol at room temperature under argon. The acetyl chloride/methanol solution was then added to a solution of 42.98 g (0.18 mol) in 700 mL of methanol in one portion. Stirring was continued for 3 hours. Triethylamine was added (0.09 mol, 12.21 mL), methanol was removed in vacuo, and the residue was partitioned between 300 mL of ethyl acetate and 150 mL of water. After separation of the layers, the aqueous layer was extracted with 150 mL of ethyl acetate, the combined ethyl acetate layers were washed with brine, dried over $Na_2SO_4$ and evaporated in vacuo to yield 43.06 g of a viscous tan oil. Flash chromatography on 1350 g of E. Merck Kieselgel 60 silica gel (240–400 mesh, 75/25 ether/hexanes, then ether after the desired product began eluting off the column) yielded 35.74 g title ester in the form of a viscous light yellow oil, free from triphenylphosphine oxide by NMR.

$^1$H NMR ($CDCl_3$, ref. TMS): δ 5.41–5.38, m (2H); 4.49, d, J=4.69Hz (1H); 4.22, d, J=4.69Hz (1H); 3.73–3.69, m (1H); 3.67, s, (3H); 3.60, m (1H); 2.37, br s (4H); 2.12–1.99, m (3H); 1.97–1.85, m (1H); 1.72, m (2H); 1.46, m (2H).

$^{13}$C NMR ($CDCl_3$, ref. 77.00): δ 173.50, 130.42, 128.63, 80.23, 79.22, 61.74, 51.49, 48.95, 46.45, 33.86, 29.69, 29.31, 25.94, 22.92

D.

[1S-[1α,2α(Z)3α,4α]]-6-[3-(Carboxy)-7-oxabicyclo[2.2.1]hept-2-yl-4-hexenoic acid, methyl ester To a solution of 2.43 g of impure Part C alcohol (80% pure=1.94 g, 7.6 mmol, contaminated with triphenylphosphine oxide) in 40 mL acetone under argon at 0°, was added slowly 8 mL Jones' Reagent (2.6M in $Cr^{VI}$). The red color of the reagent persisted toward the end of the addition This resulting precipitated mixture was stirred for 20 minutes before 2-propanol was added to quench excess reagent. Still at 0°, 3M aqueous $NaHSO_3$ solution was added with stirring until all salts dissolved. Brine was added, and extraction (3 times) with ethyl acetate followed. After drying the extracts over $Na_2SO_4$ and solvent evaporation, flash chromatography (150 g silica, 25% to 40% [5% acetic acid in ethyl acetate] in hexane gradient) afforded, after azeotropic removal of acetic acid with toluene, 1.91 g of an oil. This oil was impure title acid (80% pure=1.53 g, contaminated with triphenylphosphine oxide), obtained in 75% yield.

TLC (50% [5% acetic acid in ethyl acetate] in hexane-anisaldehyde):

| | |
|---|---|
| Part C alcohol | 0.33 |
| title acid | 0.35 |

$^{13}$C NMR (67.8 MHz in $CDCl_3$): 175.3, 173.1, 129.1, 128.8, 78.0, 78.0, 51.6, 51.1, 47.4, 33.5, 28.8, 28.5, 26.9, 22.5

E. [1S-[1α,2α,(Z),3α(R*), 4α]]-6-[3-[[[2-[(4-Cyclohexylbutyl)amino]-1-(hydroxymethyl)-2-oxoethyl]amino]carbonyl]-7-oxabicyclo[2.2.1]hept-2-yl]-4-hexenoic acid, methyl ester To a solution of 733 mg impure Part D acid (80% pure =586 mg, 2.2 mmol, 1.1 equiv, contaminated with triphenylphosphine oxide) in 4 mL dry tetrahydrofuran (THF) under argon was added 356 mg 1,1′-carbonyldiimidazole (2.2 mmol, 1.1 equiv), and the mixture was left for 1 hour. Since a large volume of precipitate had formed, 5 mL dry THF was added, and the mixture was gently warmed to obtain a solution. (TLC showed a stable acylimidazole.) After stirring 30 minutes, a solution of 495 mg Part B amine (2.0 mmol) in 10 mL dry THF was added using an additional 5 mL THF to quantitatively transfer the amine. TLC of the homogeneous mixture after 1 hour stirring at room temperature indicated very slow reaction. Therefore, THF was evaporated by passing argon over the mixture overnight until its volume was reduced to 2 mL and a precipitate had formed. Addition of 5 mL THF redissolved all precipitate. After 5 hours more stirring, the mixture was evaporated, and flash chromatography (150 g silica, 50% to 100% ethyl acetate in hexane gradient, then 0% to 10% $CH_3OH$ in ethyl acetate gradient) gave 230 mg of pure title hydroxybisamide as an oil. The yield of title hydroxybisamide was 23%.

Also isolated were the isomeric aminoesteramide (27%) and the 2:1 adduct (16%). These by-products could be converted in good yields to title hydroxybisamide by transesterification with KCN in $CH_3OH$ at room temperature, although the aminoesteramide may isomerize spontaneously. TLC (50% [5% acetic acid in ethyl acetate]in hexane-anisaldehyde):

| | |
|---|---|
| Part B amine | 0.00 |
| Part D acid | 0.38 |
| acylimidazole | 0.18 |
| title hydroxybisamide | 0.22 |
| aminoesteramide | 0.04 |
| 2:1 adduct | 0.33 |

$^{13}$C NMR (67.8 MHz in $CDCl_3$): 173.3, 172.8, 170.4, 129.2, 129.0, 78.9, 78.8, 62.7, 54.0, 53.8, 51.3, 47.9, 39.4, 37.3, 36.9, 33.6, 33.1, 29.5, 29.4, 28.6, 27.2, 26.4, 26.1, 24.0, 22.6

F. [1S-[1α,2α(Z),3α(R*), 4α]]-6-[3-[4-[[(4-Cyclohexylbutyl)aminocarbonyl-4, 5-dihydro-2-oxazolyl]-7-oxabicyclo[2.2.1hept-2-yl]4-hexenoic acid, methyl ester This chemistry is described by M. J. Miller, P. G. Mattingly, M. A. Morrison, and J. F. Kerwin, Jr., J. Am. Chem. Soc., 1980, 102, 7026.

To a solution of 240 mg of pure Part E hydroxybisamide (0.48 mmol) in 3 mL dry THF under argon at room temperature, was added 189 mg triphenylphosphine (0.72 mmol, 1.5 equiv), 73 mg triethylamine (0.72 mmol, 1.5 equiv), and 89 mg $CCl_4$ (0.58 mmol, 1.2 equiv), and the mixture was heated to reflux. After 1 hour another aliquot each of $CCl_4$ and triethylamine were added, and after 2.5 hours more another aliquot of each were added again. 2 hours later another aliquot each of $CCl_4$ and triethylamine and half an aliquot (95 mg) of triphenylphosphine were added. After 2 hours more, TLC finally indicated complete consumption of Part E hydroxybisamide, and the initially colorless, homogeneous mixture had formed a white precipitate and had darkened. Solvent evaporation was followed by flash chromatography (silica, 15% acetone in toluene) which afforded 190 mg of pure title oxazoline, an oil. The oxazoline was obtained in 83% yield.

TLC (20% acetone in toluene-anisaldehyde):

| | |
|---|---|
| Part E hydroxybisamide | 0.07 |

-continued

| | |
|---|---|
| title oxazoline | 0.29 |

$^{13}$C NMR (67.8 MHz in CDCl$_3$): 173.1, 171.2, 169.1, 129.3, 128.9, 79.0, 78.9, 69.6, 68.3, 51.3, 48.2, 46.3, 39.0, 37.4, 36.9, 33.7, 33.1, 29.6, 29.5, 28.7, 27.1, 26.5, 26.2, 24.0, 22.7

G.
[1S-[1α,2α(Z),3α,4α]]-6-[3-[4-[[(4-Cyclohexylbutyl)amino]carbonyl]-2-oxazolyl]-7-oxabicyclo[2.2.1]hept-2-yl]-4-hexenoic acid, methyl ester This chemistry is described by D. L. Evans, D. K. Minster, U. Jordis, S. M. Hecht, A. L. Mazzu, Jr., and A. I. Meyers, J. Org. Chem., 1979, 44, 497.

To a solution of 190 mg of pure Part F oxazoline (0.40 mmol) in 10 mL CHCl$_3$, was added 200 mg untritrated NiO$_2$, and the heterogenous mixture was stirred at room temperature. TLC indicated some progress in the first 1 hour, but then reaction stopped. Over 1 day, five additional aliquots of the reagent were added until the reaction was complete. The mixture was diluted with ethyl acetate, and this was stirred with 3M aqueous NaHSO$_3$ solution until the black color of the NiO$_2$ disappeared and most of the solids dissolved. Extraction (3 times) with ethyl acetate was followed by drying over Na$_2$SO$_4$ and evaporation. Flash chromatography (silica, 25% to 35% ethyl acetate in hexane gradient) afforded 90 mg of pure title oxazole, a solid. The oxazole was obtained in 48% yield. TLC (100% ethyl acetate-anisaldehyde):

| | |
|---|---|
| Part F oxazoline | 0.52 |
| title oxazole | 0.81 |

$^{13}$C NMR (67.8 MHz in CDCl$_3$): 173.2, 163.8, 160.5, 140.4, 136.0, 129.4, 128.5, 79.5, 79.3, 51.4, 49.6, 46.6, 39.0, 37.4, 37.0, 33.7, 33.3, 29.8, 29.7, 28.9, 27.8, 26.6, 26.3, 24.1, 22.7

H.
[1S-[1α,2α,(Z),3α,4α]-6-[3-[4-[[(4-Cyclohexylbutyl)amino]carbonyl]-2-oxazolyl]7-oxabicyclo[2.2.1]hept-2-yl-4-hexenoic acid To 90 mg of pure Part G oxazole (0.19 mmol) in 4 mL CH$_3$OH at room temperature, was added 2 mL of 1.0M aqueous NaOH solution. After stirring the mixture for 1.3 hours, 1M aqueous HCl solution was added to lower the pH to 1. Extraction with ethyl acetate (3 times) followed. The extracts were dried over Na$_2$SO$_4$, and solvent evaporation gave crude title acid. Flash chromatography (25% to 50% [5% acetic acid in ethyl acetate] in hexane gradient) afforded, after azeotropic removal of acetic acid with toluene, 71 mg of pure title acid as a solid. The yield of title acid was 81%.

TLC (50% [5% acetic acid in ethyl acetate] in hexane - anisaldehyde):

| | |
|---|---|
| Part G oxazole | 0.43 |
| title acid | 0.25 |

$^{13}$C NMR (67.8MHz in CDCl$_3$): 176.9, 163.9, 160.7, 140.9, 135.7, 129.5, 128.4, 79.5, 79.3, 49.6, 46.5, 39.1, 37.4, 36.9, 33.7, 33.2, 29.7, 29.7, 28.8, 27.8, 26.6, 26.2, 24.1, 22.5

EXAMPLE 2A

[1S-[1α,2α(Z),3α,4α]]-6-[3-[4-[[(4-Cyclohexylbutyl)methylamino]carbonyl]-2-oxazolyl]-7-oxabicyclo[2.2.1]hept-2-yl]-4-hexenoic acid A. N-[(1,1-(Dimethylethoxy)carbonyl]-O-(phenylmethyl)-L-serine, 2-(trimethylsilyl)ethyl ester This chemistry is described by P. Sieber, Helv. Chim. Acta, (1977), 60, 2711.

To a solution of 20.7 g of N-t-butyloxycarbonyl-O-benzyl-(L)-serine, (70 mmol), 11.0 g pyridine (139 mmol, 2.0 equiv), and 9.9 g 2-trimethylsilylethanol (84 mmol, 1.2 equiv) in 50 mL dry CH$_3$CN stirring under argon at 0°, was added 15.8 g 1,3-dicyclohexylcarbodiimide (76 mmol, 1.1 equiv) in a single portion A precipitate formed. After 3 hours the mixture was warmed to room temperature and stirred for 12 hours. A solution of 1.4 g oxalic acid dihydrate (11 mmol, 0.15 equiv) in 3 mL dimethylformamide (DMF) was added, and the mixture was stirred for 1 hour before filtration. The filtercake was washed with ethyl acetate until the filtrate was free of title ester. The filtrate was washed twice with 1M aqueous HCl solution plus brine and twice with 1M aqueous NaHCO$_3$ solution. Drying over Na$_2$SO$_4$ and evaporation gave 34.8 g of crude title ester (79% pure=27.6 g, contaminated with solvent and 2-trimethylsilylethanol) as an oil in 100% yield. TLC (50% [5% acetic acid in ethyl acetate] in hexane-anisaldehyde):

| | |
|---|---|
| N—BOC—O-benzyl-(L)-serine | 0.40 |
| Part A ester | 0.84 |

$^{13}$C NMR (67.8 MHz in CDCl$_3$): 170.5, 155.3, 137.5, 128.2, 127.6, 127.4, 79.5, 73.0, 69.9, 63.6, 54.0, 28.1, 17.2, −1.7

B. N-[(1,1-Dimethylethoxy)carbonyl-L-serine, 2-(trimethylsilyl)ethyl ester

To a solution of 34.8 g of crude Part A ester (79% pure =27.6 g, contaminated with solvent and 2-trimethylsilylethanol, 70 mmol) in 200 mL ethyl acetate plus 300 mL acetic acid at room temperature under argon was added 10 g of 10% Pd on carbon catalyst. The mixture was then stirred under an atmosphere of H$_2$ for 4 days. TLC showed nearly complete clean conversion. The mixture was filtered through a polycarbonate membrane, and after evaporation of the solvent, residual acetic acid was removed by azeotroping with toluene and CH$_2$Cl$_2$. Flash chromatography (750 g silica, 10% to 30% ethyl acetate acid in hexane gradient) gave 3.58 g of pure starting material, Part A ester, (13% yield) and 16.49 g of pure title debenzylated ester as an oil. The yield of title ester was 78%.

TLC (25% ethyl acetate in hexane-anisaldehyde):

| | |
|---|---|
| Part A ester | 0.61 |
| Part B ester | 0.28 |

$^{13}$C NMR (67.8 MHz in CDCl$_3$): 3 170.9, 155.6, 79.9, 63.8, 63.0, 55.8, 28.1, 17.2, −1.7

C. L-serine, 2-(Trimethylsilyl)ethyl ester, monohydrochloride

This chemistry is described by P. Sieber, R. H. Andreatta, K. Eisler, B. Kamber, B. Riniker, and H. Rink, Peptides: Proceedings of the Fifth American Peptide Symposium, M. Goodman and J. Meienhofer, Eds., Halsted Press, New York. (1977), pp. 543–545.

To a solution of 10.4 g of Part B ester (34.1 mmol) in 200 mL diethyl ether was added 40 mL of an approximately 6.5M HCl/methanol/methyl acetate solution (260 mmol). (This solution was prepared by adding 42 g acetyl chloride (0.54 mmol) dropwise to 35 g methanol (1.1 mmol) stirring at 0° followed by stirring at room temperature for 2 hours). The mixture was then stirred for 4 hours during which gas slowly evolved. While stirring in a room temperature bath, 32.8 g $NaHCO_3$ (390 mmol) was added cautiously in small portions to control gas evolution during neutralization. The mixture was then filtered through a glass frit, using 50% methanol in diethyl ether to wash the filtercake. Evaporation of the solvent gave 8.06 g of the semisolid, crude, nearly pure title amine hydrochloride. This material may have been only a partial salt, but assuming a pure 1:1 salt the yield was 98%.

TLC (10% [10% concentrated aqueous $NH_3$ in $CH_3OH$] in $CH_2Cl_2$-anisaldehyde):

| Part B ester | 0.63 |
|---|---|
| Part C amine | 0.22 |

$^{13}C$ NMR (67.8 MHz in $CDCl_3$): 171.3, 63.9, 61.9, 55.5, 17.1, −1.8

D. [1S-[1α,2α(Z),3α(R*),4α]]-6-[3-[[[1-(Hydroxymethyl)-2-oxo-2-[(trimethylsilyl)ethoxyethyl]amino]carbonyl]-7-oxabicyclo-[2.2.1]hept-2-yl]-4-hexenoic acid, methyl ester To a solution of 9.40 g, Example 1, Part D acid (85% pure=7.99 g, 29.8 mmol), 8.04 g of crude, nearly pure Part C amine hydrochloride (95% pure=7.60 g, 31.6 mmol, 1.06 equiv), 4.43 g 1-hydroxybenzotriazole hydrate (32.8 mmol, 1.1 equiv), and 4.24 g diisopropylethylamine (32.8 mmol, 1.1 equiv) in 50 mL dry THF stirring under argon at room temperature, was added approximately 6.8 g 1,3-dicyclohexylcarbodiimide (33 mmol, 1.1 equiv) in a single portion. A precipitate slowly formed. After 16 hours, the solvent was evaporated, and flash chromatography (silica, 30% to 100% ethyl acetate in hexane gradient) gave an oil containing a solid. This material was taken up in diethyl ether in which the solid did not dissolve, and filtered. Evaporation gave 9.45 g of nearly pure title amide (90% pure=8.51 g), a clear oil. The yield of title amide was 63%.

TLC (10% [10% concentrated aqueous $NH_3$ in $CH_3OH$] in $CH_2Cl_2$-anisaldehyde):

| Part C amine | 0.37 |
|---|---|
| Part D amide | 0.65 |

TLC (50% 5% acetic acid in ethyl acetate] in hexane-anisaldehyde):

| Example 1, Part D acid | 0.42 |
|---|---|
| Part D amide | 0.36 |

$^{13}C$ NMR (67.8 MHz in $CDCl_3$) 173.5, 172.4, 170.3, 29.4, 129.1, 79.2, 79.1, 63.9, 63.2, 54.6, 54.5, 1.4, 47.8 33.7, 29.7, 28.5, 27.3, 22.7, 17.2, −1.7

E. [1S-[1α,2α(Z),3α(R*),4α]]-6-[3-4,5-Dihydro-4-[[2-(trimethylsilyl)ethoxy]carbonyl]-2-oxazolyl]-7-oxabicyclo-[2.2.1]hept-2-yl]-4-hexenoic acid, methyl ester To a solution of 8.3 g of nearly pure Part D amide (90% pure=7.5 g, 16.6 mmol) in 150 mL dry $CH_3CN$ under argon at room temperature (room temperature bath), was added 13.1 g triphenylphosphine (50 mmol, 3.0 equiv), 6.4 g diisopropyl ethylamine (50 mmol, 3.0 equiv), and finally 7.7 g $CCl_4$ (50 mmol, 3.0 equiv). After stirring for 2 hours, 1M aqueous $NaHCO_3$ solution was added, and the mixture was extracted three times with $CH_2Cl_2$. Drying over $Na_2SO_4$ was followed by evaporation and flash chromatography (silica, 20% to 50% ethyl acetate in hexane gradient) which afforded 5.9 g of nearly pure title oxazoline (90% pure=5.3 g), an oil. The oxazoline was obtained in 73% yield.

TLC (50% ethyl acetate in hexane-anisaldehyde):

| Part D amide | 0.20 |
|---|---|
| Part E oxazoline | 0.44 |

$^{13}C$ NMR (67.8 MHz in $CDCl_3$): 172.7, 170.7, 169.0, 129.0 128.8, 78.3, 78.3, 69.0, 67.5, 63.2, 50.9, 48.1, 46.0, 33.4, 29.3, 28.4, 26.7, 22.4, 16.8, −2.0

F. [1S-[1α,2α,(Z),3α,4α]]-6-[3-[4-[[2-(Trimethylsilyl)ethoxy]carbonyl]-2-oxazolyl]-7-oxabicyclo[2.2.1hept-2-yl]-4-hexenoic acid, methyl ester This chemistry is described by D. L.. Evans, D. K. Minster, U. Jordis, S. M. Hecht, A. L. Mazzu, Jr., and A. I. Meyers, J. Org. Chem., (1979), 44, 497.

To a solution of 5.1 g of nearly pure Part E oxazoline (90% pure=4.6 g, 10.5 mmol) in 50 mL $CH_2Cl_2$, was added 10.1 g untitrated $NiO_2$, and the heterogenous mixture was stirred at room temperature. (Exothermic reaction resulted in the mixture warming somewhat.) TLC indicated nearly complete reaction after 1 hour. An additional aliquot, 2.0 g, of $NiO_2$ was then added. After 30 minutes the reaction was complete, and 150 mL ethyl acetate was added. To reduce and dissolve the Ni salts, 100 mL 3M aqueous $NaHSO_3$ solution and 200 mL 1M aqueous trisodium citrate solution were added. Stirring caused all of the solids to dissolve, and the mixture warmed. Separation and extraction twice more with ethyl acetate (TLC indicated complete extraction of title oxazole) was followed by drying over $Na_2SO_4$ and evaporation. Flash chromatographic purification of the 3.8 g of crude product (150 g silica, 20% to 75% ethyl acetate in hexane gradient) afforded 2.60 g of pure title oxazole, an oil. The oxazole was obtained in 57% yield.

TLC (50% ethyl acetate in hexane-anisaldehyde):

| Part E oxazoline | 0.34 |
|---|---|

-continued

| Part F oxazole | 0.58 |
|---|---|

$^{13}$C-NMR (67.8 MHz in CDCl$_3$) 172.9, 164.5, 161.0, 143.3, 133.0, 129.1, 128.4, 79.0, 78.9, 63.0 51.1, 49.5, 46.8, 33.5, 29.5, 28.7, 27.6, 22.5, 17.2, −1.8

G. [1S-[1α,2α(Z),3α,4α]]-6-[3-(4-Carboxy-2-oxazolyl)-7-oxabicyclo[2.2.1hept-2-yl]-4-hexenoic acid, methyl ester This chemistry is described by P. Sieber, R. H. Andreatta, K. Eisler, B. Kamber, B. Riniker, and H. Rink, Peptides: Proceedings of the Fifth American Peptide Symposium, M. Goodman and J. Meienhofer, Eds., Halsted Press, New York, (1977), pp.543–545.

To a solution of 3.1 g of pure Part F oxazole (7.1 mmol) in 20 mL dry DMF under argon, was added 12.0 g of tetrabutylammonium fluoride on silica (Fluka, 13.9 mmol, 1.96 equiv), and the heterogenous mixture was stirred at room temperature for 6 hours. The mixture was diluted with 20 mL of 1% F$_3$CCO$_2$H, 1% CH$_3$OH, 98% ethyl acetate and filtered using 40 mL of the same solvent to wash the filtercake. The filtrate was evaporated and azeotroped three times with toluene to remove the DMF. The crude product was purified on an ion exchange resin: After washing a 250 g column of AG 50W-X8 (hydrogen form) with water and then 50% CH$_3$OH in water until the eluant was colorless, the crude product dissolved in 40 mL of 50% CH$_3$OH in water was loaded, and elution was carried out with the same solvent. This afforded 2.65 g of nearly pure title oxazole acid (90% pure=2.38 g), an oil. The oxazole acid was obtained in 100% yield.

TLC (1% F$_3$CCO$_2$H, 1% CH$_3$OH, 98% ethyl acetate -anisaldehyde):

| Part F oxazole | 0.46 |
|---|---|
| Part G oxazole acid | 0.15 |

$^{13}$C NMR (67.8 MHz in CD$_3$OD): 175.0, 166.7, 163.8, 145.6, 134.2, 130.4, 129.7, 80.7, 80.7, 52.0, 50.7, 47.7, 34.6, 30.5, 29.7, 28.9, 23.8

H. N-Methyl-4-cyclohexylbutylamine, monohydrochloride

To a solution of 750 mg of 4-cyclohexylbutylamine hydrochloride (3.9 mmol) and 1.08 g triethylamine (10.8 mmol, 2.8 equiv) in 10 mL dry THF stirring under argon at 0°, was added 584 mg ClCO$_2$C$_2$H$_5$ (5.4 mmol, 1.4 equiv). After warming to room temperature, the heterogeneous mixture was stirred for 3 hours. Dilution with diethyl ether was followed by washing (twice) with 1M aqueous HCl solution. The organic layer was dried over Na$_2$SO$_4$ and evaporated to obtain 950 mg of crude ethyl carbamate intermediate, an oil, contaminated with some of the imide.

To a solution of 950 mg of crude ethyl carbamate intermediate in 10 mL dry THF stirring under argon at 0°, was added 950 mg lithium aluminum hydride (25 mmol, 6.4 equiv). Gas was evolved. The mixture was then heated to reflux for 2 hours. After recooling to 0° and adding 20 mL diethyl ether, 1.0 mL water was cautiously added to quench excess hydride. The mixture was rewarmed to room temperature, and while stirring vigorously, 1.0 mL 15% aqueous NaOH solution, then 3.0 mL water were added. The mixture was filtered, washing the filter cake with 10% [10% concentrated aqueous NH$_3$ in CH$_3$OH] in diethyl ether, and the filtrate was evaporated. This material was evaporated several times with CH$_3$OH to remove NH$_3$, and finally acidified with concentrated aqueous HCl solution. Azeotropic removal of water with toluene and CH$_3$OH yielded, after exposure to high vacuum, 830 mg of impure secondary amine hydrochloride (80% pure=660 mg, contaminated with tertiary amine hydrochloride) as a solid. The product was obtained in 83% yield and was taken on without purification.

TLC (10% [10% concentrated aqueous NH$_3$ in CH$_3$OH] in CH$_2$Cl -anisaldehyde):

| 4-cyclohexylbutylamine | 0.07 |
|---|---|
| carbamate intermediate | 0.89 |
| Part H amine | 0.11 |

I. [1S-[1α,2α,(Z),3α,4α]]-6-[3-[4-[[(4-Cyclohexylbutyl)methylamino]carbonyl]-2-oxazolyl]-7-oxabicyclo2.2.1-]hept-2-yl]-4-hexenoic acid, methyl ester A sample of impure Part G oxazole acid (contaminated with tetrabutylammonium, but as the free acid, 0.20 mmol) was dried by azeotroping with dry DMF and toluene twice (high vacuum). This material was placed in 2 mL toluene, and while stirring the heterogeneous mixture at room temperature under argon, 127 mg oxalyl chloride (1.0 mmol, 5 equiv) was added. Gas was evolved. After 1 hour an additional 127 mg oxalyl chloride was added. Again gas was evolved. This mixture was stirred overnight. TLC indicated clean conversion to the acid chloride having the name [1S-[1α, 2α,(Z),3α,4α]]-6-[3-[4-(chlorocarbonyl)-2-oxazolyl-7-oxabicyclo[2.2.1]hept-2-yl]-4-hexenoic acid, methyl ester. The solvent was evaporated, and toluene was added and evaporated again to purge any remaining oxalyl chloride To the crude acid chloride of the Part G acid was added 4 mL CHCl$_3$. The material did not all dissolve. While stirring under argon at room temperature, 100 mg of impure Part H secondary amine hydrochloride (80% pure=80 mg, contaminated with tertiary amine hydrochloride, 0.39 mmol, 2 equiv) and 145 mg triethylamine (1.4 mmol, 7 equiv) were added. After stirring at room temperature for 1 hour, the mixture was diluted with ethyl acetate, water was added, and extraction (twice) with ethyl acetate was followed by drying over Na$_2$SO$_4$ and evaporation. This gave 120 mg of impure title amide as a gum. The crude product was taken on without purification.

TLC (1% F$_3$CCO$_2$H, 1% CH$_3$OH, 98% ethyl acetate-anisaldehyde):

| Part G oxazole acid | 0.28 |
|---|---|
| acid chloride intermediate | 0.78 |
| Part I amide | 0.64 |

J. [1S-[1α,2α,(Z),3α,4α]]-6-[3-[4-[[(4-Cyclohexylbutyl)methylamino]carbonyl]-2-oxazolyl]-7-oxabicyclo[2.2.1-]hept-2-yl]-4-hexenoic acid To 120 mg of impure Part I amide in 6 mL CH$_3$OH at room temperature, was added 2 mL of 1.0M aqueous NaOH solution. After stirring the mixture for 3 hours, 1M aqueous HCl solution was added to lower the pH to 1. Extraction with ethyl acetate (3 times) followed. The extracts were dried over Na₂SO₄, and solvent evaporation gave crude acid title product. Flash chromatography (50% to 100% [5% acetic acid in ethyl acetate] in hexane gradient) afforded, after azeotropic removal of acetic acid with toluene, 70 mg of pure title product as an oil. The yield of title product was 72% overall from the impure Part G oxazole acid.

TLC (50% [5% acetic acid in ethyl acetate] in hexane-anisaldehyde):

| Part I amide     | 0.36 |
| ---------------- | ---- |
| Part J Title Product | 0.20 |

$^{13}$C NMR (67.8 MHz in CDCl₃. Two conformations were seen. Lines clearly due to only one conformation are listed in parentheses.): 177.0, 163.1, (162.3), (162.0), 142.5, 136.4, 129.6, 128.5, 79.5, 79.4, (50.4), 49.7, (48.7), 46.7, 37.5, 37.0, (36.4), 34.1, 33.3, 29.7, 29.0, 27.9, (27.2), 26.6, 26.3, (24.2), (23.7), 22.9

EXAMPLE 3A

[1S-[1α,2α(Z),3α,4α]-6-[3-[4-[(1-Pyrrolidinyl)carbonyl]-2-oxazolyl]-7-oxabicyclo[2.2.1]hept-2-yl]-4-hexenoic acid A. 1-[N-[(1,1-Dimethylethoxy)carbonyl]-L-seryl]pyrrolidine To a stirred solution of pyrrolidine (1.11 g, 15.7 mmol), t-butyloxycarbonyl (BOC)-(L)-serine (3.22 g, 15.7 mmol), 1-hydroxybenzotriazole hydrate (2.12 g, 15.7 mmol) and diisopropylethyl amine (2.73 mL, 15.7 mmol) in 30 mL of THF under argon was added 1,3-dicyclohexylcarbodiimide (3.23 g, 15.7 mmol). This mixture was stirred at room temperature for 17 hours and concentrated in vacuo. The mixture was diluted with 200 mL ethyl acetate and the precipitate was filtered off. The precipitate was rinsed with ethyl acetate (3×40 mL). The combined filtrates were washed with 1N aqueous HCl solution (3×70 mL), and saturated NaHCO₃ solution (2×80 mL). The organic layer was dried (MgSO₄), filtered and concentrated in vacuo. This was chromatographed on 140 g of Merck silica gel 60 using 2% CH₃OH in CH₂Cl₂ as eluant to give 1.64 g (41%) of title amide.

TLC: silica gel, 4% CH₃OH in CH₂Cl₂, R$_f$ 0.24, Ce(-SO₄)₂

$^{13}$C NMR (67.5 MHz, CDCl₃) δ: 169.4, 155.6, 79.7, 62.8, 53.5, 46.5, 45.9, 28.0, 28.0, 28.0, 25.7, 23.8

B.
[1S-[1α,2α,(Z),3α(R*),4α]]-6-3-[[[1-(Hydroxymethyl)-2-oxo-2-(1-pyrrolidinyl)ethyl]amino]carbonyl]-7-oxabicyclo[2.2.1]-hept-2-yl]-4-hexenoic acid, methyl ester To a stirred solution of Part A amide (0.96 g, 3.72 mmol) in 20 mL of dry CH₂Cl₂ under argon at 0° C. was added 5 mL of trifluoroacetic acid (TFA). The mixture was stirred at 0° C. for 2 hours and diluted with 50 mL of toluene. This mixture was concentrated in vacuo. To a stirred solution of this amine-TFA salt, 1-hydroxybenzotriazole hydrate (0.50 g, 3.73 mmol), and 5 mL of triethylamine in 20 mL of DMF was added a solution of Example 1, Part D acid (1.00 g, 3.73 mmol) in mL of DMF. To this mixture was then added ethyl-3(3-dimethylamino)propyl carbodiimide hydrochloride salt. The reaction mixture was stirred at room temperature for 19 hours and concentrated in vacuo. The mixture was diluted with 400 mL of ethyl acetate and washed with 1N HCl solution (3×30 mL), 0.2N NaOH solution (2×30 mL) and brine (1×60 mL). The organic layer was dried (MgSO₄), filtered, and concentrated in vacuo. Purification was effected by flash chromatography on 50 g of Merck silica gel 60 using 0.4 L each of 2% and 4% CH₃OH in C₂Cl₂ as eluants to give 320 mg (22%) of title alcohol.

TLC: silica gel, 4% CH₃OH in CH₂Cl₂, R$_f$ 0.22, Ce(-SO₄)₂

$^{13}$C NMR (67.5 MHz, CDCl₃) δ: 173.4, 172, 2, 168.8, 129.3, 129.2, 78.9, 78.9, 63.5, 54.3, 52.2, 51.4, 48.0, 46.6, 45.9, 33.7, 29.5, 28.8, 27.2, 25.8, 24.0, 22.7

C. [1S-[1α,2α(Z),3α(R*),4α]-6-[3-[4,5-Dihydro-4-[(1-pyrrolidinyl)carbonyl]-2-oxazolyl]-7-oxabicyclo[2.2.1]hept-2-yl]-4-hexenoic acid, methyl ester To a stirred solution of Part B alcohol (305 mg, 0.75 mmol) and diisopropylethyl amine (0.39 mL, 2.24 mmol) in 10 mL of CH₂Cl₂ under argon at 0° C. was added methanesulfonyl chloride (0.07 mL, 0.90 mmol). This mixture was stirred at room temperature for 4 hours and concentrated in vacuo. The crude mesylate was dissolved in 30 mL of acetone and combined with 0.60 g of K₂CO₃. This mixture was heated to reflux for 4 hours, cooled to room temperature, and diluted with 100 mL of acetone. The precipitate was filtered off and rinsed with acetone (3×40 mL). The filtrate was concentrated in vacuo and chromatographed on 50 g of Merck silica gel 60 using 2% CH₃OH in CH₂Cl₂ as eluant to give 210 mg (72%) of title oxazoline.

TLC: silica gel, 4% CH₃OH in CH₂Cl₂, R$_f$ 0.20, Ce(-SO₄)₂.

$^{13}$C NMR (67.5 MHz, CDCl₃) δ: 173.4, 168.2, 167.7, 9.5, 129.1, 78.9, 78.9, 68.7, 67.5, 51.4, 48.4, 46.5, 46.4, 46.1, 33.9, 29.7, 28.8, 27.1, 25.9, 24.1, 22.8

D.
[1S-[1α,2α,(Z),3α,4α]-6-[3-[4-[(1-Pyrrolidinyl)carbonyl]-2-oxazolyl]-7-oxabicyclo[2.2.1]hept-2-yl]-4-hexenoic acid, methyl ester To a stirred solution of Part C oxazoline (200 mg, 0.51 mmol) in 5 mL of CH₂Cl₂ was added 200 mg of NiO₂ The reaction mixture was stirred at room temperature for 3 hours at which time another 200 mg of NiO₂ was added. The mixture was stirred at room temperature for 1 hour and 200 mg of NiO₂ was added. This mixture was stirred for another 1 hour and one more portion of 200 mg of NiO₂ was added. The reaction mixture was stirred at room temperature for 17 hours and diluted with 80 mL of ethyl acetate. To the resulting mixture 5 was added 5 mL of 3M NaHSO₃ solution and 40 mL of 1M sodium citrate solution. The organic layer was separated and the aqueous layer was extracted with ethyl acetate (3×70 mL). The combined organic extracts were dried (MgSO₄), filtered, and concentrated in vacuo. This was chromatographed on 18 g of Merck silica gel 60 using 2% CH₃OH in CH₂Cl₂ as eluant to give 69.2 mg (35%) of title ester.

TLC: silica gel, 4% CH₃OH in CH₂Cl₂, R$_f$ 0.24, Ce(-SO₄)₂.

$^{13}$C NMR (67.5 MHz, CDCl$_3$) δ: 173.2, 163.1, 160.3, 142.2, 137.1, 129.3, 128.7, 79.4, 79.1, 51.4, 49.6, 48.2, 46.7, 46.6, 33.7, 29.7, 28.9, 27.8, 26.4, 23.7, 22.7

E.
[1S-[1α,2α,(Z),3α,4α]]-6-[3-[4-[(1-Pyrrolidinyl)carbonyl]-2-oxazolyl]-7-oxabicyclo[2.2.1]hept-2-yl]-4-hexenoic acid To a stirred solution of Part D ester (69.0 mg, 0.18 mmol) and 2 mL of water in 12 mL of THF was added 2 mL of 1N LiOH solution. This mixture was sparged with argon for 10 minutes and stirred at room temperature for 7 hours. The mixture was acidified to pH 2 by the addition of 1N HCl solution and saturated with NaCl. The THF layer was separated and the aqueous layer was extracted with ethyl acetate (4×60 mL). The combined organic extracts were dried (MgSO$_4$), filtered and concentrated in vacuo. Purification was effected by flash chromatography on 10 g of Merck silica gel 60 using 10% CH$_3$OH in CH$_2$Cl$_2$ as eluant to give 26 mg (39%) of title acid.

TLC: silica gel, 6% CH$_3$OH in CH$_2$Cl$_2$, R$_f$ 0.22, Ce(SO$_4$)$_2$.

$^{13}$C NMR (67.5 MHz, DMSO-d$_6$) δ: 175.1, 163, 2, 159.6, 142.2, 136.3, 130.5, 127.6, 78.8, 78.4, 48.8, 47.7, 46.3, 45.8, 29.3, 28.4, 27.5, 25.9, 23.3, 23.2, 22.8

EXAMPLE 4A
[1S-[1α,2α,(Z),3α,4α]]-6-3-[4-[(Cyclohexylamino)carbonyl]-2-oxazolyl]-7-oxabicyclo[2.2.1]hept-2-yl]-4-hexenoic acid

A. [(1,1-Dimethylethoxy)carbonyl]-N-cyclohexyl-L-serinamide

To a stirred solution of cyclohexylamine (1.11 g, 15.7 mmol), Boc-(L)-serine (3.22 g, 15.7 mmol), 1-hydroxybenzotriazole hydrate (2.12 g, 15.7 mmol) and diisopropylethyl amine (2.73 mL, 15.7 mmol) in 30 mL of THF under argon at 0° C. was added 1,3-dicyclohexylcarbodiimide (3.23 g, 15.7 mmol). This mixture was stirred at room temperature for 18 hours. The mixture was diluted with 200 mL ethyl acetate and the precipitate was filtered. The precipitate was rinsed with ethyl acetate (3×40 mL). The combined filtrates were washed with 1N aqueous HCl solution (3×70 mL), and saturated NaHCO$_3$ solution (2×80 mL). The organic layer was dried (MgSO$_4$), filtered and concentrated in vacuo. This was chromatographed on 140 g of Merck silica gel 60 using 2% CH$_3$OH in CH$_2$Cl$_2$ as eluant to give 1.64 g (41%) of title amide.

TLC: silica gel, 4% CH$_3$OH in CH$_2$Cl$_2$, R$_f$ 0.24, Ce(SO$_4$)$_2$.

$^{13}$C NMR (67.5 MHz, CDCl$_3$) δ: 170.1, 156.1, 80.2, 62.7, 48.1, 32.6, 32.6, 28.1, 28.1, 28.1, 25.3, 24.5, 24.5

B.
[1S-[1α,2α,(Z),3α(R*),4α]-6-[3-[[[2-(Cyclohexylamino)-1-(hydroxymethyl)-2-oxoethyl]amino]carbonyl]-7-oxabicyclo-[2.2.1]hept-2-yl-4-hexenoic acid, methyl ester To a stirred solution of Part A amide (1.06 g, 3.73 mmol) in 20 mL of dry CH$_2$Cl$_2$ under argon at 0° C. was added 5 mL of TFA. The mixture was stirred at 0° C. for 2 hours and diluted with 50 mL of toluene. This mixture was concentrated in vacuo. To a stirred solution of this amine-TFA salt, 1-hydroxybenzotriazole hydrate (0.50 g, 3.73 mmol), and 6 mL of triethyl amine in 20 mL of DMF was added a solution of Example 1A, Part D acid (1.00 g, 3.73 mmol) in 10 mL of DMF. To this mixture was then added ethyl-3-(3-dimethylamino)-propyl carbodiimide hydrochloride salt (0.55 g, 3.73 mmol). The reaction mixture was stirred at room temperature for 19.5 hours and concentrated in vacuo. The mixture was diluted with 400 mL of ethyl acetate and washed with 1N HCl solution (3×40 mL), 0.2 N NaOH solution (2×30 mL), saturated NaHCO$_3$ solution (1×30 mL) and brine (1×100 mL). The organic layer was dried (MgSO$_4$), filtered, and concentrated in vacuo. Purification was effected by flash chromatography on 60 g of Merck silica gel 60 using 2% CH$_3$OH in CH$_2$Cl$_2$ as eluant to give 690 mg (42%) of title alcohol.

TLC: Silica gel, 4% CH$_3$OH in CH$_2$Cl$_2$, R$_f$ 0.30, Ce(SO$_4$)$_2$ $^{13}$C NMR (67.5 MHz, CDCl$_3$) δ: 173.3, 173.0, 169.6, 129.4, 129.0, 79.1, 78.9, 62.7, 54.4, 53.7, 51.4, 48.2, 48.0, 33.7, 32.6, 32.6, 32.6, 29.5, 28.6, 27.5, 25.3, 24.6, 24.6, 22.7

C.
[1S-[1α,2α(Z),3α(R*),4α]]-6-3-[4-(Cyclohexylamino)carbonyl]-4,5-dihydro-2-oxazolyl]-7-oxabicyclo[2.2.1]hept-2-yl]-4-hexenoic acid, methyl ester To a stirred solution of Part B alcohol (680 mg, 1.56 mmol) and diisopropylethyl amine (0.82 mL, 4.68 mmol) in 20 mL of CH$_2$Cl$_2$ under argon at 0° C. was added methanesulfonyl chloride (0.13 mL, 1.63 mmol). This mixture was stirred at room temperature for 1 hour and concentrated in vacuo. The crude mesylate was dissolved in 20 mL of acetone and combined with 647 mg of K$_2$CO$_3$. This mixture was heated at 54° C. for 3.5 hours, cooled to room temperature and diluted with 100 mL of acetone. The precipitate was filtered off and rinsed with acetone (3×50 mL). The filtrate was concentrated in vacuo and chromatographed on 50 g of Merck silica gel 60 using 2% CH$_3$OH in CH$_2$Cl$_2$ as eluant to give 540 mg (83%) of title oxazoline.

TLC: silica gel, 4% CH$_3$OH in CH$_2$Cl$_2$, R$_f$ 0.42, Ce(SO$_4$)$_2$ $^{13}$C NMR (67.5 MHz, CDCl$_3$) δ: 173.2, 170.4, 169.2, 129.5, 128.9, 79.1, 79.0, 69.7, 68.4, 51.4, 48.4, 47.8, 46.4, 33.8, 33.0, 32.8, 29.6, 28.9, 27.3, 25.4, 24.7, 24.7, 22.8

D.
[1S-[1α,2α(Z),3α,4α]]-6-[3-[4-(Cyclohexylamino)carbonyl]-2-oxazolyl]-7-oxabicyclo-[2.2.1]hept-2-yl]-4-hexenoic acid, methyl ester To a stirred solution of Part C oxazoline (530 mg, 1.26 mmol) in 5 mL of CH$_2$Cl$_2$ was added 1.06 g of NiO$_2$ The reaction mixture was stirred at room temperature for 3 hours at which time another 530 mg of NiO$_2$ was added. The mixture was stirred at room temperature for 1 hour and 530 mg of NiO$_2$ was added. This mixture was stirred for another 80 minutes and diluted with 120 mL of ethyl acetate. To the resulting mixture was added 10 mL of 3M NaHSO$_3$ solution and 70 mL of 1M sodium citrate solution. The organic layer was separated and the aqueous layer was extracted with ethyl acetate (2×100 mL). the combined organic extracts were 3% washed with brine (1×100 mL), dried (MgSO$_4$), filtered, and concentrated in vacuo. This was chromatographed on 40 g of Merck silica gel 60 using 2% CH$_3$OH in CH$_2$Cl$_2$ as eluant to give 370 mg (70%) of title ester.

TLC: silica gel, 4% CH₃OH in CH₂Cl₂, R_f 0.64, Ce(SO₄)₂.

¹³C NMR (67.5 MHz, CDCl₃) δ: 173.2, 163.7, 159.6, 140.6, 136.1, 129.4, 128.5, 79.5, 79.3, 51.4, 49.6, 47.8, 46.6, 33.7, 33.0, 33.0, 29.7, 28.8, 10 27.8, 25.4, 24.9, 24.9, 22.7

E.
[1S-[1α,2α,(Z),3α,4α]-6-[3-[4-[(Cyclohexylamino)carbonyl]-2-oxazolyl]-7-oxabicyclo[2.2.1]hept-2-yl]-4-hexenoic acid To a stirred solution of Part D ester (360 mg, 0.86 mmol) and 10 mL of water in 60 mL of THF was added 10 mL of 1N LiOH solution. This mixture was sparged with argon for 10 minutes and stirred at room temperature for 7 hours. The mixture was acidified to pH 2 by the addition of 1N HCl solution and saturated with NaCl. The THF layer was separated and the aqueous layer was extracted with ethyl acetate (4×80 mL). The combined organic extracts were dried (MgSO₄), filtered and concentrated in vacuo. Purification was effected by flash chromatography on 40 g of Merck silica gel 60 using 4% CH₃OH in CH₂Cl₂ as eluant to give 300 mg (86%) of title acid.

TLC: silica gel, 6% CH₃OH in CH₂Cl₂, R_f 0.32, Ce(SO₄)₂.

¹³C NMR (67.5 MHz, CDCl₃) δ: 176.9, 163.9, 160.0, 141.0, 129.5, 128.5, 79.5, 79.5, 48.1, 46.6, 33.7, 32.9, 32.9, 29.7, 28.9, 27.9, 25.5, 24.9, 24.9

EXAMPLE 5A

1S-[1α,2α(Z),3α,4α9]-6-[3-[4-[[(2-Cyclohexylethyl)amino]carbonyl]-2-oxazolyl]-7-oxabicyclo-2.2.1]hept-2-yl]-4-hexenoic acid

A. [(1,1-Dimethylethoxy)carbonyl]-N-(2-cyclohexylethyl)-L-serinamide

To a stirred solution of 2-cyclohexylethylamine (2.00 g, 15.7 mmol), Boc-(L)-serine (3.22 g, 15.7 mmol), 1-hydroxybenzotriazole hydrate (2.12 g, 15.7 mmol) and diisopropylethyl amine (2.73 mL, 15.7 mmol) in 40 mL of THF under argon at 0° C. was added 1,3-dicyclohexylcarbodiimide (3.23 g, 15.7 mmol). This mixture was stirred at room temperature and 10 mL of DMF was added. The reaction mixture was then stirred at room temperature for 18 hours. The mixture was diluted with 300 mL ethyl acetate and the precipitate was filtered. The precipitate was rinsed with ethyl acetate (3×40 mL). The combined filtrate was washed with 1N aqueous HCl solution (3×70 mL), and saturated NaHCO₃ solution (2×80 mL). The organic layer was dried (MgSO₄), filtered and concentrated in vacuo. This was chromatographed on 160 g of Merck silica gel 60 using 1:4 hexane diethyl ether as eluant to give 1.91 g (39%) of title amide. TLC: silica gel, 4% CH₃OH in CH Cl₂, R_f 0.34, Ce(SO₄)₂.

¹³C NMR (67.5 MHz, CDCl₃) δ: 171.1, 80.3, 62.9, 37.3, 36.8, 35.2, 33.1, 33.1, 28.3, 28.3, 26.4, 26.1, 26.1

B.
[1S-[1α,2α(Z),3α(R*),4α]]-6-[3-[[2-[(2-Cyclohexylethyl)amino]-1-(hydroxymethyl)-2-oxoethylamino]carbonyl]-7-oxabicyclo-[2.2.1hept-2-yl]-4-hexenoic acid, methyl ester To a stirred solution of Part A amide (1.28 g, 3.73 mmol) in 20 mL of dry CH₂Cl₂ under argon at 0° C. was added 5 mL of TFA. The mixture was stirred at 0° C. for 2 hours and diluted with 50 mL of toluene. This mixture was concentrated in vacuo. To a stirred solution of this amine-TFA salt, 1-hydroxybenzotriazole hydrate (0.50 g, 3.73 mmol), and 5 mL of triethylamine in 20 mL of DMF was added a solution of Example 1, Part D acid (1.00 g, 3.73 mmol) in 10 mL of DMF. To this mixture was then added ethyl-3(3-dimethylamino)-propyl carbodiimide hydrochloride salt (0.55 g, 3.73 mmol). The reaction mixture was stirred at room temperature for 17 hours and concentrated in vacuo. The mixture was diluted with 400 mL of ethyl acetate and washed with 1N HCl solution (3×40 mL), 0.2 N NaOH solution (2×30 mL), saturated NaHCO₃ solution (1×30 mL) and brine (1×100 mL). The organic layer was dried (MgSO₄), filtered, and concentrated in vacuo. Purification was effected by flash chromatography on 60 g of Merck silica gel 60 using 2% CH₃OH in CH₂Cl₂ as eluant to give 1.00 g (54%) of title alcohol.

TLC: silica gel, 4% CH₃OH in CH₂Cl₂, R_f 0.30, Ce(SO₄)₂.

¹³C NMR (67.5 MHz, CDCl₃) δ: 173.4, 172.9, 170.4, 129.3, 129.0, 79.0, 78.9, 62.7, 54.2, 53.7, 51.4, 48.0, 37.3, 36.6, 35.3, 33.7, 32.9, 32.9, 29.5, 28.6, 27.3, 26.3, 26.0, 26.0, 22.7

C.
[1S-[1α,2α(Z),3α(R*),4α]]-6-[3-[4-[(2-Cyclohexylethyl)aminocarbonyl-4,5-dihydro-2-oxazolyl]-7-oxabicyclo[2.2.1]-hept-2-yl]-4-hexenoic acid, methyl ester To a stirred solution of Part B alcohol (890 mg, 1.80 mmol) and diisopropylethyl amine (0.94 mL, 5.40 mmol) in 30 mL of CH₂Cl₂ under argon at 0° C. was added methanesulfonyl chloride (0.14 mL, 1.80 mmol). This mixture was stirred at room temperature for 1 hour and concentrated in vacuo. The crude mesylate was dissolved in 30 mL of acetone and combined with 0.77 g of K₂CO₃. This mixture was heated to reflux for 4 hours, cooled to room temperature, and diluted with 100 mL of acetone. The precipitate was filtered off and rinsed with acetone (3×50 mL). The filtrate was concentrated in vacuo and chromatographed on 60 g of Merck silica gel 60 using 2% CH₃OH in CH₂Cl₂ as eluant to give 480 mg (54%) of title oxazoline.

TLC: silica gel, 4% CH₃OH in CH₂Cl₂, R_f 0.42, Ce(SO₄)₂.

¹³C NMR (67.5 MHz, CDCl₃) δ: 173.1, 171.2, 169.2, 129.4, 128.9, 79.1, 79.0, 69.6, 68.3, 51.4, 48.3, 46.3, 36.9, 36.8, 35.2, 33.7, 33.0, 32.9, 29.6, 28.8, 27.2, 26.3, 26.1, 26.1, 22.8

D.
[1S-[1α,2α(Z),3α,4α]]-6-[3-[4-[[(2-Cyclohexylethyl)amino]carbonyl]-2-oxazolyl]-7-oxabicyclo[2.2.1]hept-2-yl]-4-hexenoic acid, methyl ester To a stirred solution of Part C oxazoline (480 mg, 1.01 mmol) in 20 mL of CH₂Cl₂ was added 480 mg of NiO₂. The reaction mixture was stirred at room temperature for 1 hour at which time another 480 mg of NiO was added. The mixture was stirred at room temperature for 3 hours and 480 mg of NiO₂ was added. This mixture was stirred for another 15.5 hours and one more portion of 480 mg of NiO₂ was added. The reaction mixture was stirred for 1.5 hours and diluted with 100 mL of ethyl acetate. To the resulting mixture was added 20 mL of 3M NaHSO₃ solution and 30 mL of 1M sodium citrate solution. The organic layer was separated and the aqueous layer was extracted with ethyl acetate (2×100 mL). The combined organic extracts were washed with brine (1×50 mL), dried (MgSO₄), filtered, and concentrated in vacuo. This was chromatographed on 45 g of Merck silica gel 60 using 2% CH₃OH in CH₂Cl₂ as eluant to give 200 mg (42%) of title ester.

TLC: silica gel, 4% CH₃OH in CH Cl₂, R$_f$ 0.60, Ce(-SO₄)₂.

¹³C NMR (67.5 MHz, CDCl₃) δ: 173.1, 163.7, 160.4, 140.3, 136.0, 129.3, 128.4, 79.4, 79.3, 51.3, 49.6, 46.6, 36.9, 36.7, 35.2, 33.6, 33.0, 33.0, 29.7, 28.8, 27.7, 26.4, 26.0, 26.0, 22.7

E.
[1S-[1α,2α,(Z),3α,4α]]-6-[3-[4-[[(2-Cyclohexylethyl)aminocarbonyl]-2-oxazolyl]-7-oxabicyclo[2.2.1hept-2-yl]-4-hexenoic acid To a stirred solution of Part D ester (190 mg, 0.40 mmol) and 4 mL of water in 30 mL of THF was added 4 mL of 1N LiOH solution. This mixture was sparged with argon for 10 minutes and stirred at room temperature for 5 hours. The mixture was acidified to pH 2 by the addition of 1N HCl solution and saturated with NaCl. The THF layer was separated and the aqueous layer was extracted with ethyl acetate (4×25 mL). The combined organic extracts were dried (MgSO₄), filtered and concentrated in vacuo. Purification was effected by flash chromatography on 20 g of Merck silica gel 60 using 4% CH₃OH in CH₂Cl₂ as eluant to give 106.7 mg (59%) of title acid.

TLC: silica gel, 6% CH₃OH in CH₂Cl₂, R$_f$ 0.32, Ce(-SO₄)₂.

¹³C NMR (67.5 MHz, CDCl₃) δ: 176.9, 163, 9, 160.7, 140.8, 135.7, 129.4, 128.4, 79.5, 79.4, 49.6, 46.5, 36.9, 36.8, 35.2, 33.7, 33.0, 33.0, 29.6, 28.8, 27.8, 26.4, 26.1, 26.1, 22.6

EXAMPLE 6A
1S-[1α,2α,(Z),3α,4α]]-6-[3-[4-[[[2-(4-Chlorophenyl)-ethylamino]carbonyl-2-oxazolyl]-7-oxabicyclo-[2.2.1]hept-2-yl]-4-hexenoic acid

A.
[(1,1-Dimethylethoxy)carbonyl-N-[2-(4-chlorophenyl)ethyl]-L-serinamide

To a stirred solution of 2-(4-chlorophenyl)ethylamine (2.44 g, 15.7 mmol), Boc-(L)-serine (3.22 g, 15.7 mmol), 1-hydroxybenzotriazole hydrate (2.12 g, 15.7 mmol) and diisopropylethyl amine (2.73 mL, 15.7 mmol) in 30 mL of THF under argon at 0° C. was added 1,3-dicyclohexylcarbodiimide (3.23 g, 15.7 mmol). This mixture was stirred at room temperature and 10 mL of DMF was added. The reaction mixture was then stirred at room temperature for 18 hours. The mixture was diluted with 200 mL ethyl acetate and the precipitate was filtered. The precipitate was rinsed with ethyl acetate (3×40 mL). The combined filtrates was washed with 1N aqueous HCl solution (3×70 mL), and saturated NaHCO₃ solution (2×80 mL). The organic layer was dried (MgSO₄), filtered and concentrated in vacuo. This was chromatographed on 160 g of Merck silica gel 60 using 1:4 hexanediethyl ether as eluant to give 2.56 g (48%) of title amide.

TLC: silica gel, 4% CH₃OH in CH₂Cl₂, R$_f$ 0.34, Ce(-SO₄)₂.

¹³C NMR (67.5 MHz, CDCl₃) δ: 173.1, 157.6, 139.2, 3.1, 131.4, 131.4, 129.4, 129.4, 80.8, 63.3, 58.0, 41.7, 35.7, 34.7, 28.7, 28.7, 28.7

B.
[1S-[1α,2α(Z),3α(R*),4α]]-6-[3-[[[2-[[2-(4-Chlorophenyl)ethyl]amino]-1-(hydroxymethyl)-2-oxoethylamino]carbonyl]-7-oxabicyclo[2.2.1]hept-2-yl]-4-hexenoic acid, methyl ester To a stirred solution of Part A amide (1.28 g, 3.73 mmol) in 20 mL of dry CH₂Cl₂ under argon at 0° C. was added 5 mL of TFA. The mixture was stirred at 0° C. for 2 hours and diluted with 50 mL of toluene. This mixture was concentrated in vacuo. To a stirred solution of this amine-TFA salt, 1-hydroxybenzotriazole hydrate (0.50 g, 3.73 mmol), and 5 mL of triethylamine in 20 mL of DMF was added a solution of Example 1, Part D acid (1.00 g, 3.73 mmol) in 10 mL of DMF. To this mixture was then added ethyl-3(3-dimethylamino)-propyl carbodiimide hydrochloride salt (0.55 g, 3.73 mmol). The reaction mixture was stirred at room temperature for 17 hours and concentrated in vacuo. The mixture was diluted with 400 mL of ethyl acetate and washed with 1N HCl solution (3×40 mL), 0.2N NaOH solution (2×30 mL), saturated NaHCO₃ solution (1×30 mL) and brine (1×100 mL). The organic layer was dried (MgSO₄), filtered, and concentrated in vacuo. Purification was effected by flash chromatography on 60 g of Merck silica gel 60 using 2% CH₃OH in CH₂Cl₂ as eluant to give 1.00 g (54%) of title alcohol.

TLC: silica gel, 4% CH₃OH in C₂Cl₂, R$_f$ 0.30, Ce(-SO₄)₂.

¹³C NMR (67.5 MHz, CDCl₃) δ: 173.5, 172.9, 170.6, 137.2, 132.1, 130.0, 130.0, 129.3, 129.1, 128.5, 128.5, 79.0, 78.9, 62.7, 54.1, 53.9, 51.4, 48.0, 40.8, 34.8, 33.7, 29.5, 28.7, 27.3, 22.7

C.
[1S-[1α,2α,(Z),3α(R*),4α]]-6-[3-[4-[[2-(4-Chlorophenyl)ethyl]amino]carbonyl-4,5-dihydro-2-oxazolyl-7-oxabicyclo[2.2.1]hept-2-yl]-4-hexenoic acid, methyl ester To a stirred solution of Part B alcohol (890 mg, 1.80 mmol) and diisopropylethyl amine (0.94 mL, 5.40 mmol) in 30 mL of CH₂Cl₂ under argon at 0° C. was added methanesulfonyl chloride (0.14 mL, 1.80 mmol). This mixture was stirred at room temperature for 1 hour and concentrated in vacuo. The crude mesylate was dissolved in 30 mL of acetone and combined with 0.77 g of K₂CO₃. This mixture was heated to reflux for 4 hours, cooled to room temperature, and diluted with 100 mL of acetone. The precipitate was filtered off and rinsed with acetone (3×50 mL). The filtrate was concentrated in vacuo and chromatographed on 60 g of Merck silica gel 60 using 2% CH₃OH in CH₂Cl₂ as eluant to give 480 mg (54%) of title oxazoline.

TLC: silica gel, 4% CH₃OH in CH Cl₂, R$_f$ 0.42, Ce(-SO₄)₂.

¹³C NMR (67.5 MHz, CDCl₃) δ: 171.6, 169.4, 169.3, 137.0, 132.3, 130.0, 130.0, 129.5, 129.0, 128.6, 128.6, 79.1, 79.0, 69.6, 68.3, 51.5, 48.2, 46.3, 40.0, 34.8, 33.8, 29.6, 28.9, 27.2, 22.8

D.
[1S-[1α,2α,(Z),3α,4α]]-6-[3-[4-[[[2-(4-Chlorophenyl)ethylamino]carbonyl-2-oxazolyl]-7-oxabicyclo[2.2.1]hept-2-yl]-4-hexenoic acid, methyl ester To a stirred solution of Part C oxazoline (480 mg, 1.01 mmol) in 20 mL of CH₂Cl₂ was added 480 mg of NiO₂. The reaction mixture was stirred at room temperature for 1 hour at which time another 480 mg of NiO₂ was added. The mixture was stirred at room temperature for 3 hours and 480 mg of NiO₂ was added. This mixture was stirred for another 15.5 hours and one more portion of 480 mg of NiO₂ was added. The reaction mixture was stirred for 1.5 hours and diluted with 100 mL of ethyl acetate. To the resulting mixture was added 20 mL of 3M NaHSO₃ solution and 30 mL of 1M sodium citrate solution. The organic layer was separated and the aqueous layer was extracted with ethyl acetate (2×100 mL). The combined organic extracts were washed with brine (1×50 mL), dried (MgSO₄), filtered, and concentrated in vacuo. This was chromatographed on 45 g of Merck silica gel 60 using 2% CH₃OH in CH₂Cl₂ as eluant to give 200 mg (42%) of title ester.

TLC: silica gel, 4% CH₃OH in CH₂Cl₂, R$_f$0.60, Ce(SO₄)₂.

$^{13}$C NMR (67.5 MHz, CDCl₃) δ: 173.2, 163.9, 160.6, 0.5, 137.2, 135.8, 132.2, 130.0, 130.0, 129.4, 8.6, 128.6, 128.S, 79.5, 79.3, 51.4, 49.6, 46.6, 40.1 35.2, 33.7, 29.7, 28.9, 27.8, 22.7

E.

[1S-[1α,2α,(Z),3α,4α]]-6-[3-[4-[[[2-(4-Chlorophenyl)ethyl]amino]carbonyl]-2-oxazolyl]-7-oxabicyclo[2.2.1-]hept-2-yl]-4-hexenoic acid To a stirred solution of Part D ester (190 mg, 0.40 mmol) and 4 mL of water in 30 mL of THF was added 4 mL of 1N LiOH solution. This mixture was sparged with argon for 10 minutes and stirred at room temperature for 5 hours. The mixture was acidified to pH 2 by the addition of 1N HCl solution and saturated with NaCl. The THF layer was separated and the aqueous layer was extracted with ethyl acetate (4×25 mL). The combined organic extracts was dried (MgSO₄), filtered and concentrated in vacuo. Purification was effected by flash chromatography on 20 g of Merck silica gel 60 using 4% CH₃OH in CH₂Cl₂ as eluant to give 6.7 mg (59%) of title acid.

TLC: silica gel, 6% CH₃OH in CH₂Cl₂, R$_f$0.32, Ce(SO₄)₂.

$^{13}$C NMR (67.5 MHz, CDCl₃) δ: 176.9, 175.4, 164.0, 0.9, 140.9, 137.2, 130.1, 130.1, 129.4, 128.6, 8.6, 79.6, 79.5, 49.6, 46.6, 40.2, 35.1,33.7, 29.7, 28.9, 27.9, 22.6

EXAMPLE 7A

[1S-[1α,2α(Z),3α,4α]]-6-[3-[4-[[(4-Chlorophenyl)amino]carbonyl]-2-oxazolyl]-7-oxabicyclo[2.2.1]-hept-2-yl]-4-hexenoic acid A. [(1,1-Dimethylethoxy)carbonyl]-N-(4-chlorophenyl)-L-serinamide To a stirred solution of 4-chloroaniline (2.00 g, 15.7 mmol), Boc-(L)-serine (3.22 g, 15.7 mmol), 1-hydroxybenzotriazole hydrate (2.12 g, 15.7 mmol) and diisopropylethyl amine (5.40 mL, 31.2 mmol) in 40 mL of DMF under argon was added ethyl-3(3-dimethylamino)propyl carbodiimide, hydrochloride salt (2.31 g, 15.7 mmol). This mixture was stirred at room temperature for 17 diluted with 400 mL ethyl acetate and washed with 1N aqueous HCl solution (3×70 mL), and saturated NaHCO₃ solution (2×70 mL). The organic layer was dried (MgSO₄), filtered and concentrated in vacuo. This was chromatographed on 80 g of Merck silica gel 60 using 1 L of each of 1:3 and 1:4 hexane-diethyl ether as eluants to give 1.02 g (21%) of title amide.

TLC: silica gel, 4% CH₃OH in CH₂Cl₂, R$_f$0.34, Ce(SO₄)₂.

B.

[1S-[1α,2α(Z),3α(R*),4α]]-6-[3-[[[2-[(4-Chlorophenyl)amino]-1-(hydroxymethyl)-2-oxoethyl]amino]carbonyl]-7-oxabicyclo-[2.2.1]hept-2-yl]-4-hexenoic acid, methyl ester To a stirred solution of Part A amide (1.02 g, 3.24 mmol) in 12 mL of dry CH₂Cl₂ under argon at 0° C. was added 3 mL of TFA. The mixture was stirred at 0° C. for 3 hours and diluted with 50 mL of toluene. This mixture was concentrated in vacuo. To a stirred solution of this amine-TFA salt, 1-hydroxybenzotriazole hydrate (0.50 g, 3.73 mmol), and 5 mL of triethylamine in 20 mL of DMF was added a solution of Example 1, Part D acid (1.00 g, 3.73 mmol) in 10 mL of DMF. To this mixture was then added 1-(3-dimethylaminopropyl)-3-ethylcarbodiimide, hydrochloride salt. The reaction mixture was stirred at room temperature for 17 hours and concentrated in vacuo. The mixture was diluted with 400 mL of ethyl acetate and washed with 1N HCl solution (3×30 mL), 0.2N NaOH solution (2×30 mL) and brine (1×100 mL). The organic layer was dried (MgSO₄), and concentrated in vacuo. Purification was effected by flash chromatography on 80 g of Merck silica gel 60 using 2% CH₃OH in CH₂Cl₂ as eluant to give 380 mg (22%) of title alcohol.

TLC: silica gel, 4% CH₃OH in CH₂Cl₂, R$_f$0.31, Ce(SO₄)₂.

C.

[1S-[1α,2α(Z),3α(R*),4α]-6-[3-[4-[(4-Chlorophenyl)aminocarbonyl]-4,5-dihydro-2-oxazolyl]-7-oxabicyclo[2.2.1]hept-2-yl]-4-hexenoic acid, methyl ester To a stirred solution of Part B alcohol (370 mg, 0.80 mmol) and diisopropylethyl amine (0.42 mL, 2.39 mmol) in 5 mL of CHCl₃ under argon at 0° C. was added methanesulfonyl chloride (0.068 mL, 0.88 mmol). This mixture was stirred at room temperature for 30 minutes and concentrated in vacuo. The crude mesylate was dissolved in 10 mL of acetone and combined with 0.70 g of K₂CO₃. This mixture was heated almost to reflux for 3 hours, cooled to room temperature and diluted with 100 mL of acetone. The precipitate was filtered off and rinsed with acetone (3×30 mL). The filtrate was concentrated in vacuo and chromatographed on 35 g of Merck silica gel 60 using 2% CH₃OH in CH₂Cl₂ as eluant to give 210 mg (59%) title oxazoline.

TLC: silica gel, 4% CH₃OH in CH R$_f$0.68, Ce(SO₄)₂.

$^{13}$C NMR (67.5 MHz, CDCl₃) δ: 173.2, 170.0, 169.6, 135.8, 129.5, 129.4, 128.9, 128.9, 128.5, 120.9, 120.9, 79.2, 79.2, 69.4, 68.7, 51.4, 48.3, 46.4, 33.7, 29.6, 28.8, 27.2, 22.8

D.

[1S-[1α,2α,(Z),3α,4α]]-6-[3-[4-[[(4-Chlorophenyl)amino]carbonyl]-2-oxazolyl]-7-oxabicyclo[2.2.1]hept-2-yl]-4-hexenoic acid, methyl ester To a stirred solution of Part C oxazoline (200 mg, 0.45 mmol) in 3 mL of CH₂Cl₂ was added 200 mg of NiO₂. The reaction mixture was stirred at room temperature for 1.5 hours at which time another 200 mg of NiO₂ was added. The mixture was stirred at room temperature for 1.5 hours and 200 mg of NiO₂ was added. This mixture was stirred for another 1.5 hours and one more portion of 200 H mg of NiO was added. The reaction mixture was stirred for 2 hours and diluted with 100 mL of ethyl acetate. To the resulting mixture was added 5 mL of 3M NaHSO$_3$ solution and 30 mL of 1M sodium citrate solution. The organic layer was separated and the aqueous layer was extracted with ethyl acetate (2×100 mL). The combined organic extracts were dried (MgSO$_4$), filtered, and concentrated in vacuo. This was chromatographed on 15 g of Merck silica gel 60 using 2% CH$_3$OH in CH$_{Cl2}$ as eluant to give 140 mg (70%) of title ester.

TLC: silica gel, 4% CH$_3$OH in CH$_2$Cl$_2$, R$_f$0.76, Ce(-SO$_4$)$_2$.

$^{13}$C NMR (67.5 MHz, CDCl$_3$) δ: 173.2, 164.2, 158.4, 141.4, 136.0, 135.9, 129.5, 129.3, 128.9, 128.9, 128.4, 121.1, 121.1, 79.6, 79.4, 51.4, 49.6, 46.6, 33.7, 29.7, 28.9, 27.9, 22.8

E.
[1S-[1α,2(Z),3α,4α]]-6-[3-[4-[[(4-Chlorophenyl)amino]carbonyl]-2-oxazolyl]-7-oxabicyclo[2.2.1]hept-2-yl]-4-hexenoic acid To a stirred solution of Part D ester (135 mg, 0.03 mmol) and 3 mL of water in 15 mL of THF was added 3 mL of 1N LiOH solution. This mixture was sparged with argon for 10 minutes and stirred at room temperature for 5 hours. The mixture was acidified to pH 2 by the addition of 1N HCl solution and saturated with NaCl. The THF layer was separated and the aqueous layer was extracted with ethyl acetate (4×15 mL). The combined organic extracts were dried (MgSO$_4$), filtered and concentrated in vacuo. Purification was effected by flash chromatography on 15 g of Merck silica gel 60 using 4% CH$_3$OH in CH$_2$Cl$_2$ as eluant to give 79.2 mg (61%) of title acid.

TLC: silica gel, 6% CH$_3$OH in CH$_2$Cl$_2$, R$_f$0.36, Ce(-SO$_4$)$_2$.

$^{13}$C NMR (67.5 MHz, CDCl$_3$) δ: 179.0, 177.6, 164.2, 141.7, 136.0, 135.9, 129.4, 128.9, 128.5, 121.2, 121.2, 79.7, 79.5, 49.6, 46.6, 33.6, 32.3, 29.7, 28.9, 27.9, 22.6

EXAMPLE 8A
[1S-[1α,2α(Z),3α,4α]]-6-[3-[4-[[[4-(4-Chlorophenyl)butyl]amino]carbonyl]-2-oxazolyl]-7-oxabicyclo-[2.2.1]hept-2-yl]-4-hexenoic acid

A.
1S-[1α,2α,(Z),3α,4α]]-6-[3-[4-[[[4-(4-Chlorophenyl)butyl]amino]carbonyl]-2-oxazolyl]-7-oxabicyclo[2.2.1-]hept-2-yl]-4-hexenoic acid, methyl ester 0.21 g of impure Example 2A, Part G compound (50% pure=0.11 g, 0.33 mmol) was stirred in about 4 mL toluene, and 0.1 mL (1.14 mmol) of oxalyl chloride was added. One drop of dimethylformamide was added, and the mixture was stirred for 2 hours at room temperature after which the reaction was complete by TLC. The reaction mixture was concentrated in vacuo; the residue was reconcentrated twice from 2 mL of toluene to afford an orange oil namely [1S-[1α,2α(Z),3α,4α]]-6-(4-(chlorocarbonyl)-2-oxazolyl)-7-oxabicyclo[2.2.1-]hept-2-yl]-4-hexenoic acid, methyl ester. To this oil was added about 3 mL of CHCl$_3$ followed by 0.11 mL (0.08 g, 0.78 mmol) of triethylamine and 0.13 g (0.71 mmol) of 4-(4-chlorophenyl)butylamine, and the mixture was stirred overnight at room temperature. The reaction mixture was diluted with ethyl acetate and water, the organic layer was separated, and the aqueous layer was extracted twice with 20 mL of ethyl acetate. The organic layers were combined, washed with brine, dried over MgSO$_4$, and concentrated in vacuo to afford 0.43 g of an orange oil. This oil was flash chromatographed (silica; 0% to 100% ethyl acetate in hexane gradient) to obtain 0.26 g of impure title methyl ester (50% pure=0.13 g) as an oil. The product was obtained in 78% yield.

$^{13}$C NMR (67.8 MHz, CDCl$_3$) δ: 172.8, 163.6, 160.3, 140.2, 140.2, 135.7, 131.0, 129.4, 129.1, 128.2, 128.0, 79.2, 79.1, 51.1, 49.4, 46.3, 38.4, 34.4, 33.5, 29.4, 28.6, 28.1, 27.6, 22.5

B.
[1S-[1α,2α(Z),3α,4α]]-6-[3-[4-[[[4-(4-Chlorophenyl)butyl]amino]carbonyl]-2-oxazolyl]-7-oxabicyclo[2.2.1-]hept-2-yl]-4-hexenoic acid 0.26 g of impure Part A ester (50% pure=0.13 g, 0.26 mmol) was stirred in about 30 mL 1N NaOH and 2 mL of THF for 8 hours at room temperature. The reaction mixture was concentrated to remove THF and acidified to pH about 2 with concentrated HCl. Ethyl acetate was added and the organic layer was separated. The aqueous layer was extracted twice with about 20 mL ethyl acetate. The organic layers were combined, washed with saturated NaCl, dried over MgSO$_4$, and concentrated in vacuo to give 0.2 g of a clear oil. This was flash chromatographed (silica, 0.50% CH$_3$OH; 0.25% CH$_3$CO$_2$H; 99.25% ethyl acetate to provide 0.10 g of pure product. The product was obtained in 79% yield.

$^{13}$C NMR (67.8 MHz, CDCl$_3$) δ: 178.4, 164.4, 161.4, 141.0, 140.4, 135.6, 131.3, 129.6, 129.3, 128.5, 128.3, 79.5, 79.4, 49.6, 46.5, 38.8, 34.6, 33.6, 29.6, 28.9, 28.4, 27.8, 22.5

EXAMPLE 9A
[1S-[1α,2α(Z),3α,4α]]-6-[3[4-[[(4-Cyclohexylbutyl)amino]carbonyl]-2-thiazolyl]-7-oxabicyclo[2.2.1]-hept-2-yl]-4-hexenoic acid

A.
[1S-[1α,2α(Z),3α,4α]]-6-[3-(Aminocarbonyl)-7-oxabicyclo[2.2.1]hept-2-yl]-4-hexenoic acid, methyl ester To a solution of Example 1A, Part D acid (2.45 g, 9.13 mmol) in dry benzene (100 mL) was added, dropwise over a 10 minute period, oxalyl chloride (0.96 mL, 11 mmol). After stirring for 5 hours, the reaction was concentrated in vacuo, dissolved in dry THF (10 mL) and added dropwise over a 5 minute period to a 0° C. solution of concentrated ammonium hydroxide (3 mL) in THF (100 mL). The reaction was then concentrated in vacuo. The residual solid was partitioned between ethyl acetate (150 mL) and 0.25M K$_2$CO$_3$ (25 mL). The aqueous layer was extracted with ethyl acetate (25 mL). The combined organic layers were dried (Na$_2$SO$_4$) and concentrated in vacuo. The residue (2.2 g) was suspended in boiling ether (100 mL). Ethyl acetate (ca. 10 mL was added to effect solution. The mixture was concentrated to ca. 50 mL on a steam bath, cooled to room temperature, seeded and chilled overnight. Pure title amide (1.19 g, 49%) was obtained by filtration. Additional title amide (145 mg) was obtained by concentration of the mothor liquors to 15 mL and allowing crystallization to occur.

B. [1S-[1α,2α(Z),3α,4α]]-6-3-(Aminothiocarbonyl)-7-oxabicyclo[2.2.1]hept-2-yl]-4-hexenoic acid, methyl ester To a 60° C. solution of Part A amide (267 mg, 0.999 mmol) in dry toluene (10 mL) was added Lawesson's Reagent (222 mg, 0.55 mmol). The reaction was stirred at 60° C. for 30 minutes, diluted with diethyl ether (50 mL), and washed with half-saturated NaHCO$_3$ (2×5 mL). The organic layer was dried (Na$_2$SO$_4$) and concentrated in vacuo. The residue was passed through a short silica plug using 50% ethyl acetate/hexanes to yield a yellow solid (249 mg, 88%).

C. [1S-[1α,2α(Z),3α,4α]]-6-[3-(4-carboxy-2-thiazolyl)-7-oxabicyclo[2.2.1]hept-2-yl]-4-hexenoic acid, methyl ester To a solution of Part B thioamide (400 mg, 1.41 mmol) and powdered anhydrous K$_2$CO$_3$ (390 mg, 2.82 mmol) in dry DMF (10 mL) was added, in several portions, bromopyruvic acid (contains 0.4 mol water/mol bromoacid, 295 mg, 1.69 mmol). The reaction was allowed to stir at room temperature for 30 minutes. After this time, an additional 29.5 mg portion of bromopyruvic acid was added. After an additional 1 hour, the solvent was removed in vacuo below 30° C. The residue was suspended/dissolved in methylene chloride (10 mL). Triethylamine (0.59 mL, 4.2 mmol) was added followed by the dropwise addition of methanesulfonyl chloride (0.33 mL, 4.2 mmol). After stirring for 5 minutes, the reaction was diluted with diethyl ether (40 mL). The organic layer was extracted with 0.5M K$_2$CO$_3$ (9×10 mL). The combined aqueous layers were brought to pH 1.5 with 6N HCl and extracted with diethyl ether (6×25 mL). These combined organic layers were dried (Na$_2$SO$_4$) and concentrated in vacuo. The yield of the product acid was 212 mg (43%).

D. [1S-[1α,2α(Z),3α,4α]]-6-[3-[4-[[(4-Cyclohexylbutyl)amino]carbonyl]-2-thiazolyl]-7-oxabicyclo[2.2.1]hept-2yl]-4-hexenoic acid, methyl ester To a solution of Part C acid (42.0 mg, 0.120 mmol) in dry DMF 1 mL) was added 1,1'-carbonyldiimidazole (20.3 mg, 0.125 mmol). The reaction was allowed to stir for 1 hour. A solution of (cyclohexylbutyl)amine hydrochloride (23.4 mg, 0.131 mmol) and triethylamine (0.020 mL, 0.14 mmol) in dry DMF (0.5 mL) was then added. The reaction was stirred for 1 hour, and concentrated to remove DMF. The residue was taken up in diethyl ether (20 mL) and 0.5N HCl (5 mL). The organic layer was dried (Na$_2$SO$_4$) and concentrated in vacuo. The resultant amide (46.8 mg, 81%) was chromatographed (silica, 50% ethyl acetate/hexanes) to yield 37.1 mg (64%) of title ester as a colorless oil.

E. 1S-[1α,2α(Z),3α,4α]]-6-[3-[4-[[(4-Cyclohexylbutyl)amino]carbonyl]-2-thiazolyl]-7-oxabicyclo[2.2.1]hept-2-yl]-4-hexenoic acid To a solution of Part D amide in methanol (1 mL) was added 2N KOH (0.3 mL). The reaction was stirred for 2 hours. An additional 0.3 mL portion of KOH was added. After an additional 1 hour, the reaction was concentrated to remove methanol. The residue was dissolved in water (1 mL) and 1N HCl was added to bring the pH to 2. The mixture was extracted with methylene chloride (3×5 mL). the combined organic layers were dried (Na$_2$SO$_4$) and concentrated in vacuo to yield an oil (34.7 mg, 96%).

EXAMPLE 10A

[1S-[1α,2α(Z),3α,4α]]-6-[3-[5-[[(4-Cyclohexylbutyl)amino]carbonyl]-1H-imidazol-2-yl]-7-oxabicyclo[2.2.1]hept-2-yl]-4-hexenoic acid, methyl ester

A. 2-(((1,1-Dimethylethoxy)carbonyl)amino)-3-(((phenylmethoxy)carbonyl)amino)propanoic acid N-α-Boc-asparagine (18.0 g, 77.5 mmol) was added to a solution of bis(trifluoroacetoxy)iodosylbenzene (50.0 g, 116.3 mmol) in 1/1 DMF/H$_2$O (620 mL). After 15 minutes, pyridine (12.5 mL, 155.1 mmol) was added. The dark yellow solution was stirred overnight (16 hours). The now pale yellow solution was concentrated in vacuo below 40° C. The residue was diluted with water (600 mL), washed with diethyl ether (6×400 mL), and then concentrated in vacuo. This crude product was dissolved in water (100 mL). To the solution was added 0.5M Na$_2$CO$_3$ to bring the pH to ca. 8. Then, THF (100 mL) was added. To this vigorously stirred mixture was added, dropwise benzylchloroformate (CBZ-Cl) (80% pure determined by NMR integration; 19.8 g, 93.0 mmol) dissolved in THF (50 mL). Additional Na$_2$CO$_3$ solution was added as needed to maintain a basic pH (as judged by pH 5-10 range pH strips). One hour after the addition was completed, the reaction was concentrated to remove THF. The residue was extracted with diethyl ether (3×200 mL). The aqueous layer was brought to pH 2 with concentrated H$_2$SO$_4$. The mixture was extracted with diethyl ether (4×200 mL). These latter extracts were dried (Na$_2$SO$_4$) and concentrated in vacuo. Chromatography (80% ethyl acetate/hexanes containing 1% acetic acid) yielded 4.23 g (16%) of a slightly impure title product.

R$_f$(silica, ethyl acetate+0.5% acetic acid) 0.27.

B. 2-(Trimethylsilyl)ethyl 2-(((1,1-dimethylethoxy)carbonyl)amino)-3-(((phenylmethoxy)carbonyl)amino)propanoate To a 0° C. solution of the Part A acid (3.96 g, 11.7 mmol) in dry THF 50 mL) was added 1,1'-carbonyldiimidazole (2.08 g, 12.9 mmol). After 1 hour, 2-(trimethylsilyl)ethanol (3.4 mL) was added. The reaction was then brought to 70° C. for 1 hour. After cooling, the reaction was concentrated and chromatographed (flash, silica, 50 mm dia, 25% ethyl acetate/hexanes) to yield 3.08 g (60%) of title ester in the form a transparent oil: R$_f$(silica, 25% ethyl acetate/hexanes) 0.32.

C. 3-Amino-2-[[(1,1-dimethylethoxy)carbonyl]amino]propanoic acid, 2-(trimethylsilyl)ethyl ester To a solution of the Part B Z-amine (2.89 g, 6.60 mmol) in 2-propanol/water (65 mL/6 mL) was added ammonium formate (2.08 g, 33.0 mmol) and then a slurry of Pd/C (10%, 0.5 g) in 2-propanol 4 mL). The mixture was stirred at room temperature for 1 hour. The reaction was filtered through Celite and concentrated in vacuo. The residue was taken up in 70 mL of ethyl acetate and 30 mL of saturated NaCl containing 8 mL of 5N NaOH. The aqueous layer was further extracted with ethyl acetate (2×70 mL). The combined organic layers were dried (Na$_2$SO$_4$) and concentrated in vacuo to give title compound in the form of an oil (1.85 g, 92%): R$_f$(silica, 10% methanol/chloroform) 0.75.

D.
[1S-[1α,2α(Z),3α,4α]]-6-[3-[[[2-[[(1,1-Dimethylethoxy)carbonyl]amino]-3-oxo-3-[2-(trimethylsilyl)ethoxy]propyl]amino]thioxomethyl]-7-oxabicyclo[2.2.1]hept-2-yl]-4-hexenoic acid, methyl ester WSC (1.18 g, 6.15 mmol) was added to a solution of [1S-[1α,2α(Z),3α,4α]]-6-[3-(carboxy)-7-oxabicyclo[2.2.1]hept-2-yl]-4-hexenoic acid, methyl ester (1.65 g, 6.15 mmol), Part C compound (1.85 g, 6.08 mmol), and HOBT (831 mg, 6.15 mmol) in methylene chloride (60 mL). The reaction was stirred for 16 hours, diluted with methylene chloride (300 mL) extracted (1×50 mL of 1N HCl; 1×50 mL of saturated NaHCO₃; 1×50 mL of water) dried (Na₂SO₄) and concentrated in vacuo. Chromatography (flash, silica, 50 mm dia, 40% ethyl acetate/hexanes, 2L; 60% ethyl acetate, 1L) yielded an oil: 2.11 g 63%): R$_f$(silica, 10% methanol/chloroform) 0.67.

The preceding amide (1.94 g, 3.50 mmol) was stirred at 65° C. in benzene (40 mL) with Lawesson's Reagent (850 mg, 2.10 mmol) for 1.5 hours. The reaction was cooled and diluted with diethyl ether (250 mL). The mixture was washed (2×50 mL of 0.5N Na₂CO₃), dried (Na₂SO₄, concentrated in vacuo, and chromatographed (flash, silica, 50 mm dia, 25% ethyl acetate/hexanes) to yield 1.61 g (80%) of title compound in the form of an oil: R$_f$(silica, 25% ethyl acetate/hexanes) 0.14.

E.
[1S-[1α,2α(Z),3α,4α]]-6-[3-[1-[(1,1-Dimethylethoxy)carbonyl]-4,5-dihydro-5-[[2-(trimethylsilyl)ethoxy]carbonyl-1H-imidazole-2-yl]-7-oxabicyclo[2.2.1]hept-2-yl]-4-hexenoic acid, methyl ester Carbon tetrachloride (3.00 mL, 31.2 mmol) was added to a solution of Part D compound (1.61 g, 2.82 mmol), triphenylphosphine (2.22 g, 8.46 mmol), triethylamine (1.18 mL, 8.46 mmol) in dry acetonitrile (28 mL). The reaction was stirred for 4 hours. The reaction was diluted with diethyl ether (125 mL), saturated NaCl (125 mL) and water (5 mL). The aqueous phase was further extracted with ether (125 mL). The combined 20 organic layers were dried (Na₂SO₄) and concentrated in vacuo. The residue was triturated sequentially with ether (20 mL, 10 mL and 7 mL), each time taking and concentrating the filtrate for the next cycle. Chromatography (flash, silica, 50 mm dia, 50% ethyl acetate/hexanes) yielded 1.09 g (72%) of title compound in the form of an oil: R$_f$(silica, 50% ethyl acetate/hexanes) 0.29.

F.
1S-1α,2(Z),3α,4α]]-6-[3-(5-Carboxy-4,5-dihydro-1H-imidazole-2-yl)-7-oxabicyclo-[2.2.1]hept-2-yl]-4-hexenoic acid, methyl ester, monohydrochloride To a solution of Part E compound (1.09 g, 2.03 mmol) in methylene chloride (2 mL) was added trifluoroacetic acid (4 mL). The reaction was stirred at room temperature for 1 hour, diluted with toluene (40 mL) and was then concentrated in vacuo. The residue was taken up in ethyl acetate (60 mL) and was washed (2×5 mL) with saturated NaHCO₃ The organic layer was dried (Na₂SO₄) and concentrated in vacuo to yield [1S-(1α,2α,(Z)-,3α,4α]]-6-[3-(5-carboxy-4,5-dihydro-1H-imidazol-2-yl)-7-oxabicyclo[2.2.1]hept-2-yl]-4-hexenoic acid, methyl ester (261 mg, 27%). The aqueous phase was brought to pH 2 and concentrated in vacuo. Extraction of the solid with chloroform (2×15 mL) followed by concentration in vacuo yielded title compound (553 mg, 73%).

G.
[1S-[1α,2α(Z),3α,4α]]-6-[3-[5-[[(4-Cyclohexylbutyl)amino]carbonyl]-1H-imidazol-2-yl]7-oxabicyclo[2.2.1-]hept-2-yl]-4-hexenoic acid, methyl ester A mixture of Part F acid (516 mg, 1.38 mmol), (4-cyclohexylbutyl)amine hydrochloride (345 mg, 1.80 mmol), WSC (345 mg, 1.80 mmol), HOBT (243 mg, 1.80 mmol) and triethylamine (0.50 mL, 3.6 mmol) in methylene chloride (15 mL) was stirred for 24 hours. The reaction was diluted with methylene chloride (50 mL) and was washed (2×10 mL of saturated NaHCO₃), dried (Na₂SO₄) and concentrated in vacuo to yield a yellowish oil, namely [1S-[1α,2α(Z),3α,4α]]-6-[3-[5-[[(4-cyclohexylbutyl)amino]carbonyl]-4,5-dihydro-1H-imidazol-2-yl-7-oxabicyclo[2.2.1]hept-2-yl]-4-hexenoic acid, methyl ester. This oil was dissolved in chloroform (20 mL). Active MnO₂ (Aldrich, 1.0 g) was added. The reaction was stirred for 24 hours. An additional 0.5 g portion of MnO₂ was added and stirring was 5 continued for 3 days. Further MnO₂(0.5 g) was added. After 5 hours, the reaction was filtered through Celite ®. The pad was rinsed with portions of chloroform. The combined filtrates were concentrated in vacuo. Chromatography (flash, silica, 25 mm dia, 2% methanol/chloroform) yielded 235 mg (36%) of title ester compound in the form of an oil.

EXAMPLE 11A

[1S-[1α,2α(Z),3α,4α]]-6-[3-[4-[[(4-Cyclohexylbutyl)amino]carbonyl-1H-imidazol-2-yl]-7-oxabicyclo[2.2.1-]hept-2-yl]-4-hexenoic acid To a solution of Example 10A ester in methanol (8 mL) was added 2N KOH (4 mL). The reaction was stirred at room temperature for 4 hours. The methanol was removed in vacuo. The residue was taken up in methylene chloride (25 mL) and brought to pH 2 with 1N HCl. After shaking, the aqueous layer was further extracted with methylene chloride (25 mL). The combined organic layers were dried (Na₂SO₄) and concentrated in vacuo. The residue was taken up in methylene chloride (10 mL) and swirled with ethereal HCl (4 mL) for 30 seconds. The mixture was concentrated in vacuo. Trituration with 10 mL of ethyl acetate (boiling to room temperature) yielded a white solid which was collected by filtration, washed with ethyl acetate 5 mL and dried to yield title acid as a white solid: 126.4 mg (52%); mp 168°-173° C.

$^1$H NMR (tetradeuteriomethanol/deuteriochloroform, 270 MHz: δ 6 8.05 (s, 1H), 5.23-5.36 (m, 2H), 4.73 (s, 1H), 4.41 (s, 1H), 3.74 (d, J=8 Hz, 1H), 3.34-3.37 (m, 2H), 0.84-2.44 (m, 28H);

$^{13}$C NMR (complete decoupling, 67.8 MHz tetradeuteriomethanol/deuteriochloroform): δ 175.4, 157.0, 147.8, 130.1, 127.3, 120.7, 80.0, 79.9, 44.9, 39.8, 37.4, 36.9, 33.5, 33.1, 29.1, 28.7, 28.1, 26.5, 26.2, 24.1, 22.6.

IR (KBr): 3427 (m), 3232 (m), 3009 (m), 2923 (s), 2851 (m), 1730 (m), 1718 (m), 1651 (m), 1566 (m), 1448 (w), 1334 (w), 1189 (w) cm⁻.

LRMS (Cl, NH₃ DEP 50, pos. ion spectrum) m/z (rel. int.) 458 (2), 184 (7), 173 (14), 172 (6), 169 (9), 168

(13), 167 (5), 157 (10), 156 (100), 155 (25), 154 (35), 152 (6).

Anal Calc'd for $C_{26}H_{40}ClN_3O_4 \cdot 0.25 H_2O$:

C, 63.63; H, 8.19; Cl, 7.11; N, 8.43 Found: C, 62.76; H, 8.30; Cl, 6.82; N, 8.37.

EXAMPLE 12A

[1S-[1α,2α(Z),3α,4α]]-N-(4-Cyclohexylbutyl)2-2-[5-(1H-tetrazol-5-yl)-2-pentenyl]-7-oxabicyclo[2.2.1]hept-3-yl]-4-oxazolecarboxamide

A.

[1S-1α,2α(Z),3α,4α]]-2-[5-(1H-Tetrazol-5-yl)-2-pentenyl]-7-oxabicyclo[2.2.1]-heptane-3-methanol To a 0° C. slurry of 1.0 mmol [4aR-(4aα,5aα,5β,8β,8aα)]-octahydro-5,8-epoxy-1H-2-benzopyran-3-ol, prepared as described in U.S. Pat. No. 4,143,054, and 1.4 mmol 3-(tetrazol-5-yl)propyltriphenylphosphonum bromide in tetrahydrofuran is added dropwise a 1.8M solution of KOt-amylate in toluene (2.8 mmol). The mixture is allowed to warm to room temperature overnight. The reaction mixture is quenched by the addition of acetic acid. The reaction mixture is concentrated in vacuo and purified by silica gel chromatography using $CH_3OH/CH_2Cl_2$ mixture as eluants.

B.

[1S-[1α,2α(Z),3α,4α]]-2-[5-(1-Methoxymethyl-1H-tetrazol-5-yl)-2-pentenyl]-7-oxabicyclo[2.2.1]heptane-3-methanol A solution of 1.0 mmol of title A tetrazole in THF is cooled to 0° C. and treated with 1.0 mmol of triethylamine and 1.0 mmol of bromomethylmethyl ether. The mixture is stirred for 4 hours at room temperature and then partitioned between saturated aqueous $NaHCO_3$ and ethyl acetate. The ethyl acetate layer is dried, filtered and concentrated in vacuo to afford title B tetrazole.

C.

1S-[1α,2α(Z),3α,4α]]-N-(4-Cyclohexylbutyl)-2-[2-[5-(1-methoxymethyl-1H-tetrazol-5-yl)-2-pentenyl]-7-oxabicyclo[2.2.1]hept-3-yl]-4-oxazolecarboxamide Following Example 1A except substituting Example 12A, Part B tetrazole for Example 1A, Part C ester, the title compound is obtained.

D.

[1S-[1α,2α(Z),3α,4α]]-N-(4-Cyclohexylbutyl)-2-[2-[5-(1H-tetrazol-5-yl)-2-pentenyl]-7-oxabicyclo2.2.1]hept-3-yl]-4-oxazolecarboxamide To a solution 1.0 mmol of title C tetrazole in $CH_3OH$ (25 mL) is added 1 drop of concentrated HCl solution. The solution is heated to reflux for 2 hours. On cooling, the reaction mixture is concentrated in vacuo. The crude product is purified by reverse-phase HPLC using $CH_3CN/0.02\%$ aqueous $H_3PO_4$ mixtures as the mobile phase to afford title tetrazole.

Examples of additional compounds in accordance with the present invention which may be prepared following the procedures outlined in the specification and working Examples include, but are not limited to the following:

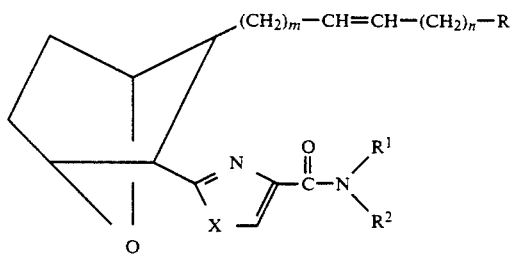

| Example No. | $(CH_2)_m$ m | $(CH_2)_n$ n | X | $R^1$ | $R^2$ | R |
|---|---|---|---|---|---|---|
| 13A | 1 | 2 | O | $C_6H_{13}$ | $CH_3$ | $CO_2H$ |
| 14A | 2 | 2 | O | $-(CH_2)_2-\langle S \rangle$ (cyclohexyl with S) | $C_2H_5$ | $CO_2H$ |
| 15A | 3 | 1 | NH | thiophene | i-$C_3H_7$ | $CONHSO_2CH_3$ |
| 16A | 1 | 2 | S | $-C_2H_4-\langle \rangle-Cl$ | H | $CH_2$-5-tetrazolyl |
| 17A | 2 | 3 | O | $C_6H_5$ | $C_6H_5$ | $CO_2H$ |
| 18A | 1 | 2 | NH | $-CH_2C_6H_5$ | $CH_2C_6H_5$ | $CONHC_6H_5$ |
| 19A | 1 | 2 | O | i-$C_3H_7$ | H | $CONHSO_2C_6H_5$ |

-continued

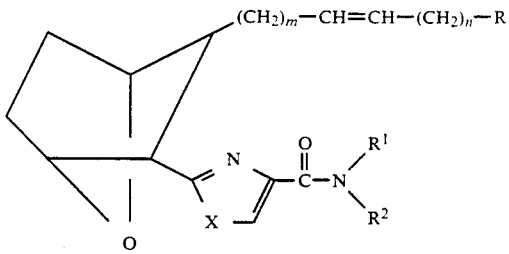

| Example No. | (CH$_2$)$_m$ m | (CH$_2$)$_n$ n | X | R$^1$ | R$^2$ | R |
|---|---|---|---|---|---|---|
| 20A | 1 | 3 | O | —CH$_2$—(tetrahydrothiopyranyl) | n-C$_4$H$_9$ | CONHSO$_2$CH$_2$C$_6$H$_5$ |
| 21A | 1 | 2 | NH | —(CH$_2$)$_3$—cyclopropyl | H | CONHCH$_2$C$_6$H$_5$ |
| 22A | 2 | 2 | O | cyclobutyl | CH$_2$C$_6$H$_5$ | CO$_2$CH$_3$ |
| 23A | 1 | 2 | S | C$_2$H$_5$ | H | CO$_2$Li |
| 24A | 1 | 3 | NH | —C$_6$H$_4$—Cl | C$_2$H$_5$ | CO$_2$C$_2$H$_5$ |
| 25A | 1 | 2 | O | —(CH$_2$)$_2$C$_6$H$_5$ | CH$_3$ | CO$_2$H |
| 26A | 1 | 3 | O | n-C$_3$H$_7$ | CH$_2$C$_6$H$_5$ | CH$_2$-5-tetrazolyl |
| 27A | 1 | 2 | NH | n-C$_5$H$_{11}$ | H | CO$_2$H |
| 28A | 2 | 3 | O | tetrahydrothiopyranyl | CH$_3$ | CONHCH$_3$ |
| 29A | 1 | 2 | O | —(CH$_2$)$_6$— | | CONH$_2$ |

EXAMPLE 30A

[1S-[1α,2α(Z),3α,4α]]-6-[3-[4-[(6-Cyclohexylhexyl)amino]carbonyl]-2-oxazolyl]-7-oxabicyclo[2.2.1]-hept-2-yl]-4-hexenoic acid, methyl ester A. Benzenepentanol, methanesulfonate ester To a stirred solution of 5-phenyl-1-pentanol (5.0 g, 30.4 mmol) in 20 mL of methylene chloride at −70° C. under argon, was added first (C$_2$H$_5$)$_3$N (4.0 g, 39.5 mmol), then methanesulfonyl chloride (2.83 mL, 4.18 g, 36.5 mmol) dropwise. The reaction mixture was slowly warmed to room temperature. After stirring for 2 hours at room temperature, water was added, and the reaction mixture was extracted with methylene chloride (50 mL). The aqueous layer was extracted twice more with CH$_2$Cl$_2$ (25 mL). The organic layers were combined and washed with brine, dried over MgSO$_4$, and concentrated to obtain 7.30 g (100%) of title compound in the form of a yellow oil. R$_f$ 0.9 in 50% hexane-ethyl acetate (UV, Ce(SO$_4$)$_2$)

$^{13}$C NMR (CDCl$_3$) δ 141.9, 128.2, 125.6, 69.9, 37.1, 35.5, 30.6, 28.8, 24.8.

B. Benzenehexanenitrile

To a stirred solution of Part A compound (7.30 g, 30.1 mmol) in 70 mL of C$_2$H$_5$OH at room temperature was added a solution of KCN (9.81 g, 150.6 mmol) in 29 mL of water. This reaction mixture was stirred for 20 hours, then extracted with CHCl$_3$ three times (50 mL). The organic layers were combined and washed with water, then brine, and dried over MgSO$_4$ and concentrated in vacuo to obtain a yellow oil containing title compound and remaining Part A compound. This oil was purified by flash chromatography (95:5 hexane-ethyl acetate) to obtain 2.16 g (41%) of the desired title product as an oil.

$^{13}$C NMR (CDCl$_3$) δ 141.8, 128.0, 125.5, 119.5, 35.4, 30.5, 27.9, 24.9, 16.7.

C. Cyclohexanehexanamine

To a stirred solution of Part B compound (2.16 g, 12.4 mmol) in 100 mL of CH$_3$COOH was added PtO$_2$ (0.60 g). The mixture was stirred at room temperature under H$_2$ balloon at 1 atmosphere. After 20 hours the reaction mixture was filtered through a celite pad, and the pad was washed with ethanol twice. The filtrate was concentrated in vacuo to obtain a semi-solid. This was stirred in hexane, and title product in the form of a white fluffy solid (2.00 g, 95%) was obtained by filtration.

D.

[1S-[1α,2α(Z),3α,4α]]-6-[3-[4-[[(6-Cyclohexylhexyl)amino]carbonyl]-2-oxazolyl]-7-oxabicyclo[2.2.1]hept-2-yl]-4-hexenoic acid, methyl ester A sample of 1.61 g of Example 2A, Part G oxazole acid (4.8 mmol) was dried by azeotroping with dry DMF and toluene twice (high vacuum). This material (which contained residual DMF) was dissolved in 30 mL toluene, and while stirring at room temperature under argon, 2.9 g oxalyl chloride (23

HA490a mmol) was added. Gas was evolved. A dark oil formed at the bottom of the reaction mixture. (The oil was the product of the reaction of DMF with oxalyl chloride.) After 5 minutes an additional 2.9 g oxalyl chloride was added. This mixture was stirred overnight. TLC indicated clean conversion to the acid chloride. The supernatant was pipetted off and transferred to an argon filled flask. Twice the oil was stirred with additional toluene and the supernatant transferred. The combined supernatants were evaporated with $CHCl_3$ to provide 1.54 g (91% yield) of the acid chloride, namely [1S-[1α,2α(Z),3α,4α]]-6-[3-[4-(chlorocarbonyl)-2-oxazolyl]-7-oxabicyclo[2.2.1]hept-2-y ]-4-hexenoic acid, methyl ester.

To a solution of (0.55 g, 3.0 mmol) Part C amine in 5 mL of chloroform at 0° C., was added (0.3 g, 3.0 mmol) triethylamine and (0.53 g, 1.5 mmol) the above acid chloride. The mixture was stirred at room temperature for 14 hours, then diluted with chloroform and water. The organic layer was separated, and the aqueous layer was extracted with 20 mL of chloroform twice. The organic layers were combined, washed with brine, dried over $MgSO_4$, and concentrated. Flash chromatography (0% to 75% EtOAc in hexane gradient) gave 0.49 g of product as a clear oil in 65% yield. $R_f$ 0.5 in 1:1 hexaneethyl acetate (UV, $Ce(SO_4)_2$).

$^{13}C$ NMR (67.8 MHz, $CDCl_3$) δ 172.8, 163.5, 160.1, 140.1, 135.8, 129.1, 128.2, 79.2, 79.0, 51 0, 49.4, 46.3, 38.7, 37.2, 37.0, 33.4, 33.0, 29.4, 29.2, 28.6, 27.5, 26.6, 26.3, 26.1, 22.5.

EXAMPLE 31A

[1S-[1α,2α(Z),3α,4α]]-6-[3-[4-[[(6-Cyclohexylhexyl)amino]carbonyl]-2-oxazolyl]-7-oxabicyclo[2.2.1]hept-2-yl]-4-hexenoic acid A solution of (0.49 g, 0.97 mmol) Example 30A ester in 8 mL of 1N NaOH and 8 mL of THF was stirred for 18 hours, then concentrated in vacuo to remove THF and acidified to pH 1.5 with 1N HCl. Ethyl acetate was added and the organic layer was separated. The aqueous layer was extracted twice with 20 mL ethyl acetate. The organic layers were combined, washed with brine, dried over $MgSO_4$, and concentrated in vacuo. A white solid was obtained. This was crystallized from hexane and chloroform to give 0.40 g (84%) of pure product as a white solid. $R_f$ 0.36 in 0.1% $CH_3COOH$ in (4% methanol in ethyl acetate). Visualized by UV: $Ce(SO_4)_2$. $[α]_D°$ = +30.2, c 0.58 g/100 mL of $CH_3OH$, mp 82°–83° C.

EXAMPLE 32A

1S-[1α,2α(Z),3α,4α]]-6-[3-[4-[[(6-Cyclohexylhexyl)amino]carbonyl]-2-oxazolyl]-7-oxabicyclo[2.2.1]hept-2-yl]-4-hexenoic acid, methyl ester To a stirred solution of 0.49 g (1.40 mmol) acid chloride prepared as described in Example 2A, Part I plus an unknown quantity of Vilsmeier salt in 10 mL of chloroform, was added 0.28 g (2.80 mmol) of triethylamine and 0.38 g (2.1 mmol) of 6-cyclohexylhexylamine prepared in Example 30, Part C. The mixture was stirred at room temperature for 10 hours, then diluted with ethyl acetate and water. The organic layer was separated, and the aqueous layer was extracted with 20 mL of ethyl acetate twice. The organic layers were combined, washed with brine, dried over $MgSO_4$, and concentrated. Flash chromatography (0% to 100% ethyl acetate-hexane gradient) gave 0.17 g of title product as a clear oil in 25% yield. $R_f$=0.46 in 1:1 ethyl acetate:hexane.

EXAMPLE 33A

[1S-[1α,2α(Z),3α,4α]]-6-[3-[4-[[(6-Cyclohexylhexyl)amino]carbonyl]-2-oxazolyl]-7-oxabicyclo[2.2.1]hept-2-yl]-4-hexenoic acid A solution of 0.17 g (0.33 mmol) of Example 32A ester in 5 mL of 1N NaOH and 2 mL of tetrahydrofuran was stirred at room temperature for 10 hours, then concentrated in vacuo to remove THF and acidified to pH 1.5 with concentrated HCl. Ethyl acetate was added and the organic layer was separated. The aqueous layer was extracted twice with 20 mL ethyl acetate. The organic layers were combined, washed with brine, dried over $MgSO_4$ and concentrated in vacuo. A clear oil was obtained. This was chromatographed in 1:1 EtOAc-hexane with 0.25% $CH_3COOH$ to give 0.13 g (78%) of title product as an oil (containing 2.5% of the cis isomer of Example 31A compound). $R_f$=0.36 in 4% $CH_3OH$, 0.1% $CH_3COOH$, 95.5% EtOAc (UV, Ce(SO_4)2) $[α]_D°$ = +55° in $CH_3OH$ at c=0.50 g/100 mL.

EXAMPLE 34A

[1α,2α,(Z),3α,4α]-6-[3-4-(1-Pyrrolidinylcarbonyl)-2-oxazolyl]-7-oxabicyclo[2.2.1]hept-2-yl]-4-hexenoic acid, methyl ester To a stirred solution of 0.18 g (0.50 mmol) of the acid chloride prepared in Example 2A, Part I in 3 mL of chloroform at 0° C., under argon was added 0.10 g (1.0 mmol) of triethylamine and 0.07 g (1.0 mmol) of pyrrolidine. The mixture was warmed to room temperature and stirred for 10 hours, then diluted with ethyl acetate and water. The organic layer was separated, and the aqueous layer was extracted with 20 mL of ethyl acetate twice. The organic layers were combined, washed with brine, dried over $MgSO_4$, and concentrated. Flash chromatography (50% to 100% ethyl acetate in hexane gradient then 2% methanol in ethyl acetate) gave 0.13 g of title product as a clear oil in 68% yield. $R_f$=0.6 in 9:1 ethyl acetate-methanol (UV, $Ce(SO_4)_2$)

$^{13}C$ NMR (67.8 MHZ, $CDCl_3$): δ 172.9, 162.9, 160.0, 141.9, 136.9, 129.0, 128.5, 79.2, 78.9, 51.1, 49.4, 47.9, 46.5, 46.4, 33.5, 29.5, 28.7, 27.6, 26.1, 23.4, 22.5.

EXAMPLE 35A

[1α,2α(Z),3α,4α]-6-[3-[4-(1-Pyrrolidinylcarbonyl)-2-oxazolyl]-7-oxabicyclo[2.2.1]hept-2-yl]-4-hexenoic acid A solution of 0.13 g (0.33 mmol) of Example 34A compound in 10 mL of 1N NaOH and 2 mL of tetrahydrofuran was stirred for 10 hours at room temperature, then concentrated in vacuo to remove THF and acidified to pH 1.5 with 1N HCl. Ethyl acetate was added and the organic layer was separated. The aqueous layer was extracted twice with 20 mL ethyl acetate. The organic layers were combined, washed with brine, dried over MgSO$_4$ and concentrated in vacuo. A clear oil was obtained. This was chromatographed (EtOAc then 1% CH$_3$OH, 0.25% CH$_3$COOH, 98.75% EtOAc) to give 0.12 g (92%) of pure product as an oil. R$_f$=0.2 in 1% CH$_3$OH, 0.5% CH$_3$COOH, 98.5% EtOAc. [α]°$_D$= +35.7° in CH$_3$OH at c=2.40 g/100 mL.

EXAMPLE 36A

[1S-[1α,2α(Z),3α,4α]]-6-[3-4-(Propylamino)carbonyl]-2-oxazolyl-7-oxabicyclo[2.2.1]hept-2-yl]-4-hexenoic acid, methyl ester To a solution of (0.22 g, 3.7 mmol) propylamine in 5 mL of chloroform at 0° under argon, was added 0.162 g, (0.46 mmol) acid chloride prepared as described in Example 2A, Part I. The mixture was warmed to room temperature and stirred for 14 hours, then diluted with chloroform and water. The organic layer was separated and the aqueous layer was extracted with 20 mL of chloroform twice. The organic layers were combined, washed with brine, dried over MgSO$_4$, and concentrated. Flash chromatography (0% to 75% EtOAc in hexane gradient) gave 0.15 g of title product as a clear oil in 85% yield. R$_f$0.29 in 4% methanol in ethyl acetate (UV, Ce(SO$_4$)$_2$).

$^{13}$C NMR (CDCl$_3$): δ 173.0, 163.7, 160.4, 140.2, 136.0, 129.2, 128.4, 79.3, 79.2, 51.2, 49.5, 46.5, 40.5, 33.6, 29.6, 28.7, 27.7, 22.7, 22.6, 11.2.

EXAMPLE 37A

[1S-[1α,2α(Z),3α,4α]]-6-[3-[4-[(Propylamino)carbonyl]-2-oxazolyl]-7-oxabicyclo[2.2.1]hept-2-yl]-4-hexenoic acid A solution of 0.15 g (0.39 mmol) Example 36 ester in 8 mL of 1N NaOH and 8 mL of THF was stirred for 18 hours, then concentrated in vacuo to remove THF and acidified to pH 1.5 with 1N HCl. Ethyl acetate was added and the organic layer was separated. The aqueous layer was extracted twice with 20 mL ethyl acetate. The organic layers were combined, washed with brine, dried over MgSO$_4$ and concentrated in vacuo. A clear oil was obtained. This was crystallized from hexane and chloroform to give 0.14 g (100%) of pure product as a white solid. R$_f$0.41 in 0.1% CH$_3$COOH, 4% methanol, 95.9% ethyl acetate (UV, Ce(SO$_4$)$_2$) mp 117°-118° C., [α]°$_D$= +42.12 at c 4.7 g/100 mL CH$_3$OH.

EXAMPLE 38A

[1S-[1α,2α(Z),3α,4α]]-6-[3-[4-[(4-Butylphenyl)amino]carbonyl]-2-oxazolyl]-7-oxabicyclo[2.2.1]-hept-2-yl]-4-hexenoic acid, methyl ester To a solution of 0.189 g (1.27 mmol) 4-butylaniline in 5 mL of chloroform under argon at 0° C., was added 0.17 g (0.48 mmol) acid chloride prepared as described in Example 2A, Part I and 0.145 g (1.44 mmol) triethylamine. The mixture was warmed to room temperature and stirred for 14 hours, then diluted with chloroform and water. The organic layer was separated, and the aqueous layer was extracted with 20 mL of chloroform twice. The organic layers were combined, washed with brine, dried over MgSO$_4$, and concentrated. Flash chromatography (0% to 75% EtOAc in hexane gradient) gave 0.16 g of title product as a clear oil in 69% yield. R$_f$0.87 in 4% methanol in ethyl acetate (UV, Ce(SO$_4$)$_2$).

$^{13}$C NMR (CDCl$_3$): δ 173.1, 163.9, 158.2, 141.1, 139.0, 136.2, 129.4, 128.7, 128.4, 119.7, 79.4, 79.3, 51.3, 49.6, 46.6, 34.9, 33.6, 33.5, 29.7, 28.8, 27.8, 22.7, 22.1, 13.8.

EXAMPLE 39A

[1S-[1α,2α(Z),3α,4α]]-6-3-[4-[(4-Butylphenyl)amino]carbonyl]-2-oxazolyl]-7-oxabicyclo2.2.1]-hept-2-y]-4-hexenoic acid A solution of 0.16 g (0.34 mmol) Example 38A ester in 8 mL of 1N NaOH and 8 mL of THF was stirred for 18 hours, then concentrated in vacuo to remove THF and acidified to pH 1.5 with 1N HCl. Ethyl acetate was added and the organic layer was separated. The aqueous layer was extracted twice with 20 mL ethyl acetate. The organic layers were combined, washed with brine, dried over MgSO$_4$ and concentrated in vacuo. A clear oil was obtained. This was crystallized from hexane and chloroform to give 0.13 g (87%) of pure product as a yellow solid. R$_f$0.47 in 0.1% CH$_3$COOH, 4% methanol, 95.9% ethyl acetate (UV, Ce(SO$_4$)$_2$). mp 113°-114° C. [α]°$_D$= +6.44, 0.59 g/100 mL of CH$_3$OH.

EXAMPLE 40A

[1S-[1α,2α(Z),3α,4α]]-6-[3-[4-[(2,3-Dihydro-1H-indol-1-yl)carbonyl]-2-oxazolyl]-7-oxabicyclo-[2.2.1]hept-2-yl]-4-hexenoic acid, methyl ester To a solution of 0.18 g (1.50 mmol) indoline in 5 mL of chloroform, was added 0.18 g (1.8 mmol) triethylamine and 0.46 g (1.30 mmol) acid chloride prepared as described in Example 2A, Part I. The mixture was stirred at room temperature for 14 hours, then diluted with chloroform and water. The organic layer was separated, and the aqueous layer was extracted with 20 mL of chloroform twice. The organic layers were combined, washed with brine, dried over MgSO$_4$, and concentrated. Flash chromatography (0% to 75% EtOAc in hexane gradient) gave 0.37 g of title product as a yellow oil in 65% yield. R$_f$0.8 in 98.9% ethyl acetate, 1% methanol, 0.1% TFA (UV, Ce(SO$_4$)$_2$).

EXAMPLE 41A

[1S-[1α,2α(Z),3α,4α-6-[3-[4-[(2,3-Dihydro-1H-indol-1-yl)carbonyl-2-oxazolyl]-7-oxabicyclo-[2.2.1]hept-2-yl]-4-hexenoic acid A solution of 0.37 g (0.80 mmol) of Example 40A ester in 15 mL of 1N NaOH and 15 mL of methanol was stirred for 18 hours, and acidified to pH 2 with concentrated HCl. Ethyl acetate was added and the organic layer was separated. The aqueous layer was extracted twice with 20 mL ethyl acetate. The organic layers were combined, washed with brine, dried over MgSO$_4$, and concentrated in vacuo. A red oil was obtained. This was chromatographed (0.1% CH$_3$COOH in (0% to 100% EtOAc in hexane gradient)) to give 0.25 g (75%) of pure title product as a yellow oil. R$_f$0.29 in 0.1% CH$_3$COOH in 50% ethyl acetate in hexane (UV, Ce(SO$_4$)$_2$). [α]°D= +31.2 in CH$_3$OH at c 0.48 g/100 mL.

EXAMPLE 42A

[1S-[1α,2α(Z),3α,4α]]-6-[3-4-[(4-Cyclohexylbutyl-)amino]carbonyl]-2-oxazolyl]-7-oxabicyclo2.2.1]-hept-2-yl]-N-(phenylsulfony)-4-hexenamide To a stirred solution of 1-(3-dimethylaminopropyl)-3-ethylcarbodiimide, hydrochloride salt (102 mg, 0.50 mmol) and 4-dimethylaminopyridine (66.7 mg, 0.50 mmol) in 50 mL of DMF was added benzenesulfonamide (80 mg, 0.51 mmol) and $(C_2H_5)_3N$ (0.14 mL, 1.00 mmol) followed by Example 1A acid (229 mg, 0.50 mmol). The mixture was stirred at room temperature for 18 hours and concentrated in vacuo. The residue was partitioned between 25 mL of 1N HCl solution and EtOAc (4×40 mL). The combined EtOAc extracts were washed with 30 mL of brine, dried (MgSO$_4$), filtered and concentrated in vacuo. This was chromatographed on 30 g of Merck silica gel 60 using 2% CH$_3$OH in CH$_2$Cl$_2$ as eluant to give 250 mg of title sulfonamide. This product was partitioned between 60 mL of EtOAc and H$_2$O (1×20 mL). The organic layer was dried (MgSO$_4$), filtered and concentrated in vacuo to give 210 mg (70%) of title compound as a solid. m.p. 154°–156° C., TLC: silica gel, 4% CH$_3$OH/CH$_2$Cl$_2$, R$_f$ 0.46, Ce(SO$_4$)$_2$.

$^{13}$C NMR title compound (CDCl$_3$, 67.5 MHz): δ 171.1 170.5, 163.9, 161.1, 140.7, 139.0, 135.9, 133.5, 128.7, 128.2, 79.7, 79.7, 49.5, 46.4, 39.2, 37.4, 37.0, 35.9, 33.3, 33.3, 29.7, 28.8, 27.9, 26.6, 26.3, 26.3, 24.1, 22.3.

EXAMPLE 43A

[1S-[1α,2α(Z),3α,4α]]-6-[3-4-[[(4-Cyclohexylbutyl-)amino]carbonyl]-2-oxazolyl]-N-(methylsulfonyl)-7-oxabicyclo2.2.1]hept-2-yl]-4-hexenamide To a stirred solution of 1-(3-dimethylaminopropyl)-3-ethylcarbodiimide, hydrochloride salt (102 mg, 0.50 mmol) and 4-dimethylaminopyridine (66.7 mg, 0.50 mmol) in 50 mL of DMF was added methanesulfonamide (47.6 mg, 0.50 mmol) and $(C_2H_5)_3N$ (0.14 mL, 1.00 mmol) followed by Example 1A acid (229 mg, 0.50 mmol). The mixture was stirred at room temperature for 18 hours and concentrated in vacuo. The residue was partitioned between 25 mL of 1N HCl solution and EtOAc (4 times with 40 mL). The combined EtOAc extracts were washed with 30 mL of brine, dried (MgSO$_4$), filtered and concentrated in vacuo. This was chromatographed on 30 g of Merck silica gel 60 using 2% CH$_3$OH in CH$_2$Cl$_2$ as eluant to give 200 mg of title sulfonamide. This product was partitioned between 60 mL of EtOAc and H$_2$O (1×20 mL). The organic layer was dried (MgSO$_4$), filtered and concentrated in vacuo to give 150 mg 56%) of title compound as a solid. m.p. 140°–142° C., TLC: silica gel, 4% CH$_3$OH/CH$_2$Cl$_2$, R$_f$ 0.40, Ce(SO$_4$)$_2$.

$^{13}$C NMR title compound (CDCl$_3$, 67.5 MHz): δ 171.8, 163.9, 161.0, 140.8, 135.9, 128.8, 128.7, 79.7, 79.7, 49.5, 46.4, 41.3, 39.2, 37.4, 37.0, 36.0, 33.3, 33.3, 29.7, 28.8, 28.0, 26.6, 26.3, 26.3, 24.1, 22.3.

EXAMPLE 44A

[1S-[1α,2α,(Z),3α,4α]]-7-[3-[4-[(4-Cyclohexylbutyl-)amino]carbonyl]-2-oxazolyl]-7-oxabicyclo[2.2.1]hept-2-yl-5-heptenoic acid, methyl ester

A.
[1S-[1α,2α(Z),3α,4α]]-7-(3-Carboxy)-7-oxabicyclo[2.2.1]hept-2-yl]-5-heptenoic acid To a stirred solution of [1S-[1α,2α,(Z),3α,4α]]-7-(3-hydroxymethyl)-7-oxabicyclo[2.2.1]hept-2-yl]-5-heptenoic acid, methyl ester (1.60 g, 5.97 mmol) in 100 mL of acetone at 0° C. was added MnSO$_4$ treated Jones reagent (about 100 mg MnSO$_4$ dissolved in 100 mL of Jones reagent) until an orange-red color persisted. The mixture was stirred at 0° C. for 30 minutes and at room temperature for 1.5 hours. The mixture was quenched with isopropyl alcohol (IPA) and concentrated in vacuo. The residue was partitioned between 70 mL of 3M NaHSO$_3$ solution and EtOAc (4×100 mL). The combined EtOAc extracts were washed with H$_2$O (1×70 mL) and brine (1×70 mL). The organic layer was dried (MgSO$_4$), filtered and concentrated in vacuo to give 1.57 g (93%) of title acid which was used for the next transformation without further purification. TLC: silica gel, 4% CH$_3$OH/CH$_2$Cl$_2$, R$_f$0.24, Ce(SO$_4$)$_2$.

$^{13}$C NMR title acid (CDCl$_3$, $_{67.5}$ MHz): δ 176.7, 74.0, 130.5, 128.3, 78.4, 78.2, 51.8, 51.3, 47.8, 3.3, 29.0, 28.7, 27.2, 26.6, 24.6.

B.
[2-[(4-Cyclohexylbutyl)amino)-1-(hydroxymethyl)-2-oxoethyl]carbamic acid, 1,1-dimethylethyl ester To a stirred mixture of 4-cyclohexylbutylamine.HCl salt (19.5 g, 102 mmol), 1-hydroxybenzotriazole H$_2$O (16.5 g, 122 mmol) and Boc-L-serine (25.0 g, 122 mmol) in 400 mL of DMF under argon at 0° C. was added sequentially $(C_2H_5)_3N$ (42.5 mL, 305 mmol) and 1-(3-dimethylaminopropyl)-3-ethyl carbodiimide.HCl salt (23.4 g, 122 mmol). The mixture was stirred at 0° C. for 1 hour and at room temperature for 18 hours. The mixture was concentrated in vacuo and diluted with 800 mL of EtOAc. The resulting solution was washed with 1N HCl solution (3 times with 120 mL), 0.2N NaOH solution (2 times with 100 mL), saturated NaHCO$_3$ solution (1 time with 100 mL) and brine (1 time with 150 mL). The organic layer was dried (MgSO$_4$), filtered and concentrated in vacuo to give 39.9 g of title amide in a quantitative yield. TLC: silica gel, 4% CH$_3$OH/CH$_2$Cl$_2$, R$_f$0.38, Ce(SO$_4$)$_2$.

$^{13}$C NMR title amide (CDCL$_3$, 67.5 MHz): δ 171.2, 156.2, 80.3, 62.8, 39.6, 37.4, 37.0, 33.3, 29.6, 28.2, 26.6, 26.3, 24.0.

C.
[1S-[1α,2α(Z),3α,4α]]-7-[3-[[[2-[(4-Cyclohexylbutyl-)amino]-1-(hydroxymethyl)-2-oxoethyl]amino]carbonyl]-7-oxabicyclo[2.2.1]hept-2-yl]-5-heptenoic acid, methyl ester To a stirred solution of Part B amide (1.90 g, 5.56 mmol) in 20 mL of CH$_2$Cl$_2$ at 0° C. was added 8 mL of trifluoroacetic acid (TFA). This mixture was stirred at 0° C. for 3 hours. The mixture was diluted with 50 mL of toluene and concentrated in vacuo to give amine TFA salt. To a stirred solution of this amine TFA salt, Part A acid (1.57 g, 5.57 mmol) and 1-hydroxybenzotriazole.H$_2$O (0.75 g, 5.57 mmol) in 60 mL of DMF at 0° C. under argon was added sequentially $(C_2H_5)_3N$ (3.88 mL, 27.8 mmol) and 1-(3-dimethylaminopropyl)-3-ethylcarbodiimide.HCl salt (1.07 g, 5.57 mmol). This mixture was then stirred at room temperature for 16 hours and concentrated in vacuo. The crude product was diluted with 400 mL of EtOAc and washed with 1N HCl solution (3 times with 70 mL), 0.2N NaOH solution (2 times with 50 mL) and saturated NaHCO$_3$ solution (1 time with 50 mL). The organic layer was dried (MgSO$_4$), filtered and concentrated in vacuo. This was chromatographed on 70 g of Merck silica gel 60 using 2% CH$_3$OH in CH$_2$Cl$_2$ as eluant to give 1.74 g (42%) of title alcohol. TLC: silica gel, 2% CH$_3$OH/CH$_2$Cl$_2$, R$_f$ 0.18, Ce(SO$_4$)$_2$.

$^{13}$C NMR title alcohol (CDCl$_3$, 67.5 MHz): δ 174.0, 173.2, 170.6, 130.6, 128.5, 79.2, 79.0, 62.7, 54.4, 53.5, 51.4, 48.0, 39.5, 37.4, 37.0, 33.3, 33.3, 33.3, 29.6, 28.6, 27.5, 26.6, 26.3, 26.3, 24.7, 24.1.

D.
[1S-[1α,2α(Z),3α,4α]]-7-[3-[5-[[(4-Cyclohexylbutyl)amino]carbonyl]-4,5-dihydro-2-oxazol-2-yl]-7-oxabicyclo[2.2.1]hept-2-yl]-5-heptenoic acid, methyl ester To a stirred solution of Part C alcohol (1.10 g, 2.17 mmol) and (C$_2$H$_5$)$_3$N (0.61 mL, 4.35 mmol) in 10 mL of dry CH$_2$Cl$_2$ at 0° C. was added methanesulfonyl chloride (0.20 mL, 2.61 mmol). This mixture was stirred at 0° C. under argon atmosphere for 1.5 hours and diluted with 200 mL of CH$_2$Cl$_2$. This mixture was washed with saturated NaHCO$_3$ solution (1 time with 20 mL) and brine (1 time with 20 mL). The organic layer was dried (MgSO$_4$), filtered and concentrated in vacuo. The crude product was dissolved in 20 mL of acetone and combined with 1.40 g of K$_2$CO$_3$. The mixture was refluxed for 5 hours and cooled to room temperature. The precipitate was filtered through a 2 inch pad of Celite ® and rinsed with acetone (4 times with 50 mL). The filtrate was concentrated in vacuo. Purification was effected by flash chromatography on 36 g of Merck silica gel 60 using 2% CH$_3$OH in CH$_2$Cl$_2$ as eluant to give 740 mg (70%) of title oxazoline. TLC: silica gel, 4% CH$_3$OH/CH$_2$Cl$_2$, R$_f$ 0.48, Ce(SO$_4$)$_2$.

$^{13}$C NMR title compound (CDCl$_3$, 67.5 MHz): δ 173.7 171.2, 169.2, 130.5, 128.4, 79.0, 79.0, 69.6, 68.3, 51.3, 48.3, 46.3, 39.0, 37.4, 36.9, 33.3, 33.2, 33.2, 29.7, 29.6, 28.8, 27.2, 26.6, 26.5, 26.2, 26.2, 24.6, 24.0.

E.
[1S-[1α,2α(Z),3α,4α]]-7-[3-[4-[[(4-Cyclohexylbutyl)amino]carbonyl]-2-oxazolyl]-7-oxabicyclo[2.2.1]hept-2-yl]-5-heptenoic acid, methyl ester To a stirred solution of Part D oxazoline (730 mg, 1.50 mmol) in 15 mL of dry CH$_2$Cl$_2$ was added 1.10 g of NiO$_2$. This mixture was stirred at room temperature for one hour, then 0.74 g of NiO$_2$ was added. This mixture was stirred at room temperature for an additional hour and a second portion of 0.74 g of NiO$_2$ was added. This mixture was stirred at room temperature for one more hour and then diluted with 80 mL of EtOAc, 50 mL of 3M NaHSO$_3$ solution and 50 mL of 1M sodium citrate solution. The aqueous layer was separated and extracted with EtOAc (3×120 mL). The combined organic extracts were dried (MgSO$_4$), filtered and concentrated in vacuo. This was chromatographed on 30 g of Merck silica gel 60 using 2% CH$_3$OH in CH$_2$Cl$_2$ as eluant to give 410 mg (56%) of title oxazole. TLC: silica gel, 2% CH$_3$OH/CH$_2$Cl$_2$, R$_f$ 0.31, Ce(SO$_4$)$_2$.

$^{13}$C NMR title compound (CDCl$_3$, 67.5 MHz): δ 173.7, 163.8, 160.5, 140.4, 136.1, 130.5, 128.0, 79.5, 79.3, 51.3, 49.7, 46.6, 39.0, 37.4, 37.0, 33.3, 33.3, 29.8, 29.7, 28.9, 27.8, 26.6, 26.3, 24.6, 24.1.

EXAMPLE 45A

[1S-[1α,2α(Z),3α,4α]]-7-[3-[4-[[(4-Cyclohexylbutyl)amino]carbonyl]-2-oxazolyl]-7-oxabicyclo[2.2.1]hept-2-yl] -5-heptenoic acid To a stirred solution of Example 44A oxazole (410 mg, 0.84 mmol) in 20 mL of CH$_3$OH was added 5 mL of 1N NaOH solution. This mixture was stirred at room temperature for 2.5 hours and concentrated in vacuo. This mixture was partitioned between 10 mL of 1N HCl solution saturated with NaCl and EtOAc 4 times with 20 mL . The EtOAc extracts were dried (MgSO$_4$), filtered and concentrated in vacuo. Purification was effected by flash chromatography on 20 g of Merck silica gel 60 using 150 mL of 2% CH$_3$OH in CH$_2$Cl$_2$ as eluant, followed with the elution of 4% CH$_3$OH in CH$_2$Cl$_2$ with 1% acetic acid to give 370 mg (93%) of pure title acid. m.p. 123°–125° C. TLC: silica gel, 6% CH$_3$OH in CH$_2$Cl$_2$, R$_f$ 0.22, Ce(SO$_4$)$_2$.

$^{13}$C NMR title compound (CDCl$_3$, 67.5 MHz): δ 177.8, 164.0, 160.9, 140.9, 135.8, 130.5, 128.1, 79.4, 79.4, 49.8, 46.7, 39.2, 37.5, 37.0, 33.3, 33.3, 29.8, 28.9, 27.8, 26.6, 26.5, 26.3, 26.3, 24.4, 24.2.

EXAMPLE 46A

[1S-[1α,2α(Z),3α,4α]]-6-[3-[4-[[(7,7-Dimethyloctyl)amino]carbonyl]-2-oxazolyl]-7-oxabicyclo[2.2.1]hept-2-yl]-4-hexenoic acid, methyl ester A. 3,3-Dimethylbutanal A solution of oxalyl chloride (9.4 mL, 13.6 g, 107 mmol) under argon in CH$_2$Cl$_2$ (500 mL) was prepared in a 1000 mL flask and cooled to −60° C. A solution of DMSO (15.4 mL, 18.5 g, 235 mmol) in 25 mL of CH$_2$Cl$_2$ was added dropwise over 10 minutes. The reaction mixture was stirred for 10 minutes, and 3,3-dimethyl-1-butanol (10 g, 98 mmol) was added slowly. Stirring was continued for an additional 20 minutes before (C$_2$H$_5$)$_3$N (68.1 mL, 49.5 g, 489 mmol) was added, and then the reaction mixture was allowed to warm to room temperature. Water (50 mL) was then added. The mixture was separated, and the aqueous layer was extracted once with CH$_2$Cl$_2$ (30 mL). The organic layers were combined, washed sequentially with 1% aqueous HCl, water, saturated NaHCO$_3$, H$_2$O, and saturated NaCl, and dried over MgSO$_4$ The filtered solution was concentrated using a rotary evaporator to obtain 3.3 g (33%) of title compound in the form of a yellow oil. The low yield was probably due to product volatility.

$^{13}$C NMR (67.8 MHz, CDCl$_3$) δ 203.3, 56.4, 31.0, 29.7.

B. 7,7-Dimethyl-4-octenoic acid

To a stirred solution of 3-carboxypropyltriphenyl phosphonium bromide (13.72 g, 31.9 mmol) in 60 mL of dry THF under argon at −15° C. was added dropwise 1.72N K t-amylate/toluene (32 mL, 57.9 mmol) over 10 minutes. The orange colored mixture was stirred for 0.5 hours. To this, Part A aldehyde (2.00 g, 19.9 mmol) was added slowly as a solution in 5 mL of THF. The reaction mixture was stirred at −15° C. for 1 hour and at room temperature for 20 hours. The reaction mixture was quenched with 12 mL of CH$_3$COOH added dropwise and then concentrated in vacuo. The residue was partitioned between EtOAc (100 mL) and water (100 mL). The aqueous layer was extracted twice more with EtOAc (100 mL). The combined organic layers were washed sequentially with 1% aqueous HCl, H$_2$O, saturated NaHCO$_3$, H$_2$O, and saturated NaCl, dried over MgSO$_4$, and concentrated in vacuo. The residue was chromatographed eluting with 0.3% CH$_3$COOH in (1% to 100% EtOAc in hexane gradient) to obtain 1.75 g (51%) of the desired title product.

$^{13}$C NMR (CDCl$_3$): δ 179.8, 128.6, 128.4, 41.0, 4.1, 31.1, 29.2, 22.6.

C. 7,7-Dimethyloctanoic acid

To a stirred solution of Part B acid (1.2 g, 7.04 mmol) in 8 mL of CH$_3$COOH, was added 0.2 g of platinum oxide. This mixture was stirred for 4 hours under 1 atmosphere of H$_2$ (balloon). The reaction mixture was filtered through a Celite® pad. The filtrate was concentrated in vacuo. The residue was diluted with 50 mL toluene and concentrated again. This process was repeated once more, to obtain 1.2 g (100%) of the desired title product as oil.

D. 7,7-Dimethyloctanamide

To a stirred solution of Part C acid (1.21 g, 7.02 mmol) in 50 mL of toluene was added 3 mL of oxalyl chloride. This reaction mixture was stirred for 1 hour at room temperature under argon and concentrated in vacuo. The residue was diluted with 20 mL of toluene and concentrated again. This was repeated to remove traces of oxalyl chloride. The residue was stirred at room temperature under argon in 5 mL of CH$_3$OH and (C$_2$H$_5$)$_3$N (1.17 mL, 8.43 mmol), and an excess of 9 M methanolic ammonia (2 mL) was added. After stirring for 16 hours, the reaction mixture was partitioned between 3 mL water and 20 mL EtOAc. The aqueous layer was extracted twice more with EtOAc (20 mL). The combined organic layers were washed with NaCl, dried over MgSO$_4$, filtered, and concentrated in vacuo to obtain a semi-solid. The semi-solid was crystallized by trituration with hexane to obtain 0.5 g (42%) of the desired title product as a solid.

$^{13}$C NMR (CDCl$_3$): δ 176.3, 43.9, 35.9, 30.2, 29.3, 25.5, 24.2.

E. 7,7-Dimethyloctanamine

To a solution of Part D amide (0.45 g, 2.62 mmol) in 50 mL of dry ether stirred under argon at 0° C. was added lithium aluminum hydride (0.11 g, 2.88 mmol). Gas was evolved. The reaction mixture was stirred at room temperature for 4 days. While stirring vigorously, the reaction was cautiously quenched by addition of 0.02 mL of H$_2$O, 0.02 mL of 15% aqueous NaOH, and 0.072 mL of H$_2$O. A white precipitate formed. After stirring for 0.5 hours, the white precipitate was filtered, and the filtrate was concentrated in vacuo to obtain 0.4 g (89%) of title compound in the form of a yellow oil. This oil was crystallized by trituration with hexane and CHCl$_3$.

F.
[1S-[1α,2α(Z),3α,4α]]-6-[3-[4-[(7,7-Dimethyloctyl-)amino]carbonyl]-2-oxazolyl]-7-oxabicyclo[2.2.1]hept-2-yl]-4-hexenoic acid, methyl ester To a solution of acid chloride prepared in Example 2A, Part I (0.46 g, 1.3 mmol) plus an unknown quantity of Vilsmeier salt in 5 mL of CHCl$_3$ under argon at room temperature, was added (C$_2$H$_5$)$_3$N (0.25 mL, 0.18 g, 1.8 mmol) and Part E amine (0.24 g, 1.5 mmol). The reaction mixture was stirred at room temperature for 16 hours, then diluted with EtOAc and water. The organic layer was separated, and the aqueous layer was extracted with 20 mL of EtOAc twice. The organic layers were combined, washed with brine, dried over MgSO$_4$ and concentrated. Flash chromatography (0% to 100% EtOAc in hexane gradient) gave 0.20 g (32%) of the desired title product as an oil. R$_f$ is 0.8 in 1% TFA, 1% CH$_3$OH, 98% EtOAc.

$^{13}$C NMR (CDCl$_3$): δ 172.8, 163.6, 160.2, 140.1, 135.9, 129.1, 128.3, 79.3, 79.1, 51.1, 49.4, 46.4, 43.9, 38.8, 33.5, 29.9, 29.5, 29.4, 29.1, 28.7, 27.6, 26.7, 24.1, 22.5.

EXAMPLE 47A

[1S-[1α,2α,(Z)3α,4α]-6-[3-[4-[[(7,7-Dimethyloctyl-)amino]carbonyl]-2-oxazolyl]-7-oxabicyclo[2.2.1]hept-2-yl]-4-hexenoic acid A solution of Example 46A ester (0.20 g, 0.38 mmol) in 10 mL of 1N NaOH and 10 mL of THF was prepared. The reaction mixture was stirred for 13 hours, then concentrated in vacuo to remove THF and acidified to pH 2 with 1N HCl. EtOAc was added and the organic layer was separated. The aqueous layer was extracted twice with 20 mL of EtOAc. The organic layers were combined, washed with brine, and concentrated in vacuo to obtain a clear oil. This oil was chromatographed (0.1% CH$_3$COOH in (0% to 50% EtOAc in hexane gradient)) to obtain 0.12 g (66%) of title acid in the form of a white solid. mp 68°–69° C. R$_f$ is 0.18 in 1:1 hexane-EtOAc with 0.05% CH$_3$COOH.

[α]$_D^o$ = +31.1 in CH$_3$OH at c=0.46 g/100 mL.

$^{13}$C NMR (CDCl$_3$): δ 176.8, 163.9, 160.7, 140.8, 135.7, 129.4, 128.4, 79.5, 79.3, 49.6, 46.5, 44.0, 39.1, 33.6, 30.1, 29.6, 29.4, 29.3, 28.8, 27.8, 26.8, 24.3, 22.5.

EXAMPLE 48A

[1S-[1α,2α(E),3α,4α]]-6-[3-[4-[[(4-Cyclohexylbutyl-)amino]carbonyl]-2-oxazolyl-7-oxabicyclo[2.2.1]hept-2-yl]-4-hexenoic acid

A.
[1S-[1α,2α(Z),3α,4α]]-7-[3-[[Dimethyl-1,1-dimethylethyl)silyl]oxy]-7-oxabicyclo[2.2.1]hept-2-yl]-5-heptenoic acid, methyl ester To a stirring solution of 20.57 g of [1S-[1α,2α(Z),3α,-4α]]-7-[3-(hydroxymethyl)-7-oxabicyclo[2.2.1]hept-2-yl]-5-heptenoic acid, methyl ester (prepared as described in U.S. Pat. No. 4,143,054) (76.8 mmol) and 5.74 g imidazole (84.4 mmol, 1.1 equiv) in 100 mL CH$_2$Cl$_2$ under argon at 0°, was added 12.05 g t-butyldimethylsilyl chloride (79.8 mmol, 1.04 equiv). A precipitate formed. The mixture was warmed to room temperature, and 10 minutes later it was diluted with diethyl ether (EtO$_2$), washed with water three times and brine once, dried over Na$_2$SO$_4$, and concentrated by rotoevaporation and then high vacuum. The residue, 30.31 g of nearly pure title silyl ether, was used without further purification. The yield of title ester was roughly quantitative.

TLC (50% EtOAc in hexanes-anisaldehyde):

| starting material | 0.21 |
|---|---|
| title ester | 0.79 |

B.
1S-(1α,2α,3α,4α)]-3-[[(1,1-Dimethylethyl)dimethylsilyl]oxy]methyl]-7-oxabicyclo[2.2.1]heptane-2-acetaldehyde A solution of 30.31 g nearly pure Part A silyl ether (76.8 mmol) in 200 mL CH$_2$Cl$_2$ at $-78°$ was treated with ozone until a blue color had persisted for 25 minutes. After purging excess O$_3$ with O$_2$, 48.0 g of (CH$_3$)$_2$S (770 mmol, 10 equiv) was added, and the mixture was warmed to room temperature. After 1 hour stirring at room temperature, solvent and excess (CH$_3$)$_2$S were removed by rotoevaporation. $^1$H NMR of the crude material revealed incomplete reduction of the ozonide. Therefore, after redissolving in CH$_2$Cl$_2$ at room temperature, 20.2 g triphenylphosphine (77 mmol, 1.0 equiv) was added. This mixture warmed due to exothermic reaction. After stirring overnight, most of the solvent was evaporated, and hexane was added to precipitate triphenylphosphine oxide and triphenylphosphine. The precipitate was filtered off, and the filtrate was concentrated before flash chromatography (5% to 15% EtOAc in hexanes gradient) allowed isolation of 16.31 g pure title aldehyde as an oil.

TLC: 50% EtOAc in hexanes-anisaldehyde):

| Part A silyl ether | 0.89 |
|---|---|
| title aldehyde | 0.76 |
| methyl 5-oxopentanoate | 0.51 |

C.
[1S-(1α,2α(E),3α,4α)]-4-[3-[[[(1,1-Dimethylethyl)dimethylsilyl]oxy]methyl]-7-oxabicyclo[2.2.1]hept-2-yl]-2-butenoic acid, methyl ester A flask containing 3.3 g (37.9 mmol) of LiBr was placed under vacuum and heated with a heat gun to drive off any moisture. On cooling, the flask was flushed with Ar, and 20 mL of CH$_2$Cl$_2$ was added. To this stirred mixture was added a solution of 5.44 g (29.9 mmol) of trimethylphosphonoacetate in 30 mL of CH$_2$Cl$_2$ followed by 4.0 mL of (C$_2$H$_5$)$_3$N (28.7 mmol). This mixture was stirred for 15 minutes after which a solution of 5.4 g (19.0 mmol max.) of crude Part B aldehyde in 35 mL of CH$_2$Cl$_2$ was added over 1 minute. This was accompanied by a slight exotherm and the formation of a sticky precipitate. This mixture was stirred vigorously at room temperature overnight. The reaction mixture was partitioned between 200 mL of hexane and 100 mL of 0.3M HCl. The aqueous layer was extracted once with 100 mL of diethyl ether. The combined organic extracts were dried over MgSO$_4$, filtered, and concentrated in vacuo. TLC analysis showed that the reaction had not gone to completion (40-50%). The residue was then dissolved in 50 mL of CH$_2$Cl$_2$, and to it was added 6.3 g (18.8 mmol) of carbomethoxymethylenetriphenylphosphorane. This solution was stirred at room temperature for 22 hours and then concentrated in vacuo. The residue was triturated with diethyl ether and diluted with an equal volume of hexane. The mixture was refrigerated for 2 hours, and then the solid was removed by filtration. The filtrate was concentrated in vacuo. The crude product was purified by chromatography on 167 g silica gel using a 4:1 hexane-diethyl ether as eluent to provide 5.9 g (91%) of title ester.

TLC: silica gel, 2:1 hexane-ether, R$_f$0.6, vanillin.

$^{13}$C NMR 67.8 MHz in CDCl$_3$): δ 148.8, 121.8, 79.9, 78.8, 61.9, 51.4, 44.8, 30.7, 29.5, 29.4, 25.9, 18.2, −5.4.

D.
[1S-(1α,2α(E),3α,4α)]-4-[3-[[[(1,1-Dimethylethyl)dimethylsilyl]oxy]methyl]-7-oxabicyclo[2.2.1]hept-2-yl]-2-buten-1-ol A solution of 5.2 g (15.3 mmol) of Part C ester in 80 mL of THF was cooled to −78° C. To this stirred solution was added dropwise 50.0 mL of a 1.5M DIBAL-H solution in toluene over a period of 20 minutes. The reaction was stirred at −78° C. for 5 hours, and then the reaction was quenched by the addition of a solution of 10 mL of acetone in 10 mL of toluene. This was followed by the slow addition of 60 g of 10:9 (w/w) silica gel:water. After several grams of the moist silica gel had been added, the cold bath was removed. The reaction mixture was diluted with 200 mL of ether. The pot temperature was monitored, and when it reached 10° C., the flask was immersed in an ice bath. This was stirred for 1 hour, and then the silica gel was removed by filtration. The filter cake was rinsed with two 100 mL portions of ether. The combined filtrates were dried over MgSO$_4$, filtered, and concentrated in vacuo to afford 5.05 g (>100%) of crude title alcohol.

TLC: silica gel, 2:1 hexane-ether, R$_f$0.1, vanillin.

$^{13}$C NMR (67.8 MHz in CDCl$_3$): δ 131.6, 130.3, 79.8, 8.8, 63.3, 61.8, 49.3, 45.4, 30.5, 29.5, 29.3, 25.9, 18.2, −5.4.

E.
[1S-(1α,2α(E),3α,4α)-4-3-[[[(1,1-Dimethylethyl)dimethylsilyl]oxy]methyl]-7-oxabicyclo[2.2.1]hept-2-yl]-2-butene-1-bromide To a flask containing 0.83 g of triphenylphosphine (3.17 mmol, 1.0 equiv) dissolved in 10 mL toluene under argon at 0°, was added 0.51 g of Br$_2$ (3.17 mmol, 1.0 equiv) in a single portion. A yellowish precipitate and an orange gum formed. Scraping with a spatula converted the gum to more free flowing precipitate. The mixture was briefly warmed to room temperature, then recooled to 0°. To this was added dropwise a solution of 1.04 g of Part D alcohol (95% pure=0.99 g, 3.17 mmol) and 0.28 g of pyridine (3.49 mmol, 1.1 equiv) in 5 mL toluene plus a 5 mL wash-in. The mixture was stirred at 0° for 30 minutes, then warmed to room temperature. Reaction was incomplete according to TLC. After 4 hours (no further progress by TLC), the mixture was filtered, and the filtrate was evaporated. Flash chromatography (3% to 50% EtOAc in hexanes gradient) allowed isolation of 880 mg of title bromide, an oil, and 190 mg of unreacted Part D alcohol. The yield of title bromide was 74%.

TLC (25% EtOAc in hexanes-anisaldehyde):

| Part D alcohol | 0.21 |
|---|---|
| title bromide | 0.75 |

$^{13}$C NMR (67.8 MHz in CDCl$_3$): δ 135.6, 127.5, 79.8, 78.8, 61.8, 49.4, 45.3, 33.1, 30.5, 29.5, 29.4, 25.9, 18.2, −5.3.

F.
[1S-(1α,2α(E),3α,4α)]-6-[3-[[[(1,1-Dimethylethyl)dimethylsilyloxy]methyl]-7-oxabicyclo[2.2.1]hept-2-yl]-4-hexenoic acid, 1,1-dimethylethyl ester To a solution of LDA in THF (2.70 mmol, 1.15 equiv, prepared by slowly adding 1.08 mL of 2.5M $C_4H_9Li$ in hexanes solution (2.70 mmol, 1.15 equiv) to a solution of 303 mg diisopropyl amine (3.0 mmol, 1.28 equiv) in 4 mL dry THF stirring at 0° under argon and then stirring for 15 minutes) stirring under argon at −78° was added dropwise a solution of 348 mg of t-butyl acetate (t-BuOAc) (3.0 mmol, 1.28 equiv) in 3 mL dry THF over 15 minutes. After stirring 1 hour, a solution of 880 mg Part E bromide (2.35 mmol) in 3 mL dry THF was added dropwise with two 2 mL wash-ins. After 8 hours of stirring at −78°, TLC showing only partial reaction, the mixture was allowed to very slowly warm (approximately 8° per hour) to room temperature. TLC indicated further progress, but still incomplete consumption of bromide. Addition of 1 mL of saturated aqueous $NH_4Cl$ solution was followed by drying over $Na_2SO_4$ and evaporation. The residue was flash chromatographed (5% EtOAc in hexane) to obtain 550 mg of nearly pure title ester product (97% pure=534 mg). The yield of title ester was 55%.

TLC (5% EtOAc in hexanes-anisaldehyde):

| Part E bromide | 0.20 |
|---|---|
| title ester | 0.13 |

$^{13}C$ NMR (67.8 MHz in $CDCl_3$): δ 172.4, 130.6, 129.6, 80.0, 79.8, 78.8, 61.9, 49.4, 45.8, 35.4, 30.8, 29.6, 29.4, 28.1, 25.9, 18.2, 5.3.

G.
[1S-(1α,2α(E),3α,4α)]-6-[3-(Hydroxymethyl)-7-oxabicyclo[2.2.1]hept-2-yl]-4-hexenoic acid, methyl ester To a solution of 550 mg of nearly pure Part F ester (97% pure=534 mg, 1.30 mmol) in 20 mL $CH_3OH$ stirring at room temperature under argon, was added 2 mL of a solution of dry HCl in $CH_3OH$ (prepared by adding 2 drops of acetyl chloride to mL $CH_3OH$ at room temperature and then allowing to stand 1 minute). TLC indicated complete conversion to an intermediate after 1 hour. This intermediate was then very slowly converted to product. Addition of 10 mL more HCl in $CH_3OH$ solution hastened the reaction. After 14 days, 2 mL $(C_2H_5)_3N$ was added, and the mixture was evaporated. This gave 630 mg of crude title alcohol.

TLC 50% EtOAc in hexanes-anisaldehyde):

| Part F ester | 0.94 |
|---|---|
| intermediate | 0.33 |
| title alcohol | 0.23 |

H.
[1S-(1α,2α(E),3α,4α)]-6-[3-Carboxy-7-oxabicyclo[2.2.1]hept-2-yl]-4-hexenoic acid, methyl ester To a solution of 630 mg of crude Part G alcohol in 20 mL acetone under argon at 0°, was added slowly 4 mL Jones' Reagent (2.6M in $Cr^{VI}$). The red color of the reagent persisted toward the end of the addition. The resulting precipitated mixture was allowed to warm to room temperature for 20 minutes before recooling and 2-propanol addition to quench excess reagent. Still at 0°, 3M aqueous $NaHSO_3$ solution was added with stirring until all salts dissolved. Brine was added, and extraction (3 times) with EtOAc followed. After drying the extracts over $Na_2SO_4$ and solvent evaporation, flash chromatography (silica, 25% to 50% (5% acetic acid in EtOAc) in hexane gradient) afforded, after azeotropic removal of acetic acid with toluene, 260 mg of title acid, obtained in 75% overall yield from Part F ester.

TLC (50% (5% $CH_3COOH$ in EtOAc) in hexane-anisaldehyde):

| Part G alcohol | 0.32 |
|---|---|
| title acid | 0.36 |

$^{13}C$ NMR (67.8 MHz in $CDCl_3$): δ 177.1, 173.4, 130.4, 129.2, 78.2, 78.1, 51.9, 51.3, 47.4, 33.8, 32.4, 28.9, 28.8, 27.7.

I.
[1S-[1α,2α(E),3α,4α]]-6-[3-[4-[[(4-Cyclohexylbutyl)amino]carbonyl]-2-oxazolyl]-7-oxabicyclo[2.2.1]hept-2-yl]-4-hexenoic acid Following the procedure of Example 1A, starting at Part E except substituting the Part H acid for the Example 1, Part D acid, the title compound is obtained. mp 122°-125°; TLC (50% [5% AcOH in EtOAc] in hexane; title acid $R_f$ 0.33;

$^{13}C$ NMR ($CDCl_3$, 67.8 MHz): δ 176.9, 163.9, 160.7, 140.8, 135.6, 130.0, 128.8, 79.4, 79.1, 49.1, 46.5, 39.1, 37.4, 36.9, 33.7, 33.2, 33.0, 29.7, 29.5, 28.8, 27.5, 26.5, 26.2, 24.0.

EXAMPLE 49A

[1S-(1α,2α,3α,4α)]-3-[4-1(4-(Cyclohexylbutyl)amino]carbonyl]-2-oxazolyl]-7-oxabicyclo[2.2.1]heptane-2-hexanoic acid A solution of 130 mg of Example 1A acid in 10 mL of ethyl acetate and 1.0 mL of acetic acid was degassed via a vacuum-fill cycle with argon. To this solution was added 34 mg of 10% Pd/C and the atmosphere was exchanged for hydrogen by two vacuum-fill cycles. A slight positive pressure was maintained through use of a hydrogen balloon. The mixture was stirred at room temperature for 22.5 hours, diluted with $CH_2Cl_2$ and filtered through a polycarbonate filter to remove the catalyst. The filtrate was concentrated in vacuo. The residue was diluted with toluene and reconcentrated. Upon addition of ethyl acetate to the residue, a small amount of gel-like material did not dissolve. The solution was decanted off and concentrated in vacuo. The crude product was dissolved in minimal hot ethyl acetate and diluted with ca. three volumes of hexane. On cooling no solid appeared, however, after standing at 5° C. overnight a white gel-like solid formed. This was removed by filtration and dried in vacuo. The resulting white powder was triturated in hexane, filtered and dried in vacuo to afford 61 mg of pure title acid; m.p. 97(softens), 122°-3° C.

Analysis Calc'd for $C_{26}H_{40}N_2O_5$: C, 67.79; H, 8.75; N, 6.08 Found: C, 67.58; H, 8.79; N, 5.97

TLC: silica gel, 4% $CH_3OH/CH_2Cl_2$, $R_f$=0.35, Ce($SO_4$)$_2$.

$[α]_D$= +23 (c=0.68, $CHCl_3$).

$^{13}$C NMR (CDCl$_3$, 67.5 MHz): δ 164.2, 160.8, 135.9, 79.5, 79.4, 49.8, 47.2, 39.2, 37.5, 37.1, 33.7, 33.4, 29.9, 29.7, 29.2, 29.0, 28.1, 26.7, 26.4, 24.5, 24.2.

EXAMPLE 50A

[1S-[1α,2α(Z),3α,4α]]-6-[3-[4-[[(4-Cyclohexylbutyl-)amino]carbonyl]-2-oxazolyl]-7-oxabicyclo[2.2.1]hept-2-yl]-4-hexenoic acid, methyl ester

A.

1S-1α,2α(Z),3α(R*),4α]]-6-[3-[[[2-[(4-Cyclohexylbutyl-)amino]-1-(hydroxymethyl)-2-oxoethyl]amino]carbonyl]-7-oxabicyclo[2.2.1]hept-2-yl]-4-hexenoic acid, methyl ester To a stirred mixture of Example 1A, Part D acid (6.70 g, 25.2 mmol), 1-hydroxybenzotriazole monohydrate (3.40 g, 25.2 mmol) and TFA salt of Example 1, Part B amine (8.97 g, 25.2 mmol) in 100 mL of DMF under argon at 0° C. was added sequentially (C$_2$H$_5$)$_3$N (17.6 mL, 126 mmol) and 1-(3-dimethylaminopropyl)-3-ethyl-carbodiimide hydrochloride salt (4.82 g, 25.2 mmol). The mixture was stirred at 0° C. for 2 hours and at room temperature for 16 hours. The mixture was concentrated in vacuo and partitioned between 800 mL of EtOAc and 1N HCl solution (2×100 mL), 0.2N NaOH solution (2×100 mL), saturated NaHCO$_3$ solution (1×100 mL). The organic layer was dried (MgSO$_4$), filtered and concentrated in vacuo. This was chromatographed on g of Merck silica gel 60 using 2% CH$_3$OH/CH$_2$Cl$_2$ as eluant to give 4.75 g (39%) of title amide.

TLC: silica gel, 50% (5% AcOH in EtOAc) in hexane, R$_f$ 0.22, anisaldehyde.

B.

[1S-1α,2α(Z),3α(R*),4α]]-6-[3-[4-[[(4-Cyclohexylbutyl-)amino]carbonyl]-4,5-dihydro-2-oxazolyl]-7-oxabicyclo[2.2.1]-hept-2-yl]-4-hexenoic acid, methyl ester To a stirred mixture of Part A amide (4.69 g, 9.53 mmol) in 60 mL of dry CH$_2$Cl$_2$ under argon at 0° C. was added sequentially (C$_2$H$_5$)$_3$N (2.66 mL, 19.1 mmol) and mesyl chloride (0.82 mL, 10.5 mmol). The mixture was stirred at 0° C. for 1 hour and diluted with 100 mL of CH$_2$Cl$_2$ and washed with saturated NaHCO$_3$ solution (1×30 mL) and brine (1×30 mL). The organic layer was dried (MgSO$_4$), filtered and concentrated in vacuo. The crude mesylate was dissolved in 60 mL of acetone and combined with K$_2$CO$_3$ (5.0 g, 36.2 mmol). The mixture was refluxed for 4.5 hours and cooled to room temperature. The solid was filtered off and rinsed with acetone (4×40 mL). The filtrate was concentrated in vacuo and chromatographed on 120 g of Merck silica gel 60 using 2% CH$_3$OH/CH$_2$Cl$_2$ as eluant to give 3.93 g (86%) of title oxazoline.

TLC: silica gel, 20% acetone in toluene, R$_f$ 0.29, anisaldehyde.

C.

[1S-[1α,2α(Z),3α,4α]]-6-[3-[4-[[(4-Cyclohexylbutyl-)amino]carbonyl]-2-oxazolyl]-7-oxabicyclo[2.2.1]hept-2-yl]-4-hexenoic acid, methyl ester To a stirred mixture of Part B oxazoline (3.90 g, 8.23 mmol) in 80 mL of dry CH$_2$Cl$_2$ under argon was added 6 g of NiO$_2$. The mixture was stirred at room temperature for 40 minutes at which time 4 g of NiO$_2$ was added. The mixture was stirred for another 70 minutes and again 2 g of NiO$_2$ was added. The mixture was stirred at room temperature for 2 hours and diluted with 120 mL of EtOAc, 60 mL of 3M NaHSO$_3$ solution and 60 mL of 1M sodium citrate solution. The aqueous layer was separated and extracted with EtOAc 4×150 mL).

The combined EtOAc extracts were dried (MgSO$_4$), filtered and concentrated in vacuo. Purification was effected by flash chromatography on 120 g of Merck silica gel 60 using 2% CH$_3$OH/CH$_2$Cl$_2$ as eluant to give 1.85 g (48%) of title oxazole.

TLC: silica gel, EtOAc, R$_f$ 0.81, anisaldehyde.

What is claimed is:

1. A method for preparing a compound of the structure

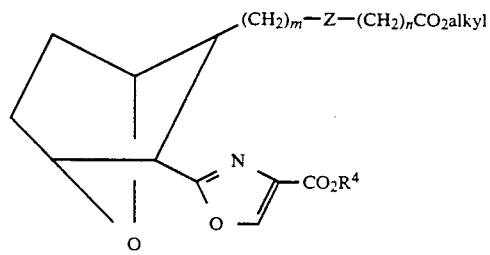

wherein m is 1, 2 or 3, n is 0, 1, 2, 3 or 4, Z is —(CH$_2$)$_2$—, —CH=CH— or

wherein Y is O, a single bond or vinyl; and R$^4$ is lower alkyl or arylalkyl, which comprises treating an oxazoline compound of the structure

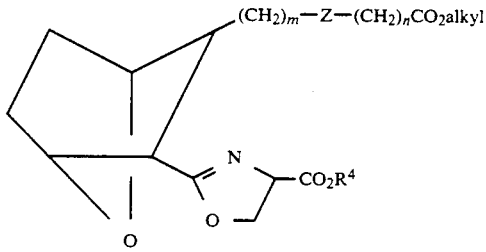

with cupric bromide and 1,8-diazabicyclo[5.4.0]undecene (DBu).

2. The method as defined in claim 1 wherein Z is —CH=CH— or

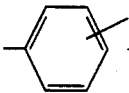

3. The method as defined in claim 1 carried out at a temperature within the range of from about 20 to about 70° C.

4. The method as defined in claim 1 wherein the cupric dibromide is employed in a molar ratio to the oxazoline of within the range of from about 2:1 to about 6:1 and the cupric dibromide is employed in a molar ratio to DBU of within the range of from about 1:1 to about 1.3.

* * * * *

UNITED STATES PATENT AND TRADEMARK OFFICE
CERTIFICATE OF CORRECTION

PATENT NO.   : 5,153,327
DATED        : Oct. 6, 1992
INVENTOR(S)  : Raj N. Misra et al It is certified that error appears in the above-identified patent and that said Letters Patent is hereby corrected as shown below:

Column 220, Claim 1, line 48, insert -- 7- -- end of line.

Signed and Sealed this

Fifth Day of October, 1993

Attest:

BRUCE LEHMAN

*Attesting Officer*     *Commissioner of Patents and Trademarks*